US010479765B2

(12) United States Patent
Beck et al.

(10) Patent No.: US 10,479,765 B2
(45) Date of Patent: *Nov. 19, 2019

(54) SUBSTITUTED N,2-DIARYLQUINOLINE-4-CARBOXAMIDES AND THE USE THEREOF AS ANTI-INFLAMMATORY AGENTS

(71) Applicant: BAYER PHARMA AKTIENGESELLSCHAFT, Berlin (DE)

(72) Inventors: Hartmut Beck, Wuppertal (DE); Tobias Thaler, Wuppertal (DE); Raimund Kast, Wuppertal (DE); Daniel Meibom, Wuppertal (DE); Mark Meininghaus, Wuppertal (DE); Carsten Terjung, Bochum (DE); Martina Delbeck, Heiligenhaus (DE); Klemens Lustig, Wuppertal (DE); Uwe Muenster, Wülfrath (DE); Britta Olenik, Bottrop (DE)

(73) Assignee: BAYER PHARMA AKTIENGESELLSCHAFT, Berlin (DE)

( * ) Notice: Subject to any disclaimer, the term of this patent is extended or adjusted under 35 U.S.C. 154(b) by 0 days.

This patent is subject to a terminal disclaimer.

(21) Appl. No.: 16/125,645

(22) Filed: Sep. 7, 2018

(65) Prior Publication Data
US 2019/0002409 A1 Jan. 3, 2019

Related U.S. Application Data

(63) Continuation of application No. 15/509,600, filed as application No. PCT/EP2015/070318 on Sep. 7, 2015, now Pat. No. 10,189,788.

(30) Foreign Application Priority Data

Sep. 9, 2014 (EP) .................................... 14184040

(51) Int. Cl.
C07D 215/52 (2006.01)
C07D 215/60 (2006.01)
C07D 401/12 (2006.01)
C07D 401/04 (2006.01)

(52) U.S. Cl.
CPC ......... C07D 215/52 (2013.01); C07D 215/60 (2013.01); C07D 401/04 (2013.01); C07D 401/12 (2013.01)

(58) Field of Classification Search
CPC .... A61K 31/47; C07D 215/52; C07D 215/60; C07D 401/04; C07D 401/12
See application file for complete search history.

(56) References Cited

U.S. PATENT DOCUMENTS

| 8,642,768 | B2 | 2/2014 | Blanco-Pillado et al. |
| 8,933,098 | B2* | 1/2015 | Blanco-Pillado .... C07D 401/04 514/318 |
| 2016/0251306 | A1* | 9/2016 | Blanco-Pillado .... C07D 405/04 514/563 |
| 2017/0260140 | A1* | 9/2017 | Beck ..................... C07D 215/52 |

FOREIGN PATENT DOCUMENTS

| EP | 2 415 755 | 2/2012 |
| WO | WO 1995/032948 | 12/1995 |
| WO | WO 1996/002509 | 2/1996 |
| WO | WO 1997/019926 | 6/1997 |
| WO | WO 2000/006568 | 2/2000 |
| WO | WO 2000/006569 | 2/2000 |
| WO | WO 2001/019355 | 3/2001 |
| WO | WO 2001/019776 | 3/2001 |
| WO | WO 2001/019778 | 3/2001 |
| WO | WO 2001/019780 | 3/2001 |
| WO | WO 2002/042301 | 5/2002 |
| WO | WO 2002/070462 | 9/2002 |
| WO | WO 2002/070510 | 9/2002 |
| WO | WO 2003/095451 | 11/2003 |
| WO | WO 2004/045614 | 6/2004 |
| WO | WO 2005/103030 | 3/2005 |
| WO | WO 2006/094237 | 9/2006 |
| WO | WO 2011/009540 | 1/2011 |
| WO | WO 2011/147809 | 12/2011 |
| WO | WO 2011/153553 | 12/2011 |
| WO | WO 2012/004258 | 1/2012 |
| WO | WO 2012/028647 | 3/2012 |
| WO | WO 2012/059549 | 5/2012 |
| WO | WO 2013/074059 | 5/2013 |
| WO | WO 2013/164326 | 11/2013 |
| WO | WO 2014/117090 | 7/2014 |
| WO | WO 2015/094912 | 6/2015 |

OTHER PUBLICATIONS

Tanaka, Respiratory Investigation 51, 76-83, 2013. (Year: 2013).*
Int'l Search Report for PCT/EP2015/070318, four pages, dated Oct. 8, 2015.
Written Opinion of the ISA for PCT/EP2015/070318, five pages, dated Oct. 8, 2015.
Abramovit et al. "Cloning and expression of cDNA for the human prostanoid FP receptor" J. Biol. Chem. 269:2632-2636 (1994).
Agas et al. "Prostaglandin F$_2$α: A bone remodeling mediator" J. Cell. Physiol. 228:25-29 (2013).
Aihara et al. "Clinical relevance of plasma prostaglandin F$_2$ α, metabolite concentrations in patients with idiopathic pulmonary fibrosis" PLoS One 8:e68017, seven pages (Jun. 2013).
Barnes "Chronic obstructive pulmonary disease" New Engl. J. Med. 343:269-280 (2000).

(Continued)

Primary Examiner — D Margaret M Seaman
(74) Attorney, Agent, or Firm — McBee Moore Woodward & Vanik IP, LLC

(57) ABSTRACT

The present application relates to novel substituted N,2-diarylquinoline-4-carboxamide derivatives, to processes for preparation thereof, to the use thereof alone or in combinations for treatment and/or prevention of diseases, and to the use thereof for production of medicaments for treatment and/or prevention of diseases, especially for treatment and/or prevention of fibrotic and/or inflammatory disorders.

10 Claims, No Drawings

(56) References Cited

OTHER PUBLICATIONS

Bastiaansen-Jenniskens et al. "Stimulation of fibrotic processes by the infrapatellar fat pad in cultured synoviocytes from patients with osteoarthritis" Arth. Rheum. 65:2070-2080 (2013).
Basu "Bioactive eicosanoids: Role of prostaglandin $F_2\alpha$ and F2-isoprostanes in inflammation and oxidative stress related pathology" Mol. Cells 30:383-391 (2010).
Basu et al. "Presence of a 15-ketoprostaglandin reductase in porcine cornea" Acta Chem. Scand. 46:108-110 (1992).
Beck et al. "Die therapie der idiopathischen pulmonalen fibrose" Pneumologe 10:105-111 (2013).
Behr et al. "Pulmonary hypertension in interstitial lung disease" J. Eur. Respir. 31:1357-1367 (2008).
Beier et al. "Preparation of $SF_5$ aromatics by vicarious nucleophilic substitution reactions of nitro(pentafluorosulfanyl)benzenes with carbanions" J. Org. Chem. 76:4781-4786 (2011).
Blanco et al. "Hemodynamic and gas exchange effects of sildenafil in patients with chronic obstructive pulmonary disease and pulmonary hypertension" J. Am. Respir. Crit. Care Med. 181:270-278 (2010).
Boa et al. "Synthesis of brequinar analogue inhibitors of malaria parasite dihydroorotate dehydrogenase" Bioorg. Med. Chem. 13:1945-1967 (2005).
Ding et al. "Prostaglandin $F_2\alpha$ facilitates collagen synthesis in cardiac fibroblasts via an F-prostanoid receptor/protein kinase C/Rho kinase pathway independent of transforming growth factor β1" Int'l J. Biochem. Cell Biol. 44: 1031-1039 (2012).
Estenne & Hertz "Pulmonary perspective: Bronchiolitis obliterans after human lung transplantation" Am. J. Respir. Crit. Care Med. 166:440-444 (2002).
Ghofrani et al. "Neue therapieoptionen in der behandlung der pulmonalarteriellen hypertonie" Herz 30:296-302 (2005).
Hoeper et al. "Diagnosis, assessment, and treatment of non-pulmonary arterial hypertension pulmonary hypertension" J. Am. Coll. Cardiol. 54:S85-S96 (2009).
Humbert et al. "Cellular and molecular pathobiology of pulmonary arterial hypertension" J. Am. Coll. Cardiol. 43:13S-24S (2004).
Ito et al. "Current drug targets and future therapy of pulmonary arterial hypertension" Curr. Med. Chem. 14:719-733 (2007).
Kanno et al. "Alpha2-antiplasmin regulates the development of dermal fibrosis in mice by prostaglandin $F_2\alpha$ synthesis through adipose triglyceride lipase/calcium-independent phospholipase $A_2$" Arth. Rheum. 65:492-502 (2013).
Kitanaka et al. "Cloning and expression of a cDNA for rat prostaglandin $F_2\alpha$ receptor" Prostaglandins 48:31-41 (1994).
Lackey et al. "Synthesis of substituted quinolone-4-carboxylic acids" Synthesis 1993:993-997 (1993).
Lettieri et al. "Prevalence and outcomes of pulmonary arterial hypertension in advanced idiopathic pulmonary fibrosis" Chest 129:746-752 (2006).
Ley et al. "Concise clinical review: Clinical course and prediction of survival in idiopathic pulmonary fibrosis" Am. J. Respir. Crit. Care Med. 183:431-440 (2011).
Montani & Simonneau "Updated clinical classification of pulmonary hypertension" in *Pulmonary Circulation: Diseases and Their Treatment* $3^{rd}$ *Ed.* pp. 197-206 (2011).
Naeije & Westerhopf "Pulmonary vascular function" in *Pulmonary Circulation: Diseases and Their Treatment* $3^{rd}$ *Ed.* pp. 3-15 (2011).
Oga et al. "Prostaglandin $F_2\alpha$ receptor signaling facilitates bleomycin-induced pulmonary fibrosis independently of transforming growth factor-β" Nature Med. 15:1426-1430 (2009).
Olman "Beyond TGF-β: A prostaglandin promotes fibrosis" Nature Med. 15:1360-1361 (2009).
O'Reilly et al. "Crystalline and amorphous silica differentially regulate the eyelooxygenase-prostaglandin pathway in pulmonary fibroblasts: Implications for pulmonary fibrosis" Am. J. Physiol. Lung Cell Mol. Physiol. 288:L1010-L1016 (2005).
Rosenzweig "Emerging treatments for pulmonary arterial hypertension" Exp. Opin. Emerg. Drugs 11:609-619 (2006).
Stolz et al. "A randomised, controlled trial of bosentan in severe COPD" Eur. Respir. J. 32:619-628 (2008).
Strieter et al. "Translating basic research into clinical practice: New mechanisms of pulmonary fibrosis" Chest 136:1364-1370 (2009).
Sugimoto et al. "Cloning and expression of a cDNA for mouse prostaglandin F receptor" J. Biol. Chem. 269:1356-1360 (1994).
Watanabe et al. "Enzymatic formation of prostaglandin $F_2\alpha$, from prostaglandin $H_a$ and $D_2$" J. Biol. Chem. 260:7035-7041 (1985).
Woodward et al. "International union of basic and clinical pharmacology. LXXXIII: Classification of prostanoid receptors, updating 15 years of progress" Pharmacol. Rev. 63:471-538 (2011).
Zhang et al. "PG $F_2\alpha$ receptor: A promising therapeutic target for cardiovascular disease" Front. Pharmacol. 1:1-7 (2010).

\* cited by examiner

SUBSTITUTED N,2-DIARYLQUINOLINE-4-CARBOXAMIDES AND THE USE THEREOF AS ANTI-INFLAMMATORY AGENTS

This application is a continuation of U.S. patent application Ser. No. 15/509,600, filed Mar. 8, 2017, now allowed, which was the U.S. national phase of International Application No. PCT/EP2015/070318, filed Sep. 7, 2015, which designated the U.S. and claims priority to priority application EP 14184040.5, filed Sep. 9, 2014, the entire contents of each of which are hereby incorporated by reference.

The present application relates to novel substituted N,2-diarylquinoline-4-carboxamide derivatives, to processes for preparation thereof, to the use thereof alone or in combinations for treatment and/or prevention of diseases, and to the use thereof for production of medicaments for treatment and/or prevention of diseases, especially for treatment and/or prevention of fibrotic and/or inflammatory disorders.

Prostaglandin F2alpha (PGF2α) is part of the family of bioactive prostaglandins, which are derivatives of arachidonic acid. After release from membrane phospholipids by A2 phospholipases, arachidonic acid is oxidized by cyclooxygenases to prostaglandin H2 (PGH2), which is converted further by PGF synthase to PGF2α. PGF2α can also be formed enzymatically in a much smaller proportion from other prostaglandins such as PGE2 or PGD2 [Watanabe et al., *J. Biol. Chem.* 1985, 260:7035-7041]. PGF2α is not stored, but is released immediately after synthesis, as a result of which it displays its effects locally. PGF2α is an unstable molecule ($t_{1/2}$<1 minute), which is rearranged rapidly by enzymatic means in the lung, liver and kidney to give an inactive metabolite, 15-ketodihydro-PGF2α [Basu et al., *Acta Chem. Scand.* 1992, 46:108-110]. 15-Ketodihydro-PGF2α is detectable in relatively large amounts in the plasma and later also in the urine, both under physiological and pathophysiological conditions.

The biological effects of PGF2α come about through the binding and activation of a receptor on the membrane, of the PGF2α receptor or else of what is called the FP receptor. The FP receptor is one of the G protein-coupled receptors characterized by seven transmembrane domains. As well as the human FP receptor, it is also possible to clone the FP receptors of mice and rats [Abramovitz et al., *J. Biol. Chem.* 1994, 269:2632-2636; Sugimoto et al., *J. Biol. Chem.* 1994, 269:1356-1360; Kitanaka et al., *Prostaglandins* 1994, 48:31-41]. In humans there exist two isoforms of the FP receptor, FPA and FPB. The FP receptor is the least selective of the prostanoid receptors, since not only PGF2α but also PGD2 and PGE2 bind to it with nanomolar affinities [Woodward et al., *Pharmacol. Rev.* 2011, 63:471-538]. Stimulation of the FP receptor leads primarily to Gq-dependent activation of phospholipase C, which results in release of calcium and activation of the diacylglycerol-dependent protein kinase C (PKC). The elevated intracellular calcium level leads to calmodulin-mediated stimulation of myosin light-chain kinase (MLCK). As well as coupling to the G protein Gq, the FP receptor, via G12/G13, can also stimulate the Rho/Rho kinase signal transduction cascade and, via Gi coupling, can alternatively stimulate the Raf/MEK/MAP signaling pathway [Woodward et al., *Pharmacol. Rev.* 2011, 63:471-538].

PGF2α is involved in the regulation of numerous physiological functions, for example ovarian functions, embryonal development, changes in the endometrium, uterine contraction and luteolysis, and in the induction of contractions and birth. PGF2α is also synthesized in epithelial cells in the endometrium, where it stimulates cellular proliferation [Woodward et al., *Pharmacol. Rev.* 2011, 63:471-538]. In addition, PGF2α is a potent stimulator of smooth muscle constriction, vascular constriction and bronchoconstriction, and is involved in acute and chronic inflammatory processes [Basu, *Mol. Cells* 2010, 30:383-391]. In the kidney, PGF2α is involved in water absorption, natriuresis and diuresis. In the eyes, PGF2α regulates intraocular pressure. PGF2α also plays an important role in bone metabolism: Prostaglandin stimulates the sodium-dependent transport of inorganic phosphate into osteoblasts and it promotes the release of interleukin-6 and vascular endothelial growth factor (VEGF) in osteoblasts; in addition, PGF2α is a strong mitogen and a survival factor for osteoblasts [Agas et al., *J. Cell Physiol.* 2013, 228:25-29]. Furthermore, it has been shown that PGF2α-FP receptor activation is involved in various cardiovascular dysfunctions, for example myocardial infarction and hypertension [Zhang et al., *Frontiers in Pharmacol.* 2010, 1:1-7]. More stable analogs of PGF2α have been developed for estrus synchronization and for influencing human reproductive functions, and also for reduction of intraocular pressure for treatment of glaucoma [Basu, *Mol. Cells* 2010, 30:383-391].

In patients having idiopathic pulmonary fibrosis (IPF), it has been shown that the stable PGF2α metabolite 15-ketodihydro-PGF2α is significantly elevated in the plasma and that the level of 15-ketodihydro-PGF2α correlates with functional parameters, for example forced vital capacity (FVC), the diffusion distance of carbon monoxide in the lung (DLCO) and the 6-minute walk test. In addition, a relationship between elevated plasma 15-ketodihydro-PGF2α and the mortality of patients has been detected [Aihara et al., *PLoS One* 2013, 8:1-6]. In accordance with this, it has also been shown that stimulation of human lung fibroblasts with naturally occurring silica dusts, which in humans can lead to silicosis in the event of chronic inhalation and as a result to pulmonary fibrosis, brings about significant upregulation of PGF2α synthesis [O'Reilly et al., *Am. J. Physiol. Lung Cell. Mol. Physiol.* 2005, 288: L1010-L1016]. In bleomycin-induced pulmonary fibrosis in mice, the elimination of the FP receptor by knockdown (FP –/–) led to a distinct reduction in pulmonary fibrosis compared to wild-type mice [Oga et al., *Nat. Med.* 2009, 15:1426-1430]. In FP –/– mice, after administration of bleomycin, a significant reduction in the hydroxyproline content and reduced induction of profibrotic genes in the pulmonary tissue was observed. Moreover, lung function was distinctly improved in FP –/– mice compared to the wild-type mice. In human pulmonary fibroblasts, PGF2α stimulates proliferation and collagen production via the FP receptor. Since this occurs independently of the profibrotic mediator TGFβ, the PGF2α/FP receptor signaling cascade constitutes an independent route in the onset of pulmonary fibrosis [Oga et al., *Nat. Med.* 2009, 15:1426-1430]. These findings show that the FP receptor is a therapeutic target protein for treatment of IPF [Olman, *Nat. Med.* 2009, 15:1360-1361]. The involvement of PGF2α in the induction of fibrotic lesions has also been shown in cardiac mouse fibroblasts [Ding et al., *Int. J. Biochem. & Cell Biol.* 2012, 44: 1031-1039], in an animal model of scleroderma [Kanno et al., *Arthritis Rheum.* 2013, 65: 492-502] and in synoviocytes from patients with gonarthrosis [Bastiaansen et al. *Arthritis Rheum.* 2013, 65: 2070-2080].

It is therefore assumed that the FP receptor plays an important role in many disorders, injuries and pathological lesions whose etiology and/or progression is associated with inflammatory events and/or proliferative and fibroproliferative tissue and vessel remodeling. These may especially be disorders of and/or damage to the lung, the cardiovascular system or the kidney, or the disorder may be a blood disorder, a neoplastic disease or another inflammatory disorder.

Disorders of and damage to the lung which may be mentioned in this context are in particular idiopathic pulmonary fibrosis, pulmonary hypertension, bronchiolitis obliterans syndrome (BOS), chronic-obstructive pulmonary disease (COPD), asthma and cystic fibrosis. Disorders of and damage to the cardiovascular system in which the FP receptor is involved are, for example, tissue lesions following myocardial infarction and associated with heart failure. Renal disorders are, for example, renal insufficiency and kidney failure. An example of a blood disorder is sickle cell anemia.

Examples of tissue degradation and remodeling in the event of neoplastic processes are the invasion of cancer cells into healthy tissue (formation of metastases) and neovascularization (neoangiogenesis). Other inflammatory diseases where the FP receptor plays a role are, for example, arthrosis and multiple sclerosis.

Idiopathic fibrosis of the lung or idiopathic pulmonary fibrosis (IPF) is a progressive lung disease which, left untreated, results in death within an average of 2.5 to 3.5 years after diagnosis. At the time of diagnosis, patients are usually more than 60 years old, men being slightly more frequently affected than women. Onset of IPF is insidious and characterized by increasing shortness of breath and a dry tickly cough. IPF is one of the group of idiopathic interstitial pneumonias (IIP), a heterogeneous group of pulmonary disorders which are characterized by fibrosis and inflammation of varying severity which can be distinguished using clinical, imaging and fine tissue criteria. Within this group, idiopathic pulmonary fibrosis is of particular significance owing to its frequency and aggressive progression [Ley et al., *Am. J. Respir. Crit. Care Med.* 183, 431-440 (2011)]. IPF may either occur sporadically or be hereditary. As yet, the causes are unknown. However, in recent years there have been numerous indications that chronic damage of the alveolar epithelium leads to the release of profibrotic cytokines/mediators followed by increased fibroblast proliferation and increased collagen fiber formation, resulting in a patchy fibrosis and the typical honeycomb structure of the lung [Strieter et al., *Chest* 136, 1364-1370 (2009)]. The clinical sequelae of fibrotization are a decrease in the elasticity of the pulmonary tissue, a reduced diffusing capacity and the development of severe hypoxia. With regard to lung function, a corresponding worsening of the forced vital capacity (FVC) and the diffusing capacity (DLCO) can be detected. Essential and prognostically important comorbidities of IPF are acute exacerbation and pulmonary hypertension [Beck et al., *Pneumologe* 10, 105-111 (2013)]. The prevalence of pulmonary hypertension in interstitial pulmonary disorders is 10-40% [Lettieri et al., *Chest* 129, 746-752 (2006); Behr et al., *Eur. Respir. J.* 31, 1357-1367 (2008)]. Currently, there is no curative treatment for IPF—except for lung transplantation.

Pulmonary hypertension (PH) is a progressive lung disease which, left untreated, results in death within an average of 2.8 years after diagnosis. By definition, the mean pulmonary arterial pressure (mPAP) in case of chronic pulmonary hypertension is >25 mmHg at rest or >30 mmHg under exertion (normal value <20 mmHg). The pathophysiology of pulmonary hypertension is characterized by vasoconstriction and remodeling of the pulmonary vessels. In chronic PH, there is a neomuscularization of primarily unmuscularized lung vessels, and the circumference of the vascular musculature of the vessels already muscularized increases. This increasing obliteration of the pulmonary circulation results in progressive stress on the right heart, which leads to a reduced output from the right heart and eventually ends in right heart failure [M. Humbert et al., *J. Am. Coll. Cardiol.* 2004, 43, 13S-24S]. Idiopathic (or primary) pulmonary arterial hypertension (IPAH) is a very rare disorder, whereas secondary pulmonary hypertension (non-PAH PH, NPAHPH) is very common, and it is thought that the latter is currently the third most common group of cardiovascular disorders after coronary heart disease and systemic hypertension [Naeije, in: A. J. Peacock et al. (Eds.), *Pulmonary Circulation. Diseases and their treatment*, $3^{rd}$ edition, Hodder Arnold Publ., 2011, p. 3]. Since 2008, pulmonary hypertension is classified in accordance with the Dana Point classification into various sub-groups according to the respective etiology [D. Montana and G. Simonneau, in: A. J. Peacock et al. (Eds.), *Pulmonary Circulation. Diseases and their treatment*, $3^{rd}$ edition, Hodder Arnold Publ., 2011, p. 197-206].

Despite all the advances in the therapy of PH there is as yet no prospect of cure of this serious disorder. Standard therapies available on the market (for example prostacyclin analogs, endothelin receptor antagonists, phosphodiesterase inhibitors) are able to improve the quality of life, the exercise tolerance and the prognosis of the patients. These are therapeutic principles which are administered systemically and act primarily hemodynamically by modulating vessel tone. The applicability of these medicaments is limited owing to side effects, some of which are serious, and/or complicated administration forms. The period over which the clinical situation of the patients can be improved or stabilized by specific monotherapy is limited (for example owing to the development of tolerance). Eventually the therapy escalates and thus a combination therapy is applied, where a plurality of medicaments must be given concurrently. Currently, these standard therapeutics are approved only for the treatment of pulmonary arterial hypertension (PAH). In the case of secondary forms of PH such as PH-COPD, these therapeutic principles (for example sildenafil, bosentan) fail in clinical studies since, as a result of non-selective vasodilation, they lead to a reduction (desaturation) of the arterial oxygen content in the patients. The probable reason for this is an unfavorable effect on the ventilation-perfusion adaptation in the lung in heterogeneous lung disorders owing to the systemic administration of non-selective vasodilators [I. Blanco et al., *Am. J. Respir. Crit. Care Med.* 2010, 181, 270-278; D. Stolz et al., *Eur. Respir. J.* 2008, 32, 619-628].

Novel combination therapies are one of the most promising future therapeutic options for the treatment of pulmonary hypertension. In this connection, the finding of novel pharmacological mechanisms for the treatment of PH is of particular interest [Ghofrani et al., *Herz* 2005, 30, 296-302; E. B. Rosenzweig, *Expert Opin. Emerging Drugs* 2006, 11, 609-619; T. Ito et al., *Curr. Med. Chem.* 2007, 14, 719-733]. In particular novel therapeutic approaches which can be combined with the therapy concepts already on the market may form the basis of a more efficient treatment and thus be of great advantage for the patients.

In the context of the present invention, the term "pulmonary hypertension" includes both primary and secondary sub-forms (NPAHPH) as defined according to the Dana Point classification in accordance with their respective etiology [D. Montana and G. Simonneau, in: A. J. Peacock et al. (Eds.), *Pulmonary Circulation. Diseases and their treatment*, $3^{rd}$ edition, Hodder Arnold Publ., 2011, pp. 197-206; Hoeper et al., *J. Am. Coll. Cardiol.*, 2009, 54 (1), Suppl. S, p 85-p 96]. These include in particular in group 1 pulmonary arterial hypertension (PAH), which, among others, embraces the idiopathic and the familial forms (IPAH and FPAH, respectively). Furthermore, PAH also embraces persistent pulmonary hypertension of the newborn and the associated pulmonary arterial hypertension (APAH) associated with collagenoses, congenital systemic pulmonary shunt lesions, portal hypertension, HIV infections, the intake of certain drugs and medicaments (for example of appetite suppressants), with disorders having a significant venous/capillary component such as pulmonary venoocclusive disorder and pulmonary capillary hemangiomatosis, or with other disorders such as disorders of the thyroid, glycogen storage diseases, Gaucher disease, hereditary teleangiectasia, hemoglobinopathies, myeloproliferative disorders and splenectomy. Group 2 of the Dana Point classification comprises PH patients having a causative left heart disorder, such as ventricular, atrial or valvular disorders. Group 3 comprises forms of pulmonary hypertension associated with a lung disorder, for example with chronic obstructive lung disease (COPD), interstitial lung disease (ILD), pulmonary fibrosis (IPF), and/or hypoxemia (e.g. sleep apnea syndrome, alveolar hypoventilation, chronic high-altitude sickness, hereditary deformities). Group 4 includes PH patients having chronic thrombotic and/or embolic disorders, for example in the case of thromboembolic obstruction of proximal and distal pulmonary arteries (CTEPH) or non-thrombotic embolisms (e.g. as a result of tumor disorders, parasites, foreign bodies). Less common forms of pulmonary hypertension, such as in patients suffering from sarcoidosis, histiocytosis X or lymphangiomatosis, are summarized in group 5.

The bronchiolitis obliterans syndrome (BOS) is a chronic rejection reaction after a lung transplantation. Within the first five years after a lung transplant about 50-60% of all patients are affected, and within the first nine years more than 90% of patients [Estenne et al., *Am. J. Respir. Crit. Care Med.* 166, 440-444 (2003)]. The cause of the disease has not been elucidated. In spite of numerous improvements in the treatment of transplantation patients, the number of BOS cases has hardly changed over the last years. BOS is the most important long-term complication in lung transplantations and is considered to be the main reason for the fact that survival rates are still markedly below those for other organ transplantations. BOS is an inflammatory event which is associated with changes in the lung tissue affecting primarily the small respiratory passages. Damage and inflammatory changes of the epithelial cells and the subepithelial structures of the smaller respiratory passages lead, owing to ineffective regeneration of the epithelium and aberrant tissue repair, to excessive fibroproliferation. There is scarring and finally destruction of the bronchi and also clots of granulation tissue in the small respiratory passages and alveolae, occasionally with vascular involvement. The diagnosis is based on the lung function. In BOS, there is a worsening of the FEV1 compared to the average of the two best values measured postoperatively. Currently, there is no curative treatment of BOS. Some of the patients show improvements under intensified immunosuppression; patients not showing any response experience persistent deterioration, such that retransplantation is indicated.

Chronic obstructive pulmonary disease (COPD) is a slowly progressing pulmonary disease characterized by an obstruction of respiratory flow which is caused by pulmonary emphysema and/or chronic bronchitis. The first symptoms of the disease generally manifest themselves during the fourth or fifth decade of life. In the subsequent years of life, shortness of breath frequently becomes worse, and there are instances of coughing combined with copious and purulent sputum, and stenotic respiration extending as far as breathlessness (dyspnea). COPD is primarily a smokers' disease: smoking is the cause of 90% of all cases of COPD and of 80-90% of all COPD-related deaths. COPD is a big medical problem and constitutes the sixth most frequent cause of death worldwide. Of people over the age of 45, about 4-6% are affected. Although the obstruction of the respiratory flow may only be partial and temporal, COPD cannot be cured.

Accordingly, the aim of treatment is to improve the quality of life, to alleviate the symptoms, to prevent acute worsening and to slow the progressive impairment of lung function. Existing pharmacotherapies, which have hardly changed over the last two or three decades, are the use of bronchodilators to open blocked respiratory passages, and in certain situations corticosteroids to control the inflammation of the lung [P. J. Barnes, *N. Engl. J. Med.* 343, 269-280 (2000)]. The chronic inflammation of the lung, caused by cigarette smoke or other irritants, is the driving force of the development of the disease. The basic mechanism comprises immune cells which, during the inflammatory reaction of the lung, release proteases and various cytokines which cause pulmonary emphysema and remodeling of the bronchi.

It is an object of the present invention to identify and provide novel substances that are potent, chemically and metabolically stable, non-prostanoid antagonists of the FP receptor, and are suitable as such for treatment and/or prevention particularly of fibrotic and inflammatory disorders.

WO 95/32948-A1, WO 96/02509-A1 and WO 97/19926-A1, inter alia, disclose 2-arylquinoline-4-carboxamides as $NK_3$ or dual $NK_2/NK_3$ antagonists suitable for treatment of disorders of the lung and central nervous system. WO 2004/045614-A1 describes particular quinolinecarboxamides as glucokinase ligands for the treatment of diabetes. WO 2006/094237-A2 discloses quinoline derivatives as sirtuin modulators which can be used for treatment of various kinds of disorders. WO 2011/009540-A2 describes bicyclic carboxamides having pesticidal action. WO 2011/153553-A2 claims various bicyclic heteroaryl compounds as kinase inhibitors for the treatment of neoplastic disorders in particular. EP 2 415 755-A1 describes, inter alia, quinoline derivatives suitable for treatment of disorders associated with the activity of plasminogen activator inhibitor 1 (PAI-1). WO 2013/074059-A2 details various quinoline-4-carboxamide derivatives which can serve as inhibitors of cytosine deaminases for boosting DNA transfection of cells. WO 2013/164326-A1 discloses N,3-diphenylnaphthalene-1-carboxamides as agonists of the EP2 prostaglandin receptor for treatment of respiratory pathway disorders. WO 2014/117090-A1 describes various 2-arylquinoline derivatives as inhibitors of metalloenzymes. In the meantime, WO 2015/094912-A1 has disclosed, inter alia, substituted N,2-diphenylquinoline-4-carboxamide derivatives that are suitable as antagonists of the prostaglandin EP4 receptor for treatment of arthritis and associated states of pain.

The present invention provides compounds of the general formula (I)

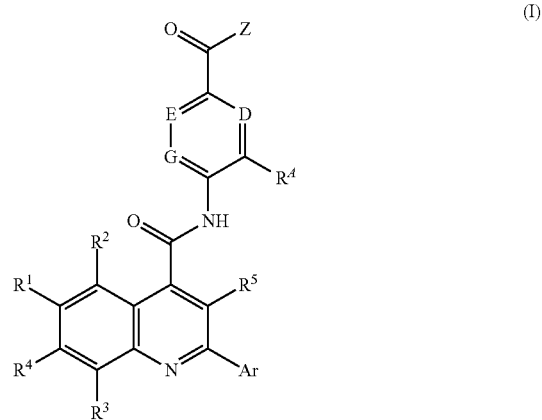

$R^4$ is hydrogen, halogen, pentafluorosulfanyl, cyano, nitro, $(C_1\text{-}C_4)$-alkyl, hydroxyl, $(C_1\text{-}C_4)$-alkoxy, amino or a group of the formula —NH—C(=O)—$R^6$, —NH—C(=O)—NH—$R^6$ or —S(=O)$_n$—$R^7$,
where $(C_1\text{-}C_4)$-alkyl and $(C_1\text{-}C_4)$-alkoxy may be up to trisubstituted by fluorine,
and in which
$R^6$ is hydrogen or $(C_1\text{-}C_4)$-alkoxy which may be up to trisubstituted by fluorine,
$R^7$ is $(C_1\text{-}C_4)$-alkyl which may be substituted by hydroxyl, methoxy or ethoxy or up to trisubstituted by fluorine,
and
n is the number 0, 1 or 2,
D is C—$R^D$ or N,
E is C—$R^E$ or N,
G is C—$R^G$ or N,
where not more than two of the ring members D, E and G at the same time are N,
and in which
$R^D$ and $R^E$ are each independently hydrogen, fluorine, chlorine, methyl, trifluoromethyl, methoxy or trifluoromethoxy,
and
$R^G$ is hydrogen, fluorine, chlorine, bromine, methyl or trifluoromethyl,
Z is OH or a group of the formula —NH—$R^8$, —NH—SO$_2$—$R^9$ or —NH—SO$_2$—NR$^{10A}$R$^{10B}$, in which
$R^8$ is hydrogen or $(C_1\text{-}C_4)$-alkoxy which may be up to trisubstituted by fluorine,
$R^9$ is $(C_1\text{-}C_4)$-alkoxy which may be up to trisubstituted by fluorine, or phenyl,
and
$R^{10A}$ and $R^{10B}$ are each independently hydrogen or $(C_1\text{-}C_4)$-alkyl which may be up to trisubstituted by fluorine,
$R^1$ is halogen, trifluoromethoxy, (trifluoromethyl)sulfanyl, pentafluorosulfanyl, $(C_1\text{-}C_4)$-alkyl, trimethylsilyl, cyclopropyl or cyclobutyl,
where $(C_1\text{-}C_4)$-alkyl may be up to trisubstituted by fluorine
and
cyclopropyl and cyclobutyl may be up to disubstituted by fluorine,
$R^2$, $R^3$ and $R^4$ are each independently hydrogen, fluorine, chlorine, methyl or trifluoromethyl,
$R^5$ is $(C_1\text{-}C_4)$-alkyl which may be up to trisubstituted by fluorine, or is fluorine, chlorine, methoxy or cyclopropyl,
and
Ar is phenyl which may be mono- or disubstituted identically or differently by fluorine and chlorine, or is pyridyl or thienyl,
and the N-oxides, salts, solvates, salts of the N-oxides and solvates of the N-oxides and salts thereof.

Compounds of the invention are the compounds of the formula (I) and the salts, solvates and solvates of the salts thereof, the compounds that are encompassed by formula (I) and are of the formulae mentioned below and the salts, solvates and solvates of the salts thereof and the compounds that are encompassed by formula (I) and are cited below as working examples and the salts, solvates and solvates of the salts thereof if the compounds that are encompassed by formula (I) and are mentioned below are not already salts, solvates and solvates of the salts.

Compounds of the invention are likewise N-oxides of the compounds of the formula (I) and the salts, solvates and solvates of the salts thereof.

Preferred salts in the context of the present invention are physiologically acceptable salts of the compounds of the invention. Also encompassed are salts which are not themselves suitable for pharmaceutical applications but can be used, for example, for the isolation, purification or storage of the compounds of the invention.

Physiologically acceptable salts of the compounds of the invention especially include the salts derived from conventional bases, by way of example and with preference alkali metal salts (e.g. sodium and potassium salts), alkaline earth metal salts (e.g. calcium and magnesium salts), zinc salts and ammonium salts derived from ammonia or organic amines having 1 to 16 carbon atoms, by way of example and with preference ethylamine, diethylamine, triethylamine, N,N-diisopropylethylamine, monoethanolamine, diethanolamine, triethanolamine, dimethylaminoethanol, diethylaminoethanol, tris(hydroxymethyl)aminomethane, choline, procaine, dicyclohexylamine, dibenzylamine, N-methylmorpholine, N-methylpiperidine, arginine, lysine and 1,2-ethylenediamine.

In addition, physiologically acceptable salts of the compounds of the invention include acid addition salts of mineral acids, carboxylic acids and sulfonic acids, for example salts of hydrochloric acid, hydrobromic acid, sulfuric acid, phosphoric acid, methanesulfonic acid, ethanesulfonic acid, benzenesulfonic acid, toluenesulfonic acid, naphthalenedisulfonic acid, formic acid, acetic acid, trifluoroacetic acid, propionic acid, succinic acid, fumaric acid, maleic acid, lactic acid, tartaric acid, malic acid, citric acid, gluconic acid, benzoic acid and embonic acid.

Solvates in the context of the invention are described as those forms of the compounds of the invention which form a complex in the solid or liquid state by coordination with solvent molecules. Hydrates are a specific form of the solvates in which the coordination is with water. Solvates preferred in the context of the present invention are hydrates.

The compounds of the invention may, depending on their structure, exist in different stereoisomeric forms, i.e. in the form of configurational isomers or else, if appropriate, as conformational isomers (enantiomers and/or diastereomers, including those in the case of atropisomers). The present invention therefore encompasses the enantiomers and diastereomers, and the respective mixtures thereof. It is possible to isolate the stereoisomerically homogeneous constituents from such mixtures of enantiomers and/or diastereomers in a known manner. Preference is given to employing chromatographic methods for this purpose, especially HPLC chromatography on achiral or chiral separation phases. In the case of carboxylic acids as intermediates or end products, separation is alternatively also possible via diastereomeric salts using chiral amine bases.

If the compounds of the invention can occur in tautomeric forms, the present invention encompasses all the tautomeric forms.

The present invention also encompasses all suitable isotopic variants of the compounds of the invention. An isotopic variant of a compound of the invention is understood here to mean a compound in which at least one atom within the compound of the invention has been exchanged for another atom of the same atomic number, but with a different atomic mass from the atomic mass which usually or predominantly occurs in nature. Examples of isotopes which can be incorporated into a compound of the invention are those of hydrogen, carbon, nitrogen, oxygen, phosphorus, sulfur, fluorine, chlorine, bromine and iodine, such as $^2$H (deuterium), $^3$H (tritium), $^{13}$C, $^{14}$C, $^{15}$N, $^{17}$O, $^{18}$O, $^{32}$P, $^{33}$P, $^{33}$S, $^{34}$S, $^{35}$S, $^{36}$S, $^{18}$F, $^{36}$Cl, $^{82}$Br, $^{123}$I, $^{124}$I, $^{129}$I and $^{131}$I.

Particular isotopic variants of a compound of the invention, especially those in which one or more radioactive isotopes have been incorporated, may be beneficial, for example, for the examination of the mechanism of action or of the active compound distribution in the body; due to the comparatively easy preparability and detectability, especially compounds labeled with $^3$H or $^{14}$C isotopes are suitable for this purpose. In addition, the incorporation of isotopes, for example of deuterium, can lead to particular therapeutic benefits as a consequence of greater metabolic stability of the compound, for example an extension of the half-life in the body or a reduction in the active dose required; such modifications of the compounds of the invention may therefore possibly also constitute a preferred embodiment of the present invention. Isotopic variants of the compounds of the invention can be prepared by commonly used processes known to those skilled in the art, for example by the methods described further down and the procedures described in the working examples, by using corresponding isotopic modifications of the respective reagents and/or starting compounds.

The present invention additionally also encompasses prodrugs of the compounds of the invention. The term "prodrugs" refers here to compounds which may themselves be biologically active or inactive, but are converted while present in the body, for example by a metabolic or hydrolytic route, to compounds of the invention.

The present invention comprises as prodrugs in particular hydrolyzable ester derivatives of the inventive carboxylic acids of the formula (I) [with Z=OH]. These are understood to mean esters which can be hydrolyzed to the free carboxylic acids, as the main biologically active compounds, in physiological media under the conditions of the biological tests described hereinbelow and in particular in vivo by an enzymatic or chemical route. $(C_1$-$C_4)$-Alkyl esters, in which the alkyl group can be straight-chain or branched, are preferred as such esters. Particular preference is given to methyl, ethyl or tert-butyl esters.

In the context of the present invention, unless specified otherwise, the substituents are defined as follows:

In the context of the invention, $(C_1$-$C_4)$-alkyl is a straight-chain or branched alkyl radical having 1 to 4 carbon atoms. By way of example and with preference, mention may be made of the following: methyl, ethyl, n-propyl, isopropyl, n-butyl, isobutyl, sec-butyl and tert-butyl.

$(C_1$-$C_4)$-Alkoxy in the context of the invention is a straight-chain or branched alkoxy radical having 1 to 4 carbon atoms. By way of example and with preference, mention may be made of the following: methoxy, ethoxy, n-propoxy, isopropoxy, n-butoxy, isobutoxy, sec-butoxy and tert-butoxy.

Halogen in the context of the invention includes fluorine, chlorine, bromine and iodine. Preference is given to chlorine, fluorine or bromine, particular preference to fluorine or chlorine.

In the context of the present invention, all radicals which occur more than once are defined independently of one another. When radicals in the compounds of the invention are substituted, the radicals may be mono- or polysubstituted, unless specified otherwise. Substitution by one substituent or by two identical or different substituents is preferred. Particular preference is given to substitution by one substituent.

A particular embodiment of the present invention comprises compounds of the formula (I) in which $R^A$ is hydrogen, fluorine, chlorine, bromine, cyano, nitro, methyl, trifluoromethyl, hydroxyl, methoxy, trifluoromethoxy or a group of the formula —S(=O)$_n$—R$^7$ in which
   $R^7$ is methyl or trifluoromethyl,
   and
   n is the number 0 or 2,
D is C—R$^D$ or N, in which
   R$^D$ is hydrogen or fluorine,
E is C—H
and
G is C—R$^G$ or N, in which
   R$^G$ is hydrogen, fluorine or chlorine,
and the salts, solvates and solvates of the salts thereof.

A further particular embodiment of the present invention encompasses compounds of the formula (I) in which
R$^A$ is fluorine, chlorine, bromine, cyano, methyl, trifluoromethyl, methoxy, trifluoromethoxy or a group of the formula —S(=O)$_n$—R$^7$ in which
   R$^7$ is methyl or trifluoromethyl,
   and
   n is the number 0, 1 or 2,
D is C—H,
E is C—H
and
G is C—R$^G$ or N, in which
   R$^G$ is hydrogen, fluorine or chlorine,
and the salts, solvates and solvates of the salts thereof.

A further particular embodiment of the present invention encompasses compounds of the formula (I) in which
Z is OH,
and the salts, solvates and solvates of the salts thereof.

A further particular embodiment of the present invention encompasses compounds of the formula (I) in which
R$^1$ is chlorine, bromine, iodine, methyl, ethyl, isopropyl, trifluoromethyl, trifluoromethoxy, (trifluoromethyl)sulfanyl, pentafluorosulfanyl or trimethylsilyl,
R$^2$ and R$^3$ are each hydrogen
and
R$^4$ is hydrogen, fluorine or chlorine,
and the salts, solvates and solvates of the salts thereof.

A further particular embodiment of the present invention encompasses compounds of the formula (I) in which
R$^1$ is bromine
and
R$^2$, R$^3$ and R$^4$ are each hydrogen,
and the salts, solvates and solvates of the salts thereof.

A further particular embodiment of the present invention encompasses compounds of the formula (I) in which
R$^1$ and R$^4$ are each chlorine
and
R$^2$ and R$^3$ are each hydrogen,
and the salts, solvates and solvates of the salts thereof.

A further particular embodiment of the present invention encompasses compounds of the formula (I) in which
R$^5$ is methyl,
and the salts, solvates and solvates of the salts thereof.

A further particular embodiment of the present invention encompasses compounds of the formula (I) in which
Ar is phenyl which may be monosubstituted by fluorine, or pyridyl,
and the salts, solvates and solvates of the salts thereof.

Preference is given in the context of the present invention to compounds of the formula (I) in which
R$^A$ is hydrogen, fluorine, chlorine, bromine, cyano, methyl, trifluoromethyl, methoxy, trifluoromethoxy or a group of the formula —S(=O)$_n$—R$^7$ in which R⁷ is methyl or trifluoromethyl,
and
n is the number 0 or 2,
D is C—R^D or N, in which
R^D is hydrogen or fluorine,
E is C—H,
G is C—R^G or N, in which
R^G is hydrogen, fluorine or chlorine,
Z is OH,
R¹ is chlorine, bromine, iodine, methyl, ethyl, isopropyl, trifluoromethyl, trifluoromethoxy, (trifluoromethyl)sulfanyl, pentafluorosulfanyl or trimethylsilyl,
R² and R³ are each hydrogen,
R⁴ is hydrogen, fluorine or chlorine,
R⁵ is methyl, chlorine or cyclopropyl,
and
Ar is phenyl which may be monosubstituted by fluorine, or pyridyl,
and the salts, solvates and solvates of the salts thereof.

In the context of the present invention, particular preference is given to compounds of the formula (I) in which
R⁴ is fluorine, chlorine, cyano, methyl, trifluoromethyl, methoxy, trifluoromethoxy or a group of the formula —S(=O)ₙ—R⁷ in which
R⁷ is methyl or trifluoromethyl,
and
n is the number 0 or 2,
D is C—H,
E is C—H,
G is C—R^G or N, in which
R^G is hydrogen, fluorine or chlorine,
Z is OH,
R¹ is chlorine, bromine, methyl, trifluoromethyl or trimethylsilyl,
R² and R³ are each hydrogen,
R⁴ is hydrogen or chlorine,
R⁵ is methyl,
and
Ar is phenyl which may be monosubstituted by fluorine, or 4-pyridyl,
and the salts, solvates and solvates of the salts thereof.

The individual radical definitions specified in the respective combinations or preferred combinations of radicals are, independently of the respective combinations of the radicals specified, also replaced as desired by radical definitions of other combinations.

Very particular preference is given to combinations of two or more of the abovementioned preferred ranges.

The invention further provides a process for preparing the compounds of the invention, characterized in that a compound of the formula (II)

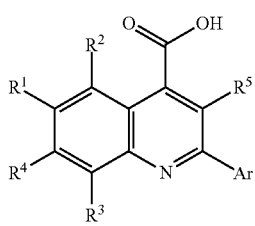

in which R¹, R², R³, R⁴, R⁵ and Ar have the definitions given above, with activation of the carboxylic acid function is coupled with an amine compound of the formula (III)

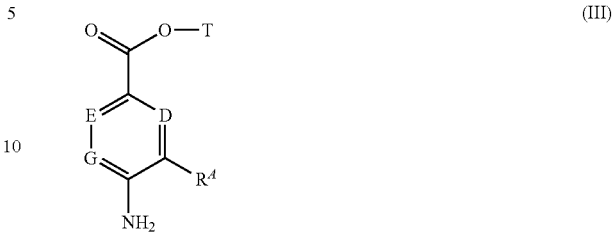

in which R⁴, D, E and G have the definitions given above
and
T is (C₁-C₄)-alkyl or benzyl
to give a compound of the formula (IV)

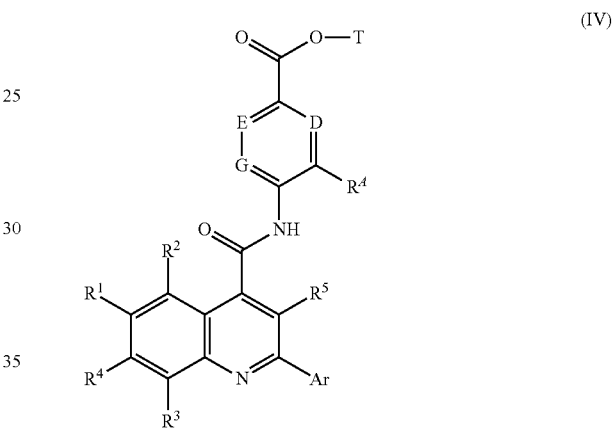

in which R⁴, D, E, G, R¹, R², R³, R⁴, R⁵, Ar and T have the definitions given above, and then the ester radical T is eliminated to give the inventive carboxylic acid of the formula (I-A)

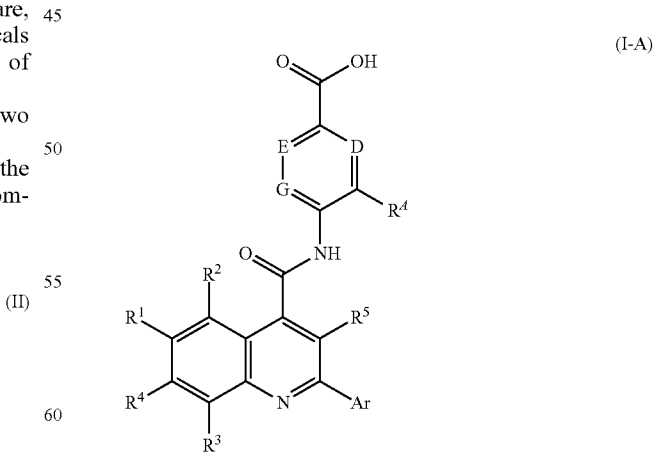

in which R⁴, D, E, G, R¹, R², R³, R⁴, R⁵ and Ar have the definitions given above,
and if necessary the carboxylic acid (I-A) is converted to the corresponding acid chloride of the formula (V)

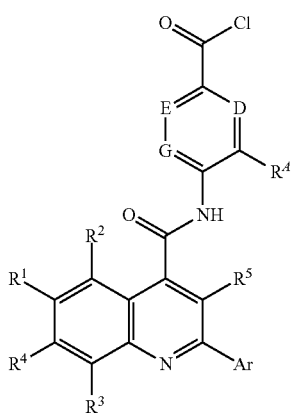

(V)

in which $R^A$, D, E, G, $R^1$, $R^2$, $R^3$, $R^4$, $R^5$ and Ar have the definitions given above, and the latter is subsequently reacted with a compound of the formula (VI)

 (VI)

in which $R^8$ has the definition given above
to give the inventive carboxamide of the formula (I-B)

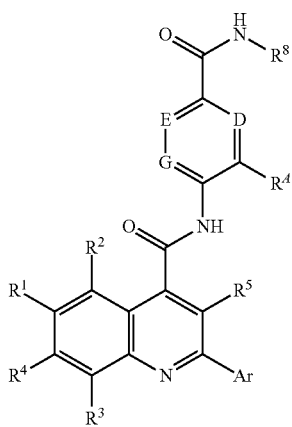

(I-B)

in which $R^A$, D, E, G, $R^1$, $R^2$, $R^3$, $R^4$, $R^5$, $R^8$ and Ar have the definitions given above,
and the compounds of the formulae (I-A) and (I-B) thus obtained are optionally converted with the appropriate (i) solvents and/or (ii) bases or acids to the solvates, salts and/or solvates of the salts thereof.

The coupling reaction (II)+(III)→(IV) [amide formation] can be effected either by a direct route with the aid of a condensing or activating agent or via the intermediate stage of a carbonyl chloride or carbonyl imidazolide obtainable from (II).

Suitable condensing or activating agents of this kind are, for example, carbodiimides such as N,N'-diethyl-, N,N'-dipropyl-, N,N'-diisopropyl-, N,N'-dicyclohexylcarbodiimide (DCC) or N-(3-dimethylaminopropyl)-N'-ethylcarbodiimide hydrochloride (EDC), phosgene derivatives such as N,N'-carbonyldiimidazole (CDI) or isobutyl chloroformate, 1,2-oxazolium compounds such as 2-ethyl-5-phenyl-1,2-oxazolium 3-sulfate or 2-tert-butyl-5-methylisoxazolium perchlorate, acylamino compounds such as 2-ethoxy-1-ethoxycarbonyl-1,2-dihydroquinoline, α-chlorenamines such as 1-chloro-N,N,2-trimethylprop-1-en-1-amine, 1,3,5-triazine derivatives such as 4-(4,6-dimethoxy-1,3,5-triazin-2-yl)-4-methylmorpholinium chloride, phosphorus compounds such as n-propanephosphonic anhydride (PPA), diethyl cyanophosphonate, diphenylphosphoryl azide (DPPA), bis(2-oxo-3-oxazolidinyl)phosphoryl chloride, benzotriazol-1-yloxytris(dimethylamino)phosphonium hexafluorophosphate or benzotriazol-1-yloxytris(pyrrolidino)phosphonium hexafluorophosphate (PyBOP), or uronium compounds such as O-(benzotriazol-1-yl)-N,N,N',N'-tetramethyluronium tetrafluoroborate (TBTU), O-(benzotriazol-1-yl)-N,N,N',N'-tetramethyluronium hexafluorophosphate (HBTU), O-(1H-6-chlorobenzotriazol-1-yl)-1,1,3,3-tetramethyluronium tetrafluoroborate (TCTU), O-(7-azabenzotriazol-1-yl)-N,N,N',N'-tetramethyluronium hexafluorophosphate (HATU) or 2-(2-oxo-1-(2H)-pyridyl)-1,1,3,3-tetramethyluronium tetrafluoroborate (TPTU), optionally in combination with further auxiliaries such as 1-hydroxybenzotriazole (HOBt) or N-hydroxysuccinimide (HOSu), and, as bases, alkali metal carbonates, e.g. sodium or potassium carbonate, or tertiary amine bases such as triethylamine, N-methylmorpholine (NMM), N-methylpiperidine (NMP), N,N-diisopropylethylamine, pyridine or 4-N,N-dimethylaminopyridine (DMAP). The preferred condensing or activating agent used is 1-chloro-N,N,2-trimethylprop-1-en-1-amine in combination with pyridine or O-(7-azabenzotriazol-1-yl)-N,N,N',N'-tetramethyluronium hexafluorophosphate (HATU) in combination with N,N-diisopropylethylamine.

In the case of a two-stage reaction regime via the carbonyl chlorides or carbonyl imidazolides obtainable from (II), the coupling with the amine component (III) is conducted in the presence of a customary base, for example sodium carbonate or potassium carbonate, triethylamine, N,N-diisopropylethylamine, N-methylmorpholine (NMM), N-methylpiperidine (NMP), pyridine, 2,6-dimethylpyridine, 4-N,N-dimethylaminopyridine (DMAP), 1,8-diazabicyclo[5.4.0]undec-7-ene (DBU), 1,5-diazabicyclo[4.3.0]non-5-ene (DBN), sodium methoxide or potassium methoxide, sodium ethoxide or potassium ethoxide, sodium tert-butoxide or potassium tert-butoxide, or sodium hydride or potassium hydride. The base used for the coupling in the case of the carbonyl chlorides is preferably pyridine, and in the case of carbonyl imidazolides preferably potassium tert-butoxide or sodium hydride.

Inert solvents for the coupling reactions mentioned are— according to the method used—for example ethers such as diethyl ether, diisopropyl ether, methyl tert-butyl ether, tetrahydrofuran, 1,4-dioxane, 1,2-dimethoxyethane or bis(2-methoxyethyl) ether, hydrocarbons such as benzene, toluene, xylene, pentane, hexane or cyclohexane, halohydrocarbons such as dichloromethane, trichloromethane, carbon tetrachloride, 1,2-dichloroethane, trichloroethylene or chlorobenzene, or polar aprotic solvents such as acetone, methyl ethyl ketone, ethyl acetate, acetonitrile, butyronitrile, pyridine, dimethyl sulfoxide (DMSO), N,N-dimethylformamide (DMF), N,N'-dimethylpropyleneurea (DMPU) or N-methylpyrrolidinone (NMP). It is also possible to use mixtures of such solvents. Preference is given to using dichloromethane, tetrahydrofuran, N,N-dimethylformamide or mixtures of these solvents. The couplings are generally conducted within a temperature range from −20° C. to +60° C., preferably at 0° C. to +40° C.

The preferred coupling method is the reaction of a carbonyl imidazolide derived from (II) with the amine compound (III).

The carbonyl imidazolides themselves are obtainable by known methods by reaction of (II) with N,N'-carbonyldiimidazole (CDI) at elevated temperature (+60° C. to +150°

C.) in a correspondingly relatively high-boiling solvent such as N,N-dimethylformamide (DMF). The preparation of the carbonyl chlorides is accomplished in a customary manner by treating (II) with thionyl chloride or oxalyl chloride in an inert solvent such as dichloromethane.

The detachment of the ester group T in process step (IV)→(I-A) is conducted by customary methods, by treating the ester in an inert solvent with an acid or a base, with conversion of the salt of the carboxylic acid initially formed in the latter variant to the free carboxylic acid by subsequent treatment with acid. In the case of the tert-butyl esters, the ester cleavage is preferably effected with an acid. Methyl and ethyl ester are preferably cleaved using a base. Benzyl esters can alternatively also be cleaved by hydrogenation (hydrogenolysis) in the presence of a suitable catalyst, for example palladium on activated carbon.

Suitable inert solvents for these reactions are water and the organic solvents customary for ester cleavage. These include in particular alcohols such as methanol, ethanol, n-propanol, isopropanol, n-butanol or tert-butanol, ethers such as diethyl ether, tetrahydrofuran, 1,4-dioxane or 1,2-dimethoxyethane, or other solvents such as dichloromethane, acetonitrile, N,N-dimethylformamide or dimethyl sulfoxide. It is equally possible to use mixtures of these solvents. In the case of a basic ester hydrolysis, preference is given to using mixtures of water with tetrahydrofuran, 1,4-dioxane, methanol and/or ethanol. Preference is given to using dichloromethane in the case of the reaction with trifluoroacetic acid, and 1,4-dioxane in the case of the reaction with hydrogen chloride, in each case under anhydrous conditions.

Suitable bases for a hydrolysis reaction are the customary inorganic bases. These especially include alkali metal or alkaline earth metal hydroxides, for example lithium hydroxide, sodium hydroxide, potassium hydroxide or barium hydroxide, or alkali metal or alkaline earth metal carbonates, such as sodium carbonate, potassium carbonate or calcium carbonate. Preference is given to using lithium hydroxide or sodium hydroxide.

Suitable acids for the ester hydrolysis are generally sulfuric acid, hydrogen chloride/hydrochloric acid, hydrogen bromide/hydrobromic acid, phosphoric acid, acetic acid, trifluoroacetic acid, toluenesulfonic acid, methanesulfonic acid or trifluoromethanesulfonic acid, or mixtures thereof, optionally with addition of water. Preference is given to using hydrogen chloride or trifluoroacetic acid.

The ester cleavage is generally conducted within a temperature range from −20° C. to +100° C., preferably at 0° C. to +80° C.

The acid chloride (V) is prepared in a customary manner by treating the carboxylic acid (I-A) with oxalyl chloride or thionyl chloride in an inert solvent such as dichloromethane, trichloromethane or 1,2-dichloroethane, optionally with use of a small amount of N,N-dimethylformamide as catalyst.

The reaction is generally conducted at a temperature of 0° C. to +30° C.

The subsequent amide formation in process step (V)+(VI)→(I-B) is usually effected in the presence of a relatively large excess of the amine component (VI). Alternatively, it is also possible to use a standard tertiary amine base as auxiliary base, for example triethylamine, N,N-diisopropylethylamine, N-methylmorpholine (NMM), N-methylpiperidine (NMP), pyridine, 2,6-dimethylpyridine or 4-N,N-dimethylaminopyridine (DMAP).

Inert solvents for this reaction are, for example, ethers such as diethyl ether, diisopropyl ether, methyl tert-butyl ether, tetrahydrofuran, 1,4-dioxane, 1,2-dimethoxyethane or bis(2-methoxyethyl) ether, hydrocarbons such as benzene, toluene, xylene, pentane, hexane or cyclohexane, halohydrocarbons such as dichloromethane, trichloromethane, carbon tetrachloride, 1,2-dichloroethane, trichloroethylene or chlorobenzene, polar aprotic solvents such as acetone, methyl ethyl ketone, ethyl acetate, acetonitrile, butyronitrile, pyridine, dimethyl sulfoxide (DMSO), N,N-dimethylformamide (DMF), N,N'-dimethylpropyleneurea (DMPU) or N-methylpyrrolidinone (NMP), or else water. It is likewise possible to use mixtures of such solvents. Preference is given to using water or a mixture of water with tetrahydrofuran, 1,4-dioxane, 1,2-dimethoxyethane or acetone. The reaction is generally conducted at a temperature of 0° C. to +40° C.

Inventive compounds of the formula (I) in which Z is a group of the formula —NH—SO$_2$—R$^9$ or —NH—SO$_2$—NR$^{10A}$R$^{10B}$ can be obtained in analogy to the above-described amide formation (V)+(VI)→(I-B) by base-mediated reaction of the acid chloride (V) with a compound of the formula (VI-A) or (VI-B)

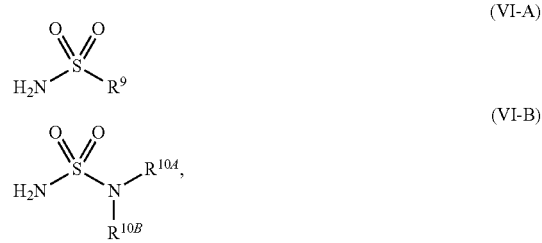

in which R$^9$, R$^{20A}$ and R$^{10B}$ have the definitions given above. The reaction is preferably effected using sodium hydride as base in tetrahydrofuran or N,N-dimethylformamide as inert solvent at a temperature of 0° C. to +50° C.

Further inventive compounds of the formula (I) can, if appropriate, also be prepared by transformations of functional groups of individual radicals or substituents, especially those listed under R$^4$, R$^1$ and R$^5$, proceeding from other compounds of the formula (I) or precursors thereof obtained by the above processes. These transformations are conducted by customary methods familiar to the person skilled in the art and include, for example, reactions such as nucleophilic or electrophilic substitution reactions, transition-metal-mediated coupling reactions, preparation and addition reactions of metal organyls (e.g. Grignard compounds or lithium organyls), oxidation and reduction reactions, hydrogenation, halogenation (e.g. fluorination, bromination), dehalogenation, amination, alkylation and acylation, the formation of carboxylic esters, carboxamides and sulfonamides, ester cleavage and hydrolysis, and the introduction and removal of temporary protecting groups.

Depending on their respective substitution pattern, the compounds of the formula (II) can be prepared by, in analogy to processes known from the literature, reacting either

[A] an isatin derivative of the formula (VII)

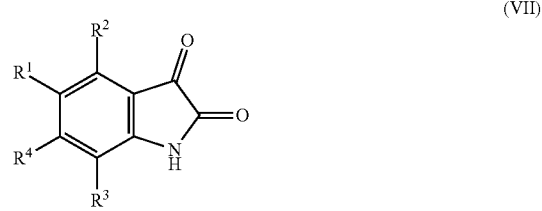

in which R$^1$, R$^2$, R$^3$ and R$^4$ have the definitions given above in an acid- or base-mediated condensation reaction with a ketomethylene compound of the formula (VIII)

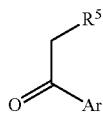
(VIII)

in which R⁵ and Ar have the definitions given above
to give the compound of the formula (II)

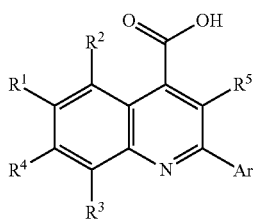
(II)

in which R¹, R², R³, R⁴, R⁵ and Ar have the definitions given above, or

[B] an ortho-aminophenylacetic ester of the formula (IX)

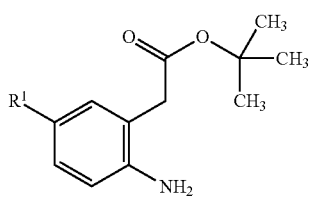
(IX)

in which R¹ has the definition given above
in an acid-induced condensation reaction with a diketo compound of the formula (X)

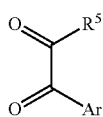
(X)

in which R⁵ and Ar have the definitions given above
to give a compound of the formula (II-A)

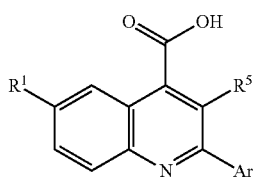
(II-A)

in which R¹, R⁵ and Ar have the definitions given above.

The condensation of the isatin derivative (VII) with the ketomethylene compound (VIII) to give the quinoline-4-carboxylic acid (II) in variant [A] can be achieved by heating the reactants in the presence of an aqueous acid, such as sulfuric acid or concentrated hydrochloric acid, or in the presence of an aqueous base, such as sodium hydroxide or potassium hydroxide solution. In the case of use of an acid, preference is given to using acetic acid as solvent for the reaction; in the case of a basic reaction regime, preference is given to using an alcoholic solvent such as methanol or ethanol. The condensation is generally conducted within a temperature range from +70° C. to +120° C. [cf., for example, K. Lackey and D. D. Sternbach, *Synthesis,* 993-997 (1993); A. N. Boa et al., *Bioorg. Med. Chem.* 13 (6), 1945-1967 (2005)].

The condensation reaction according to variant [B] to give the quinoline-4-carboxylic acid (II-A) is effected in an analogous manner by heating the ortho-aminophenylacetic ester (IX) and the diketone (X) with aqueous acid, especially concentrated hydrochloric acid. The inert solvent used for the reaction here too is preferably acetic acid.

The ortho-aminophenylacetic ester (IX) itself can be obtained in accordance with a process described in the literature, by base-mediated reaction of the α-chloroacetic ester (XI)

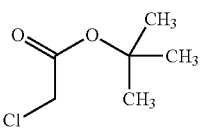
(XI)

with the nitrophenyl derivative (XII)

(XII)

in which R¹ has the definition given above
to give the ortho-nitrophenylacetic ester (XIII)

(XIII)

in which R¹ has the definition given above,
and subsequently reducing the nitro group, for example by catalytic hydrogenation [cf. P. Beier et al., *J. Org. Chem.* 76, 4781-4786 (2011)].

The compounds of the formula (III) are commercially available or their preparation is described in the literature, or they can be prepared proceeding from other commercially available compounds by methods known in the literature that are familiar to those skilled in the art. Examples of these are shown in the reaction schemes which follow. Detailed procedures and further literature references can also be found in the experimental section, in the section on the preparation of the starting compounds and intermediates.

The compounds of the formulae (VI), (VI-A), (VI-B), (VII), (VIII), (X), (XI) and (XII) are likewise commercially available or described as such in the literature, or they can be prepared in a simple manner proceeding from other commercially available compounds in analogy to methods known from the literature.

The preparation of the compounds of the invention can be illustrated by way of example by the following reaction schemes:

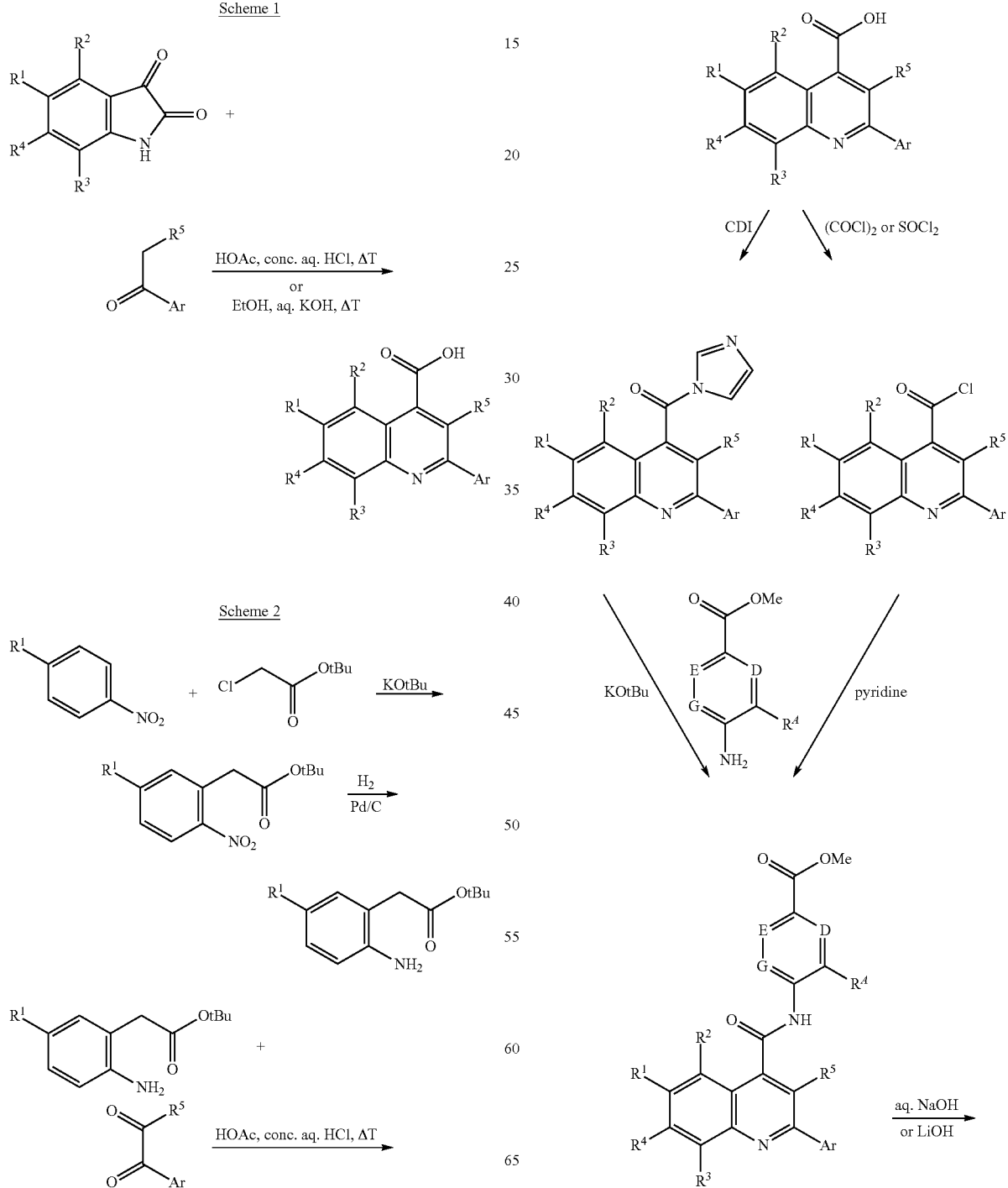

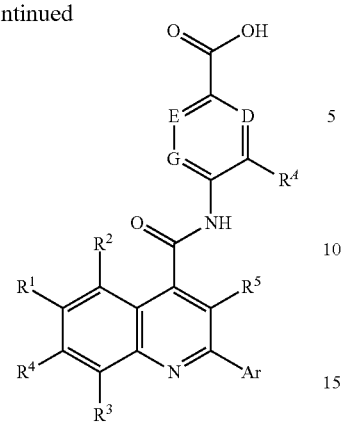
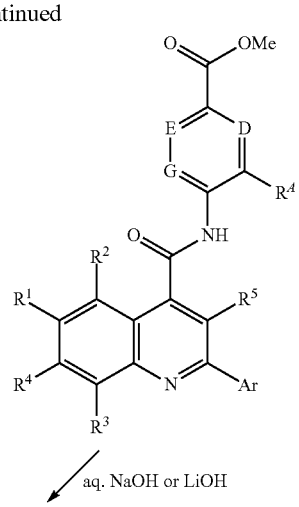
Scheme 3b
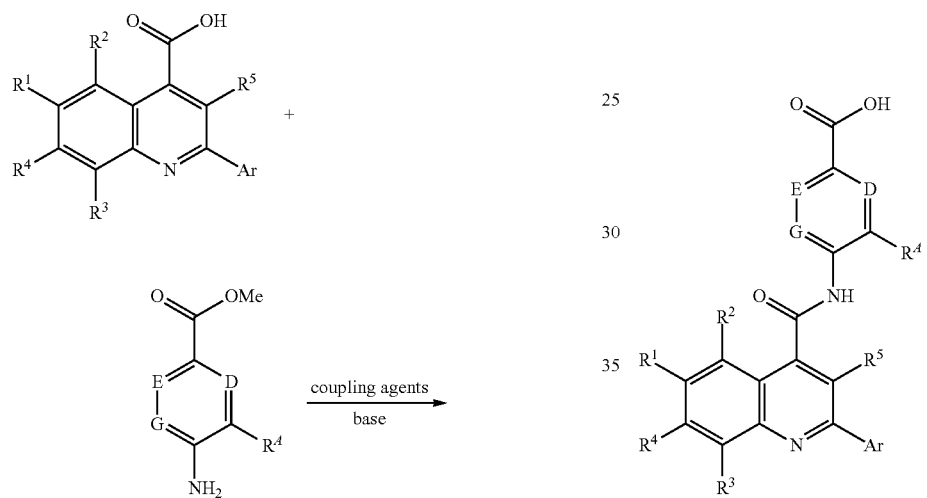
Scheme 4
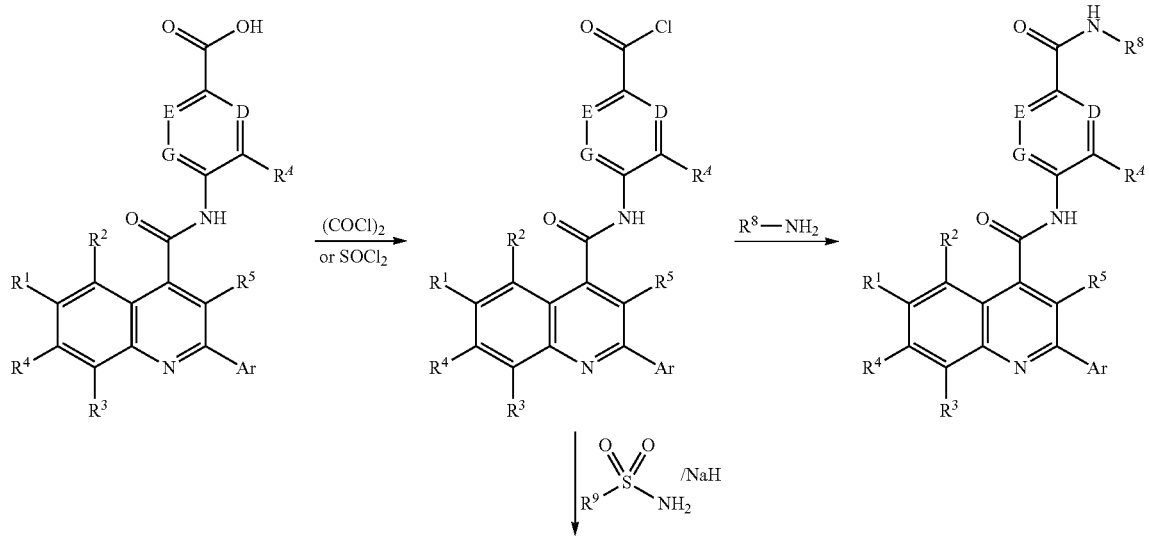

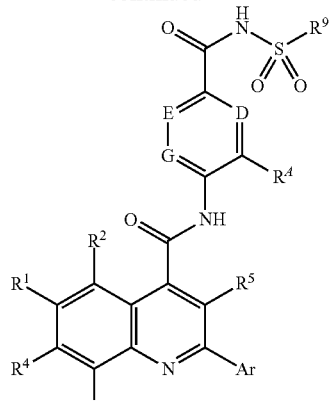
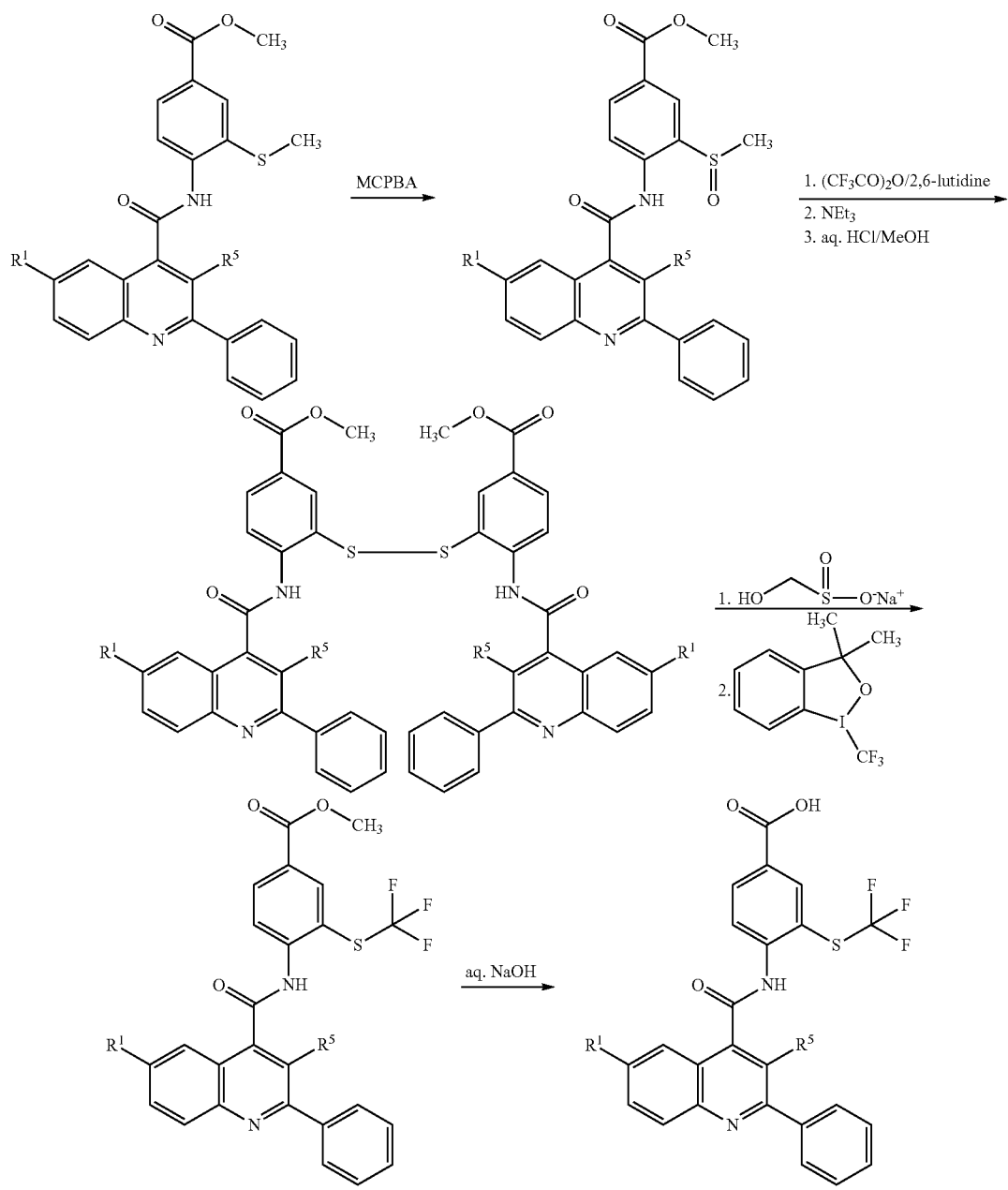
Scheme 5a

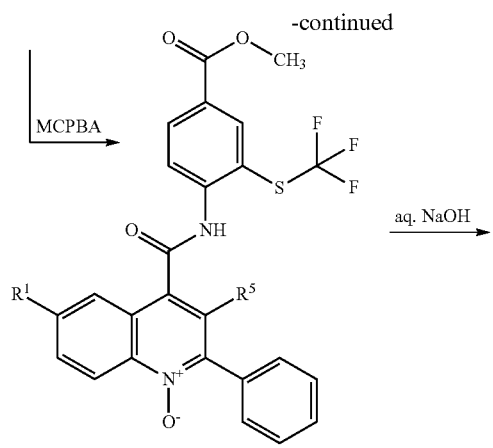
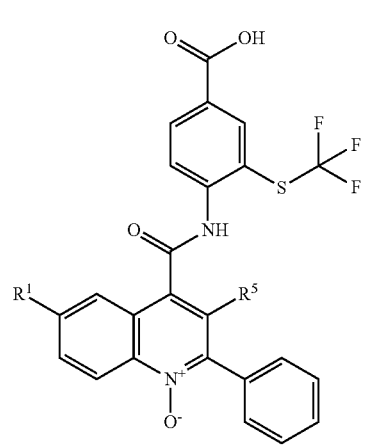
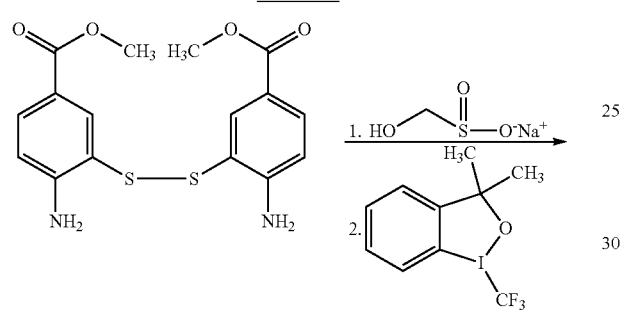
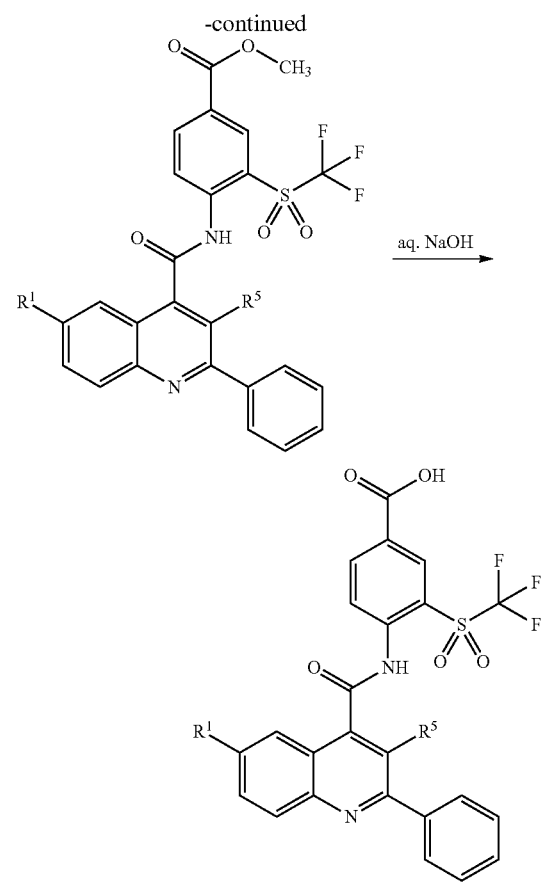
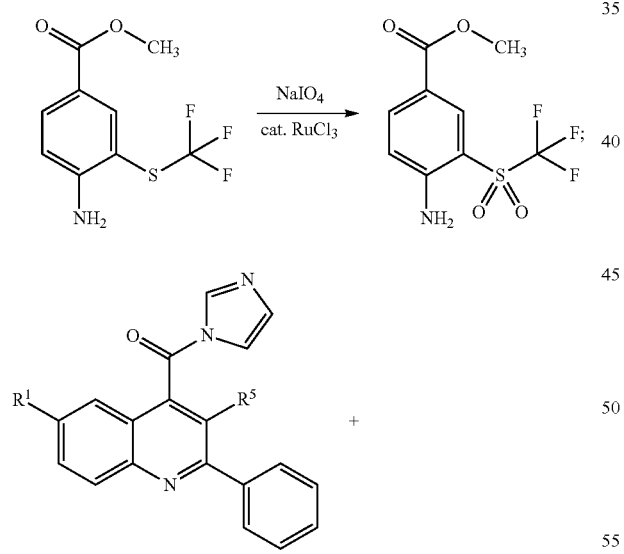
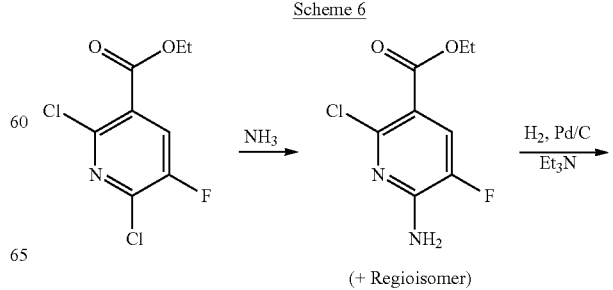

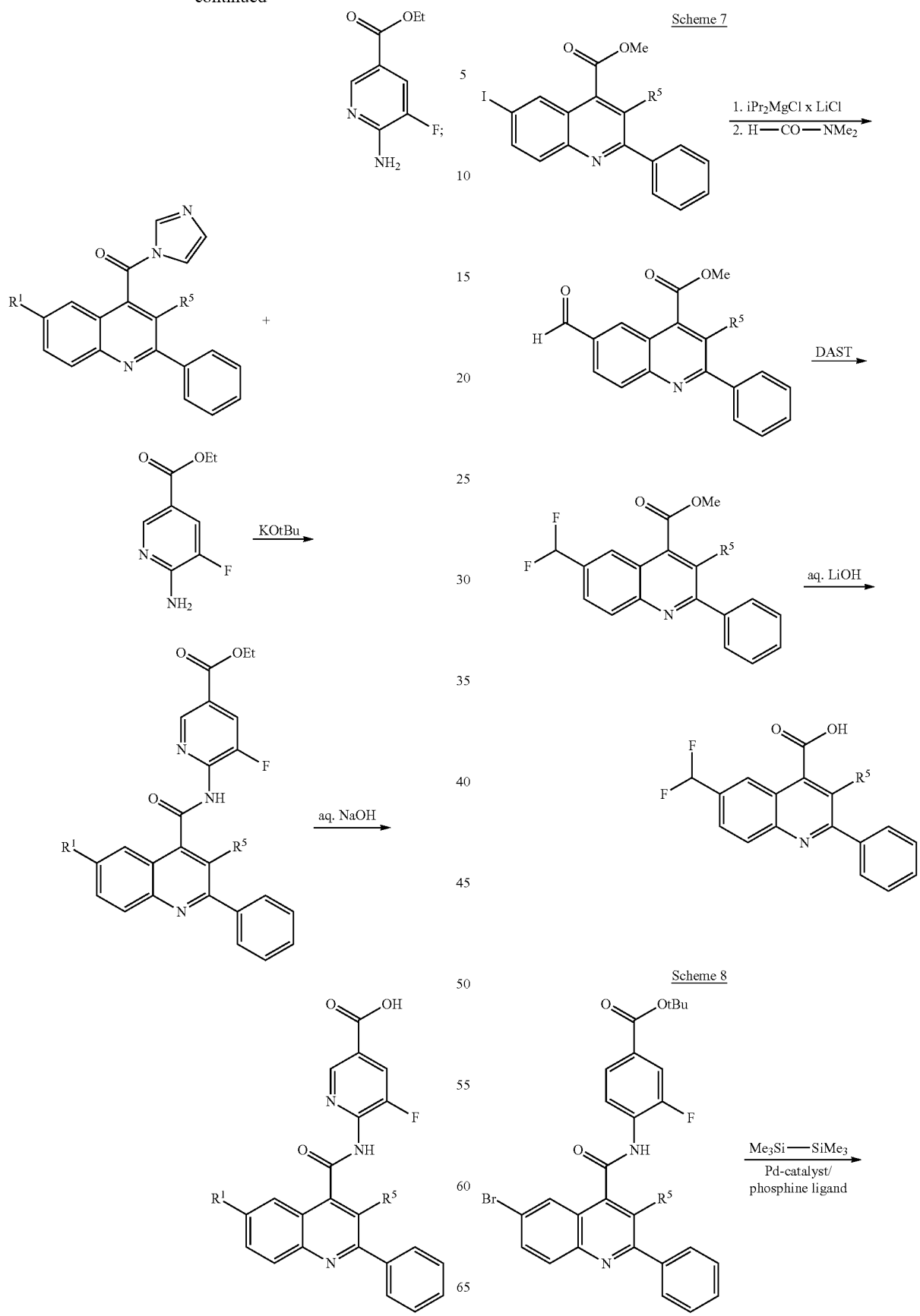

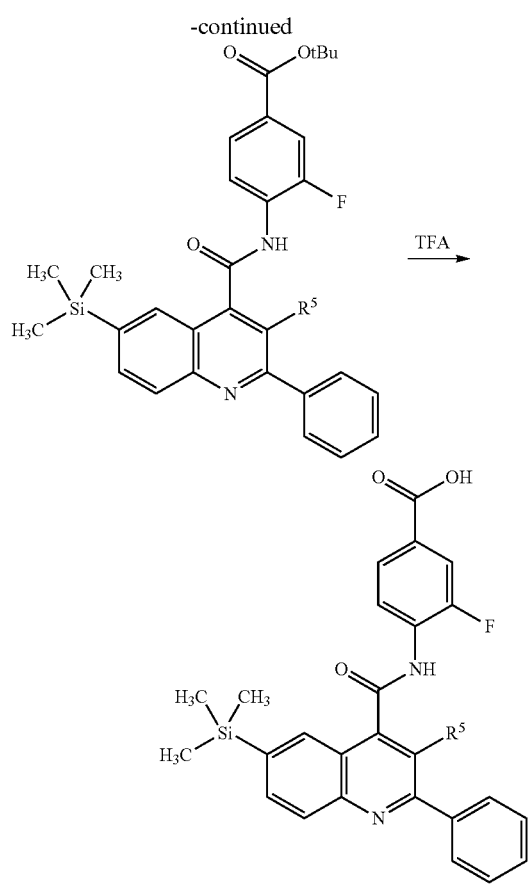
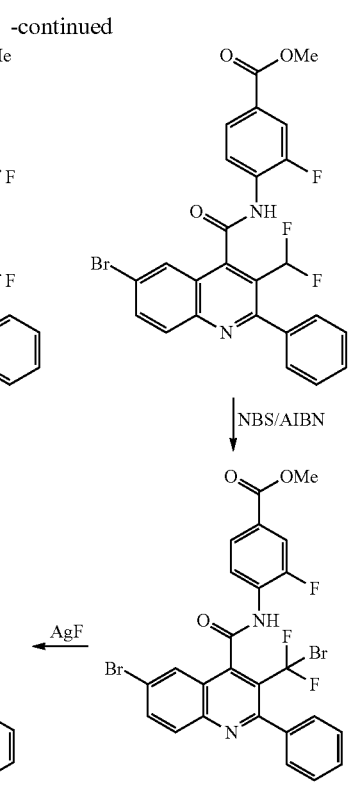
Scheme 9
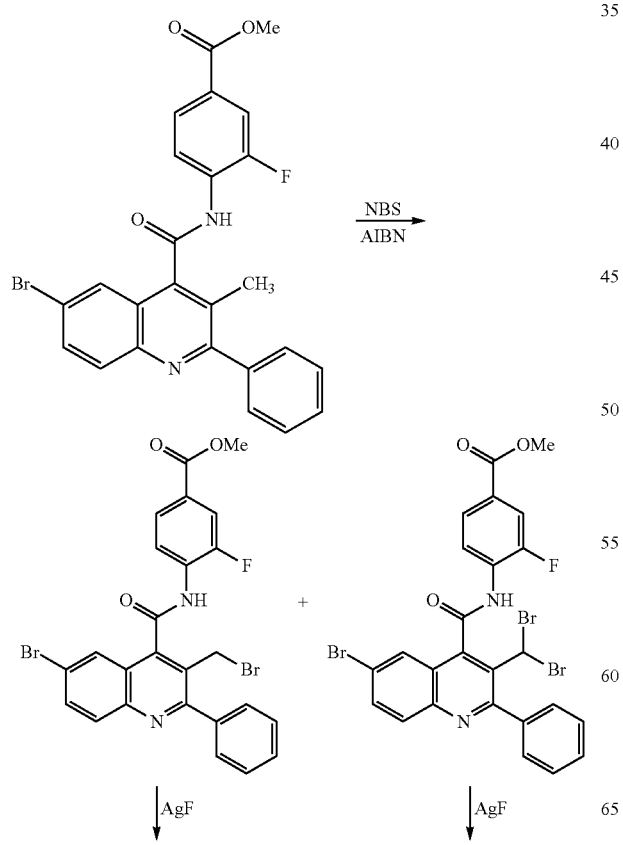
Scheme 10
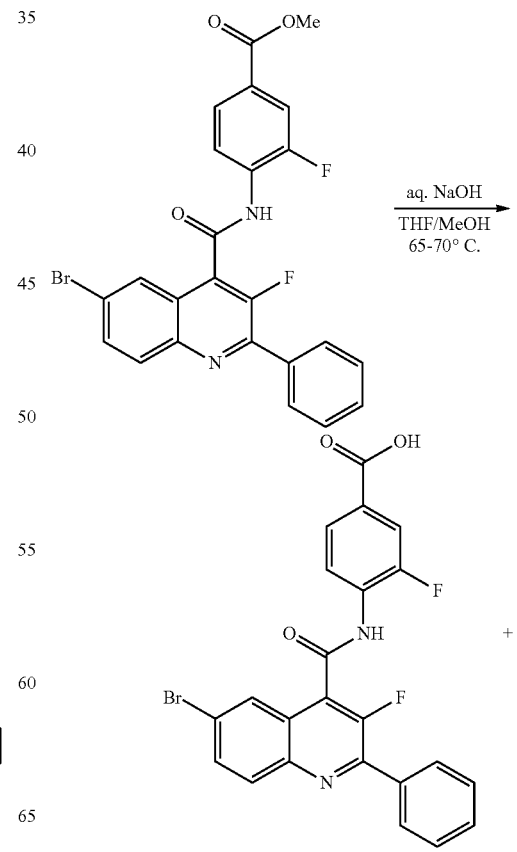

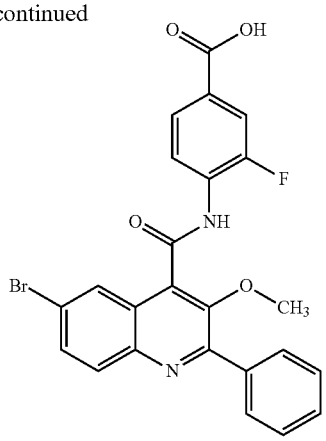

The compounds of the invention have valuable pharmacological properties and can be used for prevention and treatment of diseases in humans and animals.

The compounds of the invention are potent, chemically and metabolically stable antagonists of the FP receptor and are therefore suitable for treatment and/or prevention of disorders and pathological processes, especially those where the FP receptor is involved in the course of an inflammatory event and/or tissue or vessel reconstruction.

In the context of the present invention, these especially include disorders such as the group of the interstitial idiopathic pneumonias which includes idiopathic pulmonary fibrosis (IPF), acute interstitial pneumonia, non-specific interstitial pneumonias, lymphoid interstitial pneumonias, respiratory bronchiolitis with interstitial lung disease, cryptogenic organizing pneumonias, desquamative interstitial pneumonias and non-classifiable idiopathic interstitial pneumonias, furthermore granulomatous interstitial lung diseases, interstitial lung diseases of known etiology and other interstitial lung diseases of unknown etiology, pulmonary arterial hypertension (PAH) and other forms of pulmonary hypertension (PH), bronchiolitis obliterans syndrome (BOS), chronic-obstructive pulmonary disease (COPD), pulmonary sarcoidosis, acute respiratory distress syndrome (ARDS), acute lung injury (ALI), alpha-1-antitrypsin deficiency (AATD), pulmonary emphysema (for example pulmonary emphysema induced by cigarette smoke), cystic fibrosis (CF), inflammatory and fibrotic disorders of the kidney, chronic intestinal inflammations (IBD, Crohn's disease, ulcerative colitis), peritonitis, peritoneal fibrosis, rheumatoid disorders, multiple sclerosis, inflammatory and fibrotic skin disorders, sickle cell anemia and inflammatory and fibrotic eye disorders.

The compounds of the invention can additionally be used for treatment and/or prevention of asthmatic disorders of varying severity with intermittent or persistent characteristics (refractive asthma, bronchial asthma, allergic asthma, intrinsic asthma, extrinsic asthma, medicament- or dust-induced asthma), of various forms of bronchitis (chronic bronchitis, infectious bronchitis, eosinophilic bronchitis), of bronchiectasis, pneumonia, farmer's lung and related disorders, coughs and colds (chronic inflammatory cough, iatrogenic cough), inflammation of the nasal mucosa (including medicament-related rhinitis, vasomotoric rhinitis and seasonal allergic rhinitis, for example hay fever) and of polyps.

In addition, the compounds of the invention can be used for treatment and/or prevention of cardiovascular disorders such as, for example, high blood pressure (hypertension), heart failure, coronary heart disease, stable and unstable angina pectoris, renal hypertension, peripheral and cardiac vascular disorders, arrhythmias, atrial and ventricular arrhythmias and impaired conduction such as, for example, atrioventricular blocks degrees I-III, supraventricular tachyarrhythmia, atrial fibrillation, atrial flutter, ventricular fibrillation, ventricular flutter, ventricular tachyarrhythmia, Torsade de pointes tachycardia, atrial and ventricular extrasystoles, AV-junctional extrasystoles, sick sinus syndrome, syncopes, AV-nodal re-entry tachycardia, Wolff-Parkinson-White syndrome, acute coronary syndrome (ACS), autoimmune cardiac disorders (pericarditis, endocarditis, valvolitis, aortitis, cardiomyopathies), boxer cardiomyopathy, aneurysms, shock such as cardiogenic shock, septic shock and anaphylactic shock, furthermore for the treatment and/or prophylaxis of thromboembolic disorders and ischemias such as myocardial ischemia, myocardial infarction, stroke, cardiac hypertrophy, transient and ischemic attacks, preeclampsia, inflammatory cardiovascular disorders, spasms of the coronary arteries and peripheral arteries, edema formation such as, for example, pulmonary edema, cerebral edema, renal edema or edema caused by heart failure, peripheral circulatory disturbances, reperfusion damage, arterial and venous thromboses, microalbuminuria, myocardial insufficiency, endothelial dysfunction, micro- and macrovascular damage (vasculitis), and also to prevent restenoses, for example after thrombolysis therapies, percutaneous transluminal angioplasties (PTA), percutaneous transluminal coronary angioplasties (PTCA), heart transplants and bypass operations.

In the context of the present invention, the term "heart failure" encompasses both acute and chronic forms of heart failure, and also specific or related disease types thereof, such as acute decompensated heart failure, right heart failure, left heart failure, global failure, ischemic cardiomyopathy, dilatative cardiomyopathy, hypertrophic cardiomyopathy, idiopathic cardiomyopathy, diabetic cardiomyopathy, congenital heart defects, heart valve defects, heart failure associated with heart valve defects, mitral valve stenosis, mitral valve insufficiency, aortic valve stenosis, aortic valve insufficiency, tricuspid valve stenosis, tricuspid valve insufficiency, pulmonary valve stenosis, pulmonary valve insufficiency, combined heart valve defects, myocardial inflammation (myocarditis), chronic myocarditis, acute myocarditis, viral myocarditis, diabetic heart failure, alcoholic cardiomyopathy, cardiac storage disorders and diastolic and systolic heart failure.

The compounds of the invention are also suitable for treatment and/or prevention of renal disorders, in particular renal insufficiency and kidney failure. In the context of the present invention, the terms "renal insufficiency" and "kidney failure" encompass both acute and chronic manifestations thereof and also underlying or related renal disorders such as renal hypoperfusion, intradialytic hypotension, obstructive uropathy, glomerulopathies, glomerulonephritis, acute glomerulonephritis, glomerulosclerosis, tubulointerstitial diseases, nephropathic disorders such as primary and congenital kidney disease, nephritis, immunological kidney disorders such as kidney transplant rejection and immunocomplex-induced kidney disorders, nephropathy induced by toxic substances, nephropathy induced by contrast agents, diabetic and non-diabetic nephropathy, pyelonephritis, renal cysts, nephrosclerosis, hypertensive nephrosclerosis and nephrotic syndrome which can be characterized diagnostically, for example by abnormally reduced creatinine and/or water excretion, abnormally elevated blood concentrations of urea, nitrogen, potassium and/or creatinine, altered activity of renal enzymes, for example glutamyl synthetase, altered urine osmolarity or urine volume, elevated microalbuminuria, macroalbuminuria, lesions on glomerulae and arterioles, tubular dilatation, hyperphosphatemia and/or need for dialysis. The present invention also encompasses the use of the compounds of the invention for treatment and/or prevention of sequelae of renal insufficiency, for example hypertension, pulmonary edema, heart failure, uremia, anemia, electrolyte disturbances (for example hyperkalemia, hyponatremia) and disturbances in bone and carbohydrate metabolism.

In addition, the compounds of the invention are suitable for treatment and/or prevention of disorders of the urogenital system, for example benign prostate syndrome (BPS), benign prostate hyperplasia (BPH), benign prostate enlargement (BPE), bladder outlet obstruction (BOO), lower urinary tract syndromes (LUTS), neurogenic overactive bladder (OAB), incontinence, for example mixed urinary incontinence, urge urinary incontinence, stress urinary incontinence or overflow urinary incontinence (MUI, UUI, SUI, OUI), pelvic pain, and also erectile dysfunction and female sexual dysfunction.

The compounds of the invention can also be used for treatment of disorders of the female reproductive system, such as uterine myoma, endometriosis, dysmenorrhea and premature contractions. In addition, they are suitable for prophylaxis or treatment of hirsutism or hypertrichosis.

In addition, the compounds of the invention have antiinflammatory action and can therefore be used as antiinflammatory agents for the treatment and/or prevention of sepsis (SIRS), multiple organ failure (MODS, MOF), inflammatory disorders of the kidney, chronic intestinal inflammations (IBD, Crohn's disease, ulcerative colitis), pancreatitis, peritonitis, cystitis, urethritis, prostatitis, epidimytitis, oophoritis, salpingitis, vulvovaginitis, rheumatoid disorders, osteoarthritis, inflammatory disorders of the central nervous system, multiple sclerosis, infammatory skin disorders and inflammatory eye disorders.

The compounds of the invention are also suitable for treatment and/or prevention of fibrotic disorders of the internal organs, for example the lung, the heart, the kidney, the bone marrow and in particular the liver, and also dermatological fibroses and fibrotic eye disorders. In the context of the present invention, the term "fibrotic disorders" includes in particular disorders such as hepatic fibrosis, cirrhosis of the liver, pulmonary fibrosis, endomyocardial fibrosis, nephropathy, glomerulonephritis, interstitial renal fibrosis, fibrotic damage resulting from diabetes, bone marrow fibrosis, peritoneal fibrosis and similar fibrotic disorders, scleroderma, morphea, keloids, hypertrophic scarring, naevi, diabetic retinopathy, proliferative vitroretinopathy and disorders of the connective tissue (for example sarcoidosis). The compounds of the invention can likewise be used for promotion of wound healing, for controlling postoperative scarring, for example following glaucoma operations and cosmetically for ageing or keratinized skin.

The compounds of the invention can also be used for treatment and/or prevention of anemias such as hemolytic anemias, in particular hemoglobinopathies such as sickle cell anemia and thalassemias, megaloblastic anemias, iron deficiency anemias, anemias owing to acute blood loss, displacement anemias and aplastic anemias.

Moreover, the compounds of the invention are suitable for treatment of cancers, for example skin cancer, brain tumors, breast cancer, bone marrow tumors, leukemias, liposarcomas, carcinomas of the gastrointestinal tract, of the liver, the pancreas, the lung, the kidney, the ureter, the prostate and the genital tract and also of malignant tumors of the lymphoproliferative system, for example Hodgkin's and non-Hodgkin's lymphoma.

In addition, the compounds of the invention can be used for treatment and/or prevention of arteriosclerosis, impaired lipid metabolism and dyslipidemias (hypolipoproteinemia, hypertriglyceridemias, hyperlipidemia, combined hyperlipidemias, hypercholesterolemia, abetalipoproteinemia, sitosterolemia), xanthomatosis, Tangier disease, adiposity, obesity, metabolic disorders (metabolic syndrome, hyperglycemia, insulin-dependent diabetes, non-insulin-dependent diabetes, gestational diabetes, hyperinsulinemia, insulin resistance, glucose intolerance and diabetic sequelae, such as retinopathy, nephropathy and neuropathy), of disorders of the gastrointestinal tract and the abdomen (glossitis, gingivitis, periodontitis, esophagitis, eosinophilic gastroenteritis, mastocytosis, Crohn's disease, colitis, proctitis, anus pruritis, diarrhea, celiac disease, hepatitis, hepatic fibrosis, cirrhosis of the liver, pancreatitis and cholecystitis), of disorders of the central nervous system and neurodegenerative disorders (stroke, Alzheimer's disease, Parkinson's disease, dementia, epilepsy, depressions, multiple sclerosis), immune disorders, thyroid disorders (hyperthyreosis), skin disorders (psoriasis, acne, eczema, neurodermitis, various forms of dermatitis, for example dermatitis abacribus, actinic dermatitis, allergic dermatitis, ammonia dermatitis, facticial dermatitis, autogenic dermatitis, atopic dermatitis, dermatitis calorica, dermatitis combustionis, dermatitis congelationis, dermatitis cosmetica, dermatitis escharotica, exfoliative dermatitis, dermatitis gangraenose, stasis dermatitis, dermatitis herpetiformis, lichenoid dermatitis, dermatitis linearis, dermatitis maligna, medicinal eruption dermatitis, dermatitis palmaris and plantaris, parasitic dermatitis, photoallergic contact dermatitis, phototoxic dermatitis, dermatitis pustularis, seborrheic dermatitis, sunburn, toxic dermatitis, Meleney's ulcer, dermatitis veneata, infectious dermatitis, pyogenic dermatitis and rosacea-like dermatitis, and also keratitis, bullosis, vasculitis, cellulitis, panniculitis, lupus erythematosus, erythema, lymphomas, skin cancer, Sweet syndrome, Weber-Christian syndrome, scar formation, wart formation, chilblains), of inflammatory eye diseases (saccoidosis, blepharitis, conjunctivitis, iritis, uveitis, chorioiditis, ophthalmitis), viral diseases (caused by influenza, adeno and corona viruses, for example HPV, HCMV, HIV, SARS), of disorders of the skeletal bone and the joints and also the skeletal muscle (multifarious forms of arthritis, for example arthritis alcaptonurica, arthritis ankylosans, arthritis dysenterica, arthritis exsudativa, arthritis fungosa, arthritis gonorrhoica, arthritis mutilans, arthritis psoriatica, arthritis purulenta, arthritis rheumatica, arthritis serosa, arthritis syphilitica, arthritis tuberculosa, arthritis urica, arthritis villonodularis pigmentosa, atypical arthritis, hemophilic arthritis, juvenile chronic arthritis, rheumatoid arthritis and metastatic arthritis, furthermore Still syndrome, Felty syndrome, Sjdrgen syndrome, Clutton syndrome, Poncet syndrome, Pott syndrome and Reiter syndrome, multifarious forms of arthropathies, for example arthropathia deformans, arthropathia neuropathica, arthropathia ovaripriva, arthropathia psoriatica and arthropathia tabica, systemic scleroses, multifarious forms of inflammatory myopathies, for example myopathie epidemica, myopathie fibrosa, myopathie myoglobinurica, myopathie ossificans, myopathie ossificans neurotica, myopathie ossificans progressiva multiplex, myopathie purulenta, myopathie rheumatica, myopathie trichinosa, myopathie tropica and myopathie typhosa, and also the Giinther syndrome and the Minchmeyer syndrome), of inflammatory changes of the arteries (multifarious forms of arteritis, for example endarteritis, mesarteritis, periarteritis, panarteritis, arteritis rheumatica, arteritis deformans, arteritis temporalis, arteritis cranialis, arteritis gigantocellularis and arteritis granulomatosa, and also Horton syndrome, Churg-Strauss syndrome and Takayasu arteritis), of Muckle-Well syndrome, of Kikuchi disease, of polychondritis, dermatosclerosis and also other disorders having an inflammatory or immunological component, for example cataract, cachexia, osteoporosis, gout, incontinence, lepra, Sezary syndrome and paraneoplastic syndrome, for rejection reactions after organ transplants and for wound healing and angiogenesis in particular in the case of chronic wounds.

Owing to their profile of biochemical and pharmacological properties, the compounds of the invention are particularly suitable for treatment and/or prevention of interstitial lung diseases, especially idiopathic pulmonary fibrosis (IPF), and also of pulmonary hypertension (PH), bronchiolitis obliterans syndrome (BOS), inflammatory and fibrotic skin and eye disorders and fibrotic disorders of the internal organs.

The aforementioned well-characterized diseases in humans can also occur with comparable etiology in other mammals and can likewise be treated therein with the compounds of the present invention.

In the context of the present invention, the term "treatment" or "treating" includes inhibition, retardation, checking, alleviating, attenuating, restricting, reducing, suppressing, repelling or healing of a disease, a condition, a disorder, an injury or a health problem, or the development, the course or the progression of such states and/or the symptoms of such states. The term "therapy" is understood here to be synonymous with the term "treatment".

The terms "prevention", "prophylaxis" and "preclusion" are used synonymously in the context of the present invention and refer to the avoidance or reduction of the risk of contracting, experiencing, suffering from or having a disease, a condition, a disorder, an injury or a health problem, or a development or advancement of such states and/or the symptoms of such states.

The treatment or prevention of a disease, a condition, a disorder, an injury or a health problem may be partial or complete.

The present invention thus further provides for the use of the compounds of the invention for treatment and/or prevention of disorders, especially of the aforementioned disorders.

The present invention further provides for the use of the compounds of the invention for production of a medicament for treatment and/or prevention of disorders, especially of the aforementioned disorders.

The present invention further provides a medicament comprising at least one of the compounds of the invention for treatment and/or prevention of disorders, especially of the aforementioned disorders.

The present invention further provides for the use of the compounds of the invention in a method for treatment and/or prevention of disorders, especially of the aforementioned disorders.

The present invention further provides a process for treatment and/or prevention of disorders, especially of the aforementioned disorders, using an effective amount of at least one of the compounds of the invention.

The compounds of the invention can be used alone or, if required, in combination with one or more other pharmacologically active substances, provided that this combination does not lead to undesirable and unacceptable side effects.

The present invention therefore further provides medicaments comprising at least one of the compounds of the invention and one or more further active ingredients, especially for treatment and/or prevention of the aforementioned disorders.

Preferred examples of combination active ingredients suitable for this purpose include:

organic nitrates and NO donors, for example sodium nitroprusside, nitroglycerin, isosorbide mononitrate, isosorbide dinitrate, molsidomine or SIN-1, and inhaled NO;

compounds which inhibit the degradation of cyclic guanosine monophosphate (cGMP) and/or cyclic adenosine monophosphate (cAMP), for example inhibitors of phosphodiesterases (PDE) 1, 2, 3, 4 and/or 5, especially PDE 5 inhibitors such as sildenafil, vardenafil, tadalafil, udenafil, dasantafil, avanafil, mirodenafil or lodenafil;

NO- and heme-independent activators of soluble guanylate cyclase (sGC), such as in particular the compounds described in WO 01/19355, WO 01/19776, WO 01/19778, WO 01/19780, WO 02/070462 and WO 02/070510;

NO-independent but heme-dependent stimulators of soluble guanylate cyclase (sGC), such as in particular riociguat, nelociguat and vericiguat, and the compounds described in WO 00/06568, WO 00/06569, WO 02/42301, WO 03/095451, WO 2011/147809, WO 2012/004258, WO 2012/028647 and WO 2012/059549;

prostacyclin analogs and IP receptor agonists, by way of example and with preference iloprost, beraprost, treprostinil, epoprostenol or selexipag;

endothelin receptor antagonists, by way of example and with preference bosentan, darusentan, ambrisentan or sitaxsentan;

compounds which inhibit human neutrophile elastase (HNE), by way of example and with preference sivelestat or DX-890 (reltran);

compounds which inhibit the signal transduction cascade, by way of example and with preference from the group of the kinase inhibitors, in particular from the group of the tyrosine kinase and/or serine/threonine kinase inhibitors, by way of example and with preference nintedanib, dasatinib, nilotinib, bosutinib, regorafenib, sorafenib, sunitinib, cediranib, axitinib, telatinib, imatinib, brivanib, pazopanib, vatalanib, gefitinib, erlotinib, lapatinib, canertinib, lestaurtinib, pelitinib, semaxanib or tandutinib;

compounds which inhibit the degradation and alteration of the extracellular matrix, by way of example and with preference inhibitors of the matrix metalloproteases (MMPs), especially inhibitors of stromelysin, collagenases, gelatinases and aggrecanases (in this context particularly of MMP-1, MMP-3, MMP-8, MMP-9, MMP-10, MMP-11 and MMP-13) and of metalloelastase (MMP-12);

compounds which block the binding of serotonin to its receptors, by way of example and with preference antagonists of the 5-HT$_{2B}$ receptor such as PRX-08066;

antagonists of growth factors, cytokines and chemokines, by way of example and with preference antagonists of TGF-β, CTGF, IL-1, IL-4, IL-5, IL-6, IL-8, IL-13 and integrins;

Rho kinase-inhibiting compounds, by way of example and with preference fasudil, Y-27632, SLx-2119, BF-66851, BF-66852, BF-66853, KI-23095 or BA-1049;

compounds which inhibit soluble epoxide hydrolase (sEH), for example N,N'-dicyclohexylurea, 12-(3-adamantan-1-ylureido)dodecanoic acid or 1-adamantan-1-yl-3-{5-[2-(2-ethoxyethoxy)ethoxy]pentyl}urea;

compounds which influence the energy metabolism of the heart, by way of example and with preference etomoxir, dichloroacetate, ranolazine or trimetazidine;

anti-obstructive agents as used, for example, for treatment of chronic obstructive pulmonary disease (COPD) or bronchial asthma, by way of example and with preference from the group of the inhalatively or systemically administered agonists of the β-adrenergic receptor (β-mimetics) and the inhalatively administered antimuscarinergic substances;

antiinflammatory, immunomodulating, immunosuppressive and/or cytotoxic agents, by way of example and with preference from the group of the systemically or inhalatively administered corticosteroids and also acetylcysteine, montelukast, azathioprine, cyclophosphamide, hydroxycarbamide, azithromycin, pirfenidone or etanercept;

antifibrotic agents, by way of example and with preference adenosine A2b receptor antagonists, sphingosine-1-phosphate receptor 3 (S1P3) antagonists, autotaxin inhibitors, lysophosphatidic acid receptor 1 (LPA-1) and lysophosphatidic acid receptor 2 (LPA-2) antagonists, lysyl oxidase (LOX) inhibitors, lysyl oxidase-like 2 inhibitors, CTGF inhibitors, IL-4 antagonists, IL-13 antagonists, $\alpha_v\beta_6$-integrin antagonists, TGF-β antagonists, inhibitors of the Wnt signaling pathway or CCR2 antagonists;

antithrombotic agents, by way of example and with preference from the group of platelet aggregation inhibitors, the anticoagulants and the profibrinolytic substances;

hypotensive active ingredients, by way of example and with preference from the group of the calcium antagonists, angiotensin AII antagonists, ACE inhibitors, vasopeptidase inhibitors, endothelin antagonists, renin inhibitors, α-receptor blockers, β-receptor blockers, mineralocorticoid receptor antagonists and also the diuretics;

lipid metabolism modifiers, by way of example and with preference from the group of the thyroid receptor agonists, cholesterol synthesis inhibitors, by way of example and with preference HMG-CoA reductase or squalene synthesis inhibitors, of the ACAT inhibitors, CETP inhibitors, MTP inhibitors, PPAR-α, PPAR-γ and/or PPAR-δ agonists, cholesterol absorption inhibitors, lipase inhibitors, polymeric bile acid adsorbents, bile acid reabsorption inhibitors and lipoprotein(a) antagonists; and/or chemotherapeutics as used, for example, for therapy of neoplasms in the lung or other organs.

In a preferred embodiment of the invention, the compounds according to the invention are administered in combination with a β-adrenergic receptor agonist, by way of example and with preference albuterol, isoproterenol, metaproterenol, terbutalin, fenoterol, formoterol, reproterol, salbutamol or salmeterol.

In a preferred embodiment of the invention, the compounds of the invention are administered in combination with an antimuscarinergic substance, by way of example and with preference ipratropium bromide, tiotropium bromide or oxitropium bromide.

In a preferred embodiment of the invention, the compounds of the invention are administered in combination with a corticosteroid, by way of example and with preference prednisone, prednisolone, methylprednisolone, triamcinolone, dexamethasone, beclomethasone, betamethasone, flunisolide, budesonide or fluticasone.

Antithrombotic agents are preferably understood to mean compounds from the group of the platelet aggregation inhibitors, the anticoagulants and the profibrinolytic substances.

In a preferred embodiment of the invention, the compounds of the invention are administered in combination with a platelet aggregation inhibitor, by way of example and with preference aspirin, clopidogrel, ticlopidine or dipyridamole.

In a preferred embodiment of the invention, the compounds of the invention are administered in combination with a thrombin inhibitor, by way of example and with preference ximelagatran, melagatran, dabigatran, bivalirudin or clexane.

In a preferred embodiment of the invention, the compounds of the invention are administered in combination with a GPIIb/IIIa antagonist, by way of example and with preference tirofiban or abciximab.

In a preferred embodiment of the invention, the compounds of the invention are administered in combination with a factor Xa inhibitor, by way of example and with preference rivaroxaban, apixaban, fidexaban, razaxaban, fondaparinux, idraparinux, DU-176b, PMD-3112, YM-150, KFA-1982, EMD-503982, MCM-17, MLN-1021, DX 9065a, DPC 906, JTV 803, SSR-126512 or SSR-128428.

In a preferred embodiment of the invention, the compounds of the invention are administered in combination with heparin or with a low molecular weight (LMW) heparin derivative.

In a preferred embodiment of the invention, the compounds of the invention are administered in combination with a vitamin K antagonist, by way of example and with preference coumarin.

Hypotensive agents are preferably understood to mean compounds from the group of the calcium antagonists, angiotensin AII antagonists, ACE inhibitors, endothelin antagonists, renin inhibitors, α-receptor blockers, β-receptor blockers, mineralocorticoid receptor antagonists, and the diuretics.

In a preferred embodiment of the invention, the compounds of the invention are administered in combination with a calcium antagonist, by way of example and with preference nifedipine, amlodipine, verapamil or diltiazem.

In a preferred embodiment of the invention, the compounds according to the invention are administered in combination with an al-receptor blocker, by way of example and with preference prazosin.

In a preferred embodiment of the invention, the compounds according to the invention are administered in combination with a β-receptor blocker, by way of example and with preference propranolol, atenolol, timolol, pindolol, alprenolol, oxprenolol, penbutolol, bupranolol, metipranolol, nadolol, mepindolol, carazalol, sotalol, metoprolol, betaxolol, celiprolol, bisoprolol, carteolol, esmolol, labetalol, carvedilol, adaprolol, landiolol, nebivolol, epanolol or bucindolol.

In a preferred embodiment of the invention, the compounds of the invention are administered in combination with an angiotensin AII antagonist, by way of example and with preference losartan, candesartan, valsartan, telmisartan or embursatan.

In a preferred embodiment of the invention, the compounds of the invention are administered in combination with an ACE inhibitor, by way of example and with preference enalapril, captopril, lisinopril, ramipril, delapril, fosinopril, quinopril, perindopril or trandopril.

In a preferred embodiment of the invention, the compounds of the invention are administered in combination with an endothelin antagonist, by way of example and with preference bosentan, darusentan, ambrisentan or sitaxsentan.

In a preferred embodiment of the invention, the compounds of the invention are administered in combination with a renin inhibitor, by way of example and with preference aliskiren, SPP-600 or SPP-800.

In a preferred embodiment of the invention, the compounds of the invention are administered in combination with a mineralocorticoid receptor antagonist, by way of example and with preference spironolactone, eplerenone or finerenone.

In a preferred embodiment of the invention, the compounds of the invention are administered in combination with a diuretic, by way of example and with preference furosemide, bumetanide, torsemide, bendroflumethiazide, chlorothiazide, hydrochlorothiazide, hydroflumethiazide, methyclothiazide, polythiazide, trichlormethiazide, chlorthalidone, indapamide, metolazone, quinethazone, acetazolamide, dichlorphenamide, methazolamide, glycerol, isosorbide, mannitol, amiloride or triamterene.

Lipid metabolism modifiers are preferably understood to mean compounds from the group of the CETP inhibitors, thyroid receptor agonists, cholesterol synthesis inhibitors such as HMG-CoA reductase inhibitors or squalene synthesis inhibitors, the ACAT inhibitors, MTP inhibitors, PPAR-α, PPAR-γ and/or PPAR-δ agonists, cholesterol absorption inhibitors, polymeric bile acid adsorbers, bile acid reabsorption inhibitors, lipase inhibitors and the lipoprotein(a) antagonists.

In a preferred embodiment of the invention, the compounds of the invention are administered in combination with a CETP inhibitor, by way of example and with preference torcetrapib (CP-529 414), JJT-705 or CETP vaccine (Avant).

In a preferred embodiment of the invention, the compounds of the invention are administered in combination with a thyroid receptor agonist, by way of example and with preference D-thyroxine, 3,5,3'-triiodothyronine (T3), CGS 23425 or axitirome (CGS 26214).

In a preferred embodiment of the invention, the compounds of the invention are administered in combination with an HMG-CoA reductase inhibitor from the class of statins, by way of example and with preference lovastatin, simvastatin, pravastatin, fluvastatin, atorvastatin, rosuvastatin or pitavastatin.

In a preferred embodiment of the invention, the compounds of the invention are administered in combination with a squalene synthesis inhibitor, by way of example and with preference BMS-188494 or TAK-475.

In a preferred embodiment of the invention, the compounds of the invention are administered in combination with an ACAT inhibitor, by way of example and with preference avasimibe, melinamide, pactimibe, eflucimibe or SMP-797.

In a preferred embodiment of the invention, the compounds of the invention are administered in combination with an MTP inhibitor, by way of example and with preference implitapide, BMS-201038, R-103757 or JTT-130.

In a preferred embodiment of the invention, the compounds according to the invention are administered in combination with a PPAR-γ agonist, by way of example and with preference pioglitazone or rosiglitazone.

In a preferred embodiment of the invention, the compounds according to the invention are administered in combination with a PPAR-δ agonist, by way of example and with preference GW 501516 or BAY 68-5042.

In a preferred embodiment of the invention, the compounds of the invention are administered in combination with a cholesterol absorption inhibitor, by way of example and with preference ezetimibe, tiqueside or pamaqueside.

In a preferred embodiment of the invention, the compounds of the invention are administered in combination with a lipase inhibitor, by way of example and with preference orlistat.

In a preferred embodiment of the invention, the compounds of the invention are administered in combination with a polymeric bile acid adsorber, by way of example and with preference cholestyramine, colestipol, colesolvam, CholestaGel or colestimide.

In a preferred embodiment of the invention, the compounds of the invention are administered in combination with a bile acid reabsorption inhibitor, by way of example and with preference ASBT (=IBAT) inhibitors, for example AZD-7806, S-8921, AK-105, BARI-1741, SC-435 or SC-635.

In a preferred embodiment of the invention, the compounds of the invention are administered in combination with a lipoprotein(a) antagonist, by way of example and with preference gemcabene calcium (CI-1027) or nicotinic acid.

Particular preference is given to combinations of the compounds of the invention with one or more further active ingredients selected from the group consisting of PDE 5 inhibitors, sGC activators, sGC stimulators, prostacyclin analogs, IP receptor agonists, endothelin antagonists, compounds that inhibit the signal transduction cascade and pirfenidone.

The present invention further provides medicaments which comprise at least one compound of the invention, typically together with one or more inert, non-toxic, pharmaceutically suitable excipients, and for the use thereof for the aforementioned purposes.

The compounds of the invention can act systemically and/or locally. For this purpose, they can be administered in a suitable manner, for example by the oral, parenteral, pulmonal, nasal, sublingual, lingual, buccal, rectal, dermal, transdermal, conjunctival or otic route, or as an implant or stent.

The compounds of the invention can be administered in administration forms suitable for these administration routes.

Suitable administration forms for oral administration are those which work according to the prior art and release the compounds of the invention rapidly and/or in a modified manner and which contain the compounds of the invention in crystalline and/or amorphized and/or dissolved form, for example tablets (uncoated or coated tablets, for example with gastric juice-resistant or retarded-dissolution or insoluble coatings which control the release of the compound of the invention), tablets or films/oblates which disintegrate rapidly in the oral cavity, films/lyophilizates, capsules (for example hard or soft gelatin capsules), sugar-coated tablets, granules, pellets, powders, emulsions, suspensions, aerosols or solutions.

Parenteral administration can bypass an absorption step (e.g. take place intravenously, intraarterially, intracardially, intraspinally or intralumbally) or include an absorption (e.g. take place inhalatively, intramuscularly, subcutaneously, intracutaneously, percutaneously or intraperitoneally). Administration forms suitable for parenteral administration include preparations for injection and infusion in the form of solutions, suspensions, emulsions, lyophilizates or sterile powders.

For the other administration routes, suitable examples are inhalable medicament forms (including powder inhalers, nebulizers, metered aerosols), nasal drops, solutions or sprays, tablets, films/oblates or capsules for lingual, sublingual or buccal administration, suppositories, ear or eye preparations, vaginal capsules, aqueous suspensions (lotions, shaking mixtures), lipophilic suspensions, ointments, creams, transdermal therapeutic systems (e.g. patches), milk, pastes, foams, sprinkling powders, implants or stents.

Oral and parenteral administration are preferred, especially oral, intravenous and intrapulmonary (inhalative) administration.

The compounds of the invention can be converted to the administration forms mentioned. This can be accomplished in a manner known per se by mixing with inert, non-toxic, pharmaceutically suitable excipients. These excipients include carriers (for example microcrystalline cellulose, lactose, mannitol), solvents (e.g. liquid polyethylene glycols), emulsifiers and dispersing or wetting agents (for example sodium dodecylsulfate, polyoxysorbitan oleate), binders (for example polyvinylpyrrolidone), synthetic and natural polymers (for example albumin), stabilizers (e.g. antioxidants, for example ascorbic acid), colorants (e.g. inorganic pigments, for example iron oxides) and flavour and/or odour correctants.

In general, it has been found to be advantageous in the case of parenteral administration to administer amounts of about 0.001 to 1 mg/kg, preferably about 0.01 to 0.5 mg/kg, of body weight to achieve effective results. In the case of oral administration the dosage is about 0.01 to 100 mg/kg, preferably about 0.01 to 20 mg/kg and most preferably 0.1 to 10 mg/kg of body weight. In the case of intrapulmonary administration, the amount is generally about 0.1 to 50 mg per inhalation.

It may nevertheless be necessary in some cases to deviate from the stated amounts, specifically as a function of body weight, route of administration, individual response to the active ingredient, nature of the preparation and time or interval over which administration takes place. Thus in some cases it may be sufficient to manage with less than the abovementioned minimum amount, while in other cases the upper limit mentioned must be exceeded. In the case of administration of greater amounts, it may be advisable to divide them into several individual doses over the day.

The working examples which follow illustrate the invention. The invention is not restricted to the examples.

A. EXAMPLES

Abbreviations and Acronyms abs. absolute
Ac acetyl
AIBN 2,2'-azobis(2-methylpropionitrile), azobisisobutyronitrile
aq. aqueous, aqueous solution
br. broad (in NMR signal)
Ex. Example
Bu butyl
c concentration
approx. circa, about
cat. catalytic
CDI N,N'-carbonyldiimidazole
CI chemical ionization (in MS)
d doublet (in NMR)
d day(s)
DAST N,N-diethylaminosulfur trifluoride
TLC thin-layer chromatography
DCI direct chemical ionization (in MS)
dd doublet of doublets (in NMR)
DMF N,N-dimethylformamide
DMSO dimethyl sulfoxide
dt doublet of triplets (in NMR)
ΔT heating, temperature increase (in reaction schemes)
of th. of theory (in chemical yield)
EI electron impact ionization (in MS)
eq. equivalent(s)
ESI electrospray ionization (in MS)
Et ethyl
h hour(s)
HATU O-(7-azabenzotriazol-1-yl)-N,N,N',N'-tetramethyluronium hexafluorophosphate
HOAc acetic acid
HPLC high-pressure, high-performance liquid chromatography
iPr isopropyl
conc. concentrated (in the case of a solution)
LC liquid chromatography
LC/MS liquid chromatography-coupled mass spectrometry
lit. literature (reference)
m multiplet (in NMR)
MCPBA meta-chloroperbenzoic acid, 3-chloroperbenzoic acid
Me methyl
min minute(s)
MS mass spectrometry
NBS N-bromosuccinimide
NMR nuclear magnetic resonance spectrometry
Pd/C palladium on activated carbon
Pr propyl
q (or quart) quartet (in NMR)
qd quartet of doublets (in NMR)
quant. quantitative (in chemical yield)
quint quintet (in NMR)
$R_f$ retention index (in TLC)
RP reverse phase (in HPLC)
RT room temperature
$R_t$ retention time (in HPLC, LC/MS)
s singlet (in NMR)
sept septet (in NMR)
t triplet (in NMR)
tBu tert-butyl
td triplet of doublets (in NMR)
TFA trifluoroacetic acid
THF tetrahydrofuran
UV ultraviolet spectrometry
v/v volume to volume ratio (of a solution)
tog. together
HPLC and LC-MS Methods:
Method 1 (LC/MS):
Instrument: Waters Acquity SQD UPLC System; column: Waters Acquity UPLC HSS T3 1.8μ 50×1 mm; eluent A: 1 l water+0.25 ml 99% formic acid, eluent B: 1 l acetonitrile+

0.25 ml 99% formic acid; gradient: 0.0 min 90% A→1.2 min 5% A→2.0 min 5% A; oven: 50° C.; flow rate: 0.40 ml/min; UV detection: 208-400 nm.

Method 2 (LC/MS):

MS instrument: Waters Micromass QM; HPLC instrument: Agilent 1100 series; column: Agilent ZORBAX Extend-C18 3.0 mm×50 mm 3.5μ; eluent A: 1 l water+0.01 mol ammonium carbonate, eluent B: 1 l acetonitrile; gradient: 0.0 min 98% A→0.2 min 98% A→3.0 min 5% A→4.5 min 5% A; oven: 40° C.; flow rate: 1.75 ml/min; UV detection: 210 nm.

Method 3 (LC/MS):

MS instrument: Agilent MS Quad 6150; HPLC instrument: Agilent 1290; column: Waters Acquity UPLC HSS T3 1.8μ 50×2.1 mm; eluent A: 1 l water+0.25 ml 99% formic acid, eluent B: 1 l acetonitrile+0.25 ml 99% formic acid; gradient: 0.0 min 90% A→0.3 min 90% A→1.7 min 5% A→3.0 min 5% A; oven: 50° C.; flow rate: 1.20 ml/min; UV detection: 205-305 nm.

Method 4 (LC/MS):

MS instrument: Agilent 6130; HPLC instrument: Agilent 1200; UV DAD; column: Waters XBridge BEH XP 2.5 μm, 2.1×50 mm; eluent A: ammonium acetate (10 mM)+water/methanol/acetonitrile (9.0:0.6:0.4), eluent B: ammonium acetate (10 mM)+water/methanol/acetonitrile (1.0:5.4:3.6); gradient A/B: 80/20 (0.0 min)→80/20 (1.5 min)→0/100 (2.5 min); flow rate: 0.6 ml/min; temperature: 35° C.; UV detection: 215 and 238 nm.

Method 5 (Preparative HPLC):

Column: Reprosil C18, 10 μm, 125×30 mm; eluent: acetonitrile/water with 0.1% TFA; gradient: 0-5.00 min 10:90, sample injection at 3.00 min, 5.00-23.00 min to 95:5, 23.00-30.00 min 95:5, 30.00-30.50 min to 10:90, 30.50-31.20 min 10:90.

Method 6 (Preparative HPLC):

Column: Chromatorex C18, 125×40 mm; eluent A: water+0.05% TFA, eluent B: acetonitrile; gradient: 0.0 min 20% B→4.0 min 20% B→30 min 95% B→35 min 95% B→36 min 20% B; flow rate: 50 ml/min.

Method 7 (Preparative HPLC):

Column: Chromatorex C18, 250×30 mm; eluent A: water, eluent B: acetonitrile; gradient: 0.0 min 60% B→4.5 min 80% B→11.5 min 100% B→12 min 100% B→14.75 min 60% B; flow rate: 50 ml/min.

Method 8 (Preparative HPLC):

Column: Chromatorex C18, 250×30 mm; eluent A: water, eluent B: acetonitrile; gradient: 0.0 min 40% B→4.5 min 60% B→11.5 min 80% B→12 min 100% B→14.75 min 40% B; flow rate: 50 ml/min.

Method 9 (Preparative HPLC):

Column: Chromatorex C18, 250×30 mm; eluent A: water+0.1% TFA, eluent B: acetonitrile; gradient: 0.0 min 40% B→4.5 min 60% B→11.5 min 80% B→12 min 100% B→14.75 min 40% B; flow rate: 50 ml/min.

Method 10 (Preparative HPLC):

Column: Reprosil C18, 10 μm, 250×30 mm; flow rate: 50 ml/min; run time: 18 min; detection: 210 nm; eluent: water+0.1% formic acid/methanol; gradient: 20% methanol (4.25 min)→40% methanol (4.5 min)→60% methanol (11.5 min)→100% methanol (12 min)→100% methanol (14.5 min)→20% methanol (14.75 min)→20% methanol (18 min).

Method 11 (Preparative HPLC):

Column: GromSil C18, 250×30 mm, 10 μm; flow rate: 50 ml/min; eluent A: water, eluent B: acetonitrile; gradient: 0 min 30% B→4.25 min 30% B→4.5 min 50% B→11.5 min 70% B→12 min 100% B→14.5 min 100% B→14.75 min 30% B→18 min 30% B; detection: 210 nm.

Method 12 (Preparative HPLC):

Column: Reprosil C18, 10 μm, 125×30 mm; eluent: acetonitrile/water with 0.1% TFA; gradient: 0-5.00 min 10:90, sample injection at 3.00 min, 5.00-23.00 min to 95:5, 23.00-30.00 min 95:5, 30.00-30.50 min to 10:90, 30.50-31.20 min 10:90.

Method 13 (Preparative HPLC):

Column: Chromatorex C18, 250×30 mm; eluent A: water, eluent B: acetonitrile; gradient: 0.0 min 30% B→4.5 min 50% B→11.5 min 70% B→12 min 100% B→14.75 min 30% B; flow rate: 50 ml/min.

Method 14 (Preparative HPLC):

Column: Kinetex 5 μm C18 100 A, 150×21.2 mm; eluent A: water+0.2% formic acid, eluent B: acetonitrile; gradient: 70% A, 30% B, isocratic; flow rate: 25 ml/min.

Method 15 (Preparative HPLC):

Column: Chromatorex C18, 125×30 mm; eluent A: water+0.05% TFA, eluent B: acetonitrile; gradient: 0.0 min 20% B→3.2 min 20% B→18 min 95% B→23 min 95% B→24 min 20% B; flow rate: 50 ml/min.

Method 16 (Preparative HPLC):

Column: Reprosil C18, 10 m, 125×30 mm; eluent: acetonitrile/water with 0.1% TFA; gradient: 0-6.00 min 5:95, sample injection at 3.00 min; 6.00-27.00 min to 35:65; 27.00-30.00 min 95:5, 30.00-33.00 min to 5:95.

Method 17 (Preparative HPLC):

Column: Reprosil C18, 10 μm, 250×30 mm; flow rate: 50 ml/min; run time: 18 min; detection: 210 nm; eluent: water+0.1% formic acid/methanol; gradient: 20% methanol (4.25 min)→40% methanol (4.5 min)→60% methanol (11.5 min)→100% methanol (12 min)→100% methanol (14.5 min)→20% methanol (14.75 min)→20% methanol (18 min).

Method 18 (Preparative HPLC):

Column: Reprosil C18, 10 μm, 125×30 mm; eluent: acetonitrile/water with 0.1% TFA; flow rate: 75 ml/min; gradient: 0-5.50 min 10:90, sample injection at 3.00 min, 5.50-17.65 min to 95:5, 17.65-19.48 min 95:5, 19.48-19.66 min to 10:90, 19.66-20.72 min 10:90.

Method 19 (Preparative HPLC):

Column: Reprosil C18, 10 m, 125×30 mm; eluent: acetonitrile/water with 0.1% TFA; gradient: 0-6.00 min 35:65, sample injection at 3.00 min; 6.00-27.00 min to 80:20; 27.00-30.00 min 95:5, 30.00-33.00 min to 35:65.

Method 20 (Preparative HPLC):

Column: Reprosil C18, 10 μm, 125×30 mm; eluent: acetonitrile/water with 0.1% TFA; gradient: 0-6.00 min 35:65, sample injection at 3.00 min; 6.00-27.00 min to 80:20; 27.00-51.00 min 95:5, 51.00-53.00 min to 35:65.

Method 21 (LC/MS):

Instrument: Agilent MS Quad 6150 with HPLC Agilent 1290; column: Waters Acquity UPLC HSS T3 1.8 μm 50 mm×2.1 mm; eluent A: 1 l water+0.25 ml 99% formic acid, eluent B: 1 l acetonitrile+0.25 ml 99% formic acid; gradient: 0.0 min 90% A→0.3 min 90% A→1.7 min 5% A→3.0 min 5% A; flow rate: 1.20 ml/min; temperature: 50° C.; UV detection: 205-305 nm.

Method 22 (LC/MS):

Instrument: Micromass Quattro Premier with Waters UPLC Acquity; column: Thermo Hypersil GOLD 1.9μ 50×1 mm; eluent A: 1 l water+0.5 ml 50% formic acid, eluent B: 1 l acetonitrile+0.5 ml 50% formic acid; gradient: 0.0 min 97% A→0.5 min 97% A→3.2 min 5% A→4.0 min 5% A; oven: 50° C.; flow rate: 0.30 ml/min; UV detection: 210 nm.

Method 23 (LC/MS):

Instrument: Waters Acquity SQD UPLC System; column: Waters Acquity UPLC HSS T3 1.8μ 50×1 mm; eluent A: 1 l water+0.25 ml 99% formic acid, eluent B: 1 l acetonitrile+0.25 ml 99% formic acid; gradient: 0.0 min 95% A→6.0 min 5% A→7.5 min 5% A; oven: 50° C.; flow rate: 0.35 ml/min; UV detection: 210-400 nm.

Method 24 (Preparative HPLC):

Column: Reprosil C18, 10 μm, 250×40 mm; eluent: acetonitrile/water with 0.1% TFA; gradient: 0-6.00 min 10:90, sample injection at 3.00 min, 6.00-27.00 min to 95:5, 27.00-38.00 min 95:5, 38.00-39.00 min to 10:90, 39.00-40.20 min 10:90.

Further Details:

The percentages in the example and test descriptions which follow are, unless indicated otherwise, percentages by weight; parts are parts by weight. Solvent ratios, dilution ratios and concentration data for liquid/liquid solutions are based in each case on volume.

Purity figures are generally based on corresponding peak integrations in the LC/MS chromatogram, but may additionally also have been determined with the aid of the $^1$H NMR spectrum. If no purity is indicated, the purity is generally 100% according to automated peak integration in the LC/MS chromatogram, or the purity has not been determined explicitly.

Stated yields in % of theory are generally corrected for purity if a purity of <100% is indicated. In solvent-containing or contaminated batches, the formal yield may be ">100%"; in these cases the yield is not corrected for solvent or purity.

The descriptions of the coupling patterns of $^1$H NMR signals that follow have in some cases been taken directly from the suggestions of the ACD SpecManager (ACD/Labs Release 12.00, Product version 12.5) and have not necessarily been strictly scrutinized. In some cases, the suggestions of the SpecManager were adjusted manually. Manually adjusted or assigned descriptions are generally based on the optical appearance of the signals in question and do not necessarily correspond to a strict, physically correct interpretation. In general, the stated chemical shift refers to the center of the signal in question. In the case of broad multiplets, an interval is given. Signals obscured by solvent or water were either tentatively assigned or have not been listed. Significantly broadened signals—caused, for example, by rapid rotation of molecular moieties or because of exchanging protons—were likewise assigned tentatively (often referred to as a broad multiplet or broad singlet) or are not listed.

Melting points and melting-point ranges, if stated, are uncorrected.

All reactants or reagents whose preparation is not described explicitly hereinafter were purchased commercially from generally accessible sources. For all other reactants or reagents whose preparation likewise is not described hereinafter and which were not commercially obtainable or were obtained from sources which are not generally accessible, a reference is given to the published literature in which their preparation is described.

In the case of the synthesis intermediates and working examples of the invention described hereinafter, any compound specified in the form of a salt of the corresponding base or acid is generally a salt of unknown exact stoichiometric composition, as obtained by the respective preparation and/or purification process. Unless specified in more detail, additions to names and structural formulae, for example "hydrochloride", "formate", "acetate", "trifluoroacetate", "sodium salt" or "x HCl", "x HCOOH", "x CH$_3$COOH", "x CF$_3$COOH", "x Na$^+$" should therefore not be understood in a stoichiometric sense in the case of such salts, but are merely of descriptive character with regard to the salt-forming components present.

Starting Compounds and Intermediates

Example 1A

6-Bromo-3-methyl-2-phenylquinoline-4-carboxylic Acid

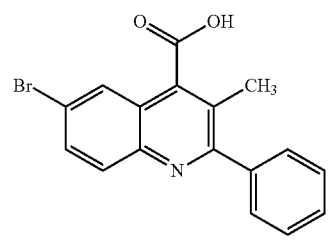 [SMILES: Cc1c(-c2ccccc2)nc2ccc(Br)cc2c1C(=O)O]

To 100.0 g (398.16 mmol, 90% purity) of 5-bromo-1H-indole-2,3-dione and 59.4 g (442.41 mmol) of 1-phenylpropan-1-one were added 1.2 liters of acetic acid, and the mixture was stirred at 75° C. for 20 min. Thereafter, 400 ml of conc. hydrochloric acid were added to the reaction mixture, and stirring of the mixture was continued at 105° C. overnight. The reaction solution was then added to a mixture of 10 liters of 1 N hydrochloric acid, 9.2 liters of water and 840 ml of conc. hydrochloric acid while stirring. 1 liter of ice-water was added to the mixture, and the precipitate was filtered off with the aid of a frit. The filter residue was washed twice with 500 ml of water, then extracted by stirring twice with 150 ml each time of a 3:1 mixture of tert-butyl methyl ether and acetone and filtered again. The residue was extracted by stirring three times more with 100 ml each time of tert-butyl methyl ether and finally dried under reduced pressure. 117.96 g (78% of theory, 100% purity) of the title compound were obtained.

$^1$H-NMR (400 MHz, DMSO-d$_6$): [ppm]=14.39 (br. s, 1H), 8.01 (d, 1H), 7.94-7.90 (m, 2H), 7.63-7.61 (m, 2H), 7.56-7.49 (m, 3H), 2.40 (s, 3H).

LC/MS (Method 1, ESIpos): R$_t$=0.76 min, m/z=343 [M+H]$^+$.

Example 2A (6-Bromo-3-methyl-2-phenylquinolin-4-yl)(1H-imidazol-1-yl)methanone

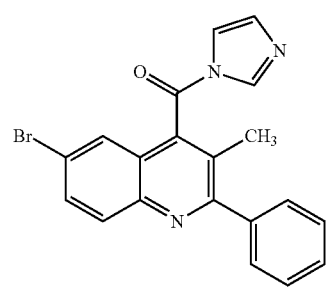 [SMILES: Cc1c(-c2ccccc2)nc2ccc(Br)cc2c1C(=O)n1ccnc1]

100.0 g (292.23 mmol) of the compound from example 1A were suspended in 1.5 liters of DMF, and 95.0 g (584.45 mmol) of N,N'-carbonyldiimidazole were added at RT. The reaction mixture was stirred first at 60° C. for 4 h and then at RT overnight. While cooling with an ice bath, 1.5 liters of ice-water were added gradually and then the mixture was put in the fridge for three days. The precipitated solids were filtered off by means of a frit, washed three times with 250 ml of water and dried under reduced pressure. 103.41 g (85% of theory, 94% purity) of the title compound were obtained.

$^1$H-NMR (400 MHz, DMSO-$d_6$): [ppm]=8.6-8.0 (br. m, 1H), 8.09 (d, 1H), 8.0-7.5 (br. m, 1H), 7.97 (dd, 1H), 7.82 (s, 1H), 7.72-7.66 (m, 2H), 7.59-7.48 (m, 3H), 7.22 (br. s, 1H), 2.25 (s, 3H).

LC/MS (Method 1, ESIpos): $R_t$=1.16 min, m/z=392/394 [M+H]$^+$.

Example 3A

6-Fluoro-3-methyl-2-phenylquinoline-4-carboxylic Acid

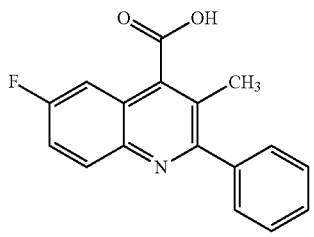 [SMILES: Cc1c(-c2ccccc2)nc2ccc(I)cc2c1C(=O)O]

1.00 g (6.06 mmol) of 5-fluoro-1H-indole-2,3-dione were initially charged in 16.5 ml of acetic acid, and 813 mg (6.06 mmol) of 1-phenylpropan-1-one were added. The reaction mixture was stirred at 75° C. for 5 min. Subsequently, 5.5 ml of conc. hydrochloric acid were added, and stirring of the mixture was continued at 105° C. for 3 h. After cooling to RT, the reaction mixture was added to 200 ml of 1 M hydrochloric acid and the precipitated solids were filtered off with suction. The solids were washed with water and dried under reduced pressure. 670 mg (35% purity, 14% of theory) of the title compound were obtained.

LC/MS (Method 1, ESIpos): $R_t$=0.64 min, m/z=282 [M+H]$^+$.

Example 4A (6-Fluoro-3-methyl-2-phenylquinolin-4-yl)(1H-imidazol-1-yl)methanone

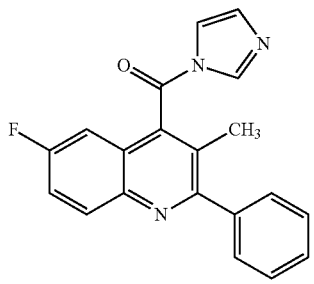 [SMILES: Cc1c(-c2ccccc2)nc2ccc(I)cc2c1C(=O)n1ccnc1]

To a solution of 1.50 g (5.33 mmol) of the compound from example 3A in 23 ml of DMF were added, at RT, 951 mg (5.87 mmol) of N,N'-carbonyldiimidazole, and the mixture was stirred at 60° C. for 3 h. Subsequently, a further 300 mg (1.07 mmol) of N,N'-carbonyldiimidazole were added, and the mixture was stirred at 60° C. for a further 15 h. After cooling to RT, the mixture was introduced into 100 ml of water while stirring and a little ice was added. The solids formed were filtered off and dried under reduced pressure. 1.57 g (89% of theory, 100% purity) of the title compound were obtained.

$^1$H-NMR (400 MHz, DMSO-$d_6$): [ppm]=8.5-8.0 (br. m, 1H), 8.22 (dd, 1H), 8.0-7.5 (br. m, 1H), 7.76 (td, 1H), 7.69 (dd, 2H), 7.59-7.47 (m, 3H), 7.41 (dd, 1H), 7.21 (br. s, 1H), 2.25 (s, 3H).

LC/MS (Method 1, ESIpos): $R_t$=1.05 min, m/z=332 [M+H]$^+$.

Example 5A

6-Iodo-3-methyl-2-phenylquinoline-4-carboxylic acid

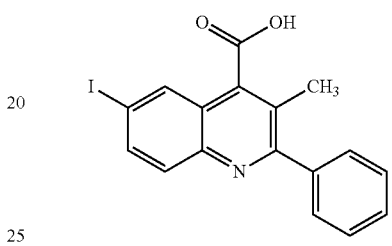

20.0 g (73.25 mmol) of 5-iodo-1H-indole-2,3-dione were initially charged in 200 ml of acetic acid, and 9.83 g (73.25 mmol) of 1-phenylpropan-1-one were added. The reaction mixture was stirred at 75° C. for 5 min. Thereafter, 66 ml of conc. hydrochloric acid were added, and stirring of the mixture was continued at 105° C. overnight. Subsequently, the reaction solution was introduced cautiously into water while stirring. The precipitate formed was filtered off and washed twice with water and twice with a little tert-butyl methyl ether. After drying under reduced pressure overnight, 11.10 g (32% of theory, 82% purity) of the title compound were obtained.

$^1$H-NMR (400 MHz, DMSO-$d_6$): [ppm]=14.36 (br. s, 1H), 8.13 (d, 1H), 8.05 (dd, 1H), 7.84 (d, 1H), 7.66-7.57 (m, 2H), 7.57-7.41 (m, 3H), 2.39 (s, 3H).

LC/MS (Method 1, ESIpos): $R_t$=0.78 min, m/z=390 [M+H]$^+$.

Example 6A (1H-Imidazol-1-yl)(6-iodo-3-methyl-2-phenylquinolin-4-yl)methanone

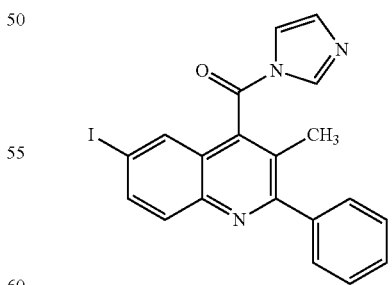

600 mg (1.23 mmol, 80% purity) of the compound from example 5A were dissolved in 5.5 ml of DMF, and 400 mg (2.47 mmol) of N,N'-carbonyldiimidazole were added at RT. The reaction mixture was stirred at 60° C. overnight and then, after cooling to RT, water and ethyl acetate were added. The phases were separated and the aqueous phase was extracted three times with ethyl acetate. The combined organic phases were dried over sodium sulfate, filtered and concentrated. The residue was purified by means of column chromatography (80 g of silica gel, eluent: cyclohexane/ethyl acetate 5:1, Biotage). After the solvent had been removed under reduced pressure, the residue was dried under reduced pressure overnight. 568 mg (98% of theory, 94% purity) of the title compound were obtained.

$^1$H-NMR (400 MHz, DMSO-d$_6$): [ppm]=9.50-6.00 (br. m, 2H), 8.10 (dd, 1H), 7.95 (s, 1H), 7.91 (d, 1H), 7.72-7.65 (m, 2H), 7.60-7.42 (m, 3H), 7.22 (br. s, 1H), 2.24 (s, 3H).

LC/MS (Method 1, ESIpos): $R_t$=1.13 min, m/z=440 [M+H]$^+$.

Example 7A 3,6-Dimethyl-2-phenylquinoline-4-carboxylic Acid

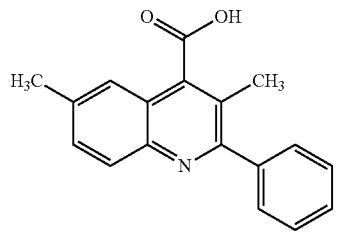 [SMILES: Cc1ccc2nc(-c3ccccc3)c(C)c(C(=O)O)c2c1]

2.00 g (12.41 mmol) of 5-methyl-1H-indole-2,3-dione were initially charged in 33.7 ml of acetic acid, and 1.66 g (12.41 mmol) of 1-phenylpropan-1-one were added. The reaction mixture was stirred at 75° C. for 5 min. Subsequently, 11.3 ml of conc. hydrochloric acid were added, and stirring of the mixture was continued at 105° C. overnight. After cooling to RT, the reaction mixture was added to 400 ml of 1 M hydrochloric acid and this mixture was then left to stand at RT for three days. The precipitated solids were filtered off, washed with water and dried under reduced pressure. 700 mg (20% of theory, 100% purity) of the title compound were obtained.

LC/MS (Method 1, ESIpos): $R_t$=0.53 min, m/z=278 [M+H]$^+$.

Example 8A (3,6-Dimethyl-2-phenylquinolin-4-yl)(1H-imidazol-1-yl)methanone

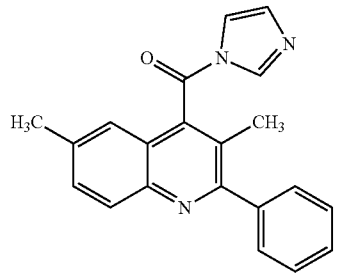 [SMILES: Cc1ccc2nc(-c3ccccc3)c(C)c(C(=O)n3ccnc3)c2c1]

To a solution of 464 mg (1.68 mmol) of the compound from example 7A in 7 ml of DMF were added, at RT, 299 mg (1.84 mmol) of N,N'-carbonyldiimidazole, and the mixture was stirred at 60° C. for 4 h. Subsequently, a further 30 mg (0.18 mmol) of N,N'-carbonyldiimidazole were added, and the mixture was stirred at 60° C. for a further hour. After cooling to RT, water was added and the mixture was extracted three times with ethyl acetate. The combined organic phases were washed once with saturated sodium chloride solution, dried over sodium sulfate, filtered and concentrated. The residue was taken up in dichloromethane, concentrated again and dried under reduced pressure. 505 mg (92% of theory, 100% purity) of the title compound were obtained.

$^1$H-NMR (400 MHz, DMSO-d$_6$): [ppm]=8.5-8.0 (br. m, 1H), 8.04 (d, 1H), 8.0-7.5 (br. m, 1H), 7.98-7.59 (m, 3H), 7.57-7.45 (m, 3H), 7.34 (s, 1H), 7.26-7.09 (m, 1H), 2.46 (s, 3H), 2.23 (s, 3H).

LC/MS (Method 1, ESIpos): $R_t$=1.05 min, m/z=328 [M+H]$^+$.

Example 9A

6-Ethyl-3-methyl-2-phenylquinoline-4-carboxylic acid

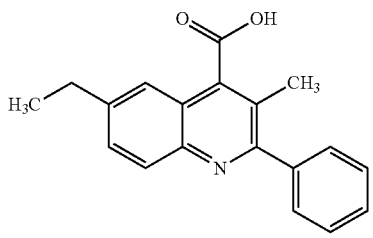 [SMILES: CCc1ccc2nc(-c3ccccc3)c(C)c(C(=O)O)c2c1]

1.00 g (5.71 mmol) of 5-ethyl-1H-indole-2,3-dione were initially charged in 15.5 ml of acetic acid, and 766 mg (5.71 mmol) of 1-phenylpropan-1-one were added. The reaction mixture was stirred at 75° C. for 5 min. Subsequently, 5.2 ml of conc. hydrochloric acid were added, and stirring of the mixture was continued at 105° C. overnight. After cooling to RT, the reaction mixture was added to 200 ml of 1 M hydrochloric acid and the precipitated solids were filtered off. The solids were washed with water and dried under reduced pressure. 780 mg (46% of theory, 99% purity) of the title compound were obtained.

LC/MS (Method 1, ESIpos): $R_t$=0.63 min, m/z=292 [M+H]$^+$.

Example 10A (6-Ethyl-3-methyl-2-phenylquinolin-4-yl)(1H-imidazol-1-yl)methanone

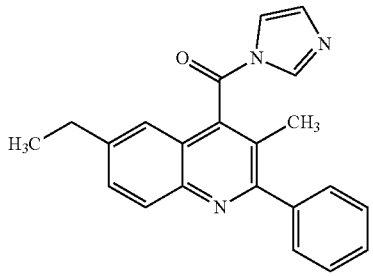 [SMILES: CCc1ccc2nc(-c3ccccc3)c(C)c(C(=O)n3ccnc3)c2c1]

To a solution of 640 mg (2.20 mmol) of the compound from example 9A in 10 ml of DMF were added, at RT, 392 mg (2.42 mmol) of N,N'-carbonyldiimidazole, and the mixture was stirred at 60° C. for 3.5 h. Subsequently, the mixture was cooled to RT, water was added and the mixture was extracted three times with ethyl acetate. The combined organic phases were washed once with saturated sodium chloride solution, dried over sodium sulfate, filtered and concentrated, and the residue was dried under reduced pressure. The residue was purified by means of column chromatography (50 g of silica gel, eluent: cyclohexane/ethyl acetate 7:3, Biotage). 362 mg (46% of theory, 95% purity) of the title compound were obtained.

$^1$H-NMR (400 MHz, DMSO-$d_6$): [ppm]=8.5-8.0 (br. m, 1H), 8.07 (d, 1H), 8.0-7.5 (br. m, 1H), 7.73 (dd, 1H), 7.70-7.65 (m, 2H), 7.57-7.47 (m, 3H), 7.32 (br. s, 1H), 7.22 (br. s, 1H), 2.76 (q, 2H), 2.24 (s, 3H), 1.19 (t, 3H).

LC/MS (Method 1, ESIpos): $R_t$=1.18 min, m/z=342 [M+H]$^+$.

Example 11A

6-Isopropyl-3-methyl-2-phenylquinoline-4-carboxylic acid

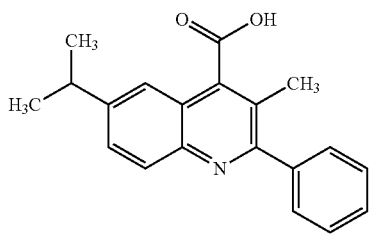 [SMILES: Cc1c(-c2ccccc2)nc2ccc(C(C)C)cc2c1C(=O)O]

2.50 g (13.21 mmol) of 5-isopropyl-1H-indole-2,3-dione were initially charged together with 36 ml of acetic acid and 1.77 g (13.21 mmol) of 1-phenylpropan-1-one, and the reaction mixture was stirred at 75° C. for 5 min. Then 12 ml of conc. hydrochloric acid were added, and stirring of the mixture was continued at 105° C. overnight. After cooling to RT, the reaction mixture was added to 500 ml of 1 M hydrochloric acid and the precipitated solids were filtered off. The solids were washed with water and dried under reduced pressure. 2.04 g (31% of theory, 62% purity) of the title compound were obtained.

LC/MS (Method 1, ESIpos): $R_t$=0.66 min, m/z=306 [M+H]$^+$.

Example 12A

3-Methyl-2-phenyl-6-(trifluoromethyl)quinoline-4-carboxylic Acid

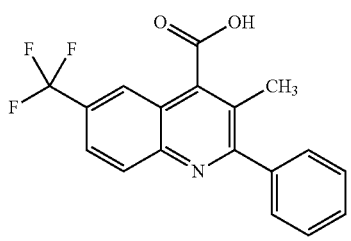 [SMILES: Cc1c(-c2ccccc2)nc2ccc(C(F)(F)F)cc2c1C(=O)O]

1.00 g (4.65 mmol) of 5-(trifluoromethyl)-1H-indole-2,3-dione were initially charged together with 12.6 ml of acetic acid and 624 mg (4.65 mmol) of 1-phenylpropan-1-one, and the reaction mixture was stirred at 75° C. for 5 min. Then 4.2 ml of conc. hydrochloric acid were added, and stirring of the mixture was continued at 105° C. overnight. After cooling to RT, the reaction mixture was added to 200 ml of 1 M hydrochloric acid and the precipitated solids were filtered off. The solids were washed with water and dried under reduced pressure. 1.17 g (75% of theory, 100% purity) of the title compound were obtained.

LC/MS (Method 1, ESIpos): $R_t$=0.91 min, m/z=332 [M+H]$^+$.

Example 13A

3-Methyl-2-phenyl-6-(trifluoromethoxy)quinoline-4-carboxylic Acid

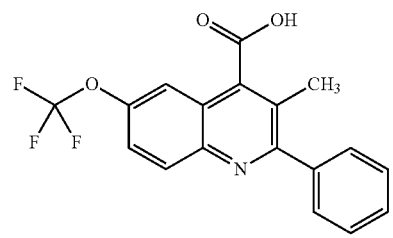 [SMILES: Cc1c(-c2ccccc2)nc2ccc(OC(F)(F)F)cc2c1C(=O)O]

To a mixture of 2.5 g (10.82 mmol) of 5-(trifluoromethoxy)-1H-indole-2,3-dione in 25 ml of acetic acid were added 1.45 g (10.82 mmol) of 1-phenylpropan-1-one. After stirring at 75° C. for 5 min, 8 ml of conc. hydrochloric acid were added, and stirring of the mixture was continued at 110° C. for 5 h. After cooling to RT and leaving to stand overnight, the mixture was introduced into 500 ml of 1 M hydrochloric acid while stirring. After a few minutes, the solids formed were filtered off, washed twice with water and dried under reduced pressure. 3.16 g (77% of theory, 92% purity) of the title compound were obtained.

$^1$H-NMR (400 MHz, DMSO-$d_6$): [ppm]=14.41 (br. s, 1H), 8.21 (d, 1H), 7.80 (dd, 1H), 7.69 (d, 1H), 7.66-7.58 (m, 2H), 7.57-7.47 (m, 3H), 2.41 (s, 3H).

LC/MS (Method 1, ESIpos): $R_t$=0.97 min, m/z=348 [M+H]$^+$.

Example 14A (1H-Imidazol-1-yl) [3-methyl-2-phenyl-6-(trifluoromethoxy)quinolin-4-yl]methanone

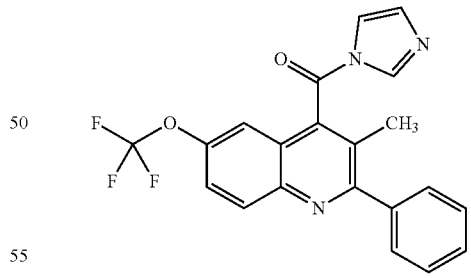

To a solution of 1.50 g (3.97 mmol, 92% purity) of the compound from example 13A in 15 ml of DMF were added, at RT, 709 mg (4.37 mmol) of N,N'-carbonyldiimidazole, and the mixture was stirred at 60° C. for 3 h. Subsequently, a further 709 mg (4.37 mmol) of N,N'-carbonyldiimidazole were added, and the mixture was stirred at 60° C. for a further 4 h. After being left to stand at RT overnight, the mixture was first stirred at 80° C. for a further hour. Thereafter, another 709 mg (4.37 mmol) of N,N'-carbonyldiimidazole were added, and the mixture was stirred at 100° C. for another 4 h. After being left to stand at RT overnight, the mixture was introduced into ice-water while stirring and adjusted to pH 4 by means of 10% aqueous citric acid solution. Subsequently, the mixture was extracted twice with ethyl acetate. The combined organic phases were washed once with saturated sodium chloride solution, dried over sodium sulfate, filtered and concentrated. The residue was prepurified by means of column chromatography (100 g of silica gel, eluent: cyclohexane/ethyl acetate 7:3, Biotage). The product thus obtained was stirred in pentane, and the solids present were filtered off and dried under reduced pressure. 1.28 g (81% of theory, 100% purity) of the title compound were obtained.

$^1$H-NMR (400 MHz, DMSO-$d_6$): [ppm]=8.5-8.0 (br. m, 1H), 8.30 (d, 1H), 8.0-7.5 (br. m, 1H), 7.84 (dd, 1H), 7.72-7.66 (m, 2H), 7.59-7.50 (m, 4H), 7.21 (br. s, 1H), 2.26 (s, 3H).

LC/MS (Method 1, ESIpos): $R_t$=1.15 min, m/z=398 [M+H]$^+$.

Example 15A

6-Bromo-3-ethyl-2-phenylquinoline-4-carboxylic Acid

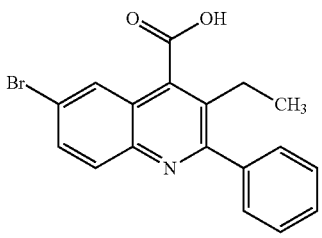 [SMILES: CCc1c(-c2ccccc2)nc2ccc(Br)cc2c1C(=O)O]

1.00 g (4.42 mmol) of 5-bromo-1H-indole-2,3-dione were initially charged in 12.0 ml of acetic acid, and 656 mg (4.42 mmol) of 1-phenylbutan-1-one were added. The reaction mixture was stirred at 75° C. for 5 min. Subsequently, 4.0 ml of conc. hydrochloric acid were added, and stirring of the mixture was continued at 105° C. overnight. After cooling to RT, the reaction mixture was added to 200 ml of 1 M hydrochloric acid and the precipitated solids were filtered off with suction. The solids were washed with water and dried under reduced pressure. 1.20 g (55% of theory, 72% purity) of the title compound were obtained.

LC/MS (Method 1, ESIpos): $R_t$=0.88 min, m/z=357 [M+H]$^+$.

Example 16A (6-Bromo-3-ethyl-2-phenylquinolin-4-yl)(1H-imidazol-1-yl)methanone

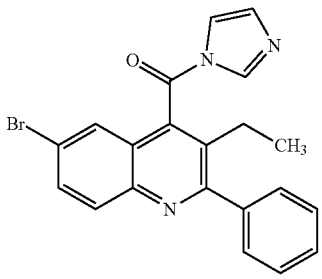 [SMILES: CCc1c(-c2ccccc2)nc2ccc(Br)cc2c1C(=O)n1ccnc1]

To a solution of 500 mg (1.40 mmol) of the compound from example 15A in 6 ml of DMF were added, at RT, 250 mg (1.54 mmol) of N,N'-carbonyldiimidazole, and the mixture was stirred at bath temperature 60° C. for 5 h. Subsequently added to the mixture were 100 ml each of water and ethyl acetate. After phase separation, the aqueous phase was extracted once with ethyl acetate. The combined organic phases were washed once with saturated sodium chloride solution, dried over sodium sulfate, filtered and concentrated. The residue was taken up in dichloromethane and purified by means of column chromatography (50 g of silica gel, eluent: cyclohexane/ethyl acetate 7:3, Biotage). 259 mg (45% of theory, 100% purity) of the title compound were obtained.

$^1$H-NMR (400 MHz, DMSO-$d_6$): δ [ppm]=8.5-7.5 (br. m, 2H), 8.08 (d, 1H), 7.97 (dd, 1H), 7.77 (br. s, 1H), 7.69-7.60 (m, 2H), 7.59-7.47 (m, 3H), 7.22 (br. s, 1H), 2.82-2.69 (m, 1H), 2.53-2.44 (m, 1H, partially hidden), 0.81 (t, 3H).

LC/MS (Method 1, ESIpos): $R_t$=1.16 min, m/z=406/408 [M+H]$^+$.

Example 17A

6-Bromo-2-phenyl-3-propylquinoline-4-carboxylic Acid

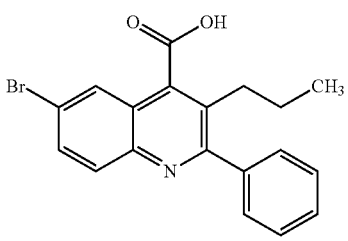 [SMILES: CCCc1c(-c2ccccc2)nc2ccc(Br)cc2c1C(=O)O]

300 mg (1.33 mmol) of 5-bromo-1H-indole-2,3-dione were initially charged in 3.6 ml of acetic acid, and 237 mg (1.46 mmol) of 1-phenylpentan-1-one were added. The reaction mixture was stirred at 75° C. for 5 min. Subsequently, 1.2 ml of conc. hydrochloric acid were added, and stirring of the mixture was continued at 105° C. overnight. After cooling to RT, the reaction mixture was added to 200 ml of 1 M hydrochloric acid and the precipitated solids were filtered off with suction. The solids were washed with water and dried under reduced pressure. 246 mg (35% of theory, 70% purity) of the title compound were obtained.

LC/MS (Method 1, ESIpos): $R_t$=0.97 min, m/z=371 [M+H]$^+$.

Example 18A (6-Bromo-2-phenyl-3-propylquinolin-4-yl)(1H-imidazol-1-yl)methanone

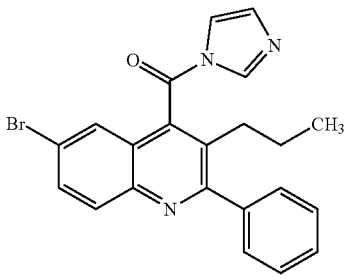 [SMILES: CCCc1c(-c2ccccc2)nc2ccc(Br)cc2c1C(=O)n1ccnc1]

To a solution of 500 mg (1.35 mmol) of the compound from example 17A in 6 ml of DMF were added, at RT, 241 mg (1.49 mmol) of N,N'-carbonyldiimidazole, and the mixture was stirred at bath temperature 60° C. for 5 h. Subsequently added to the mixture were 100 ml each of water and ethyl acetate. After phase separation, the aqueous phase was extracted once with ethyl acetate. The combined organic phases were washed once with saturated sodium chloride solution, dried over sodium sulfate, filtered and concentrated. The residue was taken up in dichloromethane and purified by means of column chromatography (50 g of silica gel, eluent: cyclohexane/ethyl acetate 7:3, Biotage). 355 mg (62% of theory, 100% purity) of the title compound were obtained.

$^1$H-NMR (400 MHz, DMSO-d$_6$): [ppm]=8.5-7.5 (br. m, 2H), 8.08 (d, 1H), 7.97 (dd, 1H), 7.77 (br. s, 1H), 7.68-7.62 (m, 2H), 7.58-7.48 (m, 3H), 7.22 (br. s, 1H), 2.81-2.70 (m, 1H), 2.47-2.36 (m, 1H), 1.30-1.08 (m, 2H), 0.55 (t, 3H).

LC/MS (Method 1, ESIpos): R$_t$=1.25 min, m/z=420/422 [M+H]$^+$.

Example 19A

6-Bromo-7-chloro-3-methyl-2-phenylquinoline-4-carboxylic acid

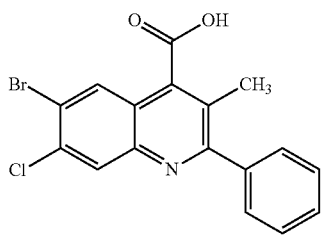

To a mixture of 521 mg (2.00 mmol) of 5-bromo-6-chloro-1H-indole-2,3-dione in 4.5 ml of acetic acid were added 268 mg (2.00 mmol) of propiophenone. After stirring at 75° C. for 5 min, 1.5 ml of conc. hydrochloric acid were added, and stirring of the mixture was continued at 110° C. for 6 h. After cooling down to RT and being left to stand overnight, the mixture was stirred at 110° C. for a further 6 h. Thereafter, the mixture was introduced into 100 ml of 1 N hydrochloric acid while stirring. After a few minutes, the solids formed were filtered off, washed twice with water and dried under reduced pressure. 612 mg (58% of theory, 71% purity) of the title compound were obtained.

$^1$H-NMR (400 MHz, DMSO-d$_6$): [ppm]=14.45 (br. s, 1H), 8.35 (s, 1H), 8.15 (s, 1H), 7.64-7.58 (m, 2H), 7.57-7.48 (m, 3H), 2.40 (s, 3H).

LC/MS (Method 1, ESIpos): R$_t$=1.08 min, m/z=376/378 [M+H]$^+$.

Example 20A (6-Bromo-7-chloro-3-methyl-2-phenylquinolin-4-yl)(1H-imidazol-1-yl)methanone

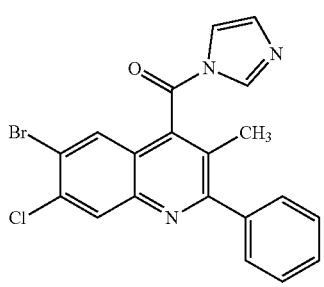

To a solution of 608 mg (1.15 mmol, 71% purity) of the compound from example 19A in 3 ml of DMF were added, at RT, 204 mg (1.26 mmol) of N,N'-carbonyldiimidazole, and the mixture was stirred at 60° C. for 8 h. Then 100 ml each of water and ethyl acetate were added to the mixture. After phase separation, the aqueous phase was extracted once with ethyl acetate. The combined organic phases were washed once with saturated sodium chloride solution, dried over sodium sulfate, filtered and concentrated. The residue was taken up in dichloromethane and purified by means of column chromatography (50 g of silica gel, eluent: cyclohexane/ethyl acetate 7:3, Biotage). 446 mg (86% of theory, 94% purity) of the title compound were obtained.

$^1$H-NMR (400 MHz, DMSO-d$_6$): [ppm]=8.5-7.7 (br. m, 2H), 8.44 (s, 1H), 8.09 (s, 1H), 7.72-7.65 (m, 2H), 7.60-7.50 (m, 3H), 7.21 (br. s, 1H), 2.24 (s, 3H).

LC/MS (Method 1, ESIpos): R$_t$=1.21 min, m/z=426/428 [M+H]$^+$.

Example 21A 6,7-Dichloro-3-methyl-2-phenylquinoline-4-carboxylic acid

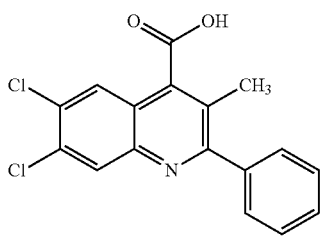 [SMILES: Cc1c(-c2ccccc2)nc2cc(Cl)c(Cl)cc2c1C(=O)O]

10.0 g (46.29 mmol) of a regioisomer mixture of 4,5-dichloro-1H-indole-2,3-dione and 5,6-dichloro-1H-indole-2,3-dione [about 1:1, preparation described in *J. Med. Chem.* 2004, 47 (4), 935-946] were initially charged in 136 ml of acetic acid, and 6.21 g (46.29 mmol) of 1-phenylpropan-1-one were added. The reaction mixture was stirred at 75° C. for 5 min. Then 42 ml of conc. hydrochloric acid were added, and stirring of the mixture was continued at 105° C. overnight. Subsequently, the reaction solution was introduced cautiously into water while stirring. The precipitate formed was filtered off and prepurified by means of column chromatography (silica gel, eluent: ethyl acetate/methanol 10:1). The product mixture thus obtained was dissolved in 120 ml of acetonitrile/methanol/water/trifluoroacetic acid mixture while heating and separated into the regioisomers by means of preparative HPLC [column: Kinetix C18, 5 µm, 100×21.2 mm; flow rate: 25 ml/min; detection: 210 nm; injection volume: 1.0 ml; temperature: 35° C.; eluent: 45% water/50% acetonitrile/5% formic acid (1% in water), isocratic; run time: 4.3 min]. 380 mg (2.2% of theory, 90% purity) of the title compound and 300 mg (1.9% of theory, 100% purity) of the regioisomeric compound from example 23A were obtained.

$^1$H-NMR (400 MHz, DMSO-d$_6$): [ppm]=14.54 (br. s, 1H), 8.37 (s, 1H), 8.00 (s, 1H), 7.68-7.58 (m, 2H), 7.58-7.47 (m, 3H), 2.40 (s, 3H).

LC/MS (Method 1, ESIpos): R$_t$=0.99 min, m/z=332 [M+H]$^+$.

Example 22A (6,7-Dichloro-3-methyl-2-phenylquinolin-4-yl)(1H-imidazol-1-yl)methanone

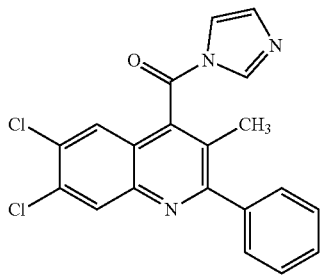 [SMILES: Cc1c(-c2ccccc2)nc2cc(Cl)c(Cl)cc2c1C(=O)n1ccnc1]

To a solution of 328 mg (0.99 mmol) of the compound from example 21A in 4.4 ml of DMF were added, at RT, 320 mg (1.98 mmol) of N,N'-carbonyldiimidazole, and the mixture was stirred at 60° C. overnight. Then water and ethyl acetate were added to the mixture. After phase separation, the aqueous phase was extracted three times with ethyl acetate. The combined organic phases were washed once with saturated sodium chloride solution, dried over sodium sulfate, filtered and concentrated. The residue was purified by means of column chromatography (80 g of silica gel, eluent: cyclohexane/ethyl acetate 2:1, Biotage). In this way, 295 mg (70% of theory, 90% purity) of the title compound were obtained.

$^1$H-NMR (400 MHz, DMSO-$d_6$): δ [ppm]=9.25-6.25 (br. m, 2H), 8.46 (s, 1H), 7.97 (s, 1H), 7.75-7.63 (m, 2H), 7.63-7.38 (m, 3H), 7.21 (br. s, 1H), 2.24 (s, 3H).

LC/MS (Method 1, ESIpos): $R_t$=1.19 min, m/z=382 [M+H]$^+$.

Example 23A 5,6-Dichloro-3-methyl-2-phenylquinoline-4-carboxylic Acid

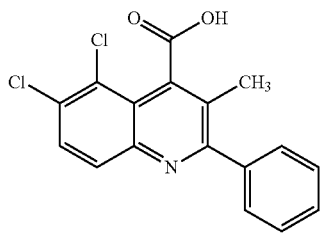 [SMILES: Cc1c(-c2ccccc2)nc2ccc(Cl)c(Cl)c2c1C(=O)O]

As described under example 21A, 10.0 g (46.29 mmol) of a regioisomer mixture of 4,5-dichloro-1H-indole-2,3-dione and 5,6-dichloro-1H-indole-2,3-dione (about 1:1) were used to obtain 300 mg (1.9% of theory, 100% purity) of the title compound.

$^1$H-NMR (400 MHz, DMSO-$d_6$): [ppm]=7.92 (d, 1H), 7.82 (d, 1H), 7.58-7.43 (m, 5H), 2.29 (s, 3H).

LC/MS (Method 1, ESIpos): $R_t$=0.95 min, m/z=332 [M+H]$^+$.

Example 24A (5,6-Dichloro-3-methyl-2-phenylquinolin-4-yl)(1H-imidazol-1-yl)methanone

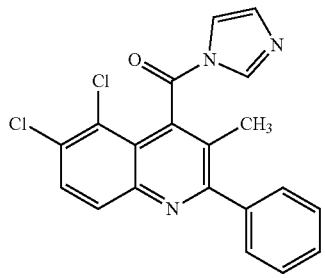 [SMILES: Cc1c(-c2ccccc2)nc2ccc(Cl)c(Cl)c2c1C(=O)n1ccnc1]

To a solution of 274 mg (0.83 mmol) of the compound from example 23A in 3.7 ml of DMF were added, at RT, 268 mg (1.65 mmol) of N,N'-carbonyldiimidazole, and the mixture was stirred at 60° C. overnight. Then the mixture was stirred in a microwave apparatus at 150° C. for 3 h. After a further 268 mg (1.65 mmol) of N,N'-carbonyldiimidazole had been added, the mixture was stirred in the microwave at 150° C. for another 1 h. After cooling down to RT, water and ethyl acetate were added to the mixture, the phases were separated and then the aqueous phase was extracted three times with ethyl acetate. The combined organic phases were washed once with saturated sodium chloride solution, dried over sodium sulfate, filtered and concentrated. The residue was purified by means of column chromatography (80 g of silica gel, eluent: cyclohexane/ethyl acetate 2:1→ethyl acetate/methanol 10:1, Biotage). 108 mg (32% of theory, 94% purity) of the title compound were obtained.

$^1$H-NMR (400 MHz, DMSO-$d_6$): [ppm]=9.0-7.0 (br. m, 2H), 8.19 (d, 1H), 8.07 (d, 1H), 7.72-7.65 (m, 2H), 7.59-7.50 (m, 3H), 7.28 (br. s, 1H), 2.25 (s, 3H).

LC/MS (Method 1, ESIpos): $R_t$=1.17 min, m/z=382 [M+H]$^+$.

Example 25A

6-Bromo-2-(4-fluorophenyl)-3-methylquinoline-4-carboxylic acid

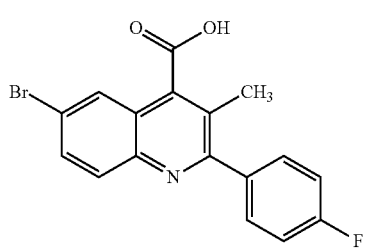 [SMILES: Cc1c(-c2ccc(F)cc2)nc2ccc(Br)cc2c1C(=O)O]

1.00 g (4.42 mmol) of 5-bromo-1H-indole-2,3-dione were initially charged in 12.0 ml of acetic acid, and 673 mg (4.42 mmol) of 1-(4-fluorophenyl)propan-1-one were added. The reaction mixture was stirred at 75° C. for 5 min. Subsequently, 4.0 ml of conc. hydrochloric acid were added, and stirring of the mixture was continued at 105° C. overnight. After cooling to RT, the reaction mixture was added to 200 ml of 1 M hydrochloric acid and the precipitated solids were filtered off. The solids were washed with water and dried under reduced pressure. 1.29 g (73% of theory, 90% purity) of the title compound were obtained.

LC/MS (Method 1, ESIpos): $R_t$=0.88 min, m/z=360 [M+H]$^+$.

Example 26A

[6-Bromo-2-(4-fluorophenyl)-3-methylquinolin-4-yl](1H-imidazol-1-yl)methanone

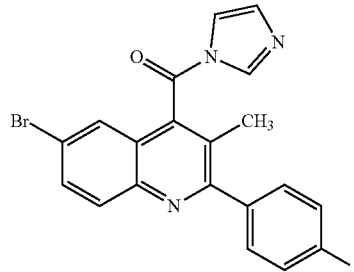

To a solution of 500 mg (1.39 mmol) of the compound from example 25A in 6 ml of DMF were added, at RT, 248 mg (1.53 mmol) of N,N'-carbonyldiimidazole, and the mixture was stirred first at bath temperature 60° C. for 5 h and then at RT for 14 h. Subsequently, a further 124 mg (0.76 mmol) of N,N'-carbonyldiimidazole were added, and the mixture was stirred at bath temperature 60° C. for another 7 h. Thereafter, 100 ml each of water and ethyl acetate were added to the mixture, the phases were separated and then the aqueous phase was extracted once with ethyl acetate. The combined organic phases were washed once with saturated sodium chloride solution, dried over sodium sulfate, filtered and concentrated. The residue was taken up in dichloromethane and purified by means of column chromatography (50 g of silica gel, eluent: cyclohexane/ethyl acetate 7:3, Biotage). 402 mg (71% of theory, 100% purity) of the title compound were obtained.

$^1$H-NMR (400 MHz, DMSO-$d_6$): [ppm]=8.5-7.5 (br. m, 2H), 8.09 (d, 1H), 7.97 (dd, 1H), 7.82 (br. s, 1H), 7.79-7.72 (m, 2H), 7.37 (t, 2H), 7.21 (br. s, 1H), 2.25 (s, 3H).

LC/MS (Method 1, ESIpos): $R_t$=1.13 min, m/z=410/412 [M+H]$^+$.

Example 27A

6-Bromo-2-(3-fluorophenyl)-3-methylquinoline-4-carboxylic Acid

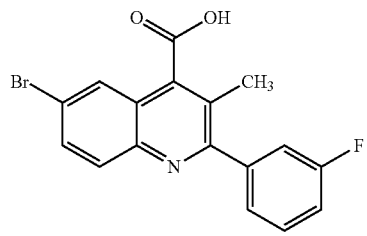 [SMILES: Cc1c(-c2cccc(F)c2)nc2ccc(Br)cc2c1C(=O)O]

1.00 g (4.42 mmol) of 5-bromo-1H-indole-2,3-dione were initially charged in 12.0 ml of acetic acid, and 673 mg (4.42 mmol) of 1-(3-fluorophenyl)propan-1-one were added. The reaction mixture was stirred at 75° C. for 5 min. Subsequently, 4.0 ml of conc. hydrochloric acid were added, and stirring of the mixture was continued at 105° C. overnight. After cooling to RT, the reaction mixture was added to 200 ml of 1 M hydrochloric acid and the precipitated solids were filtered off. The solids were washed with water and dried under reduced pressure. 1.20 g (63% of theory, 83% purity) of the title compound were obtained.

LC/MS (Method 1, ESIpos): $R_t$=0.94 min, m/z=360 [M+H]$^+$.

Example 28A

[6-Bromo-2-(3-fluorophenyl)-3-methylquinolin-4-yl](1H-imidazol-1-yl)methanone

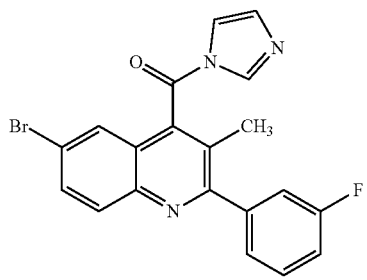 [SMILES: Cc1c(-c2cccc(F)c2)nc2ccc(Br)cc2c1C(=O)n1ccnc1]

To a solution of 500 mg (1.39 mmol) of the compound from example 27A in 6 ml of DMF were added, at RT, 248 mg (1.53 mmol) of N,N'-carbonyldiimidazole, and the mixture was stirred at bath temperature 60° C. for 7 h. Subsequently, 100 ml each of water and ethyl acetate were added to the mixture, the phases were separated and then the aqueous phase was extracted once with ethyl acetate. The combined organic phases were washed once with saturated sodium chloride solution, dried over sodium sulfate, filtered and concentrated. The residue was taken up in dichloromethane and purified by means of column chromatography (50 g of silica gel, eluent: cyclohexane/ethyl acetate 7:3, Biotage). 344 mg (60% of theory, 100% purity) of the title compound were obtained.

$^1$H-NMR (400 MHz, DMSO-$d_6$): [ppm]=8.5-8.0 (br. m, 1H), 8.10 (d, 1H), 8.0-7.5 (br. m, 1H), 7.98 (dd, 1H), 7.84 (br. s, 1H), 7.64-7.49 (m, 3H), 7.41-7.32 (m, 1H), 7.22 (br. s, 1H), 2.27-2.22 (m, 3H).

LC/MS (Method 1, ESIpos): $R_t$=1.16 min, m/z=410/412 [M+H]$^+$.

Example 29A

6-Bromo-2-(2-fluorophenyl)-3-methylquinoline-4-carboxylic Acid

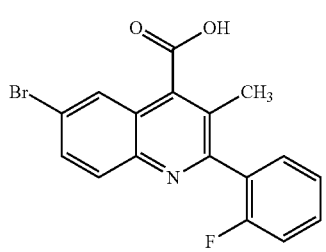 [SMILES: Cc1c(-c2ccccc2F)nc2ccc(Br)cc2c1C(=O)O]

1.00 g (4.42 mmol) of 5-bromo-1H-indole-2,3-dione were initially charged in 12.0 ml of acetic acid, and 673 mg (4.42 mmol) of 1-(2-fluorophenyl)propan-1-one were added. The reaction mixture was stirred at 75° C. for 5 min. Subsequently, 4.0 ml of conc. hydrochloric acid were added, and stirring of the mixture was continued at 105° C. overnight. After cooling to RT, the reaction mixture was added to 200 ml of 1 M hydrochloric acid and the precipitated solids were filtered off. The solids were washed with water, dried under reduced pressure and then stirred with dichloromethane. The solvent was removed by suction and the residue was dried under reduced pressure. 649 mg (37% of theory, 90% purity) of the title compound were obtained.

LC/MS (Method 1, ESIpos): $R_t$=0.90 min, m/z=360 [M+H]$^+$.

Example 30A

[6-Bromo-2-(2-fluorophenyl)-3-methylquinolin-4-yl] (1H-imidazol-1-yl)methanone

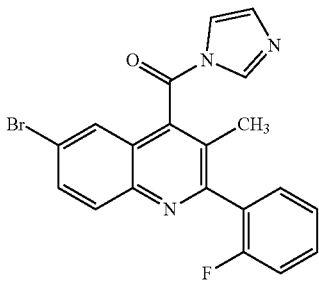 [SMILES: Cc1c(-c2ccccc2F)nc2ccc(Br)cc2c1C(=O)n1ccnc1]

To a solution of 500 mg (1.39 mmol) of the compound from example 29A in 6 ml of DMF were added, at RT, 248 mg (1.53 mmol) of N,N'-carbonyldiimidazole. The mixture was stirred at bath temperature 60° C. for 5 h and then left to stand at RT for 14 h. Thereafter, a further 124 mg (0.77 mmol) of N,N'-carbonyldiimidazole were added, and the mixture was stirred at bath temperature 80° C. for 8 h and then left to stand at RT for 14 h. Thereafter, another 162 mg (1.00 mmol) of N,N'-carbonyldiimidazole were added, and the mixture was stirred at bath temperature 100° C. for a further 7 h and then left to stand at RT for 14 h. Thereafter, yet another 162 mg (1.00 mmol) of N,N'-carbonyldiimidazole were added, and the mixture was stirred at bath temperature 145° C. for a further 7 h and then left to stand at RT for 14 h. Thereafter, still another 162 mg (1.00 mmol) of N,N'-carbonyldiimidazole were added, and the mixture was stirred at bath temperature 145° C. for a further 7 h and then left to stand at RT for 14 h. Thereafter, once again another 162 mg (1.00 mmol) of N,N'-carbonyldiimidazole were added, and the mixture was stirred at bath temperature 145° C. for a further 7 h and then left to stand at RT for 14 h. Thereafter, finally, 25 ml each of ethyl acetate and saturated aqueous sodium chloride solution were added to the mixture, the phases were separated and then the aqueous phase was extracted twice with 50 ml each time of ethyl acetate. The combined organic phases were dried over magnesium sulfate, filtered and concentrated. The residue was taken up in dichloromethane and purified by means of column chromatography (100 g of silica gel, eluent: cyclohexane/ethyl acetate 7:3, Biotage). 405 mg (71% of theory, 100% purity) of the title compound were obtained.

$^1$H-NMR (400 MHz, DMSO-d$_6$): [ppm]=8.5-7.5 (br. m, 2H), 8.11 (d, 1H), 8.00 (dd, 1H), 7.87 (br. s, 1H), 7.67-7.56 (m, 2H), 7.45-7.36 (m, 2H), 7.21 (br. s, 1H), 2.14 (s, 3H).

LC/MS (Method 1, ESIpos): $R_t$=1.10 min, m/z=410/412 [M+H]$^+$.

Example 31A

6-Bromo-3-methyl-2-(pyridin-4-yl)quinoline-4-carboxylic Acid

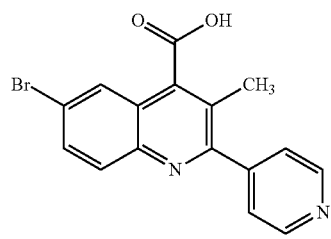 [SMILES: Cc1c(-c2ccncc2)nc2ccc(Br)cc2c1C(=O)O]

Method A:

1.00 g (4.42 mmol) of 5-bromo-1H-indole-2,3-dione were initially charged in 12.0 ml of acetic acid, and 598 mg (4.42 mmol) of 1-(pyridin-4-yl)propan-1-one were added. The reaction mixture was stirred at 75° C. for 5 min. Subsequently, 4.0 ml of conc. hydrochloric acid were added, and stirring of the mixture was continued at 105° C. for 16 h. After cooling to RT, the reaction mixture was added to 200 ml of water and the precipitated solids were filtered off. The filtrate was concentrated under reduced pressure and the residue was purified by means of preparative HPLC (method 17). 200 mg (13% of theory, 100% purity) of the title compound were obtained.

$^1$H-NMR (400 MHz, DMSO-d$_6$): [ppm]=14.56 (br. s, 1H), 8.79-8.70 (m, 2H), 8.08-8.01 (m, 1H), 7.98-7.92 (m, 2H), 7.66 (d, 2H), 2.40 (s, 3H).

LC/MS (Method 1, ESIpos): $R_t$=0.45 min, m/z=343/345 [M+H]$^+$.

Method B (General Experimental Procedure):

To a solution of the appropriate isatin (1H-indole-2,3-dione) in ethanol (concentration between 0.5 and 0.75 M) were added dropwise six equivalents of an 8.5 M aqueous potassium hydroxide solution. Subsequently, one equivalent of 1-(pyridin-4-yl)propan-1-one was added, and the mixture was stirred under reflux overnight. After cooling to RT and removing the solvent under reduced pressure, the residue was taken up in water and the aqueous phase was extracted with ethyl acetate. Subsequently, the aqueous phase was adjusted to pH 4-5 by adding hydrochloric acid. The solids formed were filtered off, washed with a little water and ethyl acetate, and dried under reduced pressure. The target compound in question was obtained in a yield of 35-70% of theory.

Example 32A

Ethyl 6-amino-2-chloro-5-fluoronicotinate

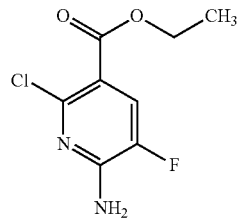

A mixture of 5.00 g (21.00 mmol) of ethyl 2,6-dichloro-5-fluoronicotinate [described in US 2008/0171732, Example 44 (b)] and 105 ml (210 mmol) of a 2 M solution of ammonia in ethanol was divided between 5 microwave vessels and heated in a microwave apparatus to 120° C. for 1.5 h. After cooling to RT, the solvent was removed, and ethyl acetate was added to the residue. The mixture was washed once with water, and the aqueous phase was then extracted once with ethyl acetate. The combined organic phases were washed once with saturated sodium chloride solution, dried over magnesium sulfate, filtered and concentrated. The crude product thus obtained was combined with the crude product from an experiment conducted analogously [amount of ethyl 2,6-dichloro-5-fluoronicotinate used: 1.00 g (4.20 mmol)]. This material was then purified by means of preparative HPLC [column: Daicel C18 Bio Spring Column, 10 µm, 300×100 mm; flow rate: 250 ml/min; detection: 210 nm; injection volume: 20 ml; temperature: 22° C.; eluent: acetonitrile/water gradient]. 2.60 g of the title compound were obtained (100% purity, 47% of theory based on a total of 6.0 g of ethyl 2,6-dichloro-5-fluoronicotinate). Also obtained were 290 mg of the isomeric compound ethyl 2-amino-6-chloro-5-fluoronicotinate (100% purity, 5% of theory based on a total of 6.0 g of ethyl 2,6-dichloro-5-fluoronicotinate).

$^1$H-NMR (500 MHz, DMSO-$d_6$): [ppm]=7.80 (d, 1H), 7.49 (br. s, 2H), 4.23 (q, 2H), 1.28 (t, 3H).

LC/MS (Method 1, ESIpos): $R_t$=0.82 min, m/z=219 [M+H]$^+$.

Example 33A

Ethyl 6-amino-5-fluoronicotinate trifluoroacetic Acid Salt

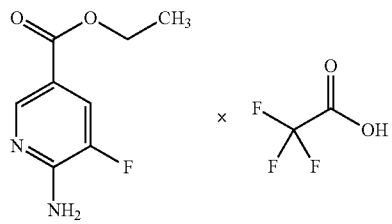

A mixture, made up under argon, of 500 mg (2.29 mmol) of the compound from example 32A, 100 mg (94 mmol) of palladium on activated carbon (10% Pd) and 324 mg (3.20 mmol) of triethylamine in 20 ml of ethanol was hydrogenated under standard pressure at RT for 6 h. Subsequently, a further 100 mg (94 mmol) of palladium on activated carbon (10% Pd) and 324 mg (3.20 mmol) of triethylamine were added, and hydrogenation was effected under standard pressure at RT for a further 16 h. Thereafter, another 100 mg (94 mmol) of palladium on activated carbon (10% Pd) and 324 mg (3.20 mmol) of triethylamine were added, and hydrogenation was effected under standard pressure at RT for another 6 h. Thereafter, the mixture was filtered through kieselguhr, and the filter residue was washed with ethanol and ethyl acetate. The filtrate was concentrated and the residue was stirred with water. The solids present were filtered off, washed with water and dried under reduced pressure. The crude product obtained was purified by means of preparative HPLC (method 16). The combined product fractions were concentrated, and the residue was taken up in dichloromethane, concentrated again and finally dried under reduced pressure. 555 mg (81% of theory, 100% purity) of the title compound were obtained.

$^1$H-NMR (400 MHz, DMSO-$d_6$): [ppm]=8.37-8.35 (m, 1H), 7.69 (dd, 1H), 7.4-5.5 (br. m, 2H), 4.25 (q, 2H), 1.29 (t, 3H).

LC/MS (Method 2, ESIpos): $R_t$=1.83 min, m/z=185 [M+H]$^+$.

Example 34A

Ethyl 4-{[(6-bromo-3-methyl-2-phenylquinolin-4-yl)carbonyl]amino}benzoate

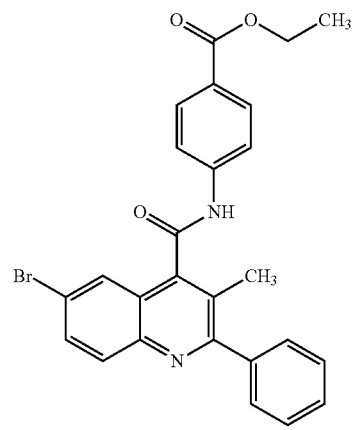 [SMILES: CCOC(=O)c1ccc(NC(=O)c2c(C)c(-c3ccccc3)nc3ccc(Br)cc23)cc1]

To 300 mg (0.88 mmol) of the compound from example 1A were added 16 ml of dichloromethane and then 0.19 ml (1.40 mmol) of 1-chloro-N,N,2-trimethylprop-1-en-1-amine. The mixture was stirred at RT for 30 min, and then 0.21 ml (2.63 mmol) of pyridine and 145 mg (0.88 mmol) of ethyl 4-aminobenzoate, dissolved in 4 ml of dichloromethane, were added. The reaction mixture was then stirred at 50° C. for 30 min and then at 70° C. for 90 min. After cooling down to RT, the solvent was removed under reduced pressure, and the residue was purified by means of preparative HPLC (method 7) without further workup. 177 mg (41% of theory, 100% purity) of the title compound were obtained.

LC/MS (Method 1, ESIpos): $R_t$=1.31 min, m/z=489/491 [M+H]+.

Example 35A

4-{[(6-Bromo-3-methyl-2-phenylquinolin-4-yl)carbonyl]amino}benzoyl Chloride

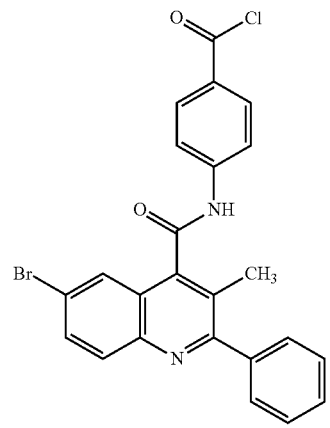

To a suspension of 200 mg (0.43 mmol) of the compound from Example 1 in 5 ml of dichloromethane were successively added one drop of DMF and, gradually, 110 mg (0.87 mmol) of oxalyl chloride. After stirring at RT for 1 h, a further 59 mg (0.46 mmol) of oxalyl chloride were added, and the mixture was stirred at RT for another 30 min. Subsequently, the mixture was concentrated and the residue was dried under reduced pressure. The title compound was obtained in a purity of 98% by LC/MS (the analytical sample was quenched with methanol).

LC/MS (Method 3, ESIpos): $R_t$=1.52 min, m/z=475/477 [M−Cl+OCH$_3$+H]$^+$.

Example 36A

Methyl 5-{[(6-bromo-3-methyl-2-phenylquinolin-4-yl)carbonyl]amino}pyrimidine-2-carboxylate

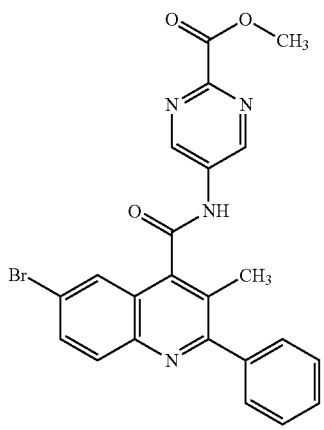 [SMILES: COC(=O)c1ncc(NC(=O)c2c(C)c(-c3ccccc3)nc3ccc(Br)cc23)cn1]

150 mg (0.38 mmol) of the compound from example 2A and 59 mg (0.38 mmol) of methyl 5-aminopyrimidine-2-carboxylate were dissolved in 3 ml of DMF. The mixture was stirred at RT for 15 min. Subsequently, 64 mg (0.57 mmol) of potassium tert-butoxide were added, and stirring of the reaction mixture was continued at RT overnight. Thereafter, the mixture, without further workup, was purified by means of preparative HPLC (method 6). After the solvent-water mixture had been removed, the mixture was dried under reduced pressure overnight. 23 mg (12% of theory, 95% purity) of the title compound were obtained.

$^1$H-NMR (400 MHz, DMSO-d$_6$): [ppm]=11.63 (s, 1H), 9.32 (s, 2H), 8.11 (d, 1H), 8.05 (d, 1H), 7.95 (dd, 1H), 7.70-7.59 (m, 2H), 7.59-7.49 (m, 3H), 3.92 (s, 3H), 2.42 (s, 3H).

LC/MS (Method 1, ESIpos): $R_t$=1.05 min, m/z=477/479 [M+H]$^+$.

Example 37A

Ethyl 6-{[(6-bromo-3-methyl-2-phenylquinolin-4-yl)carbonyl]amino}-5-fluoronicotinate

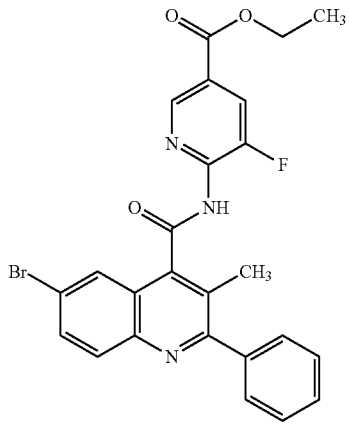 [SMILES: CCOC(=O)c1cnc(NC(=O)c2c(C)c(-c3ccccc3)nc3ccc(Br)cc23)c(F)c1]

To a solution of 200 mg (0.51 mmol) of the compound from example 2A and 152 mg (0.51 mmol) of the compound from example 33A in 2 ml of DMF were added, in small portions at RT, 114 mg (1.02 mmol) of potassium tert-butoxide. The mixture was stirred at RT for 15 min. Subsequently, a further 29 mg (0.26 mmol) of potassium tert-butoxide were added in small portions, and the mixture was stirred at RT for another 15 min. Thereafter, the mixture, without further workup, was purified by means of preparative HPLC (method 5). 195 mg (74% of theory, 99% purity) of the title compound were obtained.

$^1$H-NMR (400 MHz, DMSO-d$_6$): δ [ppm]=11.66 (s, 1H), 8.89 (br. s, 1H), 8.35 (d, 1H), 8.09-7.91 (m, 3H), 7.67-7.49 (m, 5H), 4.39 (q, 2H), 2.47 (s, 3H), 1.36 (t, 3H).

LC/MS (Method 1, ESIpos): $R_t$=1.18 min, m/z=508/510 [M+H]$^+$.

Example 38A

Methyl 4-{[(6-bromo-3-methyl-2-phenylquinolin-4-yl)carbonyl]amino}-3-fluorobenzoate

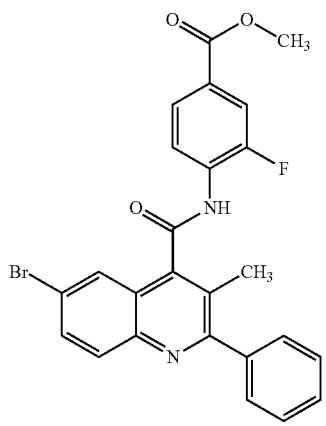 [SMILES: COC(=O)c1ccc(NC(=O)c2c(C)c(-c3ccccc3)nc3ccc(Br)cc23)c(F)c1]

1.00 g (2.55 mmol) of the compound from example 2A were dissolved in 10 ml of DMF. To the solution were added 474 mg (2.80 mmol) of methyl 4-amino-3-fluorobenzoate and 429 mg (3.82 mmol) of potassium tert-butoxide. The reaction mixture was stirred at RT for 1 h and then stirred into a mixture of 50 ml of ice-water, 50 ml of ammonium chloride solution and 100 ml of ethyl acetate. The organic phase was removed, washed twice with water and once with saturated sodium chloride solution, and dried over magnesium sulfate. The solvent was removed under reduced pressure and the residue was purified by means of column chromatography (silica gel, eluent: 5% ethyl acetate/95% cyclohexane→15% ethyl acetate/85% cyclohexane→45% ethyl acetate/55% cyclohexane, Biotage). The product-containing fractions were concentrated and the residue was stirred in 10 ml of tert-butyl methyl ether. The solids were filtered off, washed twice with 5 ml of tert-butyl methyl ether and then stirred in 4 ml of ethyl acetate for three days. The solids were then filtered off again and dried under reduced pressure. 810 mg (64% of theory, 99% purity) of the title compound were obtained.

$^1$H-NMR (400 MHz, DMSO-d$_6$): δ [ppm]=11.10 (s, 1H), 8.27 (t, 1H), 8.05 (d, 1H), 7.99 (d, 1H), 7.95-7.90 (m, 2H), 7.85 (dd, 1H), 7.64-7.62 (m, 2H), 7.58-7.51 (m, 3H), 3.89 (s, 3H), 2.43 (s, 3H).

LC/MS (Method 1, ESIpos): $R_t$=1.27 min, m/z=493/495 [M+H]$^+$.

Example 39A tert-Butyl 4-{[(6-bromo-3-methyl-2-phenylquinolin-4-yl)carbonyl]amino}-3-fluorobenzoate

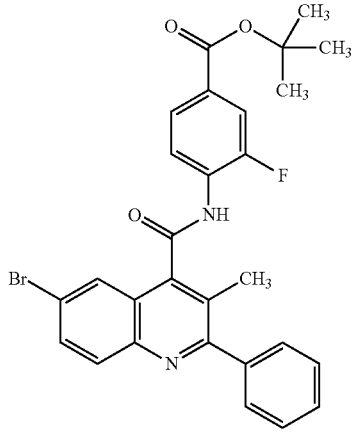 [SMILES: Cc1c(-c2ccccc2)nc2ccc(Br)cc2c1C(=O)Nc1ccc(C(=O)OC(C)(C)C)cc1F]

To a mixture of 1.00 g (2.09 mmol) of the compound from Example 7 in 50 ml of THF were added 912 mg (4.17 mmol) of tert-butyl trichloroacetimidate and 59 mg (0.42 mmol) of boron trifluoride-diethyl ether complex, and the mixture was stirred at RT for another 1 h. Subsequently, a further 912 mg (4.17 mmol) of tert-butyl trichloroacetimidate were added and the mixture was stirred under reflux for another 1 h. After dichloromethane had been added, the mixture was washed with water and the aqueous phase was extracted once with dichloromethane. The combined organic phases were washed once with saturated sodium chloride solution, dried over magnesium sulfate, filtered and concentrated. The residue was purified by means of column chromatography (silica gel, eluent: cyclohexane/ethyl acetate 85:15, Biotage). 939 mg (84% of theory, 100% purity) of the title compound were obtained.

$^1$H-NMR (400 MHz, DMSO-$d_6$): [ppm]=11.06 (s, 1H), 8.22 (t, 1H), 8.05 (d, 1H), 7.98 (d, 1H), 7.94 (dd, 1H), 7.85 (dd, 1H), 7.78 (dd, 1H), 7.66-7.61 (m, 2H), 7.60-7.49 (m, 3H), 2.43 (s, 3H), 1.57 (s, 9H).

LC/MS (Method 1, ESIpos): $R_t$=1.41 min, m/z=535/537 [M+H]$^+$.

Example 40A

4-{[(6-Bromo-3-methyl-2-phenylquinolin-4-yl)carbonyl]amino}-3-fluorobenzoyl chloride

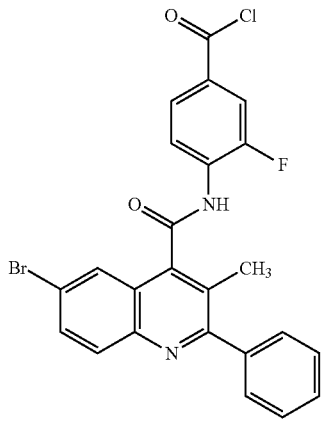 [SMILES: Cc1c(-c2ccccc2)nc2ccc(Br)cc2c1C(=O)Nc1ccc(C(=O)Cl)cc1F]

To a suspension of 250 mg (0.52 mmol) of the compound from Example 7 in 2.5 ml of dichloromethane were successively added one drop of DMF and, gradually, 110 mg (0.87 mmol) of oxalyl chloride. After diluting with a further 2.5 ml of dichloromethane and stirring at RT for 1 h, the mixture was concentrated and the residue was dried under reduced pressure. The title compound was obtained in a purity of 94% by LC/MS (the analytical sample was quenched with methanol).

LC/MS (Method 3, ESIpos): $R_t$=1.55 min, m/z=493/495 [M–Cl+OCH$_3$+H]$^+$.

Example 41A

Methyl 4-{[(6-bromo-3-methyl-2-phenylquinolin-4-yl)carbonyl]amino}-2-fluorobenzoate

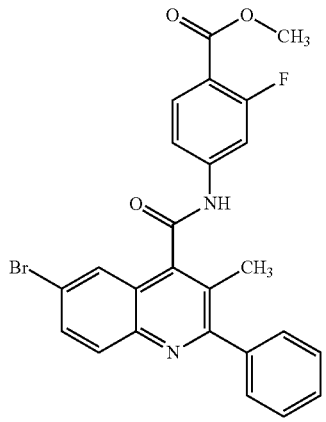 [SMILES: COC(=O)c1ccc(NC(=O)c2c(C)c(-c3ccccc3)nc3ccc(Br)cc23)cc1F]

To 300 mg (0.88 mmol) of the compound from example 1A were added 3 ml of dichloromethane and then 0.19 ml (1.40 mmol) of 1-chloro-N,N,2-trimethylprop-1-en-1-amine. The mixture was stirred at RT for 30 min, and then 0.21 ml (2.63 mmol) of pyridine and 148 mg (0.88 mmol) of methyl 4-amino-2-fluorobenzoate were added. The reaction mixture was subsequently stirred at 70° C. for 3 h. After cooling down to RT, the solvent was removed under reduced pressure, and the residue was purified by means of preparative HPLC (method 7) without further workup. 124 mg (23% of theory, 81% purity) of the title compound were obtained.

LC/MS (Method 1, ESIpos): $R_t$=1.27 min, m/z=493/495 [M+H]$^+$.

Example 42A

Methyl 4-{[(6-bromo-3-methyl-2-phenylquinolin-4-yl)carbonyl]amino}-3-chlorobenzoate

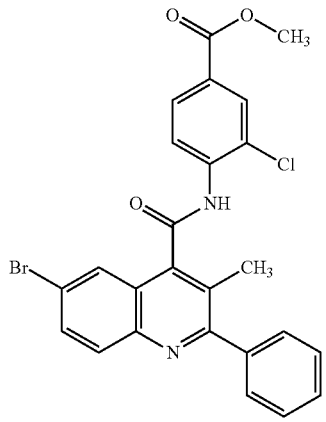

To a solution of 1.50 g (3.82 mmol) of the compound from example 2A and 710 mg (3.82 mmol) of methyl 4-amino- 3-chlorobenzoate in 15 ml of DMF were added, in small portions at RT, 430 mg (3.82 mmol) of potassium tert-butoxide. The mixture was stirred at RT for 15 min. Subsequently, another 215 mg (1.91 mmol) of potassium tert-butoxide were added in small portions, and the mixture was stirred at RT for a further 2 h. Thereafter, the mixture was introduced into 40 ml of a 10% aqueous citric acid solution while stirring, whereupon there was precipitation of solids. After diluting with water, the solids were filtered off, washed with water and dried under reduced pressure. The crude product thus obtained was purified by means of column chromatography (100 g of silica gel, eluent: cyclohexane/ethyl acetate 85:15, Biotage). 1.60 g (80% of theory, 98% purity) of the title compound were obtained.

$^1$H-NMR (400 MHz, DMSO-$d_6$): [ppm]=10.96 (s, 1H), 8.14-8.08 (m, 3H), 8.07-8.02 (m, 2H), 7.94 (dd, 1H), 7.66-7.61 (m, 2H), 7.60-7.50 (m, 3H), 3.90 (s, 3H), 2.48 (s, 3H).

LC/MS (Method 1, ESIpos): $R_t$=1.32 min, m/z=509/511 [M+H]$^+$.

Example 43A

Methyl 3-bromo-4-{[(6-bromo-3-methyl-2-phenylquinolin-4-yl)carbonyl]amino}benzoate

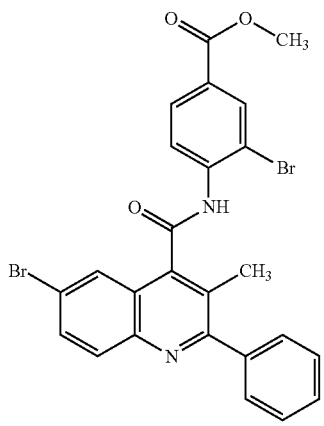

To a solution of 200 mg (0.51 mmol) of the compound from example 2A and 129 mg (0.56 mmol) of methyl 4-amino-3-bromobenzoate in 2 ml of DMF were added, in small portions at RT, 57 mg (0.51 mmol) of potassium tert-butoxide. The mixture was stirred at RT for 15 min. Subsequently, another 29 mg (0.26 mmol) of potassium tert-butoxide were added in small portions, and the mixture was stirred at RT for a further 15 min. Thereafter, the mixture was admixed with 4 ml of a 10% aqueous citric acid solution, diluted with water and extracted twice with ethyl acetate. The combined organic phases were washed once with saturated sodium chloride solution, dried over magnesium sulfate, filtered and concentrated. The residue was prepurified by means of column chromatography (25 g of silica gel, eluent: cyclohexane/ethyl acetate 85:15, Biotage) and then purified further by means of preparative HPLC (method 5). 145 mg (51% of theory, 100% purity) of the title compound were obtained.

$^1$H-NMR (400 MHz, DMSO-$d_6$): [ppm]=10.91 (s, 1H), 8.25 (d, 1H), 8.14 (d, 1H), 8.10-8.07 (m, 1H), 8.07-8.02 (m, 2H), 7.94 (dd, 1H), 7.66-7.61 (m, 2H), 7.60-7.50 (m, 3H), 3.90 (s, 3H), 2.50 (s, 3H).

LC/MS (Method 1, ESIpos): $R_t$=1.33 min, m/z=553/555/557 [M+H]$^+$.

Example 44A

Ethyl 4-{[(6-bromo-3-methyl-2-phenylquinolin-4-yl)carbonyl]amino}-3,5-dichlorobenzoate

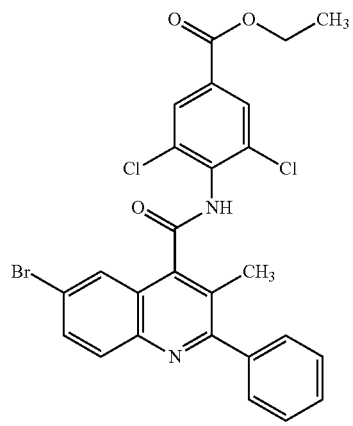 [SMILES: CCOC(=O)c1cc(Cl)c(NC(=O)c2c(C)c(-c3ccccc3)nc3ccc(Br)cc23)c(Cl)c1]

To a solution of 200 mg (0.51 mmol) of the compound from example 2A and 119 mg (0.51 mmol) of ethyl 4-amino-3,5-dichlorobenzoate in 2 ml of DMF were added, in small portions at RT, 57 mg (0.51 mmol) of potassium tert-butoxide. The mixture was stirred at RT for 15 min. Subsequently, another 29 mg (0.26 mmol) of potassium tert-butoxide were added in small portions, and the mixture was stirred at RT for a further 15 min. Thereafter, the mixture was purified directly by means of preparative HPLC (method 5). The combined product-containing fractions were neutralized with saturated sodium hydrogencarbonate solution and concentrated down to a residual volume of aqueous phase. The solids formed were filtered off, washed twice with water and dried under reduced pressure. 76 mg (24% of theory, 90% purity) of the title compound were obtained.

$^1$H-NMR (400 MHz, DMSO-$d_6$): δ [ppm]=11.26 (s, 1H), 8.43-8.37 (m, 1H), 8.13 (s, 1H), 8.09-8.02 (m, 1H), 7.99-7.92 (m, 1H), 7.73 (s, 1H), 7.68-7.48 (m, 5H), 4.38 (q, 2H), 2.58 (s, 3H, partially hidden), 1.36 (t, 3H).

LC/MS (Method 1, ESIpos): $R_t$=1.41 min, m/z=557/559/561 [M+H]$^+$.

Example 45A

Methyl 4-{[(6-bromo-3-methyl-2-phenylquinolin-4-yl)carbonyl]amino}-3-methylbenzoate

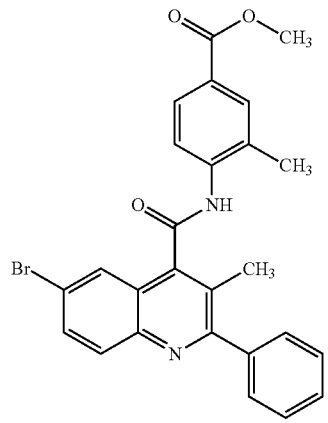 [SMILES: COC(=O)c1ccc(NC(=O)c2c(C)c(-c3ccccc3)nc3ccc(Br)cc23)c(C)c1]

To 300 mg (0.88 mmol) of the compound from example 1A were added 3 ml of dichloromethane and then 0.19 ml (1.40 mmol) of 1-chloro-N,N,2-trimethylprop-1-en-1-amine. The mixture was stirred at RT for 30 min, and then 0.21 ml (2.63 mmol) of pyridine and 145 mg (0.88 mmol) of methyl 4-amino-3-methylbenzoate were added. The reaction mixture was subsequently stirred at 70° C. for 3 h. After cooling down to RT, the solvent was removed under reduced pressure, and the residue was purified by means of preparative HPLC (method 7) without further workup. 128 mg (25% of theory, 84% purity) of the title compound were obtained.

LC/MS (Method 1, ESIpos): $R_t$=1.27 min, m/z=489/491 [M+H]$^+$.

Example 46A

Methyl 4-{[(6-bromo-3-methyl-2-phenylquinolin-4-yl)carbonyl]amino}-3-methoxybenzoate

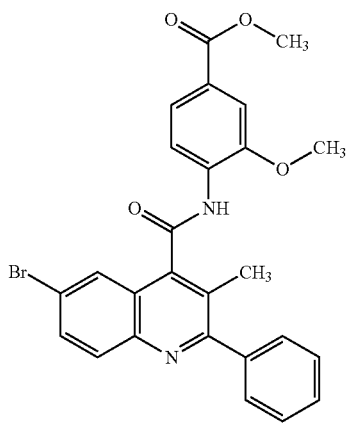 [SMILES: COC(=O)c1ccc(NC(=O)c2c(C)c(-c3ccccc3)nc3ccc(Br)cc23)c(OC)c1]

To a solution of 820 mg (2.09 mmol) of the compound from example 2A and 379 mg (2.09 mmol) of methyl 4-amino-3-methoxybenzoate in 8 ml of DMF were added, in small portions at RT, 235 mg (2.09 mmol) of potassium tert-butoxide. The mixture was stirred at RT for 15 min. Subsequently, another 117 mg (1.05 mmol) of potassium tert-butoxide were added in small portions, and the mixture was stirred at RT for a further 2 h. Thereafter, the mixture was introduced into 20 ml of a 10% aqueous citric acid solution while stirring, whereupon there was precipitation of solids. After diluting with water, the solids were filtered off, washed with water and dried under reduced pressure. The crude product thus obtained was purified by means of column chromatography (50 g of silica gel, eluent: cyclohexane/ethyl acetate 85:15, Biotage). 709 mg (67% of theory, 100% purity) of the title compound were obtained.

$^1$H-NMR (400 MHz, DMSO-d$_6$): [ppm]=10.53 (s, 1H), 8.17 (d, 1H), 8.06-8.00 (m, 2H), 7.92 (dd, 1H), 7.69 (dd, 1H), 7.65-7.60 (m, 3H), 7.59-7.47 (m, 3H), 3.94 (s, 3H), 3.89 (s, 3H), 2.42 (s, 3H).

LC/MS (Method 1, ESIpos): $R_t$=1.25 min, m/z=505/507 [M+H]+.

Example 47A

Ethyl 4-{[(6-bromo-3-methyl-2-phenylquinolin-4-yl)carbonyl]amino}-3-(trifluoromethoxy)benzoate

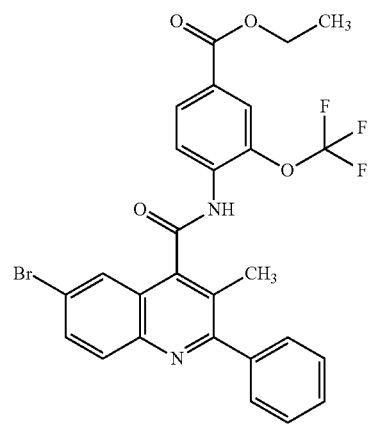 [SMILES: CCOC(=O)c1ccc(NC(=O)c2c(C)c(-c3ccccc3)nc3ccc(Br)cc23)c(OC(F)(F)F)c1]

150 mg (0.38 mmol) of the compound from example 2A and 95 mg (0.38 mmol) of ethyl 4-amino-3-(trifluoromethoxy)benzoate were dissolved in 3 ml of DMF. 86 mg (0.76 mmol) of potassium tert-butoxide were added, and the mixture was stirred at RT for 15 min. Thereafter, a further 22 mg (0.19 mmol) of potassium tert-butoxide were added gradually. Stirring of the reaction mixture continued at RT overnight, and then it was purified, without further workup, by means of preparative HPLC (method 6). After the solvent-water mixture had been removed, the residue was dried under reduced pressure overnight. 75 mg (34% of theory, 100% purity) of the title compound were obtained.

LC/MS (Method 1, ESIpos): $R_t$=1.38 min, m/z=573/575 [M+H]$^+$.

Example 48A

Methyl 4-{[(6-bromo-3-methyl-2-phenylquinolin-4-yl)carbonyl]amino}-3-(methylsulfanyl)benzoate

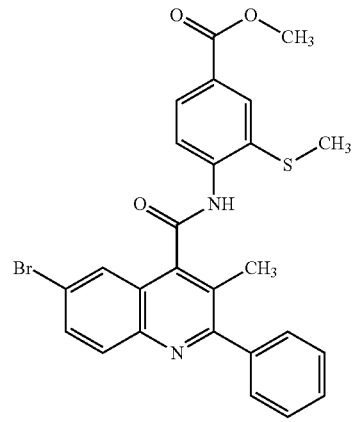 [SMILES: COC(=O)c1ccc(NC(=O)c2c(C)c(-c3ccccc3)nc3ccc(Br)cc23)c(SC)c1]

To a solution of 500 mg (1.28 mmol) of the compound from example 2A and 267 mg (1.28 mmol, 94% purity) of methyl 4-amino-3-(methylsulfanyl)benzoate [described in *Org. Prep. Proced. Int.* 2003, 35 (5), 520-524] in 5 ml of DMF were added, in small portions at RT, 144 mg (1.28 mmol) of potassium tert-butoxide. The mixture was stirred at RT for 15 min. Subsequently, a further 72 mg (0.64 mmol) of potassium tert-butoxide were added in small portions, and the mixture was stirred at RT for a further 15 min. Thereafter, the mixture was admixed with 10 ml of a 10% aqueous citric acid solution, diluted with water and extracted twice with ethyl acetate. The combined organic phases were washed once with saturated sodium chloride solution, dried over magnesium sulfate, filtered and concentrated. The residue was purified by means of column chromatography (50 g of silica gel, eluent: cyclohexane/ethyl acetate 85:15, Biotage). 418 mg (61% of theory, 96% purity) of the title compound were obtained.

$^1$H-NMR (400 MHz, DMSO-$d_6$): δ [ppm]=10.73 (s, 1H), 8.26 (d, 1H), 8.04 (d, 1H), 7.96-7.91 (m, 2H), 7.88 (dd, 1H), 7.74 (d, 1H), 7.65-7.61 (m, 2H), 7.60-7.49 (m, 3H), 3.90 (s, 3H), 2.57 (s, 3H), 2.52-2.50 (m, 3H, hidden).

LC/MS (Method 1, ESIpos): $R_t$=1.27 min, m/z=521/523 [M+H]$^+$.

Example 49A

Methyl 4-{[(6-bromo-3-methyl-2-phenylquinolin-4-yl)carbonyl]amino}-3-(methylsulfinyl)benzoate

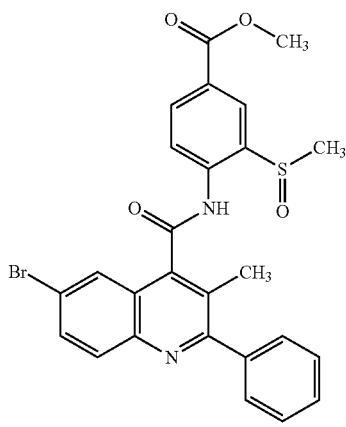 [SMILES: COC(=O)c1ccc(NC(=O)c2c(C)c(-c3ccccc3)nc3ccc(Br)cc23)c(S(C)=O)c1]

To a solution of 150 mg (0.29 mmol) of the compound from example 48A in 3 ml of dichloromethane were added 71 mg (0.29 ml, 70% purity) of 3-chloroperbenzoic acid, and the mixture was stirred at RT for 5 min. Subsequently, a further 20 mg (0.08 mmol) of 3-chloroperbenzoic acid were added, and the mixture was stirred at RT for a further 5 min. Thereafter, another 20 mg (0.08 mmol) of 3-chloroperbenzoic acid were added, and the mixture was stirred at RT for another 5 min. Subsequently, the solvent was removed. The residue was taken up in acetonitrile and purified by means of preparative HPLC (method 5). The combined product-containing fractions were concentrated, and the residue was taken up in dichloromethane, concentrated again and then dried under reduced pressure. 150 mg (97% of theory, 100% purity) of the title compound were obtained.

$^1$H-NMR (400 MHz, DMSO-$d_6$): δ [ppm]=11.24 (s, 1H), 8.54 (d, 1H), 8.22 (dd, 1H), 8.09-8.04 (m, 2H), 8.01-7.93 (m, 1H), 7.86 (d, 1H), 7.67-7.62 (m, 2H), 7.61-7.49 (m, 3H), 3.93 (s, 3H), 2.92 (s, 3H), 2.50 (s, 3H, hidden).

LC/MS (Method 1, ESIpos): $R_t$=1.13 min, m/z=537/539 [M+H]$^+$.

Example 50A

Methyl 4-{[(6-bromo-3-methyl-2-phenylquinolin-4-yl)carbonyl]amino}-3-(methylsulfonyl)benzoate

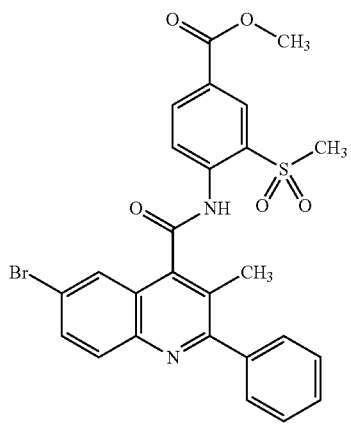 [SMILES: COC(=O)c1ccc(NC(=O)c2c(C)c(-c3ccccc3)nc3ccc(Br)cc23)c(S(C)(=O)=O)c1]

Method A:

To a solution of 150 mg (0.29 mmol) of the compound from example 48A in 3 ml of dichloromethane were added 141 mg (0.58 mmol, 70% purity) of 3-chloroperbenzoic acid. The mixture was stirred at RT for 30 min. Subsequently, the mixture was admixed with 5 ml of 1 M sodium hydroxide solution, diluted with water and extracted three times with dichloromethane. The combined organic phases were washed once with saturated sodium chloride solution, dried over magnesium sulfate, filtered and concentrated. After the residue had been dried under reduced pressure, 106 mg (61% of theory, 92% purity) of the title compound were obtained.

$^1$H-NMR (400 MHz, DMSO-$d_6$): δ [ppm]=10.76 (s, 1H), 8.55 (d, 1H), 8.42-8.32 (m, 2H), 8.26 (d, 1H), 8.04 (d, 1H), 7.94 (dd, 1H), 7.66-7.61 (m, 2H), 7.59-7.49 (m, 3H), 3.94 (s, 3H), 3.42 (s, 3H), 2.50-2.48 (m, 3H, hidden).

LC/MS (Method 1, ESIpos): $R_t$=1.23 min, m/z=553/555 [M+H]$^+$.

Method B:

To a solution of 1.00 g (1.86 mmol) of the compound from example 49A in 20 ml of dichloromethane were added 917 mg (3.72 mmol, 70% purity) of 3-chloroperbenzoic acid. The mixture was stirred at RT for 2 h. Subsequently, the mixture was admixed with 35 ml of 1 M sodium hydroxide solution, diluted with water and extracted three times with dichloromethane. The combined organic phases were washed once with saturated sodium chloride solution, dried over magnesium sulfate, filtered and concentrated. After the residue had been dried under reduced pressure, 881 mg (67% of theory, 78% purity) of the title compound were obtained.

Example 51A

Methyl 4-{[(6-bromo-3-methyl-2-phenylquinolin-4-yl)carbonyl]amino}-5-(ethylsulfonyl)-2-methoxybenzoate

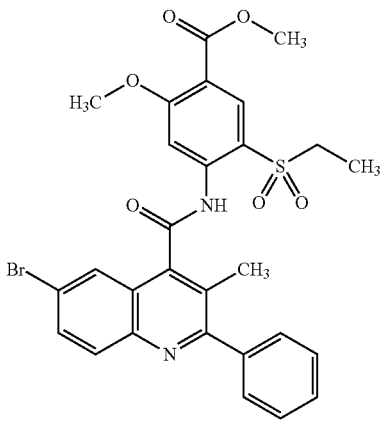 [SMILES: CCS(=O)(=O)c1cc(C(=O)OC)c(OC)cc1NC(=O)c1c(C)c(-c2ccccc2)nc2ccc(Br)cc12]

To a solution of 200 mg (0.51 mmol) of the compound from example 2A and 139 mg (0.51 mmol) of methyl 4-amino-5-(ethylsulfonyl)-2-methoxybenzoate in 2 ml of DMF were added, in small portions at RT, 57 mg (0.51 mmol) of potassium tert-butoxide, and the mixture was stirred at RT for 15 min. Subsequently, a further 29 mg (0.26 mmol) of potassium tert-butoxide were added in small portions, and the mixture was stirred at RT for another 15 min. Thereafter, the mixture was purified by means of preparative HPLC (method 5). The combined product-containing fractions were neutralized with saturated sodium hydrogencarbonate solution and concentrated down to a residual volume of aqueous phase. The solids formed were filtered off, washed twice with water and dried under reduced pressure. 235 mg (77% of theory, 100% purity) of the title compound were obtained.

$^1$H-NMR (400 MHz, DMSO-$d_6$): δ [ppm]=10.61 (s, 1H), 8.25 (br. s, 2H), 8.18 (br. s, 1H), 8.08-8.01 (m, 1H), 7.98-7.90 (m, 1H), 7.68-7.60 (m, 2H), 7.54 (s, 3H), 4.03 (s, 3H), 3.85 (s, 3H), 3.44 (q, 2H), 2.50 (s, 3H, hidden), 1.14 (t, 3H).

LC/MS (Method 1, ESIpos): $R_t$=1.32 min, m/z=597/599 [M+H]$^+$.

Example 52A

Dimethyl 3,3'-disulfanediylbis(4-{[(6-bromo-3-methyl-2-phenylquinolin-4-yl)carbonyl]amino}benzoate)

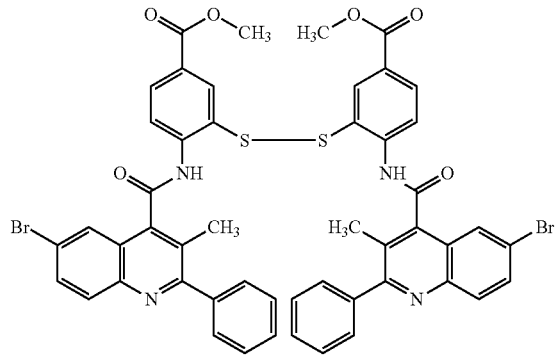 [SMILES: COC(=O)c1ccc(NC(=O)c2c(C)c(-c3ccccc3)nc3ccc(Br)cc23)c(SSc2cc(C(=O)OC)ccc2NC(=O)c2c(C)c(-c3ccccc3)nc3ccc(Br)cc23)c1]

To a mixture of 2.24 g (4.17 mmol) of the compound from example 49A and 1.38 g (12.92 mmol) of 2,6-dimethylpyridine in 18.5 ml of acetonitrile were added dropwise, at −20° C., 2.63 g (12.50 mmol) of trifluoroacetic anhydride. The mixture was stirred at −10° C. to 0° C. for 1 h. Thereafter, the mixture was concentrated under reduced pressure, and the residue was admixed at 0° C. with 14 ml of a mixture of methanol and triethylamine (1:1) which had been degassed and cooled to 0° C. Subsequently, the mixture was stirred at RT for 30 min and then the volatile constituents were removed under reduced pressure. The residue was admixed with 4 ml of a mixture of methanol and 6 M hydrochloric acid, and stirred at 50° C. for 20 min. Subsequently, the mixture was concentrated, the residue was taken up in ethyl acetate and the mixture was washed once with water. The aqueous phase was reextracted once with ethyl acetate. The combined organic phases were washed once with saturated sodium chloride solution, dried over magnesium sulfate, filtered and concentrated. The residue was taken up in dichloromethane, applied to 10 g of neutral alumina and purified by column chromatography (silica gel, cyclohexane/ethyl acetate 7:3, Biotage, with pre-column). Fractions that contained the title compound were obtained, as were further fractions that contained the compound listed as example 72A as a by-product of the reaction. The fractions that contained the title compound were concentrated and the residue was stirred in acetonitrile. The solids present were filtered off and dried under reduced pressure. In this way, 608 mg (13% of theory, about 90% purity) of the title compound were obtained.

LC/MS (Method 1, ESIpos): $R_t$=1.59 min, m/z=1011/1013/1015 [M+H]$^+$.

The fractions that contained the compound listed as example 72A were concentrated and purified further by means of preparative HPLC (column: Sunfire C18, 5 μm, 100 mm×30 mm; eluent: water/acetonitrile/2% formic acid in water; gradient: 50:30:20-5:90:5, 10 min; injection volume: 1.0 ml; flow rate: 75 ml/min; temperature: 40° C.; detection: 210 nm). 210 mg (9% of theory, 100% purity) of the by-product were obtained (for analysis see example 72A).

Example 53A

Methyl 4-{[(6-bromo-3-methyl-2-phenylquinolin-4-yl)carbonyl]amino}-3-[(trifluoromethyl)sulfanyl]benzoate

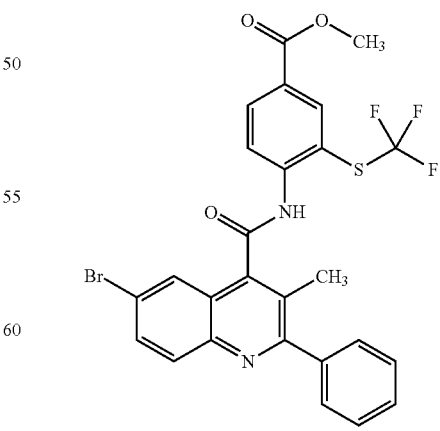

To a mixture of 300 mg (0.30 mmol, 90% purity) of the compound from example 52A in 3 ml of DMF were added 105 mg (0.89 mmol) of sodium hydroxymethanesulfinate (Rongalit™), and the mixture was stirred at RT for 15 min. Subsequently, 196 mg (0.59 mmol) of 3,3-dimethyl-1-(trifluoromethyl)-1,2-benzodioxole were added, and the mixture was stirred at RT for a further 30 min. Thereafter, the mixture, without further workup, was purified by means of preparative HPLC (method 5). 140 mg (91% of theory, 100% purity) of the title compound were obtained.

LC/MS (Method 1, ESIpos): $R_t$=1.40 min, m/z=575/577 [M+H]$^+$.

An experiment conducted analogously gave the following $^1$H NMR of the title compound [amount of compound from example 52A used: 100 mg (0.10 mmol)]:

$^1$H-NMR (400 MHz, DMSO-d$_6$): [ppm]=11.37 (s, 1H), 8.36 (s, 1H), 8.28 (dd, 1H), 8.16 (d, 1H), 8.06 (d, 1H), 8.00-7.92 (m, 2H), 7.67-7.61 (m, 2H), 7.60-7.49 (m, 3H), 3.92 (s, 3H), 2.47 (s, 3H).

Example 54A

Methyl 3-fluoro-4-{[(6-fluoro-3-methyl-2-phenylquinolin-4-yl)carbonyl]amino}benzoate

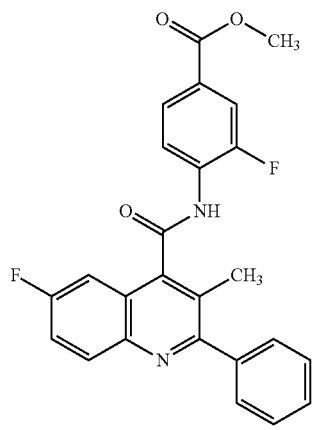 [SMILES: COC(=O)c1ccc(NC(=O)c2c(C)c(-c3ccccc3)nc3ccc(F)cc23)c(F)c1]

To a solution of 200 mg (0.60 mmol) of the compound from example 4A and 102 mg (0.60 mmol) of methyl 4-amino-3-fluorobenzoate in 2.5 ml of DMF were added, in small portions at RT, 68 mg (0.60 mmol) of potassium tert-butoxide, and the mixture was stirred at RT for 15 min. Subsequently, a further 34 mg (0.31 mmol) of potassium tert-butoxide were added in small portions, and the mixture was stirred at RT for a further 15 min. Thereafter, the mixture was admixed with 4 ml of a 10% aqueous citric acid solution, diluted with water and extracted twice with ethyl acetate. The combined organic phases were washed once with saturated sodium chloride solution, dried over magnesium sulfate, filtered and concentrated. The residue was purified by means of column chromatography (25 g of silica gel, eluent: cyclohexane/ethyl acetate 85:15, Biotage). 198 mg (76% of theory, 100% purity) of the title compound were obtained.

$^1$H-NMR (400 MHz, DMSO-d$_6$): [ppm]=11.07 (s, 1H), 8.28 (t, 1H), 8.17 (dd, 1H), 7.91 (d, 1H), 7.84 (dd, 1H), 7.73 (td, 1H), 7.65-7.59 (m, 2H), 7.59-7.47 (m, 4H), 3.89 (s, 3H), 2.43 (s, 3H).

LC/MS (Method 1, ESIpos): $R_t$=1.16 min, m/z=433 [M+H]$^+$.

Example 55A

Methyl 4-{[(3,6-dimethyl-2-phenylquinolin-4-yl)carbonyl]amino}-3-fluorobenzoate

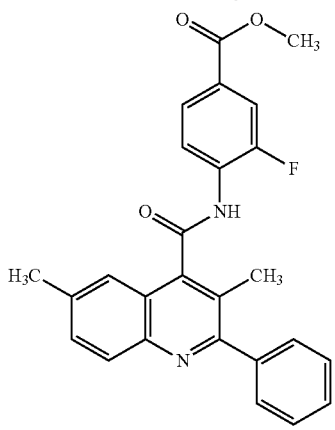 [SMILES: COC(=O)c1ccc(NC(=O)c2c(C)c(-c3ccccc3)nc3ccc(C)cc23)c(F)c1]

To a solution of 200 mg (0.61 mmol) of the compound from example 8A and 103 mg (0.61 mmol) of methyl 4-amino-3-fluorobenzoate in 2.4 ml of DMF were added, in small portions at RT, 69 mg (0.61 mmol) of potassium tert-butoxide, and the mixture was stirred at RT for 15 min. Subsequently, a further 34 mg (0.30 mmol) of potassium tert-butoxide were added in small portions, and the mixture was stirred at RT for a further 15 min. Thereafter, 21 mg (0.12 mmol) of methyl 4-amino-3-fluorobenzoate and 14 mg (0.12 mmol) of potassium tert-butoxide were added, and the mixture was stirred at RT for another 30 min. Subsequently, the mixture was admixed with 4 ml of a 10% aqueous citric acid solution, diluted with water and extracted twice with ethyl acetate. The combined organic phases were washed once with saturated sodium chloride solution, dried over magnesium sulfate, filtered and concentrated. The residue was purified by means of preparative HPLC (Method 5). The combined product-containing fractions were concentrated, and the residue was taken up in dichloromethane, concentrated again and then dried under reduced pressure. 134 mg (47% of theory, 92% purity) of the title compound were obtained.

$^1$H-NMR (400 MHz, DMSO-d$_6$): [ppm]=11.06 (s, 1H), 8.31 (t, 1H), 8.00 (d, 1H), 7.91 (dd, 1H), 7.84 (dd, 1H), 7.67 (dd, 1H), 7.65-7.60 (m, 3H), 7.59-7.48 (m, 3H), 3.89 (s, 3H), 2.41 (s, 3H).

LC/MS (Method 1, ESIpos): $R_t$=1.16 min, m/z=429 [M+H]$^+$.

Example 56A

Methyl 4-{[(6-ethyl-3-methyl-2-phenylquinolin-4-yl)carbonyl]amino}-3-fluorobenzoate

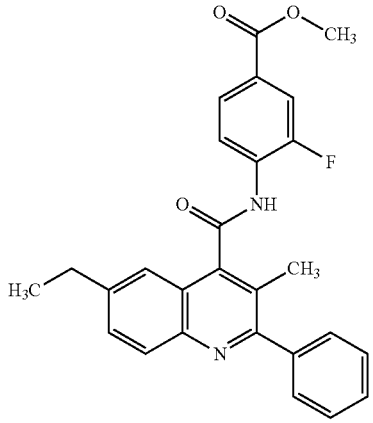 [SMILES: CCc1ccc2nc(-c3ccccc3)c(C)c(C(=O)Nc3ccc(C(=O)OC)cc3F)c2c1]

To a solution of 200 mg (0.59 mmol) of the compound from example 10A and 99 mg (0.59 mmol) of methyl 4-amino-3-fluorobenzoate in 2 ml of DMF were added, in small portions at RT, 66 mg (0.59 mmol) of potassium tert-butoxide, and the mixture was stirred at RT for 15 min. Subsequently, a further 29 mg (0.26 mmol) of potassium tert-butoxide were added in small portions, and the mixture was stirred at RT for a further 15 min. Thereafter, 40 mg (0.12 mmol) of the compound from example 10A and 20 mg (0.12 mmol) of methyl 4-amino-3-fluorobenzoate were added, and the mixture was stirred at RT for another 30 min. Subsequently, the mixture was admixed with 4 ml of a 10% aqueous citric acid solution, diluted with water and extracted twice with ethyl acetate. The combined organic phases were washed once with saturated sodium chloride solution, dried over magnesium sulfate, filtered and concentrated. The residue was purified by means of preparative HPLC (Method 5). The combined product-containing fractions were concentrated, and the residue was taken up in dichloromethane, concentrated again and then dried under reduced pressure. 195 mg (69% of theory, 91% purity) of the title compound were obtained.

$^1$H-NMR (400 MHz, DMSO-d$_6$): [ppm]=11.06 (s, 1H), 8.26 (t, 1H), 8.03 (d, 1H), 7.92 (dd, 1H), 7.85 (dd, 1H), 7.72 (dd, 1H), 7.66-7.60 (m, 3H), 7.59-7.48 (m, 3H), 3.92-3.87 (m, 3H), 2.84 (q, 2H), 2.41 (s, 3H), 1.26 (t, 3H).

LC/MS (Method 1, ESIpos): R$_t$=1.25 min, m/z=443 [M+H]+.

Example 57A

Methyl 3-fluoro-4-{[(6-isopropyl-3-methyl-2-phenylquinolin-4-yl)carbonyl]amino}benzoate

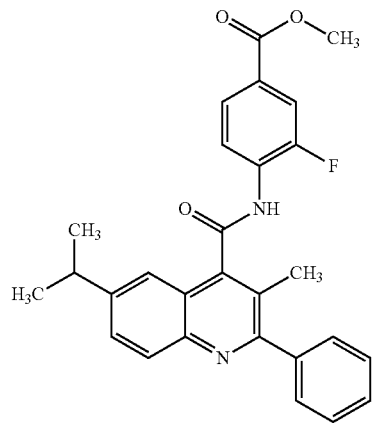 [SMILES: COC(=O)c1ccc(NC(=O)c2c(C)c(-c3ccccc3)nc3ccc(C(C)C)cc23)c(F)c1]

To 670 mg (2.19 mmol) of the compound from example 11A were added 3 ml of dichloromethane and then 0.46 ml (3.51 mmol) of 1-chloro-N,N,2-trimethylprop-1-en-1-amine. The mixture was stirred at RT for 30 min, and then 0.53 ml (6.55 mmol) of pyridine and 371 mg (2.19 mmol) of methyl 4-amino-3-fluorobenzoate were added. The reaction mixture was stirred at 60° C. for 10 h. After cooling down to RT, the solvent was removed under reduced pressure, and the residue was purified by means of preparative HPLC (method 8) without further workup. 108 mg (10% of theory, 96% purity) of the title compound were obtained.

LC/MS (Method 1, ESIpos): R$_t$=1.32 min, m/z=457 [M+H]$^+$.

Example 58A

Methyl 3-fluoro-4-({[3-methyl-2-phenyl-6-(trifluoromethyl)quinolin-4-yl]carbonyl}amino)benzoate

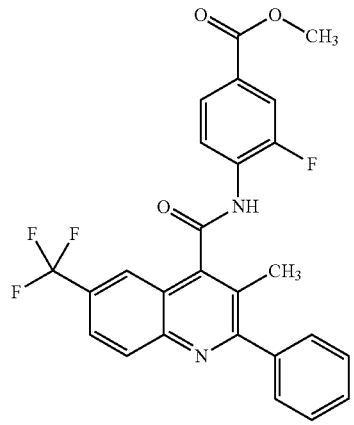 [SMILES: COC(=O)c1ccc(NC(=O)c2c(C)c(-c3ccccc3)nc3ccc(C(F)(F)F)cc23)c(F)c1]

To 300 mg (0.91 mmol) of the compound from example 12A were added 2 ml of dichloromethane and then 0.19 ml (1.45 mmol) of 1-chloro-N,N,2-trimethylprop-1-en-1-amine. The mixture was stirred at RT for 30 min, and then 0.22 ml (2.72 mmol) of pyridine and 153 mg (0.91 mmol) of methyl 4-amino-3-fluorobenzoate were added. The reaction mixture was stirred at 60° C. for 4 h. After cooling down to RT, the solvent was removed under reduced pressure, and the residue was purified by means of preparative HPLC (method 7) without further workup. 105 mg (20% of theory, 83% purity) of the title compound were obtained.

LC/MS (Method 1, ESIpos): R$_t$=0.91 min, m/z=483 [M+H]$^+$.

Example 59A

Methyl 3-fluoro-4-({[3-methyl-2-phenyl-6-(trifluoromethoxy)quinolin-4-yl]carbonyl}amino)benzoate

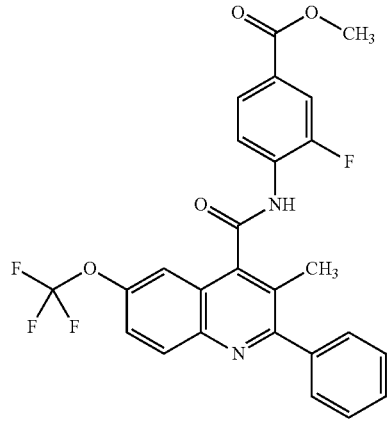 [SMILES: COC(=O)c1ccc(NC(=O)c2c(C)c(-c3ccccc3)nc3ccc(OC(F)(F)F)cc23)c(F)c1]

To a solution of 200 mg (0.50 mmol) of the compound from example 14A and 85 mg (0.50 mmol) of methyl 4-amino-3-fluorobenzoate in 2 ml of DMF were added, in small portions at RT, 56 mg (0.50 mmol) of potassium tert-butoxide, and the mixture was stirred at RT for 15 min. Subsequently, a further 28 mg (0.26 mmol) of potassium tert-butoxide were added in small portions, and the mixture was stirred at RT for a further 15 min. Thereafter, the mixture was admixed with 4 ml of a 10% aqueous citric acid solution, diluted with water and extracted twice with ethyl acetate. The combined organic phases were washed once with saturated sodium chloride solution, dried over magnesium sulfate, filtered and concentrated. The residue was purified by means of column chromatography (25 g of silica gel, eluent: cyclohexane/ethyl acetate 85:15, Biotage). The combined product-containing fractions were concentrated, and the residue was taken up in dichloromethane, concentrated again and then dried under reduced pressure. 166 mg (60% of theory, 91% purity) of the title compound were obtained.

$^1$H-NMR (400 MHz, DMSO-$d_6$): [ppm]=11.11 (s, 1H), 8.27-8.17 (m, 2H), 7.92 (dd, 1H), 7.86 (dd, 1H), 7.82 (dd, 1H), 7.75-7.73 (m, 1H), 7.66-7.61 (m, 2H), 7.60-7.44 (m, 4H), 6.77 (t, 1H), 3.89 (s, 3H), 2.45 (s, 3H).

LC/MS (Method 1, ESIpos): $R_t$=1.26 min, m/z=499 [M+H]$^+$.

Example 60A tert-Butyl 3-fluoro-4-({[3-methyl-2-phenyl-6-(trimethylsilyl)quinolin-4-yl]carbonyl}amino)benzoate

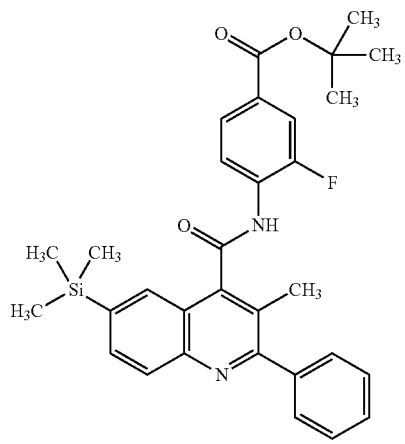 [SMILES: Cc1c(-c2ccccc2)nc2ccc([Si](C)(C)C)cc2c1C(=O)Nc1ccc(C(=O)OC(C)(C)C)cc1F]

To a mixture of 214 mg (0.40 mmol) of the compound from example 39A and 64 mg (0.44 mmol) of hexamethyldisilane in a mixture of 1 ml of toluene and 1 ml of water were added 7 mg (0.02 mmol) of allyl palladium chloride dimer, 11 mg (0.04 mmol) of (2-hydroxyphenyl)diphenylphosphine, 19 mg (0.48 mmol) of sodium hydroxide and 14 mg (0.044 mmol) of tetrabutylammonium bromide. The mixture was stirred at 100° C. for 5 h and then left to stand at RT for 14 h. Subsequently, a further 64 mg (0.44 mmol) of hexamethyldisilane, 7 mg (0.02 mmol) of allyl palladium chloride dimer and 11 mg (0.04 mmol) of (2-hydroxyphenyl)diphenylphosphine were added, and the mixture was stirred at 100° C. for another 7 h. After then being left to stand at RT for three days, the mixture was diluted with ethyl acetate and washed with water. The aqueous phase was re-extracted once with ethyl acetate, and the combined organic phases were washed with saturated sodium chloride solution, dried over magnesium sulfate, filtered and concentrated. The residue was purified by means of preparative HPLC (method 5). The combined product-containing fractions were concentrated, and the residue was taken up in dichloromethane, concentrated again and then dried under reduced pressure. In this way, 39 mg (18% of theory, 100% purity) of the title compound were obtained.

$^1$H-NMR (400 MHz, DMSO-$d_6$): δ [ppm]=11.03 (s, 1H), 8.10-7.99 (m, 3H), 7.94 (dd, 1H), 7.85 (dd, 1H), 7.80 (dd, 1H), 7.66-7.60 (m, 2H), 7.59-7.48 (m, 3H), 2.43 (s, 3H), 1.57 (s, 9H), 0.32 (s, 9H).

LC/MS (Method 1, ESIpos): $R_t$=1.51 min, m/z=529 [M+H]$^+$.

Example 61A

Methyl 4-({[6-bromo-3-(bromomethyl)-2-phenylquinolin-4-yl]carbonyl}amino)-3-fluorobenzoate

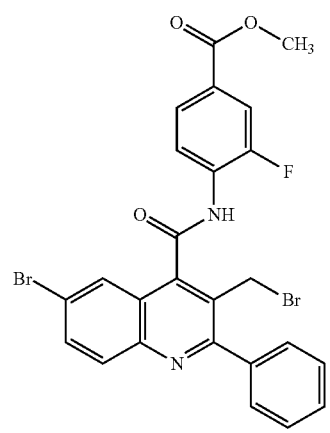 [SMILES: COC(=O)c1ccc(NC(=O)c2c(CBr)c(-c3ccccc3)nc3ccc(Br)cc23)c(F)c1]

To a solution of 1.07 g (2.17 mmol) of the compound from Example 38A in 10 ml of acetonitrile under argon were added, at RT, 463 mg (2.60 mmol) of N-bromosuccinimide (NBS) and 36 mg (0.22 mmol) of 2,2'-azobis(2-methylpropionitrile) (AIBN), and the mixture was heated to bath temperature 80° C. Then 10 ml of carbon tetrachloride were added, and the mixture was stirred at bath temperature 80° C. for 1 h. Subsequently, a further 232 mg (1.30 mmol) of N-bromosuccinimide (NBS) and 21 mg (0.13 mmol) of 2,2'-azobis(2-methylpropionitrile) (AIBN) were added, and the mixture was stirred at bath temperature 80° C. for a further 8 h. After cooling to RT, the solids present were filtered off and washed twice with 2 ml of acetonitrile. After the solids had been dried under reduced pressure, 656 mg (44% of theory, 84% purity) of a first batch of the title compound were obtained. The filtrate was concentrated and the residue was purified by means of column chromatography (silica gel, eluent: cyclohexane/ethyl acetate 9:1) together with a residue obtained analogously from a preceding experiment [amount of compound from example 38A used: 100 mg (0.20 mmol)]. In this way, 260 mg of a second batch of the title compound were obtained (90% purity, 17% of theory, based on a total of 1.17 g (2.37 mmol) of the amount of compound from example 38A used). Additionally obtained as a by-product of the reaction were 194 mg (10% of theory, 70% purity) of the compound from example 62A (see therein).

$^1$H-NMR (400 MHz, DMSO-$d_6$): [ppm]=11.23 (s, 1H), 8.25 (t, 1H), 8.10-8.01 (m, 3H), 7.93 (dd, 1H), 7.87 (dd, 1H), 7.72-7.66 (m, 2H), 7.64-7.56 (m, 3H), 4.73 (dd, 2H), 3.90 (s, 3H).

LC/MS (Method 1, ESIpos): $R_t$=1.27 min, m/z=571/573/575 [M+H]$^+$.

Example 62A

Methyl 4-({[6-bromo-3-(dibromomethyl)-2-phenylquinolin-4-yl]carbonyl}amino)-3-fluorobenzoate

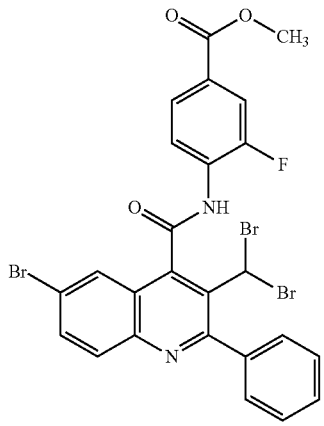 [SMILES: COC(=O)c1ccc(NC(=O)c2c(C(Br)Br)c(-c3ccccc3)nc3ccc(Br)cc23)c(F)c1]

The title compound (194 mg, 70% purity) was obtained as a by-product of the reaction described in example 61A.

$^1$H-NMR (400 MHz, DMSO-$d_6$): [ppm]=11.26 (s, 1H), 8.38 (t, 1H), 8.14-8.07 (m, 3H), 7.94 (dd, 1H), 7.87 (dd, 1H), 7.65-7.59 (m, 5H), 7.03 (s, 1H), 3.90 (s, 3H).

LC/MS (Method 1, ESIpos): $R_t$=1.32 min, m/z=649/651/653/655 [M+H]$^+$.

Example 63A

Methyl 4-({[6-bromo-3-(fluoromethyl)-2-phenylquinolin-4-yl]carbonyl}amino)-3-fluorobenzoate

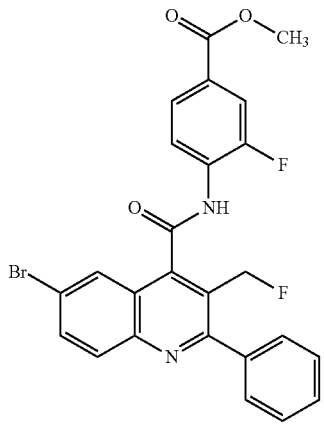

To a mixture of 232 mg (0.37 mmol, 90% purity) of the compound from example 61A in 18 ml of acetonitrile under argon were added 130 mg (1.02 mmol) of silver fluoride, and the mixture was heated at bath temperature 80° C. for 1.5 h. After cooling to RT, the mixture was admixed with 100 ml each of ethyl acetate and saturated aqueous sodium hydrogencarbonate solution. After phase separation, the aqueous phase was extracted once with ethyl acetate. The combined organic phases were dried over sodium sulfate, filtered and concentrated. The residue was taken up in dichloromethane and purified by means of column chromatography (25 g of silica gel, eluent: cyclohexane/ethyl acetate 9:1, Biotage). In this way, 77 mg (41% of theory, 100% purity) of the title compound were obtained.

$^1$H-NMR (400 MHz, DMSO-$d_6$): δ [ppm]=11.19 (s, 1H), 8.28 (t, 1H), 8.15-8.10 (m, 2H), 8.07 (dd, 1H), 7.93 (dd, 1H), 7.86 (dd, 1H), 7.70-7.64 (m, 2H), 7.62-7.54 (m, 3H), 5.63 (s, 1H), 5.51 (s, 1H), 3.89 (s, 3H).

LC/MS (Method 1, ESIpos): $R_t$=1.22 min, m/z=511/513 [M+H]$^+$.

Example 64A

Methyl 4-({[6-bromo-3-(difluoromethyl)-2-phenylquinolin-4-yl]carbonyl}amino)-3-fluorobenzoate

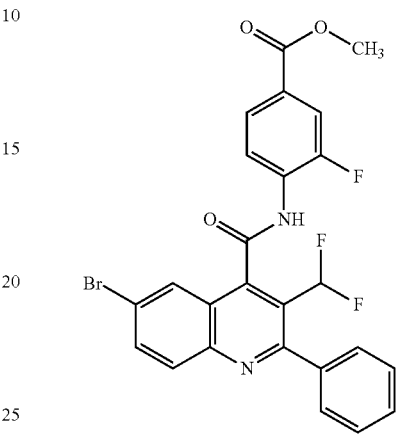

To a mixture of 170 mg (0.18 mmol, 70% purity) of the compound from example 62A in 6 ml of acetonitrile under argon were added 93 mg (0.73 mmol) of silver fluoride, and the mixture was heated at bath temperature 80° C. for 1 h. After cooling to RT, the mixture was admixed with 50 ml each of ethyl acetate and saturated aqueous sodium hydrogencarbonate solution. After phase separation, the aqueous phase was extracted once with 50 ml of ethyl acetate. The combined organic phases were dried over sodium sulfate, filtered and concentrated. The residue was taken up in dichloromethane and purified by means of column chromatography (25 g of silica gel, eluent: cyclohexane/ethyl acetate 9:1, Biotage). In this way, 28 mg (27% of theory, 95% purity) of the title compound were obtained.

$^1$H-NMR (400 MHz, DMSO-$d_6$): δ [ppm]=11.16 (s, 1H), 8.34-8.28 (m, 1H), 8.17-8.11 (m, 3H), 7.92 (dd, 1H), 7.85 (dd, 1H), 7.65-7.55 (m, 5H), 7.08 (t, 1H), 3.89 (s, 3H).

LC/MS (Method 1, ESIpos): $R_t$=1.22 min, m/z=529/531 [M+H]+.

Example 65A

Methyl 4-{[(6-bromo-3-ethyl-2-phenylquinolin-4-yl)carbonyl]amino}-3-fluorobenzoate

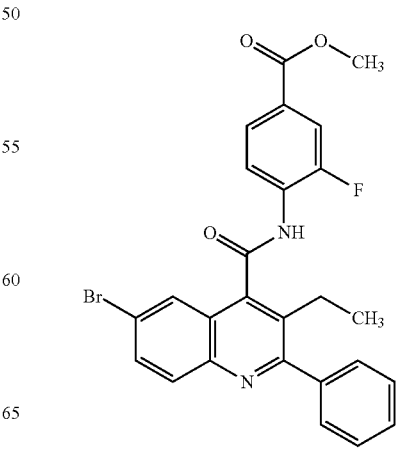

To a solution of 238 mg (0.59 mmol) of the compound from example 16A and 99 mg (0.59 mmol) of methyl 4-amino-3-fluorobenzoate in 2.3 ml of DMF under argon was added 0.88 ml (0.88 mmol) of a 1 M solution of potassium tert-butoxide in THF, and the mixture was stirred at RT for 1 h. Subsequently, the mixture was admixed with 4 ml of a 10% aqueous citric acid solution, diluted with water and extracted twice with 20 ml each time of ethyl acetate. The combined organic phases were washed once with 40 ml of saturated sodium chloride solution, dried over sodium sulfate, filtered and concentrated. The residue was taken up in dichloromethane and purified by means of column chromatography (50 g of silica gel, eluent: cyclohexane/ethyl acetate 4:1, Biotage). 206 mg (69% of theory, 100% purity) of the title compound were obtained.

$^1$H-NMR (400 MHz, DMSO-d$_6$): [ppm]=11.13 (s, 1H), 8.22 (t, 1H), 8.06-7.89 (m, 4H), 7.85 (dd, 1H), 7.60-7.49 (m, 5H), 3.89 (s, 3H), 2.91-2.76 (m, 2H), 0.98 (t, 3H).

LC/MS (Method 1, ESIpos): R$_t$=1.27 min, m/z=507/509 [M+H]$^+$.

Example 66A

Methyl 4-{[(6-bromo-2-phenyl-3-propylquinolin-4-yl)carbonyl]amino}-3-fluorobenzoate

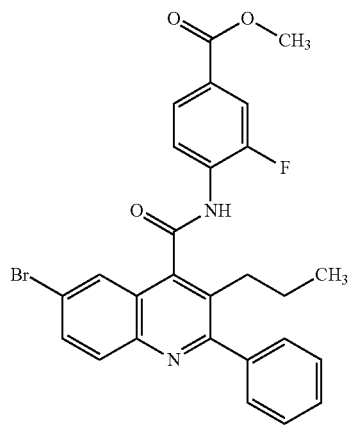 [SMILES: CCCc1c(-c2ccccc2)nc2ccc(Br)cc2c1C(=O)Nc1ccc(C(=O)OC)cc1F]

To a solution of 170 mg (0.40 mmol) of the compound from example 18A and 68 mg (0.40 mmol) of methyl 4-amino-3-fluorobenzoate in 2 ml of DMF under argon was added 0.61 ml (0.61 mmol) of a 1 M solution of potassium tert-butoxide in THF, and the mixture was stirred at RT for 1 h. Subsequently, the mixture was admixed with 4 ml of a 10% aqueous citric acid solution, diluted with water and extracted twice with 20 ml each time of ethyl acetate. The combined organic phases were washed once with 40 ml of saturated sodium chloride solution, dried over sodium sulfate, filtered and concentrated. The residue was taken up in dichloromethane and purified by means of column chromatography (25 g of silica gel, eluent: cyclohexane/ethyl acetate 9:1, Biotage). 151 mg (72% of theory, 100% purity) of the title compound were obtained.

$^1$H-NMR (400 MHz, DMSO-d$_6$): [ppm]=11.11 (s, 1H), 8.18 (t, 1H), 8.03 (d, 1H), 7.99 (d, 1H), 7.97-7.90 (m, 2H), 7.86 (dd, 1H), 7.59-7.50 (m, 5H), 3.89 (s, 3H), 2.79 (t, 2H), 1.47-1.30 (m, 2H), 0.67 (t, 3H).

LC/MS (Method 1, ESIpos): R$_t$=1.31 min, m/z=521/523 [M+H]$^+$.

Example 67A

Methyl 4-{[(6-bromo-7-chloro-3-methyl-2-phenylquinolin-4-yl)carbonyl]amino}-3-fluorobenzoate

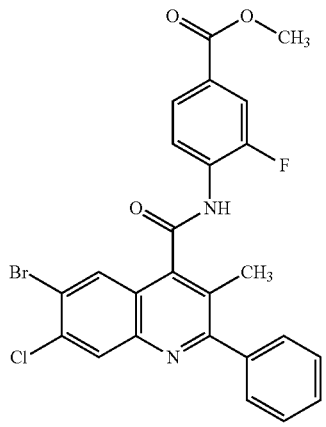

To a solution of 200 mg (0.47 mmol) of the compound from example 20A and 87 mg (0.52 mmol) of methyl 4-amino-3-fluorobenzoate in 1 ml of DMF under argon were added, in small portions at RT, 53 mg (0.47 mmol) of potassium tert-butoxide, and the mixture was stirred at RT for 15 min. Subsequently, a further 26 mg (0.24 mmol) of potassium tert-butoxide were added in small portions, and the mixture was stirred at RT for another 15 min. Thereafter, the mixture was admixed with 4 ml of a 10% aqueous citric acid solution and diluted with 6 ml of water. The solids formed were filtered off, washed twice with water and dried under reduced pressure. The solids were then taken up in dichloromethane and purified by means of column chromatography (50 g of silica gel, eluent: cyclohexane/ethyl acetate 9:1, Biotage). 74 mg (30% of theory, 100% purity) of the title compound were obtained.

$^1$H-NMR (400 MHz, DMSO-d$_6$): [ppm]=11.11 (s, 1H), 8.39 (s, 1H), 8.28 (t, 1H), 8.20 (s, 1H), 7.92 (dd, 1H), 7.85 (dd, 1H), 7.66-7.61 (m, 2H), 7.60-7.49 (m, 3H), 3.89 (s, 3H), 2.43 (s, 3H).

LC/MS (Method 1, ESIpos): R$_t$=1.32 min, m/z=527/529 [M+H]+.

Example 68A

Methyl 4-({[6-bromo-2-(4-fluorophenyl)-3-methylquinolin-4-yl]carbonyl}amino)-3-fluorobenzoate

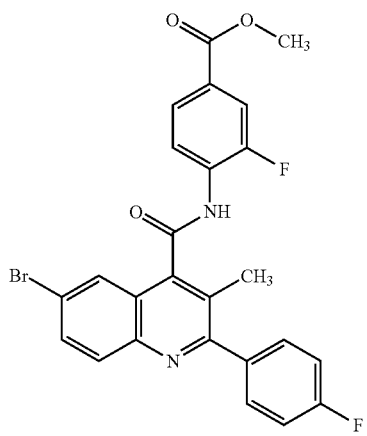 [SMILES: COC(=O)c1ccc(NC(=O)c2c(C)c(-c3ccc(F)cc3)nc3ccc(Br)cc23)c(F)c1]

To a solution of 200 mg (0.49 mmol) of the compound from example 26A and 82 mg (0.49 mmol) of methyl 4-amino-3-fluorobenzoate in 2 ml of DMF under argon was added 0.73 ml (0.73 mmol) of a 1 M solution of potassium tert-butoxide in THF, and the mixture was stirred at RT for 1 h. Subsequently, the mixture was admixed with 4 ml of a 10% aqueous citric acid solution, diluted with water and extracted twice with 20 ml each time of ethyl acetate. The combined organic phases were washed once with 40 ml of saturated sodium chloride solution, dried over sodium sulfate, filtered and concentrated. The residue was taken up in dichloromethane and purified by means of column chromatography (50 g of silica gel, eluent: cyclohexane/ethyl acetate 4:1, Biotage). 193 mg (77% of theory, 100% purity) of the title compound were obtained.

$^1$H-NMR (400 MHz, DMSO-$d_6$): [ppm]=11.08 (s, 1H), 8.27 (t, 1H), 8.05 (d, 1H), 8.00-7.97 (m, 1H), 7.96-7.88 (m, 2H), 7.85 (dd, 1H), 7.73-7.65 (m, 2H), 7.38 (t, 2H), 3.89 (s, 3H), 2.43 (s, 3H).

LC/MS (Method 1, ESIpos): $R_t$=1.25 min, m/z=511/513 [M+H]+.

Example 69A

Methyl 4-({[6-bromo-2-(3-fluorophenyl)-3-methylquinolin-4-yl]carbonyl}amino)-3-fluorobenzoate

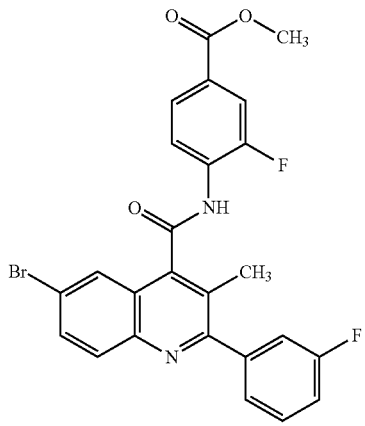 [SMILES: COC(=O)c1ccc(NC(=O)c2c(C)c(-c3cccc(F)c3)nc3ccc(Br)cc23)c(F)c1]

To a solution of 170 mg (0.41 mmol) of the compound from example 28A and 70 mg (0.41 mmol) of methyl 4-amino-3-fluorobenzoate in 2 ml of DMF under argon was added 0.62 ml (0.62 mmol) of a 1 M solution of potassium tert-butoxide in THF, and the mixture was stirred at RT for 1 h. Subsequently, the mixture was admixed with 4 ml of a 10% aqueous citric acid solution, diluted with water and extracted twice with 20 ml each time of ethyl acetate. The combined organic phases were dried over sodium sulfate, filtered and concentrated. The residue was taken up in dichloromethane and purified by means of column chromatography (25 g of silica gel, eluent: cyclohexane/ethyl acetate 9:1, Biotage). 108 mg (51% of theory, 100% purity) of the title compound were obtained.

$^1$H-NMR (400 MHz, DMSO-$d_6$): [ppm]=11.09 (s, 1H), 8.27 (t, 1H), 8.06 (d, 1H), 8.01-7.90 (m, 3H), 7.85 (dd, 1H), 7.66-7.55 (m, 1H), 7.51-7.44 (m, 2H), 7.41-7.33 (m, 1H), 3.89 (s, 3H), 2.44 (s, 3H).

LC/MS (Method 1, ESIpos): $R_t$=1.25 min, m/z=511/513 [M+H]$^+$.

Example 70A

Methyl 4-({[6-bromo-2-(2-fluorophenyl)-3-methylquinolin-4-yl]carbonyl}amino)-3-fluorobenzoate

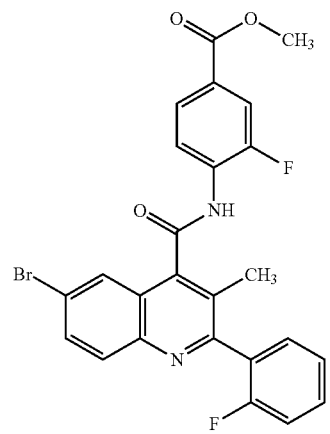

To a solution of 200 mg (0.49 mmol) of the compound from example 30A and 82 mg (0.49 mmol) of methyl 4-amino-3-fluorobenzoate in 2.4 ml of DMF under argon was added 0.73 ml (0.73 mmol) of a 1 M solution of potassium tert-butoxide in THF, and the mixture was stirred at RT for 1 h. Subsequently, the mixture was admixed with 4 ml of a 10% aqueous citric acid solution, diluted with water and extracted twice with 20 ml each time of ethyl acetate. The combined organic phases were dried over sodium sulfate, filtered and concentrated. The residue was admixed with 4 ml of acetonitrile and the mixture was treated in an ultrasound bath, whereupon there was precipitation of solids. The solids were filtered off, washed with 4 ml of acetonitrile and dried under reduced pressure. 164 mg (63% of theory, 96% purity) of the title compound were obtained.

$^1$H-NMR (400 MHz, DMSO-$d_6$): [ppm]=11.18 (s, 1H), 8.25 (t, 1H), 8.09-8.04 (m, 1H), 8.02 (d, 1H), 7.99-7.94 (m, 1H), 7.91 (dd, 1H), 7.85 (dd, 1H), 7.66-7.57 (m, 1H), 7.57-7.50 (m, 1H), 7.45-7.37 (m, 2H), 3.89 (s, 3H), 2.32 (s, 3H).

LC/MS (Method 3, ESIpos): $R_t$=1.54 min, m/z=511/513 [M+H]$^+$.

Example 71A

Ethyl 4-({[6-bromo-3-methyl-2-(pyridin-4-yl)quinolin-4-yl]carbonyl}amino)-3-fluorobenzoate

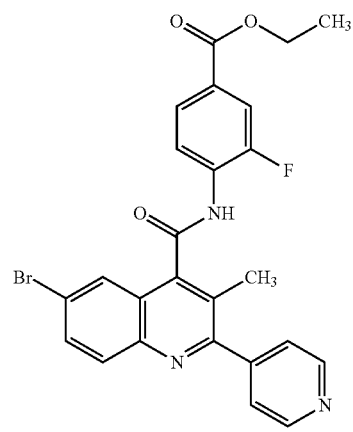 [SMILES: CCOC(=O)c1ccc(NC(=O)c2c(C)c(-c3ccncc3)nc3ccc(Br)cc23)c(F)c1]

To a suspension of 500 mg (1.46 mmol) of the compound from example 31A in 50 ml of dichloromethane were added a few drops of DMF and then 0.57 ml (6.56 mmol) of oxalyl chloride. After stirring at RT for 15 min, the solvent was removed, and the residue was taken up in 15 ml of pyridine. Subsequently, 321 mg (1.75 mmol) of ethyl 4-amino-3-fluorobenzoate were added, and the mixture was stirred at 80° C. overnight. After cooling to RT, the solvent was removed under reduced pressure and the residue was taken up in 25 ml of dichloromethane. The solution was washed with water, dried over sodium sulfate, filtered and concentrated. The residue was purified by means of column chromatography (silica gel, eluent: dichloromethane/methanol 97:3). 90 mg (12% of theory) of the title compound were obtained, which were used directly in the subsequent stage.

Example 72A

Methyl 4-{[(6-bromo-3-methyl-2-phenylquinolin-4-yl)carbonyl]amino}-3-[(methoxymethyl)sulfanyl]benzoate

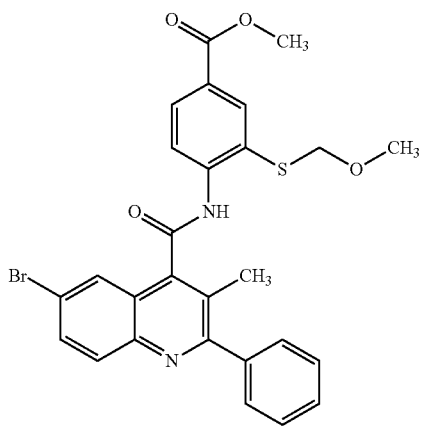 [SMILES: COCSc1cc(C(=O)OC)ccc1NC(=O)c1c(C)c(-c2ccccc2)nc2ccc(Br)cc12]

The title compound was obtained as a by-product in the preparation of the compound from example 52A (for description see therein).

$^1$H-NMR (400 MHz, DMSO-d$_6$): δ [ppm]=10.78 (s, 1H), 8.25 (dd, 2H), 8.04 (d, 1H), 7.95 (td, 2H), 7.83 (d, 1H), 7.66-7.61 (m, 2H), 7.60-7.51 (m, 3H), 5.10 (s, 2H), 3.88 (s, 3H), 3.36 (s, 3H), 2.50 (s, 3H, hidden).

LC/MS (Method 21, ESIpos): R$_t$=1.40 min, m/z=551/553 [M+H]$^+$.

Example 73A

Methyl 4-amino-3-[(trifluoromethyl)sulfanyl]benzoate

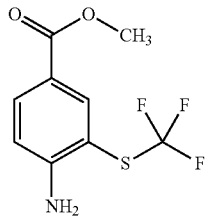

To a mixture of 400 mg (1.10 mmol) of dimethyl 3,3'-disulfanediylbis(4-aminobenzoate) [described in Org. Prep. Proc. Int. 2003, 35 (5), 520-524] in 10 ml of DMF were added 389 mg (3.29 mmol) of sodium hydroxymethanesulfinate (Rongalit™), and the reaction mixture was stirred at RT for 15 min. Subsequently, 725 mg (2.20 mmol) of 3,3-dimethyl-1-(trifluoromethyl)-1,2-benzodioxole were added. After stirring at RT for 30 min, the mixture was purified directly by means of preparative HPLC (method 5). The combined product-containing fractions were concentrated and dried under reduced pressure. The residue was taken up in dichloromethane, the solution was concentrated again and the residue was dried once again under reduced pressure. 185 mg (67% of theory, 100% purity) of the title compound were obtained.

$^1$H-NMR (400 MHz, DMSO-d$_6$): δ [ppm]=7.94 (d, 1H), 7.77 (dd, 1H), 6.83 (d, 1H), 6.71 (s, 2H), 3.77 (s, 3H).

LC/MS (Method 22, ESIpos): R$_t$=2.16 min, m/z=252 [M+H]$^+$.

Example 74A

Methyl 4-amino-3-[(trifluoromethyl)sulfonyl]benzoate

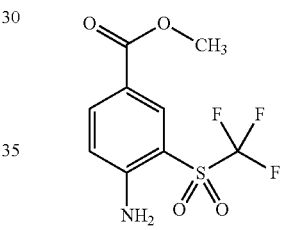

To a mixture of 200 mg (0.80 mmol) of the compound from example 73A in 5 ml of acetonitrile were added, at 0° C., 3.3 mg (0.016 mmol) of ruthenium(III) chloride and 511 mg (2.39 mmol) of sodium periodate. Subsequently, 5 ml of water precooled to 0° C. were added, and the mixture was stirred at 0° C. for 15 min and then at RT overnight. Thereafter, a further 3.3 mg (0.016 mmol) of ruthenium(III) chloride and 511 mg (2.39 mmol) of sodium periodate were added, and the mixture was stirred at RT for another 2 h. Then the mixture was admixed with ethyl acetate and washed once with water. The aqueous phase was reextracted once with ethyl acetate. The combined organic phases were washed once with saturated sodium chloride solution, dried over magnesium sulfate, filtered and concentrated. The residue was purified by means of preparative HPLC (method 18). The combined product-containing fractions were concentrated and dried under reduced pressure. The residue was taken up in dichloromethane, the solution was concentrated again and the residue was dried once again under reduced pressure. 50 mg (21% of theory, 96% purity) of the title compound were obtained.

$^1$H-NMR (400 MHz, DMSO-d$_6$): δ [ppm]=8.11 (d, 1H), 7.98 (dd, 1H), 7.34 (br. s, 2H), 7.03 (d, 1H), 3.81 (s, 3H).

LC/MS (Method 1, ESIpos): R$_t$=0.94 min, m/z=284 [M+H]$^+$.

Example 75A

Methyl 4-{[(6-bromo-3-methyl-2-phenylquinolin-4-yl)carbonyl]amino}-3-[(trifluoromethyl)sulfonyl]benzoate

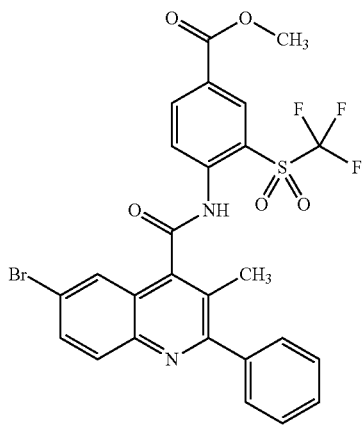 [SMILES: COC(=O)c1ccc(NC(=O)c2c(C)c(-c3ccccc3)nc3ccc(Br)cc23)c(S(=O)(=O)C(F)(F)F)c1]

To a solution of 62 mg (0.16 mmol) of the compound from example 2A and 45 mg (0.16 mmol) of the compound from example 74A in 0.65 ml of DMF under argon was added 0.24 ml (0.24 mmol) of a 1 M solution of potassium tert-butoxide in THF. The mixture was stirred at RT for 30 min. Subsequently, the mixture was diluted with 0.018 ml (0.24 mmol) of TFA and purified directly by means of preparative HPLC (method 18). 45 mg (46% of theory, 96% purity) of the title compound were obtained.

$^1$H-NMR (400 MHz, DMSO-d$_6$): δ [ppm]=11.03 (s, 1H), 8.62 (dd, 1H), 8.57 (s, 1H), 8.41 (d, 1H), 8.09-8.02 (m, 2H), 7.95 (dd, 1H), 7.67-7.60 (m, 2H), 7.60-7.49 (m, 3H), 3.96 (s, 3H), 2.48 (s, 3H).

LC/MS (Method 1, ESIpos): R$_t$=1.42 min, m/z=607/609 [M+H]+.

Example 76A

Methyl 4-{[(6-bromo-3-methyl-1-oxido-2-phenylquinolin-4-yl)carbonyl]amino}-3-[(trifluoromethyl)sulfanyl]benzoate

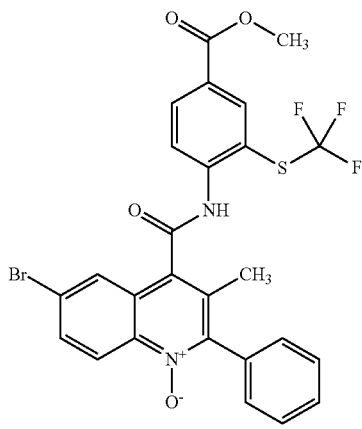 [SMILES: COC(=O)c1ccc(NC(=O)c2c(C)c(-c3ccccc3)[n+]([O-])c3ccc(Br)cc23)c(SC(F)(F)F)c1]

To a solution of 90 mg (0.16 mmol) of the compound from example 53A in 5 ml of dichloromethane were added 58 mg (0.24 ml, 70% purity) of 3-chloroperbenzoic acid, and the mixture was stirred at RT for 3 h. Subsequently, a further 39 mg (0.16 mmol, 70% purity) of 3-chloroperbenzoic acid were added, and the mixture was stirred at RT for another 2.5 h. Thereafter, a further 20 mg (0.08 mmol, 70% purity) of 3-chloroperbenzoic acid were added, and the mixture was stirred at RT for yet another 1 h. Thereafter, the mixture was admixed with 5 ml of saturated aqueous sodium hydrogencarbonate solution and stirred for a few minutes, and then 1 ml of 10% sodium thiosulfate solution was added. After being left to stand at RT for about 80 h, the mixture was diluted with dichloromethane and water, the phases were separated, and then the aqueous phase was extracted once with dichloromethane. The combined organic phases were dried over magnesium sulfate, filtered and concentrated. The residue was purified by means of preparative HPLC (method 5). Drying under reduced pressure gave 48 mg (52% of theory, purity 100%) of the title compound.

$^1$H-NMR (400 MHz, DMSO-d$_6$): δ [ppm]=11.28 (s, 1H), 8.52 (d, 1H), 8.34 (s, 1H), 8.26 (dd, 1H), 8.22 (d, 1H), 8.01 (dd, 1H), 7.98 (d, 1H), 7.62-7.56 (m, 2H), 7.56-7.50 (m, 1H), 7.44 (d, 2H), 3.92 (s, 3H), 2.19 (s, 3H).

LC/MS (Method 1, ESIpos): R$_t$=1.21 min, m/z=591/593 [M+H]+.

Example 77A

6-Bromo-5-chloro-3-methyl-2-phenylquinoline-4-carboxylic acid

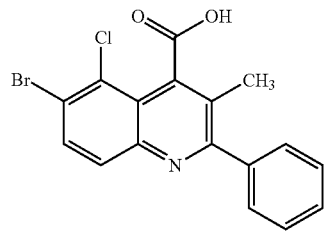

2.50 g (9.60 mmol) of 5-bromo-4-chloro-1H-indole-2,3-dione were initially charged in 21.6 ml of acetic acid, and 1.29 g (9.60 mmol) of 1-phenylpropan-1-one were added. The reaction mixture was stirred at 75° C. for 5 min. Subsequently, 7.2 ml of concentrated hydrochloric acid were added, and the mixture was stirred at 105° C. for 28 h. After cooling to RT, the reaction mixture was added to 100 ml of 1 M hydrochloric acid, and the precipitated solids were filtered off. The solids were washed twice with water and suspended in ethyl acetate, and the suspension was extracted three times with 75 ml of 1 M sodium hydroxide solution. The combined sodium hydroxide solution phases were then adjusted to pH 4 with concentrated hydrochloric acid. The precipitated solids were filtered off, washed twice with water and dried under reduced pressure to obtain a first intermediate batch of the target compound. The ethyl acetate phase previously obtained was extracted twice with 100 ml of water, and the two aqueous phases were adjusted to pH 1 with concentrated hydrochloric acid and extracted twice with 100 ml of ethyl acetate. The combined ethyl acetate phases were dried over sodium sulfate, filtered and concentrated. The residue was dried to obtain a second intermediate batch of the target compound. The two intermediate batches were then combined, taken up again in 100 ml of 1 M sodium hydroxide solution and extracted twice with 50 ml of ethyl acetate. The aqueous phase was adjusted to pH 4 with concentrated hydrochloric acid, and the solids formed were filtered off, washed twice with 10 ml of water and dried under reduced pressure. In this way, 2.23 g (53% of theory, 86% purity) of the title compound were obtained.

$^1$H-NMR (400 MHz, DMSO-d$_6$): δ [ppm]=14.17 (br. s, 1H), 8.11 (d, 1H), 7.98 (d, 1H), 7.66-7.59 (m, 2H), 7.58-7.50 (m, 2H), 2.39 (s, 3H).

LC/MS (Method 1, ESIpos): R$_t$=0.97 min, m/z=376/378 [M+H]+.

Example 78A (6-Bromo-5-chloro-3-methyl-2-phenylquinolin-4-yl)(1H-imidazol-1-yl)methanone

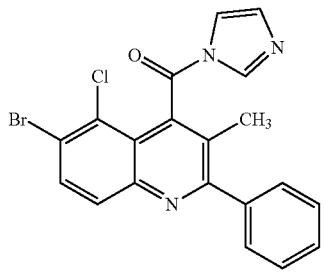 [SMILES: Cc1c(-c2ccccc2)nc2ccc(Br)c(Cl)c2c1C(=O)n1ccnc1]

To a solution of 2.20 g (5.02 mmol, 86% purity) of the compound from example 77A in 12 ml of DMF were added, at RT, 1.42 g (8.74 mmol) of N,N'-carbonyldiimidazole, and the mixture was stirred at bath temperature 120° C. for 6 h. Subsequently, a further 552 mg (3.40 mmol) of N,N'-carbonyldiimidazole were added, and the mixture was stirred at bath temperature 120° C. for another 4 h. Thereafter, another 552 mg (3.40 mmol) of N,N'-carbonyldiimidazole were added, and the mixture was stirred at bath temperature 140° C. for a further 5 h. Thereafter, 100 ml each of water and ethyl acetate were added to the mixture, the phases were separated and then the aqueous phase was extracted once with ethyl acetate. The combined organic phases were washed once with saturated sodium chloride solution, dried over sodium sulfate, filtered and concentrated. The residue was taken up in dichloromethane and purified by means of column chromatography (100 g of silica gel, eluent: cyclohexane/ethyl acetate 7:3, Biotage). 362 mg (17% of theory, 100% purity) of the title compound were obtained.

$^1$H-NMR (400 MHz, DMSO-$d_6$): δ [ppm]=8.5-7.5 (br. m, 2H), 8.18 (d, 1H), 8.09 (d, 1H), 7.71-7.66 (m, 2H), 7.59-7.49 (m, 3H), 7.27 (br. s, 1H), 2.25 (s, 3H).

LC/MS (Method 1, ESIpos): $R_t$=1.25 min, m/z=426/428 [M+H]$^+$.

Example 79A

Methyl 4-{[(6-bromo-5-chloro-3-methyl-2-phenylquinolin-4-yl)carbonyl]amino}-3-fluorobenzoate

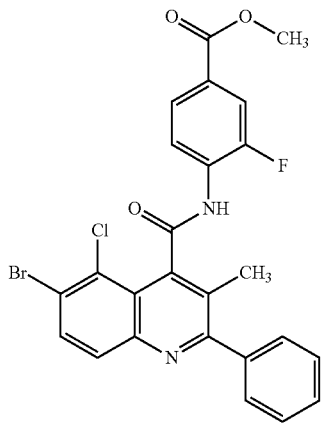

To a solution of 357 mg (0.84 mmol) of the compound from example 78A and 156 mg (0.92 mmol) of methyl 4-amino-3-fluorobenzoate in 1.0 ml of DMF under argon was added 0.84 ml (0.84 mmol) of a 1 M solution of potassium tert-butoxide in THF. The mixture was stirred at RT for 2.5 h. Subsequently, another 0.84 ml (0.84 mmol) of a 1 M solution of potassium tert-butoxide in THF was added, and stirring of the mixture was continued at RT overnight. Thereafter, the mixture was admixed with 30 ml of 10% aqueous citric acid solution and 30 ml of water. The precipitate formed was filtered off, washed twice with 10 ml of water and dried under reduced pressure. 289 mg of a product batch were obtained, in which the title compound, by LC/MS analysis, was present in 4% purity (3% of theory). This material was used in subsequent reactions without further purification.

LC/MS (Method 23, ESIpos): $R_t$=4.16 min, m/z=527/529 [M+H]$^+$.

Example 80A

Methyl 4-[({6-bromo-3-[bromo(difluoro)methyl]-2-phenylquinolin-4-yl}carbonyl)amino]-3-fluorobenzoate

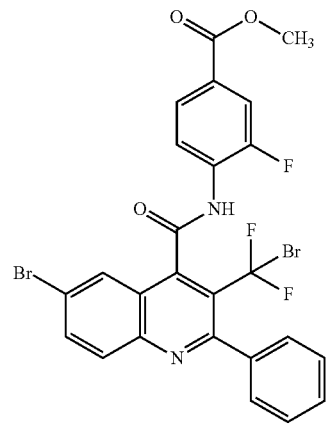

To a mixture of 133 mg (0.25 mmol) of the compound from example 64A in 4 ml of tetrachloromethane were added 103 mg (0.58 mmol) of N-bromosuccinimide and 2.1 mg (0.013 mmol) of 2,2'-azobis-2-methylpropanenitrile. The mixture was irradiated with a UV lamp at 300 W for 24 h, in the course of which the internal temperature rose to 80°-90° C. After this period, another 103 mg (0.58 mmol) of N-bromosuccinimide and 2.1 mg (0.013 mmol) of 2,2'-azobis-2-methylpropanenitrile were added, and the mixture was irradiated with a UV lamp at 300 W and an internal temperature of 80°–90° C. for a further 48 h. Subsequently, yet another 103 mg (0.58 mmol) of N-bromosuccinimide and 2.1 mg (0.013 mmol) of 2,2'-azobis-2-methylpropanenitrile were added, and the mixture was irradiated with a UV lamp at 300 W and an internal temperature of 80°-90° C. for another 24 h. Thereafter, the solvent was removed and the residue was purified by means of preparative HPLC (method 20). 35 mg (18% of theory, 76% purity) of the title compound were obtained.

LC/MS (Method 1, ESIpos): $R_t$=1.31 min, m/z=607/609/611 [M+H]$^+$.

Example 81A

Methyl 4-({[6-bromo-2-phenyl-3-(trifluoromethyl)quinolin-4-yl]carbonyl}amino)-3-fluorobenzoate

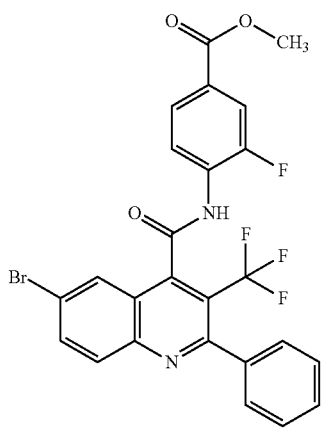 [SMILES: COC(=O)c1ccc(NC(=O)c2c(C(F)(F)F)c(-c3ccccc3)nc3ccc(Br)cc23)c(F)c1]

To a solution of 32 mg (0.04 mmol, 76% purity) of the compound from example 80A in 1.6 ml of acetonitrile under argon were added 27 mg (0.21 mmol) of silver(I) fluoride, and the mixture was stirred at 80° C. for 30 min. After cooling to RT, the solid constituents were filtered off, and the filtrate was purified by means of preparative HPLC (method 19). 4.5 mg (18% of theory, 90% purity) of the title compound were obtained.

LC/MS (Method 23, ESIpos): $R_t$=4.22 min, m/z=547/549 $[M+H]^+$.

Example 82A

Methyl 4-{[(6-chloro-3-methyl-2-phenylquinolin-4-yl)carbonyl]amino}-3-fluorobenzoate

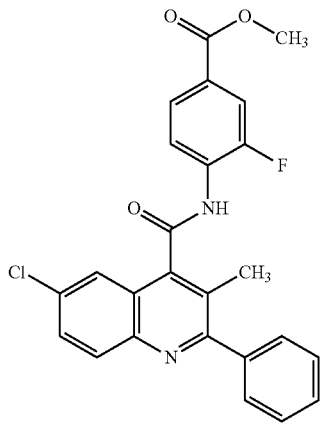 [SMILES: COC(=O)c1ccc(NC(=O)c2c(C)c(-c3ccccc3)nc3ccc(Cl)cc23)c(F)c1]

To a solution of 210 mg (0.71 mmol) of 6-chloro-3-methyl-2-phenylquinoline-4-carboxylic acid in 5 ml of DMF were added, at RT, 239 mg (1.41 mmol) of methyl 4-amino-3-fluorobenzoate, 402 mg (1.06 mmol) of HATU and 182 mg (1.41 mmol) of N,N-diisopropylethylamine. The mixture was stirred at 60° C. for 1 h. After cooling to RT, the mixture was introduced into 10% aqueous citric acid solution, and the precipitate formed was filtered off, washed three times with water and dried under reduced pressure. The material thus obtained was suspended in 4.5 ml of DMF, 117 mg (0.69 mmol) of methyl 4-amino-3-fluorobenzoate and 0.94 ml (0.94 mmol) of a 1 M solution of potassium tert-butoxide in THF were added to the suspension at RT, and the mixture was stirred at RT for 30 min. Thereafter, the mixture was introduced into 30 ml of 10% aqueous citric acid solution, and extracted twice with ethyl acetate. The combined organic phases were dried over sodium sulfate, filtered and concentrated. The residue was taken up in a mixture of DMSO, water and acetonitrile and, after some suspended material had been filtered off, purified by means of preparative HPLC (method 19). The combined product-containing fractions were concentrated down to a residual volume of aqueous phase, and the aqueous residue was extracted twice with ethyl acetate. The combined ethyl acetate phases were dried over sodium sulfate, filtered and concentrated. The residue was dried under reduced pressure. 78 mg (25% of theory, 100% purity) of the title compound were obtained.

$^1$H-NMR (400 MHz, DMSO-$d_6$): δ [ppm]=11.10 (s, 1H), 8.28 (t, 1H), 8.15-8.07 (m, 1H), 7.91 (d, 1H), 7.88-7.79 (m, 3H), 7.66-7.60 (m, 2H), 7.60-7.49 (m, 3H), 3.89 (s, 3H), 2.43 (s, 3H).

LC/MS (Method 1, ESIpos): $R_t$=1.19 min, m/z=449 $[M+H]^+$.

Example 83A

Methyl 4-{[(6-bromo-3-methyl-2-phenylquinolin-4-yl)carbonyl]amino}-3-[(methoxymethyl)sulfonyl]benzoate

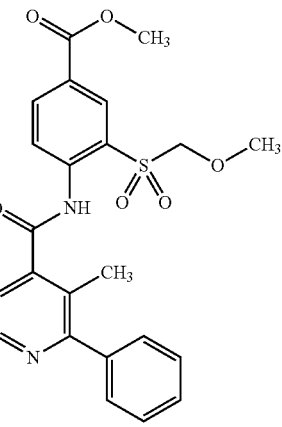

To a solution of 134 mg (0.24 mmol) of the compound from example 72A in 3.5 ml of dichloromethane were added 120 mg (0.49 mmol, 70% purity) of 3-chloroperbenzoic acid. The mixture was stirred at RT for 15 min. Subsequently, the mixture was diluted with dichloromethane and washed with saturated sodium hydrogencarbonate solution. The aqueous phase was reextracted once with dichloromethane, and the combined organic phases were dried over magnesium sulfate, filtered and concentrated. The residue was purified by means of preparative HPLC (method 18). Drying under reduced pressure gave 77 mg (54% of theory, purity 100%) of the title compound.

LC/MS (Method 1, ESIpos): $R_t$=1.24 min, m/z=583/585 [M+H]$^+$.

$^1$H-NMR (500 MHz, DMSO-d$_6$): δ [ppm]=10.63 (s, 1H), 8.51-8.46 (m, 2H), 8.43 (dd, 1H), 8.20 (d, 1H), 8.05 (d, 1H), 7.95 (dd, 1H), 7.67-7.62 (m, 2H), 7.59-7.49 (m, 3H), 5.03 (s, 2H), 3.94 (s, 3H), 3.41 (s, 3H).

Example 84A 6-tert-Butyl-3-methyl-2-phenylquinoline-4-carboxylic acid

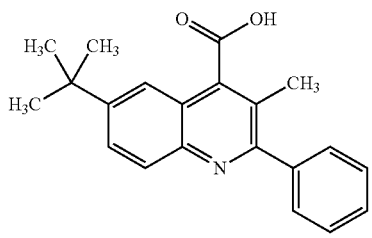 [SMILES: Cc1c(-c2ccccc2)nc2ccc(C(C)(C)C)cc2c1C(=O)O]

5.00 g (24.60 mmol) of 5-tert-butyl-1H-indole-2,3-dione were initially charged in 50 ml of acetic acid, and 3.30 g (24.60 mmol) of 1-phenylpropan-1-one were added. The reaction mixture was stirred at 75° C. for 5 min. Subsequently, 18 ml of concentrated hydrochloric acid were added, and the mixture was stirred at 105° C. overnight. After cooling to RT, the reaction mixture was added to 1 liter of 1 M hydrochloric acid and the precipitated solids were filtered off. The solids were washed with water, dried under air and then stirred with 50 ml of acetonitrile. The solids were filtered off again and dried under air and finally under reduced pressure. 4.85 g (61% of theory, 99% purity) of the title compound were obtained.

$^1$H-NMR (400 MHz, DMSO-d$_6$): δ [ppm]=14.09 (br. s, 1H), 7.99 (d, 1H), 7.92 (dd, 1H), 7.66 (d, 1H), 7.62-7.57 (m, 2H), 7.55-7.45 (m, 3H), 2.37 (s, 3H), 1.39 (s, 9H).

LC/MS (Method 1, ESIpos): $R_t$=0.69 min, m/z=320 [M+H]$^+$.

Example 85A

Methyl 4-{[(6-tert-butyl-3-methyl-2-phenylquinolin-4-yl)carbonyl]amino}-3-fluorobenzoate

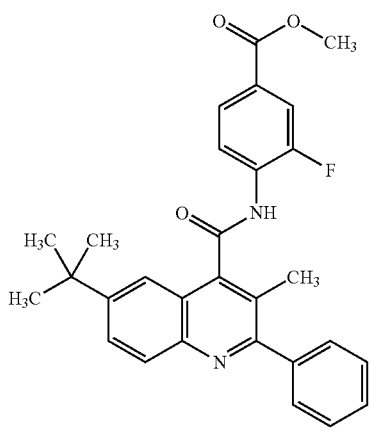 [SMILES: COC(=O)c1ccc(NC(=O)c2c(C)c(-c3ccccc3)nc3ccc(C(C)(C)C)cc23)c(F)c1]

To a solution of 200 mg (0.63 mmol) of the compound from example 84A and 127 mg (0.75 mmol) of methyl 4-amino-3-fluorobenzoate in 5.0 ml of DMF under argon were added 357 mg (0.94 mmol) of HATU and 162 mg (1.25 mmol) of N,N-diisopropylethylamine. The mixture was stirred at 60° C. overnight. Subsequently, another 127 mg (0.51 mmol) of methyl 4-amino-3-fluorobenzoate were added, and the mixture was stirred at 60° C. for a further 7.5 h and then left to stand at RT for about 80 h. Thereafter, 0.94 ml (0.94 mmol) of a 1 M solution of potassium tert-butoxide in THF was added, and the mixture was stirred for a while and then left to stand at RT for a further night. Another 0.94 ml (0.94 mmol) of a 1 M solution of potassium tert-butoxide in THF was added, and the mixture was first stirred at RT for 8 h and then left to stand at RT for a further night. Thereafter, the mixture was introduced into about 40 ml of 5% aqueous citric acid solution, and extracted twice with ethyl acetate. The combined organic phases were washed once with saturated sodium chloride solution, dried over magnesium sulfate, filtered and concentrated. The residue was purified by means of preparative HPLC (method 18). The combined product-containing fractions were concentrated, and the residue was taken up in dichloromethane, concentrated again and then dried under reduced pressure. 86 mg (28% of theory, 98% purity) of the title compound were obtained.

$^1$H-NMR (400 MHz, DMSO-d$_6$): δ [ppm]=11.07 (s, 1H), 8.10 (t, 1H), 8.05 (d, 1H), 7.96 (dd, 1H), 7.92 (dd, 1H), 7.87 (dd, 1H), 7.77 (d, 1H), 7.65-7.60 (m, 2H), 7.59-7.49 (m, 3H), 3.89 (s, 3H), 2.42 (s, 3H), 1.38 (s, 9H).

LC/MS (Method 1, ESIpos): $R_t$=1.28 min, m/z=471 [M+H]$^+$.

Example 86A tert-Butyl [2-nitro-5-(pentafluoro-λ$^6$-sulfanyl)phenyl]acetate

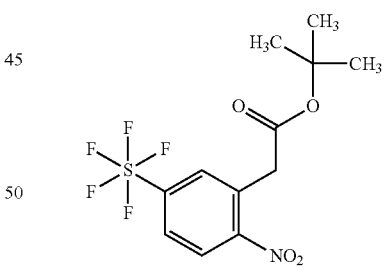

24.90 g (99.94 mmol) of 1-nitro-4-(pentafluoro-λ$^6$-sulfanyl)benzene were initially charged in 200 ml of anhydrous DMF under argon. The solution was cooled to −30° C., and 15.05 g (14.30 ml, 99.94 mmol) of tert-butyl chloroacetate were added. Then a solution of 44.86 g (339.74 mmol) of potassium tert-butoxide in 400 ml of anhydrous DMF was slowly added dropwise. A deep blue solution formed. The reaction mixture was stirred overnight, in the course of which it warmed up gradually to room temperature. Thereafter, the reaction solution was added cautiously to a tert-butyl methyl ether/water mixture while stirring. The phases were separated, and the organic phase was washed once with water and dried over sodium sulfate. The solvent was removed, and the residue was purified by column chromatography (silica gel, eluent: cyclohexane/ethyl acetate 20:1). After the solvent had been removed, the residue was stirred in pentane. The solids were filtered off and dried under reduced pressure. 13.67 g (38% of theory, >99% purity) of the title compound were obtained.

$^1$H-NMR (400 MHz, DMSO-d$_6$): δ [ppm]=8.28 (d, 1H), 8.26 (d, 1H), 8.14 (dd, 1H), 4.12 (s, 2H), 1.39 (s, 9H).

LC/MS (Method 22, ESIneg): R$_t$=2.64 min, m/z=362 [M–H]–.

Example 87A tert-Butyl [2-amino-5-(pentafluoro-λ$^6$-sulfanyl)phenyl]acetate

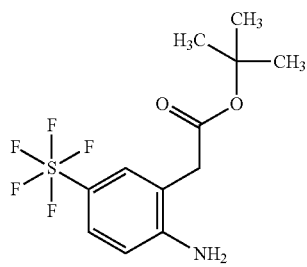 [SMILES: CC(C)(C)OC(=O)Cc1cc(S(F)(F)(F)(F)F)ccc1N]

13.67 g (37.63 mmol) of the compound from example 86A were initially charged together with 1.98 g (1.88 mmol) of palladium on activated carbon (10%) in 500 ml of ethanol. The reaction mixture was hydrogenated at RT under standard pressure for 3 h. After the reaction had ended, the palladium catalyst was filtered off through Celite and the filtrate was concentrated. The residue was stirred with a pentane/tert-butyl methyl ether mixture, and the solids were filtered off and dried under reduced pressure. 10 g (80% of theory, >99% purity) of the title compound were obtained.

$^1$H-NMR (400 MHz, DMSO-d$_6$): δ [ppm]=7.49-7.36 (m, 2H), 6.68 (d, 1H), 5.75 (s, 2H), 3.50 (s, 2H), 1.40 (s, 9H).

LC/MS (Method 22, ESIpos): R$_t$=2.53 min, m/z=278 [M–C$_4$H$_8$+H]$^+$.

Example 88A

3-Methyl-6-(pentafluoro-λ$^6$-sulfanyl)-2-phenylquinoline-4-carboxylic Acid

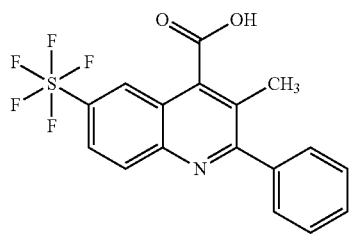 [SMILES: Cc1c(-c2ccccc2)nc2ccc(S(F)(F)(F)(F)F)cc2c1C(=O)O]

4.79 g (14.38 mmol) of the compound from example 87A were initially charged in 71.4 ml of acetic acid. 2.13 g (1.94 ml, 14.38 mmol) of 1-phenylpropane-1,2-dione were added, and the reaction mixture was stirred at 75° C. for 5 min. Then 23.8 ml of conc. hydrochloric acid were added, and stirring of the mixture was continued at 105° C. overnight. The reaction mixture was then added cautiously to an ethyl acetate/water mixture while stirring. The phases were separated, and the aqueous phase was extracted three times with ethyl acetate. The combined organic phases were dried over sodium sulfate and the solvent was removed. The residue was stirred with a pentane/tert-butyl methyl ether mixture. The solids were filtered off and then purified by means of column chromatography (silica gel, eluent: ethyl acetate/methanol 10:1). After the solvent had been removed, the solids were dried under reduced pressure. 980 mg (17% of theory, 99% purity) of the title compound were obtained.

$^1$H-NMR (400 MHz, DMSO-d$_6$): δ [ppm]=15.02 (br. s, 1H), 8.31 (d, 1H), 8.26-8.14 (m, 2H), 7.67-7.58 (m, 2H), 7.58-7.48 (m, 3H), 2.40 (s, 3H).

LC/MS (Method 1, ESIpos): R$_t$=1.00 min, m/z=390 [M+H]+.

Example 89A

1H-Imidazol-1-yl[3-methyl-6-(pentafluoro-λ$^6$-sulfanyl)-2-phenylquinolin-4-yl]methanone

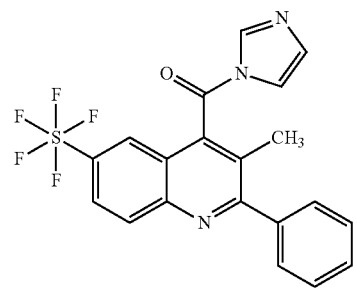 [SMILES: Cc1c(-c2ccccc2)nc2ccc(S(F)(F)(F)(F)F)cc2c1C(=O)n1ccnc1]

838 mg (2.15 mmol) of the compound from example 88A were dissolved in 5 ml of DMF, and 698 mg (4.30 mmol) of N,N'-carbonyldiimidazole were added at RT. The reaction mixture was stirred at 60° C. overnight. Thereafter, a further 174 mg (1.08 mmol) of N,N'-carbonyldiimidazole were added, and the mixture was stirred at 60° C. for a further hour. Another 349 mg (2.15 mmol) of N,N'-carbonyldiimidazole were added and the mixture was stirred at 60° C. for another 3 h. The reaction mixture was then admixed with water and tert-butyl methyl ether. The phases were separated, and the aqueous phase was extracted three times with tert-butyl methyl ether. The combined organic phases were dried over sodium sulfate. After the solvent had been removed, the residue was dried under reduced pressure overnight. 520 mg (52% of theory, 95% purity) of the title compound were obtained.

$^1$H-NMR (400 MHz, DMSO-d$_6$): δ [ppm]=8.90-7.37 (br. m, 2H), 8.36 (d, 1H), 8.28 (dd, 1H), 8.04 (br. s, 1H), 7.78-7.67 (m, 2H), 7.63-7.49 (m, 3H), 7.23 (br. s, 1H), 2.28 (s, 3H).

LC/MS (Method 1, ESIpos): R$_t$=1.18 min, m/z=440 [M+H]$^+$.

Example 90A

Methyl 3-fluoro-4-({[3-methyl-6-(pentafluoro-λ⁶-sulfanyl)-2-phenylquinolin-4-yl]carbonyl}amino)benzoate

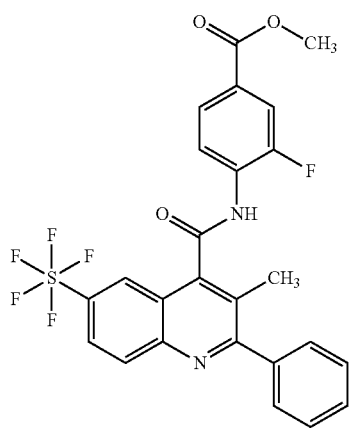 [SMILES: COC(=O)c1ccc(NC(=O)c2c(C)c(-c3ccccc3)nc3ccc(S(F)(F)(F)(F)F)cc23)c(F)c1]

100 mg (0.23 mmol) of the compound from example 89A and 39 mg (0.23 mmol) of methyl 4-amino-3-fluorobenzoate were dissolved in 2 ml of DMF. 0.57 ml (0.57 mmol) of a 1 M solution of potassium tert-butoxide in THF was added, and stirring of the mixture was continued at RT for 1 h. This was followed by addition of ethyl acetate and water. The phases were separated, and the aqueous phase was extracted three times with ethyl acetate. The combined organic phases were washed with water, dried over sodium sulfate, filtered and concentrated. The residue was stirred in a pentane/tert-butyl methyl ether mixture. The solids were filtered off and dried under reduced pressure. 117 mg (87% of theory, 91% purity) of the title compound were obtained.

$^1$H-NMR (400 MHz, DMSO-d$_6$): δ [ppm]=11.17 (s, 1H), 8.35-8.22 (m, 3H), 8.15 (t, 1H), 7.96-7.84 (m, 2H), 7.71-7.63 (m, 2H), 7.63-7.44 (m, 3H), 3.89 (s, 3H), 2.48 (s, 3H).

LC/MS (Method 1, ESIpos): R$_t$=1.33 min, m/z=541 [M+H]+.

Example 91A

Methyl 6-iodo-3-methyl-2-phenylquinoline-4-carboxylate

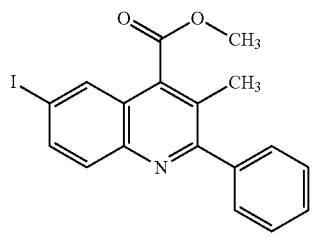 [SMILES: COC(=O)c1c(C)c(-c2ccccc2)nc2ccc(I)cc12]

22.4 g (57.5 mmol) of the compound from example 5A were initially charged together with 28.1 g (86.23 mmol) of cesium carbonate in 224 ml of acetonitrile under argon. 3.6 ml (57.5 mmol) of iodomethane were added at RT. The reaction mixture was heated to 40° C. and stirred for 1 h. Subsequently, a further 3.6 ml (57.5 mmol) of iodomethane were added, and the mixture was stirred at 40° C. for another 2 h. The reaction mixture was then cooled to RT, and ethyl acetate and water were added. The phases were separated, and the organic phase was washed once with saturated sodium carbonate solution. A precipitate was formed, which was filtered off through kieselguhr. The filtrate was dried over sodium sulfate, filtered and concentrated. The residue was purified by means of column chromatography (silica gel, eluent cyclohexane/ethyl acetate 10:1). Drying under reduced pressure gave 12.7 g (55% of theory, 96% purity) of the title compound.

$^1$H-NMR (400 MHz, DMSO-d$_6$): δ [ppm]=8.12 (d, 1H), 8.06 (dd, 1H), 7.84 (d, 1H), 7.64-7.59 (m, 2H), 7.57-7.47 (m, 3H), 4.07 (s, 3H), 2.35 (s, 3H).

LC/MS (Method 1, ESIpos): R$_t$=1.26 min, m/z=404 [M+H]+.

Example 92A

Methyl 6-formyl-3-methyl-2-phenylquinoline-4-carboxylate

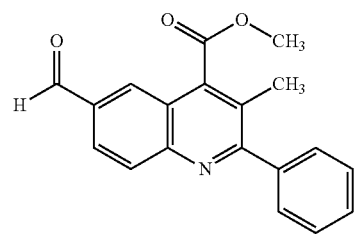 [SMILES: COC(=O)c1c(C)c(-c2ccccc2)nc2ccc(C(F)F)cc12]

5.0 g (12.4 mmol) of the compound from example 91A were dissolved in 98 ml of anhydrous THF under argon, and the mixture was cooled to −50° C. This was followed by successive dropwise addition of 35.4 ml (37.2 mmol) of a 1.05 M solution of isopropylmagnesium chloride/lithium chloride complex in THF and 3.2 ml (37.2 mmol) of 1,4-dioxane. The reaction mixture was stirred at −50° C. for 1 h and then cooled to −78° C. Then 9.5 ml (124 mmol) of absolute DMF were added dropwise. The reaction mixture was allowed to come to RT while stirring overnight, and then ethyl acetate and water were added. The phases were separated, and the organic phase was washed once with water, dried over sodium sulfate, filtered and concentrated. In the attempt to purify the residue by means of column chromatography (silica gel, eluent: cyclohexane/ethyl acetate 6:1), the product precipitated out on the column. The chromatographic purification was then stopped and the silica gel was stirred with ethyl acetate. After filtration, the filtrate was concentrated. The residue was stirred in methanol, and the solids were filtered off and dried under reduced pressure. 2.29 g (59% of theory, 98% purity) of the title compound were obtained.

$^1$H-NMR (400 MHz, DMSO-d$_6$): δ [ppm]=10.24 (s, 1H), 8.44 (d, 1H), 8.24-8.12 (m, 2H), 7.71-7.60 (m, 2H), 7.59-7.47 (m, 3H), 4.12 (s, 3H), 2.40 (s, 3H).

LC/MS (Method 1, ESIpos): R$_t$=1.06 min, m/z=306 [M+H]+.

Example 93A

Methyl 6-(difluoromethyl)-3-methyl-2-phenylquinoline-4-carboxylate

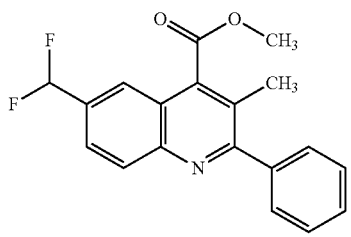

1.0 g (3.2 mmol) of the compound from example 92A were dissolved in 40 ml of dichloromethane. The mixture was cooled down to −78° C., and 1.4 g (7.86 mmol, 90% purity) of N-ethyl-N-(trifluoro-$\lambda^4$-sulfanyl)ethanamine (DAST) was added gradually. The reaction mixture was stirred overnight, in the course of which it warmed up to RT, and then saturated aqueous sodium hydrogencarbonate solution was added. The phases were separated, and the aqueous phase was extracted three times with ethyl acetate. The combined organic phases were dried over sodium sulfate, filtered and concentrated. The residue was purified by means of column chromatography (silica gel, eluent cyclohexane/ethyl acetate 5:1). After the solvent had been removed, the residue was dried under reduced pressure. 737 mg (69% of theory, >99% purity) of the title compound were obtained.

$^1$H-NMR (400 MHz, DMSO-d$_6$): δ [ppm]=8.21 (d, 1H), 8.02 (br. s, 1H), 7.95 (d, 1H), 7.69-7.61 (m, 2H), 7.59-7.48 (m, 3H), 7.28 (t, 1H), 4.09 (s, 3H), 2.38 (s, 3H).

LC/MS (Method 1, ESIpos): R$_t$=1.15 min, m/z=328 [M+H]$^+$.

Example 94A 6-(Difluoromethyl)-3-methyl-2-phenylquinoline-4-carboxylic acid

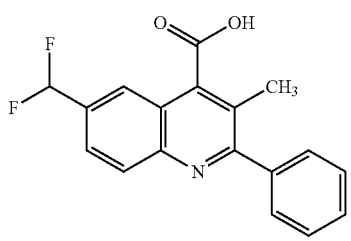 [SMILES: Cc1c(-c2ccccc2)nc2ccc(C(F)F)cc2c1C(=O)O]

100 mg (0.31 mmol) of the compound from example 93A were dissolved in 5 ml of a THF/methanol mixture (5:1), and 1.53 ml (1.53 mmol) of a 1 M solution of lithium hydroxide in water were added. The reaction mixture was stirred at 50° C. for 7 h and then cooled to RT, and ethyl acetate and water were added. The phases were separated, and the aqueous phase was adjusted to pH 1-2 with 1 M hydrochloric acid and extracted three times with ethyl acetate. The combined organic extracts were dried over sodium sulfate, filtered and concentrated. The residue was stirred in a pentane/tert-butyl methyl ether mixture, and the solids were filtered off and dried under reduced pressure. 61 mg (96% of theory, 99% purity) of the title compound were obtained.

$^1$H-NMR (400 MHz, DMSO-d$_6$): δ [ppm]=14.37 (br. s, 1H), 8.20 (d, 1H), 8.02 (d, 1H), 7.92 (dd, 1H), 7.67-7.61 (m, 2H), 7.59-7.49 (m, 3H), 7.33 (t, 1H), 2.42 (s, 3H).

LC/MS (Method 1, ESIpos): R$_t$=0.72 min, m/z=314 [M+H]$^+$.

Example 95A

Methyl 4-{[(6-bromo-3-methyl-2-phenylquinolin-4-yl)carbonyl]amino}-2,3-difluorobenzoate

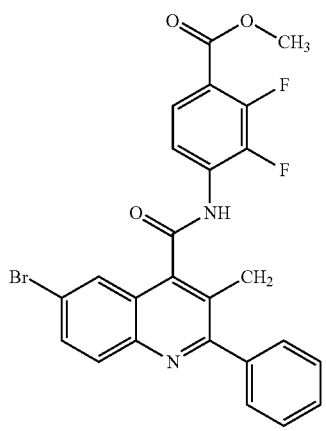 [SMILES: COC(=O)c1ccc(NC(=O)c2c(C)c(-c3ccccc3)nc3ccc(Br)cc23)c(F)c1F]

150 mg (0.38 mmol) of the compound from example 2A and 72 mg (0.38 mmol) of methyl 4-amino-2,3-difluorobenzoate were dissolved in 3.4 ml of DMF. 0.96 ml (0.96 mmol) of a 1 M solution of potassium tert-butoxide in THF was added, and stirring of the mixture was continued at RT for 1 h. This was followed by addition of ethyl acetate and water. The phases were separated, and the aqueous phase was extracted three times with ethyl acetate. The combined organic phases were washed with water and dried over sodium sulfate, and the solvent was removed on a rotary evaporator. The residue was dried under reduced pressure. 110 mg (50% of theory, 89% purity) of the title compound were obtained.

$^1$H-NMR (400 MHz, DMSO-d$_6$): δ [ppm]=11.29 (s, 1H), 8.12-8.00 (m, 2H), 7.98 (d, 1H), 7.93 (dd, 1H), 7.87-7.77 (m, 1H), 7.66-7.60 (m, 2H), 7.60-7.48 (m, 3H), 3.90 (s, 3H), 2.43 (s, 3H).

LC/MS (Method 23, ESIpos): R$_t$=4.00 min, m/z=511/513 [M+H]$^+$.

Example 96A

Methyl 4-{[(6-bromo-3-methyl-2-phenylquinolin-4-yl)carbonyl]amino}-2,5-difluorobenzoate

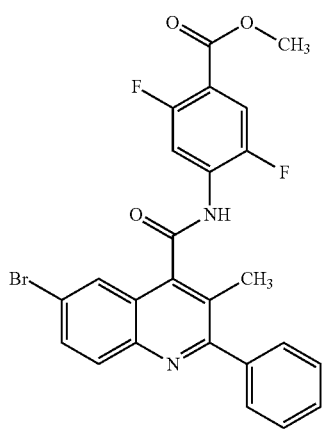 [SMILES: COC(=O)c1cc(F)c(NC(=O)c2c(C)c(-c3ccccc3)nc3ccc(Br)cc23)cc1F]

150 mg (0.38 mmol) of the compound from example 2A and 72 mg (0.38 mmol) of methyl 4-amino-2,5-difluorobenzoate were dissolved in 3.4 ml of DMF. 0.96 ml (0.96 mmol) of a 1 M solution of potassium tert-butoxide in THF was added, and stirring of the mixture was continued at RT for 1 h. This was followed by addition of ethyl acetate and water. The phases were separated, and the aqueous phase was extracted three times with ethyl acetate. The combined organic phases were washed with water and dried over sodium sulfate, and the solvent was removed. The residue was purified by means of column chromatography (25 g of silica gel, eluent: cyclohexane/ethyl acetate 4:1, Biotage Isolera™ One). After the solvent had been removed, the residue was dried under reduced pressure. 102 mg (44% of theory, 85% purity) of the title compound were obtained.

$^1$H-NMR (400 MHz, DMSO-d$_6$): δ [ppm]=11.27 (s, 1H), 8.31 (dd, 1H), 8.04 (d, 1H), 8.01 (d, 1H), 7.93 (dd, 1H), 7.81 (dd, 1H), 7.65-7.59 (m, 2H), 7.59-7.49 (m, 3H), 3.88 (s, 3H), 2.41 (s, 3H).

LC/MS (Method 1, ESIpos): R$_t$=1.23 min, m/z=511/513 [M+H]$^+$.

Example 97A

6-Bromo-3-fluoro-2-phenylquinoline-4-carboxylic acid

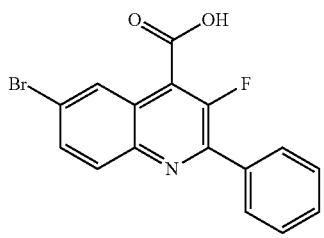 [SMILES: O=C(O)c1c(F)c(-c2ccccc2)nc2ccc(Br)cc12]

1.75 g (6.97 mmol, 90% purity) of 5-bromo-1H-indole-2,3-dione were initially charged in 15 ml of acetic acid, and 0.96 g (6.97 mmol) of 2-fluoro-1-phenylethanone was added. The reaction mixture was stirred at 75° C. for 5 min. Subsequently, 5 ml of conc. hydrochloric acid were added, and stirring of the mixture was continued at 115° C. overnight. After cooling to RT, the reaction mixture was added to 100 ml of 1 M hydrochloric acid. The precipitated solids were filtered off, washed twice with 10 ml of water and dried under reduced pressure. The residue was purified by means of preparative HPLC (method 18). 501 mg (20% of theory, 98% purity) of the title compound were obtained.

$^1$H-NMR (400 MHz, DMSO-d$_6$): δ [ppm]=14.66 (br. s, 1H), 8.21 (d, 1H), 8.11 (d, 1H), 8.04-7.96 (m, 3H), 7.62-7.56 (m, 3H).

LC/MS (Method 1, ESIpos): R$_t$=0.98 min, m/z=346/348 [M+H]$^+$.

Example 98A

Methyl 4-{[(6-bromo-3-fluoro-2-phenylquinolin-4-yl)carbonyl]amino}-3-fluorobenzoate

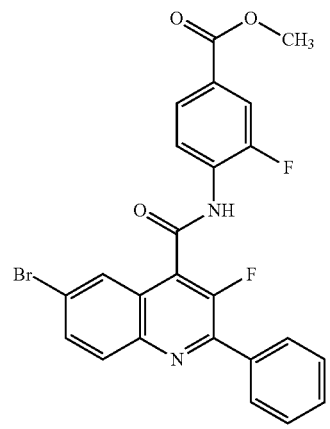 [SMILES: COC(=O)c1ccc(NC(=O)c2c(F)c(-c3ccccc3)nc3ccc(Br)cc23)c(F)c1]

To a solution of 200 mg (0.58 mmol) of the compound from example 97A in 4.1 ml of DMF were added, at RT, 195 mg (1.16 mmol) of methyl 4-amino-3-fluorobenzoate, 330 mg (0.87 mmol) of HATU and 149 mg (1.16 mmol) of N,N-diisopropylethylamine. The mixture was first stirred at 60° C. for 4.5 h and then left to stand at RT for two days. Thereafter, the mixture was introduced into aqueous 10% aqueous citric acid solution, and extracted twice with 30 ml of ethyl acetate. The combined organic phases were washed once with 60 ml of saturated sodium chloride solution, dried over sodium sulfate and concentrated. The residue was taken up in 3 ml of DMSO and 3 ml of acetonitrile, and purified by means of preparative HPLC (Method 18). 51 mg (16% of theory, 91% purity) of the title compound were obtained.

$^1$H-NMR (400 MHz, DMSO-d$_6$): [ppm]=11.25 (s, 1H), 8.39 (t, 1H), 8.17-8.12 (m, 2H), 8.09-8.03 (m, 2H), 8.00 (dd, 1H), 7.92 (dd, 1H), 7.85 (dd, 1H), 7.65-7.57 (m, 3H), 3.89 (s, 3H).

LC/MS (Method 23, ESIpos): R$_t$=4.30 min, m/z=497/499 [M+H]$^+$.

Example 99A

3-Chloro-6-iodo-2-phenylquinoline-4-carboxylic acid

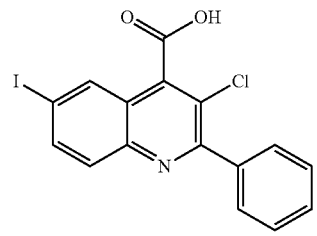 [SMILES: O=C(O)c1c(Cl)c(-c2ccccc2)nc2ccc(I)cc12]

10.00 g (36.63 mmol) of 5-iodo-1H-indole-2,3-dione were initially charged in 100 ml of acetic acid, and 5.66 g (36.63 mmol) of 2-chloro-1-phenylethanone were added. The reaction mixture was stirred at 75° C. for 5 min. Subsequently, 5 ml of conc. hydrochloric acid were added, and stirring of the mixture was continued at 105° C. overnight. After cooling to RT, the reaction mixture was added to 200 ml of 1 M hydrochloric acid. The precipitated solids were filtered off, washed twice with water and dried under reduced pressure. The solids were then stirred in 50 ml of acetonitrile, filtered off again and dried again under reduced pressure. 4.45 g (16% of theory, 54% purity) of the title compound were obtained.

LC/MS (Method 1, ESIpos): $R_t$=0.94 min, m/z=409 [M+H]$^+$.

Example 100A (3-Chloro-6-iodo-2-phenylquinolin-4-yl)(1H-imidazol-1-yl)methanone

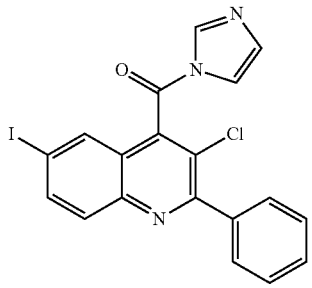 [SMILES: O=C(c1c(Cl)c(-c2ccccc2)nc2ccc(I)cc12)n1ccnc1]

To a solution of 700 mg (0.92 mmol, 54% purity) of the compound from example 99A in 6 ml of DMF were added, at RT, 165 mg (1.02 mmol) of N,N'-carbonyldiimidazole, and the mixture was stirred at 60° C. for 2 h. Subsequently, a further 165 mg (1.02 mmol) of N,N'-carbonyldiimidazole were added, and the mixture was stirred at 60° C. for another 4 h. After cooling to RT, the mixture was introduced into 50 ml of water while stirring. The solids formed were filtered off, washed twice with 2 ml each time of water and dried under reduced pressure. 699 mg (">100%" of theory, still containing solvent, 81% purity by LC/MS) of the title compound were obtained.

LC/MS (Method 1, ESIpos): $R_t$=1.17 min, m/z=460 [M+H]$^+$.

Example 101A

Methyl 4-{[(3-chloro-6-iodo-2-phenylquinolin-4-yl)carbonyl]amino}-3-fluorobenzoate

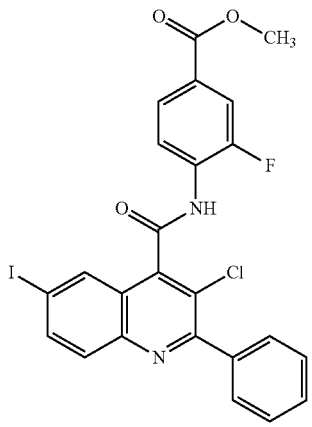 [SMILES: COC(=O)c1ccc(NC(=O)c2c(Cl)c(-c3ccccc3)nc3ccc(I)cc23)c(F)c1]

To a solution of 110 mg (0.23 mmol) of the compound from example 100A and 61 mg (0.36 mmol) of methyl 4-amino-3-fluorobenzoate in 2 ml of DMF was added 0.36 ml (0.36 mmol) of a 1 M solution of potassium tert-butoxide in THF, and the mixture was stirred at RT for 1 h. Subsequently, the mixture was purified directly by means of preparative HPLC (method 24). 46 mg (31% of theory, 90% purity) of the title compound were obtained.

LC/MS (Method 23, ESIpos): $R_t$=4.26 min, m/z=561 [M+H]$^+$.

Example 102A

6-Bromo-3-chloro-2-phenylquinoline-4-carboxylic acid

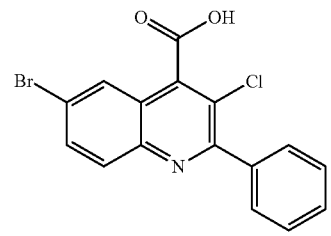 [SMILES: O=C(O)c1c(Cl)c(-c2ccccc2)nc2ccc(Br)cc12]

10.00 g (44.24 mmol) of 5-bromo-1H-indole-2,3-dione were initially charged in 120 ml of acetic acid, and 6.84 g (44.24 mmol) of 2-chloro-1-phenylethanone were added. The reaction mixture was stirred at 75° C. for 5 min. Subsequently, 5 ml of conc. hydrochloric acid were added, and stirring of the mixture was continued at 105° C. overnight. After cooling to RT, the reaction mixture was added to 200 ml of 1 M hydrochloric acid. The precipitated solids were filtered off, washed twice with water and dried under reduced pressure. The solids were then stirred in 50 ml of acetonitrile, filtered off again and dried again under reduced pressure. 5.60 g (29% of theory, 82% purity) of the title compound were obtained.

LC/MS (Method 1, ESIpos): $R_t$=0.88 min, m/z=362/364 [M+H]$^+$.

Example 103A (6-Bromo-3-chloro-2-phenylquinolin-4-yl)(1H-imidazol-1-yl)methanone

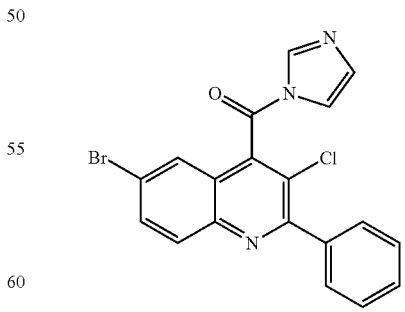

To a solution of 500 mg (1.13 mmol, 82% purity) of the compound from example 102A in 5 ml of DMF were added, at RT, 202 mg (1.24 mmol) of N,N'-carbonyldiimidazole, and the mixture was stirred at 60° C. for 2 h. Subsequently, a further 202 mg (1.24 mmol) of N,N'-carbonyldiimidazole were added, and the mixture was stirred at 60° C. for another 4 h. After cooling to RT, the mixture was admixed with 50 ml of aqueous citric acid solution. The solids formed were filtered off, washed twice with 2 ml each time of water and dried under reduced pressure. 553 mg (95% of theory, 80% purity) of the title compound were obtained.

LC/MS (Method 1, ESIpos): $R_t$=1.14 min, m/z=412/414 [M+H]$^+$.

Example 104A

Methyl 4-{[(6-bromo-3-chloro-2-phenylquinolin-4-yl)carbonyl]amino}-3-fluorobenzoate

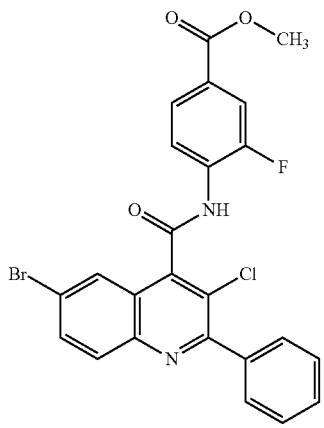

To a mixture of 80 mg (0.19 mmol) of the compound from example 103A and 49 mg (0.29 mmol) of methyl 4-amino-3-fluorobenzoate in 2 ml of DMF was added 0.29 ml (0.29 mmol) of a 1 M solution of potassium tert-butoxide in THF, and the mixture was stirred at RT for 1 h. Subsequently, the mixture was purified directly by means of preparative HPLC (method 24). 45 mg (38% of theory, 85% purity) of the title compound were obtained.

LC/MS (Method 23, ESIpos): $R_t$=4.19 min, m/z=513/515 [M+H]$^+$.

Example 105A

6-Bromo-3-cyclopropyl-2-phenylquinoline-4-carboxylic acid

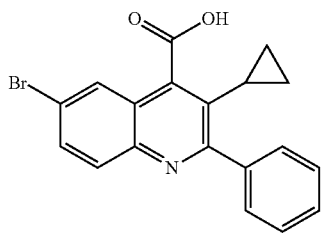 [SMILES: O=C(O)c1c(C2CC2)c(-c2ccccc2)nc2ccc(Br)cc12]

Method A:

1.75 g (6.97 mmol, 90% purity) of 5-bromo-1H-indole-2,3-dione were initially charged in 15 ml of acetic acid, and 1.12 g (6.97 mmol) of 2-cyclopropyl-1-phenylethanone was added [preparation described in WO 2009/143049-A1, p. 182, Compound 99A]. The reaction mixture was stirred at 75° C. for 5 min. Subsequently, 5 ml of conc. hydrochloric acid were added, and stirring of the mixture was continued at 110° C. for 2.5 h and then at RT overnight. The reaction mixture was then added to 100 ml of 1 M hydrochloric acid. The precipitated solids were filtered off, washed twice with 10 ml of water and dried under reduced pressure. 2.23 g of a crude product were obtained. 200 mg of this crude product were purified by preparative HPLC (Method 4). This was used to obtain 43 mg (1.5% of theory based on 6.97 mmol of reactant, 93% purity) of the title compound.

Method B:

To a solution of 2.03 g (8.12 mmol, 90% purity) of 5-bromo-1H-indole-2,3-dione in 20 ml of ethanol were added, at RT, 1.95 g (12.18 mmol) of 2-cyclopropyl-1-phenylethanone [preparation described in WO 2009/143049-A1, p. 182, Compound 99A] and 2.05 g (36.56 mmol) of potassium hydroxide. The reaction mixture was stirred at bath temperature 100° C. for 1 h. After cooling to RT, the mixture was admixed with 300 ml of water and adjusted to pH 2 with conc. hydrochloric acid. The mixture was extracted twice with 20 ml each time of ethyl acetate. The combined organic phases were dried over sodium sulfate, filtered and concentrated. The residue was suspended in a mixture of 30 ml of DMSO and 10 ml of acetonitrile, and the remaining solids were filtered off and dried under reduced pressure. In this way, 107 mg (4% of theory, purity 100%) of a first batch of the title compound were obtained. The filtrate was concentrated, and the residue was purified by means of preparative HPLC (method 3), which gave 750 mg (25% of theory, 100% purity) of a second batch of the title compound.

$^1$H-NMR (400 MHz, DMSO-d$_6$): [ppm]=14.22 (br. s, 1H), 8.01 (d, 1H), 7.97 (d, 1H), 7.93 (dd, 1H), 7.76-7.71 (m, 2H), 7.54-7.46 (m, 3H), 2.38-2.28 (m, 1H), 0.76-0.66 (m, 2H), 0.33-0.25 (m, 2H).

LC/MS (Method 1, ESIpos): $R_t$=0.91 min, m/z=368/370 [M+H]$^+$.

Example 106A

Methyl 4-{[(6-bromo-3-cyclopropyl-2-phenylquinolin-4-yl)carbonyl]amino}-3-fluorobenzoate

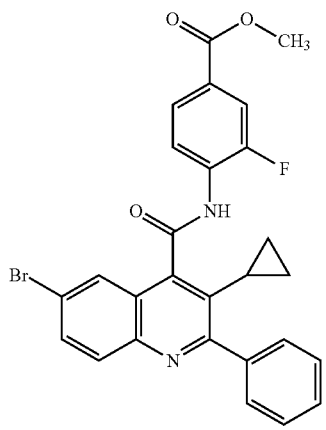 [SMILES: COC(=O)c1ccc(NC(=O)c2c(C3CC3)c(-c3ccccc3)nc3ccc(Br)cc23)c(F)c1]

To a solution of 400 mg (1.09 mmol) of the compound from example 105A in 6 ml of DMF were added, at RT, 367 mg (2.17 mmol) of methyl 4-amino-3-fluorobenzoate, 620 mg (1.63 mmol) of HATU and 281 mg (2.17 mmol) of N,N-diisopropylethylamine. The mixture was stirred at 60° C. for 5 h. Thereafter, a further 140 mg (1.09 mmol) of N,N-diisopropylethylamine were added, and the mixture was stirred at 60° C. for another 2 h. After cooling to RT, 2.17 ml (2.17 mmol) of a 1 M solution of potassium tert-butoxide in THF were added, and stirring of the mixture was continued at RT for 18 h. Subsequently, another 2.17 ml (2.17 mmol) of a 1 M solution of potassium tert-butoxide in THF were added, and stirring of the mixture was continued at RT for another 2 h. Thereafter, the mixture was introduced into 80 ml of a 10% aqueous citric acid solution, and extracted twice with 50 ml each time of ethyl acetate. The combined organic phases were dried over sodium sulfate, filtered and concentrated. The residue was taken up in a mixture of DMSO and water, and purified by means of preparative HPLC (method 18). 3.4 mg (0.6% of theory, 100% purity) of a first batch of the title compound and 33 mg (5% of theory, 77% purity) of a second batch of the title compound were obtained.

$^1$H-NMR (500 MHz, DMSO-d$_6$): [ppm]=11.04 (s, 1H), 8.31 (t, 1H), 8.07-8.03 (m, 2H), 7.96-7.91 (m, 2H), 7.86 (dd, 1H), 7.76 (dd, 2H), 7.56-7.48 (m, 3H), 3.90 (s, 3H), 2.43-2.32 (m, 1H), 0.68 (d, 2H), 0.32 (d, 2H).

LC/MS (Method 1, ESIpos): R$_t$=1.31 min, m/z=519/521 [M+H]$^+$.

Example 107A

6-Bromo-3,8-dimethyl-2-phenylquinoline-4-carboxylic acid

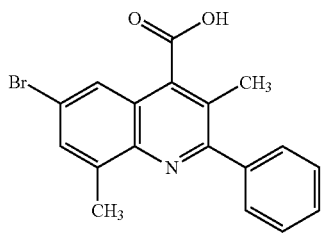 [SMILES: Cc1c(-c2ccccc2)nc2c(C)cc(Br)cc2c1C(=O)O]

3.00 g (12.50 mmol) of 5-bromo-7-methyl-1H-indole-2,3-dione were initially charged in 34 ml of acetic acid, and 1.68 g (12.50 mmol) of 1-phenylpropan-1-one were added. The reaction mixture was stirred at 75° C. for 5 min. Subsequently, 11 ml of conc. hydrochloric acid were added, and stirring of the mixture was continued at 115° C. overnight. After cooling to RT, the reaction mixture was added to 200 ml of 1 M hydrochloric acid. The precipitated solids were filtered off, washed twice with 10 ml of water and dried under reduced pressure. 3.02 g (64% of theory, 94% purity) of the title compound were obtained.

$^1$H-NMR (400 MHz, DMSO-d$_6$): [ppm]=14.31 (br. s, 1H), 7.83 (s, 1H), 7.77-7.63 (m, 3H), 7.57-7.49 (m, 3H), 2.70 (s, 3H), 2.41 (s, 3H).

LC/MS (Method 1, ESIpos): R$_t$=1.15 min, m/z=356/358 [M+H]$^+$.

Example 108A

Methyl 4-{[(6-bromo-3,8-dimethyl-2-phenylquinolin-4-yl)carbonyl]amino}-3-fluorobenzoate

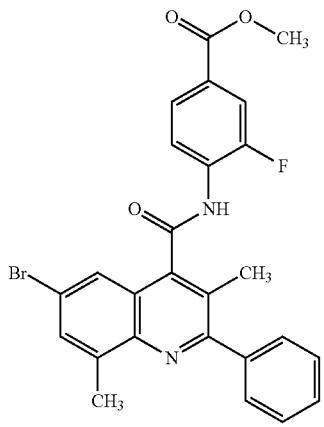 [SMILES: COC(=O)c1ccc(NC(=O)c2c(C)c(-c3ccccc3)nc3c(C)cc(Br)cc23)c(F)c1]

To a solution of 500 mg (1.32 mmol, 94% purity) of the compound from example 107A in 9 ml of DMF were added, at RT, 448 mg (2.65 mmol) of methyl 4-amino-3-fluorobenzoate, 755 mg (1.98 mmol) of HATU and 342 mg (2.65 mmol) of N,N-diisopropylethylamine. The mixture was stirred at 60° C. for 2 h. Thereafter, a further 171 mg (1.32 mmol) of N,N-diisopropylethylamine were added, and the mixture was stirred at 60° C. for another 7 h. After cooling to RT, 2.65 ml (2.65 mmol) of a 1 M solution of potassium tert-butoxide in THF were added, and stirring of the mixture was continued at RT for 2 h. Subsequently, another 2.65 ml (2.65 mmol) of a 1 M solution of potassium tert-butoxide in THF were added, and stirring of the mixture was continued at RT for two days. Thereafter, the mixture was introduced into 200 ml of a 10% aqueous citric acid solution. The precipitate formed was filtered off and dried under reduced pressure. 651 mg (78% of theory, 80% purity) of the title compound were obtained.

LC/MS (Method 1, ESIpos): R$_t$=1.35 min, m/z=507/509 [M+H]$^+$.

WORKING EXAMPLES

Example 1

4-{[(6-Bromo-3-methyl-2-phenylquinolin-4-yl)carbonyl]amino}benzoic acid

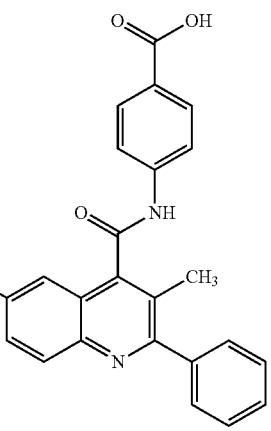

To 177 mg (0.36 mmol) of the compound from example 34A were added first 4.5 ml of THF and then a solution of 13 mg (0.54 mmol) of lithium hydroxide in 1.5 ml of water. The reaction mixture was stirred at RT for eight days and then adjusted to pH 1-2 with 2 M hydrochloric acid. The precipitated solids were filtered off, washed with water, and dried under reduced pressure at 60° C. overnight. 109 mg (65% of theory, 100% purity) of the title compound were obtained.

$^1$H-NMR (400 MHz, DMSO-d$_6$): [ppm]=11.25 (s, 1H), 8.06 (d, 1H), 8.01-7.99 (m, 2H), 7.95 (dd, 1H), 7.92-7.87 (m, 3H), 7.65-7.63 (m, 2H), 7.58-7.51 (m, 3H), 2.41 (s, 3H).

LC/MS (Method 1, ESIpos): R$_t$=1.08 min, m/z=461/463 [M+H]$^+$.

Example 2

6-{[(6-Bromo-3-methyl-2-phenylquinolin-4-yl)carbonyl]amino}nicotinic acid imidazole salt

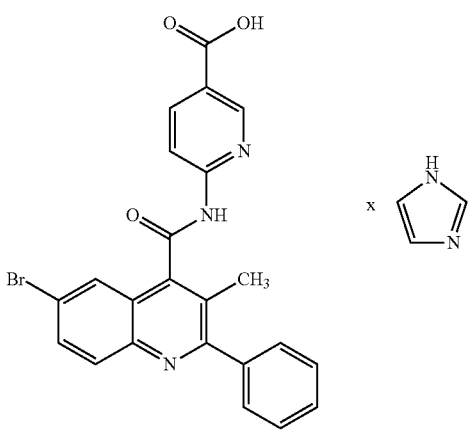 [SMILES: Cc1c(-c2ccccc2)nc2ccc(Br)cc2c1C(=O)Nc1ccc(C(=O)O)cn1 ; c1c[nH]cn1]

To 100 mg (0.26 mmol) of the compound from example 2A were successively added 2 ml of THF, 47 mg (0.31 mmol) of methyl 6-aminonicotinate and 22 mg (0.56 mmol) of sodium hydride (60% in mineral oil). The reaction mixture was stirred at RT overnight, and then it was purified, without further workup, by means of preparative HPLC (method 8). 15 mg (11% of theory, 100% purity) of the title compound were obtained.

$^1$H-NMR (400 MHz, DMSO-$d_6$): [ppm]=12.54 (br. s, 1H), 11.65 (s, 1H), 8.85 (d, 1H), 8.43 (d, 1H), 8.36 (dd, 1H), 8.03 (d, 1H), 7.93-7.90 (m, 2H), 7.64-7.61 (m, 4H), 7.58-7.49 (m, 4H), 7.01 (s, 1H), 2.40 (s, 3H).

LC/MS (Method 1, ESIpos): $R_t$=1.07 min, m/z=462/464 [M+H]$^+$.

Example 3

5-{[(6-Bromo-3-methyl-2-phenylquinolin-4-yl)carbonyl]amino}pyrazine-2-carboxylic Acid

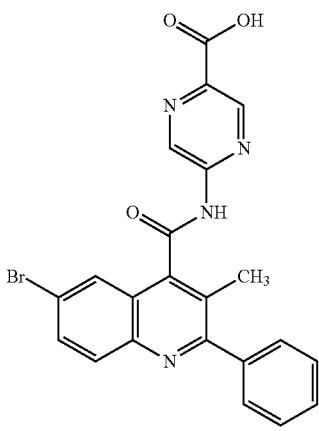 [SMILES: Cc1c(-c2ccccc2)nc2ccc(Br)cc2c1C(=O)Nc1cnc(C(=O)O)cn1]

100 mg (0.26 mmol) of the compound from example 2A and 43 mg (0.26 mmol) of ethyl 5-aminopyrazine-2-carboxylate were dissolved in 2 ml of DMF. 72 mg (0.64 mmol) of potassium tert-butoxide were added in portions to the solution. The reaction mixture was stirred at RT overnight, and then 1.3 ml (1.3 mmol) of 1 M sodium hydroxide solution were added. After stirring at 80° C. for 1 h and cooling to RT, the mixture was adjusted to pH 1-2 with 1 M hydrochloric acid. The mixture was extracted with ethyl acetate, and the organic phase was removed and washed with saturated sodium chloride solution. After the organic phase had been dried over sodium sulfate and the solvent had been removed on a rotary evaporator, the residue was taken up in a little DMF and purified by means of preparative HPLC (method 6). After the solvent-water mixture had been removed, the residue was taken up in a little acetonitrile, water was added and then the mixture was lyophilized. Since solvent residues were still present, the lyophilizate was redissolved in dichloromethane and ethyl acetate, water was added again and the mixture was lyophilized again. The resulting lyophilizate was redissolved once again in dichloromethane and tert-butanol, water was added and the mixture was lyophilized again. The lyophilizate thus obtained was dried at 100° C. under high vacuum for a total 9 h. In this way, 39 mg (29% of theory, 90% purity) of the title compound were obtained.

$^1$H-NMR (600 MHz, DMSO-$d_6$): δ [ppm]=13.54 (br. s, 1H), 12.03 (s, 1H), 9.71 (s, 1H), 9.01 (s, 1H), 8.10 (d, 1H), 8.04 (d, 1H), 7.93 (dd, 1H), 7.66-7.60 (m, 2H), 7.58-7.50 (m, 3H), 2.41 (s, 3H).

LC/MS (Method 1, ESIpos): $R_t$=0.96 min, m/z=463/465 [M+H]$^+$.

Example 4

5-{[(6-Bromo-3-methyl-2-phenylquinolin-4-yl)carbonyl]amino}pyrimidine-2-carboxylic Acid

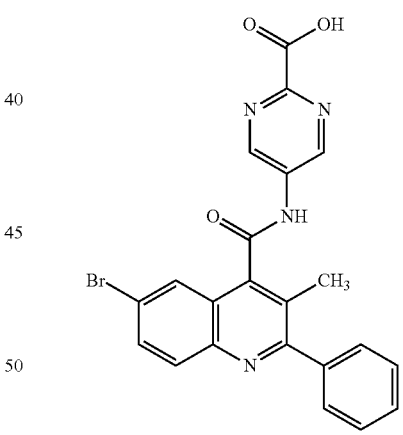

A solution of 23 mg (0.05 mmol) of the compound from example 36A in 0.7 ml of a THF/methanol mixture (5:1) was admixed with 0.24 ml (0.24 mmol) of 1 M sodium hydroxide solution and stirred under reflux for 1 h. After cooling to RT, the mixture, without further workup, was purified by means of preparative HPLC (method 15). The acetonitrile-water mixture was removed on a rotary evaporator and the residue was dried under reduced pressure overnight. 10 mg (22% of theory, 98% purity) of the title compound were obtained.

$^1$H-NMR (400 MHz, CD$_3$OD): [ppm]=9.41 (br. s, 2H), 8.12 (s, 1H), 8.05 (d, 1H), 7.95 (d, 1H), 7.71-7.51 (m, 5H), 2.50 (s, 3H).

LC/MS (Method 1, ESIpos): $R_t$=0.90 min, m/z=463/465 [M+H]$^+$.

Example 5

5-{[(6-Bromo-3-methyl-2-phenylquinolin-4-yl)carbonyl]amino}-6-methylpyridine-2-carboxylic Acid

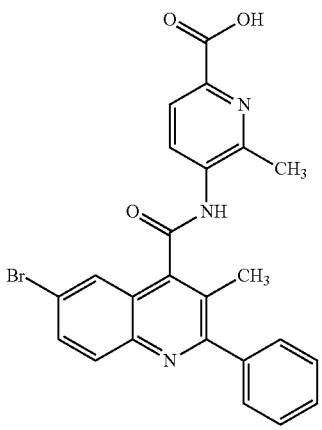 [SMILES: Cc1nc(C(=O)O)ccc1NC(=O)c1c(C)c(-c2ccccc2)nc2ccc(Br)cc12]

To 250 mg (0.64 mmol) of the compound from example 2A were added 10 ml of THF, 127 mg (0.77 mmol) of methyl 5-amino-6-methylpyridine-2-carboxylate and 56 mg (1.40 mmol) of sodium hydride (60% in mineral oil). The reaction mixture was stirred at RT for two days, then water was added, and the mixture was acidified with hydrochloric acid and extracted with ethyl acetate. The organic phase was separated off and the solvent was removed on a rotary evaporator. The residue was purified by means of preparative HPLC (method 11). 41 mg (13% of theory, 100% purity) of the title compound were obtained.

$^1$H-NMR (400 MHz, DMSO-$d_6$): δ [ppm]=10.76 (s, 1H), 8.43 (d, 1H), 8.07-8.02 (m, 3H), 7.97-7.94 (m, 1H), 7.66-7.64 (m, 2H), 7.59-7.49 (m, 3H), 2.58 (s, 3H), 2.48 (s, 3H).

LC/MS (Method 1, ESIpos): $R_t$=0.96 min, m/z=476/478 [M+H]$^+$.

Example 6

6-{[(6-Bromo-3-methyl-2-phenylquinolin-4-yl)carbonyl]amino}-5-fluoronicotinic Acid

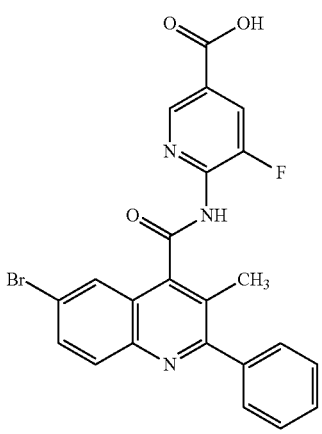

To a solution of 156 mg (0.31 mmol) of the compound from example 37A in 3.9 ml of THF and 0.8 ml of methanol were added, at RT, 1.54 ml (1.54 mmol) of 1 M sodium hydroxide solution, and the mixture was stirred under reflux for 1 h. After cooling to RT, the organic solvent was removed. The remaining residue was diluted with water, and the mixture was acidified with 1 M hydrochloric acid while stirring. The solids formed were filtered off and washed twice with water. Drying under reduced pressure gave 131 mg (89% of theory, purity 100%) of the title compound.

$^1$H-NMR (400 MHz, DMSO-$d_6$): [ppm]=13.67 (br. s, 1H), 11.60 (s, 1H), 8.86 (br. s, 1H), 8.30 (d, 1H), 8.10-7.89 (m, 3H), 7.67-7.60 (m, 2H), 7.58-7.49 (m, 3H), 2.47 (s, 3H).

LC/MS (Method 1, ESIpos): $R_t$=0.99 min, m/z=480/482 [M+H]$^+$.

Example 7

4-{[(6-Bromo-3-methyl-2-phenylquinolin-4-yl)carbonyl]amino}-3-fluorobenzoic Acid

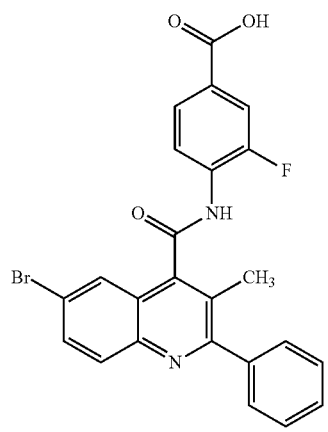

100 mg (0.20 mmol) of the compound from example 38A were dissolved in 2.5 ml of THF and 0.5 ml of methanol. 0.61 ml (0.61 mmol) of 1 M sodium hydroxide solution was added to the solution. The reaction mixture was stirred under reflux for 1 h. The volume of the solution was then reduced on a rotary evaporator, and the concentrated solution was adjusted to pH 3 with 0.6 ml of 1 M hydrochloric acid. The mixture was diluted with 5 ml of water, and the precipitated solids were filtered off. The solids were washed with water and dried under reduced pressure. 94 mg (97% of theory, 100% purity) of the title compound were obtained.

$^1$H-NMR (400 MHz, DMSO-$d_6$): [ppm]=13.27 (br. s, 1H), 11.04 (s, 1H), 8.17 (t, 1H), 8.05 (d, 1H), 7.99 (d, 1H), 7.94 (dd, 1H), 7.88 (dd, 1H), 7.80 (dd, 1H), 7.65-7.61 (m, 2H), 7.58-7.50 (m, 3H), 2.44 (s, 3H).

LC/MS (Method 1, ESIpos): $R_t$=1.08 min, m/z=479/481 [M+H]$^+$.

Example 8

4-{[(6-Bromo-3-methyl-2-phenylquinolin-4-yl)carbonyl]amino}-2-fluorobenzoic acid

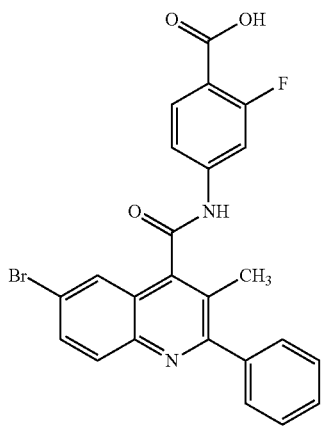 [SMILES: Cc1c(-c2ccccc2)nc2ccc(Br)cc2c1C(=O)Nc1ccc(C(=O)O)c(F)c1]

To 95 mg (0.19 mmol) of the compound from example 41A were added 2 ml of THF and 1.9 ml of 4 M sodium hydroxide solution. The reaction mixture was stirred at 80° C. overnight. Thereafter, the organic phase was removed and, without further workup, purified by means of preparative HPLC (method 9). 16 mg (17% of theory, 100% purity) of the title compound were obtained.

$^1$H-NMR (400 MHz, DMSO-$d_6$): [ppm]=11.38 (s, 1H), 8.07-8.04 (m, 1H), 7.96-7.92 (m, 3H), 7.85 (dd, 1H), 7.65-7.62 (m, 2H), 7.58-7.50 (m, 4H), 2.40 (s, 3H).

LC/MS (Method 1, ESIpos): $R_t$=1.11 min, m/z=479/481 [M+H]$^+$.

Example 9

4-{[(6-Bromo-3-methyl-2-phenylquinolin-4-yl)carbonyl]amino}-3-chlorobenzoic acid

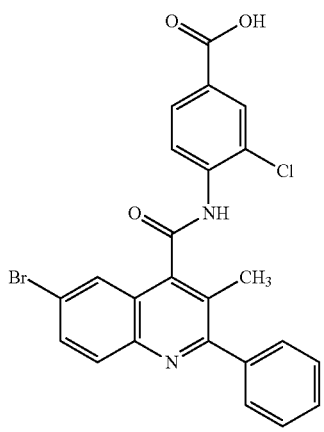

To a solution of 1.53 g (3.00 mmol) of the compound from example 42A in 38 ml of THF and 8 ml of methanol were added, at RT, 15 ml (15 mmol) of 1 M sodium hydroxide solution, and the mixture was stirred under reflux for 1 h. After cooling to RT, the organic solvent was removed. The remaining residue was diluted with water, and the mixture was acidified with 1 M hydrochloric acid while stirring. The solids present were filtered off and washed twice with water and once with tert-butyl methyl ether. Drying under reduced pressure gave 1.40 g (94% of theory, 100% purity) of the title compound.

$^1$H-NMR (400 MHz, DMSO-$d_6$): δ [ppm]=13.34 (br. s, 1H), 10.93 (s, 1H), 8.13-7.99 (m, 5H), 7.94 (dd, 1H), 7.68-7.60 (m, 2H), 7.59-7.49 (m, 3H), 2.48 (s, 3H, partially hidden).

LC/MS (Method 1, ESIpos): $R_t$=1.11 min, m/z=495/497 [M+H]$^+$.

Example 10

3-Bromo-4-{[(6-bromo-3-methyl-2-phenylquinolin-4-yl)carbonyl]amino}benzoic acid

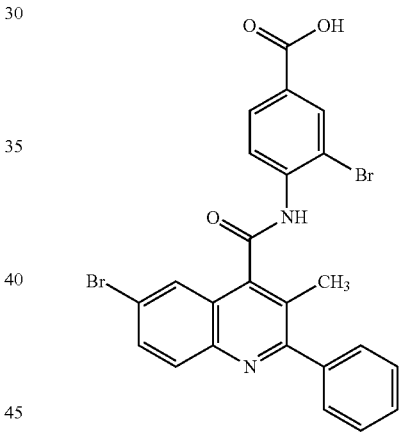

To a solution of 120 mg (0.22 mmol) of the compound from example 43A in 2.5 ml of THF and 0.5 ml of methanol was added, at RT, 1.0 ml (1.0 mmol) of 1 M sodium hydroxide solution, and the mixture was stirred under reflux for 1 h. After cooling to RT, the mixture was introduced into 30 ml of water and then acidified with 1 M hydrochloric acid while stirring. The solids present were filtered off and washed twice with water and once with tert-butyl methyl ether. Drying under reduced pressure gave 113 mg (95% of theory, purity 98%) of the title compound.

$^1$H-NMR (400 MHz, DMSO-$d_6$): δ [ppm]=13.35 (s, 1H), 10.88 (s, 1H), 8.23 (d, 1H), 8.14 (d, 1H), 8.09-8.02 (m, 2H), 8.01-7.97 (m, 1H), 7.94 (dd, 1H), 7.66-7.61 (m, 2H), 7.59-7.49 (m, 3H), 2.50 (s, 3H, hidden).

LC/MS (Method 1, ESIpos): $R_t$=1.13 min, m/z=539/541/543 [M+H]$^+$.

Example 11

4-{[(6-Bromo-3-methyl-2-phenylquinolin-4-yl)carbonyl]amino}-3-iodobenzoic Acid

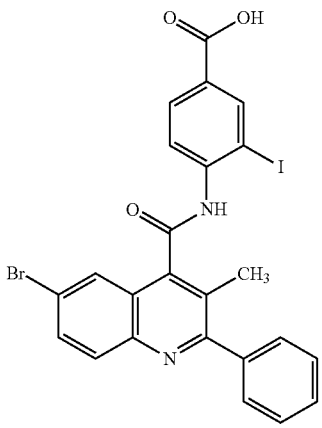

100 mg (0.26 mmol) of the compound from example 2A and 71 mg (0.26 mmol) of methyl 4-amino-3-iodobenzoate were dissolved in 2 ml of DMF. Subsequently, 72 mg (0.64 mmol) of potassium tert-butoxide were added in portions, and the reaction mixture was stirred at RT overnight. Thereafter, the mixture was admixed with 1.3 ml (1.3 mmol) of 1 M sodium hydroxide solution and stirred at 80° C. for 1 h. After cooling to RT, the mixture, without further workup, was purified by means of preparative HPLC (method 6). After the solvent-water mixture had been removed, the mixture was dried under reduced pressure overnight. 81 mg (53% of theory, 99% purity) of the title compound were obtained.

$^1$H-NMR (500 MHz, DMSO-$d_6$): [ppm]=13.30 (br. s, 1H), 10.77 (s, 1H), 8.45 (d, 1H), 8.17 (d, 1H), 8.10-8.01 (m, 2H), 7.94 (dd, 1H), 7.86 (d, 1H), 7.68-7.60 (m, 2H), 7.60-7.49 (m, 3H), 2.53 (s, 3H).

LC/MS (Method 1, ESIpos): $R_t$=1.11 min, m/z=586/588 [M+H]$^+$.

Example 12

4-{[(6-Bromo-3-methyl-2-phenylquinolin-4-yl)carbonyl]amino}-3,5-difluorobenzoic Acid

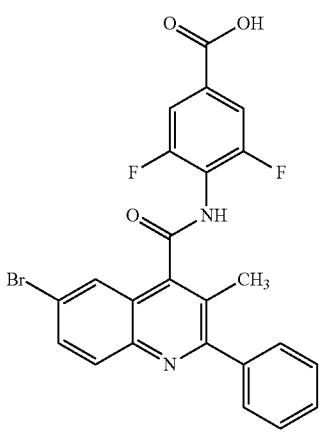 [SMILES: Cc1c(-c2ccccc2)nc2ccc(Br)cc2c1C(=O)Nc1c(F)cc(C(=O)O)cc1F]

500 mg (1.28 mmol) of the compound from example 2A and 286 mg (1.53 mmol) of methyl 4-amino-3,5-difluorobenzoate were dissolved in 10 ml of THF, and 112 mg (2.80 mmol) of sodium hydride (60% in mineral oil) were added at RT. After stirring overnight, the solvent was removed on a rotary evaporator. The residue, without further workup, was purified by means of preparative HPLC (method 13). The product thus obtained was stirred with acetonitrile, and the resulting solids were filtered off and washed with acetonitrile. Drying under reduced pressure gave 124 mg (18% of theory, purity 94%) of the title compound.

$^1$H-NMR (400 MHz, DMSO-$d_6$): [ppm]=10.69 (s, 1H), 8.08 (d, 1H), 8.06-8.03 (d, 1H), 7.96-7.94 (dd, 1H), 7.65-7.63 (m, 2H), 7.58-7.50 (m, 5H), 2.48 (s, 3H).

LC/MS (Method 1, ESIpos): $R_t$=1.08 min, m/z=497/499 [M+H]$^+$.

Example 13

4-{[(6-Bromo-3-methyl-2-phenylquinolin-4-yl)carbonyl]amino}-3,5-dichlorobenzoic Acid

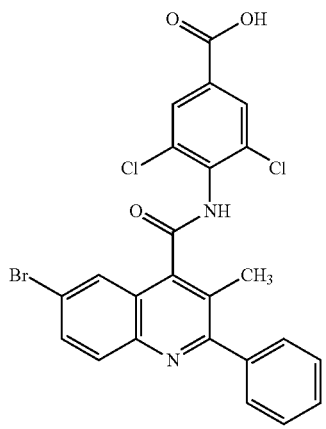

To a solution of 62 mg (0.11 mmol) of the compound from example 44A in 1.4 ml of THF and 0.3 ml of methanol was added, at RT, 0.56 ml (0.56 mmol) of 1 M sodium hydroxide solution, and the mixture was stirred under reflux for 1 h. After cooling to RT, the organic solvent was removed. The remaining residue was diluted with water, and the mixture was acidified with 1 M hydrochloric acid while stirring. The solids formed were filtered off and washed twice with water. After drying under air, the solids were taken up in DMSO and purified by means of preparative HPLC (method 5). The combined product-containing fractions were concentrated, the residue was taken up in dichloromethane/methanol, and the mixture was concentrated again. After the residue had been dried under reduced pressure, 20 mg (34% of theory, 100% purity) of the title compound were obtained.

$^1$H-NMR (400 MHz, DMSO-$d_6$): [ppm]=13.68 (br. s, 1H), 11.22 (s, 1H), 8.42 (d, 1H), 8.16-8.01 (m, 3H), 7.95 (dd, 1H), 7.67-7.61 (m, 2H), 7.59-7.48 (m, 3H), 2.58 (s, 3H).

LC/MS (Method 1, ESIpos): $R_t$=1.10 min, m/z=529/531/533 [M+H]$^+$.

Example 14

4-{[(6-Bromo-3-methyl-2-phenylquinolin-4-yl)carbonyl]amino}-3-methylbenzoic Acid

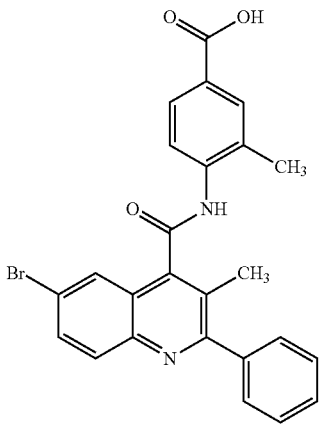 [SMILES: Cc1cc(C(=O)O)ccc1NC(=O)c1c(C)c(-c2ccccc2)nc2ccc(Br)cc12]

To 128 mg (0.26 mmol) of the compound from example 45A were added 3.3 ml of THF and then a solution of 9 mg (0.39 mmol) of lithium hydroxide in 1.1 ml of water. The reaction mixture was first stirred at RT for two days, then 2.6 ml of 4 M sodium hydroxide solution were added, and the mixture was stirred at RT for a further 24 h. Thereafter, the reaction mixture was heated to 100° C. for 3 h. After cooling to RT, the reaction mixture was adjusted to pH 1-2 with hydrochloric acid. The precipitated solids were filtered off with suction, washed with water and dried under reduced pressure. 70 mg (56% of theory, 99% purity) of the title compound were obtained.

$^1$H-NMR (400 MHz, DMSO-d$_6$): [ppm]=10.57 (s, 1H), 8.06 (d, 1H), 8.02 (d, 1H), 7.95 (dd, 1H), 7.92-7.87 (m, 3H), 7.66-7.64 (m, 2H), 7.59-7.51 (m, 3H), 2.54 (s, 3H), 2.38 (s, 3H).

LC/MS (Method 1, ESIpos): R$_t$=1.09 min, m/z=475/477 [M+H]$^+$.

Example 15

4-{[(6-Bromo-3-methyl-2-phenylquinolin-4-yl)carbonyl]amino}-3-(trifluoromethyl)benzoic Acid

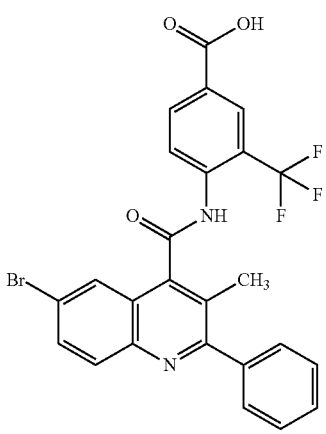 [SMILES: Cc1c(-c2ccccc2)nc2ccc(Br)cc2c1C(=O)Nc1ccc(C(=O)O)cc1C(F)(F)F]

To a solution of 300 mg (0.87 mmol) of the compound from example 1A in 3 ml of DMF were added, at RT, 267 mg (0.96 mmol) of 4-(4,6-dimethoxy-1,3,5-triazin-2-yl)-4-methylmorpholinium chloride and 211 mg (0.96 mmol) of methyl 4-amino-3-(trifluoromethyl)benzoate. The mixture was stirred at RT for 20 h. Subsequently, about 100 mg (about 2.63 mmol) of sodium hydride (60% dispersion in mineral oil) were gradually added in portions, and the mixture was first stirred at RT for 1 h and then left to stand at RT for 2 days. Thereafter, the mixture was diluted with ethyl acetate and washed with water. The aqueous phase was extracted once with ethyl acetate, and the combined organic phases were dried over magnesium sulfate, filtered and concentrated. The residue was purified by means of preparative HPLC (method 5). The combined product-containing fractions were concentrated down to a residual volume of aqueous phase and extracted twice with ethyl acetate. The combined organic phases were again dried over magnesium sulfate, filtered and concentrated. The residue was taken up in a methanol/dichloromethane mixture, concentrated again and finally dried under reduced pressure. 153 mg (33% of theory, 100% purity) of the title compound were obtained.

$^1$H-NMR (400 MHz, DMSO-d$_6$): δ [ppm]=13.54 (br. s, 1H), 10.95 (s, 1H), 8.35 (dd, 1H), 8.31-8.29 (m, 1H), 8.08-8.00 (m, 3H), 7.95 (dd, 1H), 7.67-7.61 (m, 2H), 7.60-7.50 (m, 3H), 2.50 (s, 3H, hidden).

LC/MS (Method 1, ESIpos): R$_t$=1.17 min, m/z=529/531 [M+H]$^+$.

Example 16

4-{[(6-Bromo-3-methyl-2-phenylquinolin-4-yl)carbonyl]amino}-3-cyanobenzoic acid

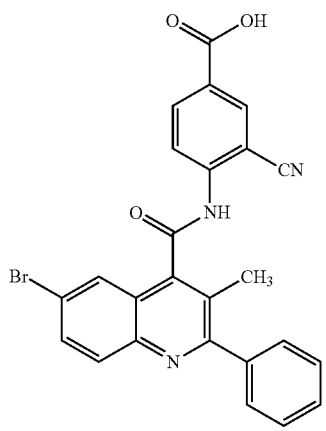

To 250 mg (0.64 mmol) of the compound from example 2A and 133 mg (0.70 mmol) of ethyl 4-amino-3-cyanobenzoate were added 2 ml of THF and 56 mg (1.40 mmol) of sodium hydride (60% in mineral oil). The reaction mixture was stirred at RT overnight. Then the mixture was admixed with water, acidified with 2 M hydrochloric acid and extracted with ethyl acetate. The organic phase was removed and washed with saturated sodium chloride solution. After the organic phase had been dried over sodium sulfate and the solvent had been removed, the residue was stirred with acetonitrile. The solids were filtered off, washed with acetonitrile and then purified by means of preparative HPLC (method 8). 102 mg (31% of theory, 96% purity) of the title compound were obtained.

$^1$H-NMR (400 MHz, DMSO-d$_6$): [ppm]=13.54 (br. s, 1H), 11.54 (s, 1H), 8.39 (d, 1H), 8.32 (dd, 1H), 8.17 (d, 1H), 8.06 (d, 1H), 7.96 (dd, 1H), 7.91 (d, 1H), 7.65-7.63 (m, 2H), 7.59-7.51 (m, 3H), 2.49 (s, 3H).

LC/MS (Method 1, ESIpos): R$_t$=1.07 min, m/z=486/488 [M+H]$^+$.

Example 17

4-{[(6-Bromo-3-methyl-2-phenylquinolin-4-yl)carbonyl]amino}-3-nitrobenzoic Acid

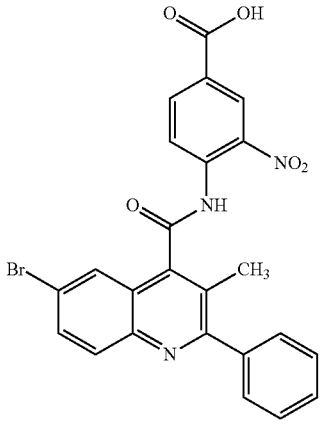

To 100 mg (0.26 mmol) of the compound from example 2A and 60 mg (0.31 mmol) of methyl 4-amino-3-nitrobenzoate were added 2 ml of THF. Then, at RT, 22 mg (0.56 mmol) of sodium hydride (60% in mineral oil) were added. After stirring at RT overnight, the reaction mixture was admixed with a few drops of water and, without further workup, purified by means of preparative HPLC (method 8). 110 mg (85% of theory, 100% purity) of the title compound were obtained.

$^1$H-NMR (400 MHz, DMSO-$d_6$): [ppm]=13.62 (br. s, 1H), 11.65 (s, 1H), 8.45 (d, 1H), 8.32-8.29 (dd, 1H), 8.12 (d, 1H), 8.06 (d, 1H), 7.96 (dd, 1H), 7.81 (d, 1H), 7.65-7.61 (m, 2H), 7.59-7.51 (m, 3H), 2.43 (s, 3H).

LC/MS (Method 1, ESIpos): $R_t$=1.15 min, m/z=507 [M+H]$^+$.

Example 18

3-Amino-4-{[(6-bromo-3-methyl-2-phenylquinolin-4-yl)carbonyl]amino}benzoic Acid

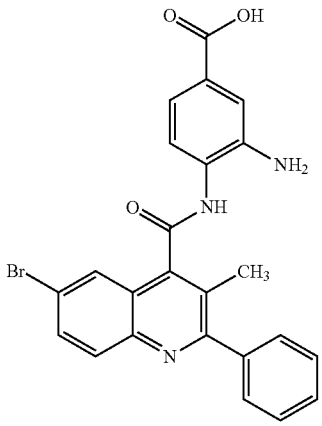 [SMILES: Cc1c(-c2ccccc2)nc2ccc(Br)cc2c1C(=O)Nc1ccc(C(=O)O)cc1[N+](=O)[O-]]

To 282 mg (0.56 mmol) of the compound from example 17 were added 1.6 ml of acetic acid, 2.5 ml of ethanol, 2.5 ml of water and 628 mg (2.79 mmol) of tin(II) chloride. The reaction mixture was stirred at 80° C. for 3 h and then, without further workup, purified by means of preparative HPLC (method 13). 211 mg (80% of theory, 100% purity) of the title compound were obtained.

$^1$H-NMR (400 MHz, DMSO-$d_6$): [ppm]=12.69 (br. s, 1H), 10.30 (s, 1H), 8.05 (d, 1H), 8.01 (d, 1H), 7.94 (dd, 1H), 7.74 (d, 1H), 7.65-7.63 (m, 2H), 7.58-7.50 (m, 3H), 7.47 (d, 1H), 7.28 (dd, 1H), 5.25 (br. s, 2H), 2.46 (s, 3H).

LC/MS (Method 1, ESIpos): $R_t$=0.97 min, m/z=476/478 [M+H]$^+$.

Example 19

3-Acetamido-4-{[(6-bromo-3-methyl-2-phenylquinolin-4-yl)carbonyl]amino}benzoic Acid

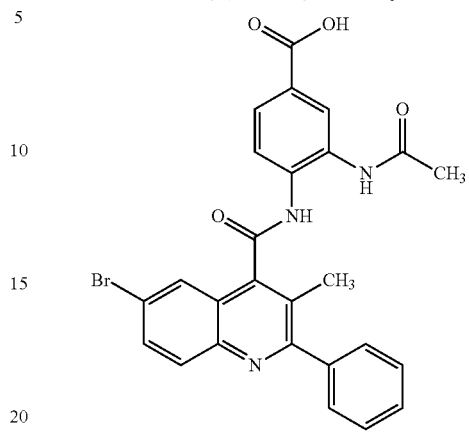

To 100 mg (0.21 mmol) of the compound from example 18 were added 1 ml of DMF and 0.12 ml (0.84 mmol) of triethylamine. At 0° C., 0.02 ml (0.25 mmol) of acetyl chloride were added dropwise. After 5 min, the ice bath was removed, and the reaction mixture was stirred at RT overnight. The mixture was then, without further workup, purified by means of preparative HPLC (method 8). The acetonitrile-water mixture was removed on a rotary evaporator, and the resulting residue was purified further by another preparative HPLC (method 13). 14 mg (13% of theory, 100% purity) of the title compound were obtained.

$^1$H-NMR (400 MHz, DMSO-$d_6$): [ppm]=13.07 (br. s, 1H), 10.60 (s, 1H), 9.64 (s, 1H), 8.04-7.99 (m, 4H), 7.93 (dd, 1H), 7.82 (d, 1H), 7.63-7.61 (m, 2H), 7.57-7.50 (m, 3H), 2.45 (s, 3H), 2.04 (s, 3H).

LC/MS (Method 1, ESIpos): $R_t$=0.99 min, m/z=518/520 [M+H]$^+$.

Example 20

4-{[(6-Bromo-3-methyl-2-phenylquinolin-4-yl)carbonyl]amino}-3-[(ethylcarbamoyl)amino]benzoic Acid

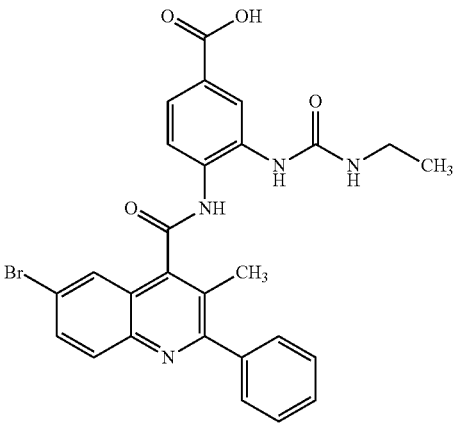 [SMILES: CCNC(=O)Nc1cc(C(=O)O)ccc1NC(=O)c1c(C)c(-c2ccccc2)nc2ccc(Br)cc12]

To 100 mg (0.21 mmol) of the compound from example 18 were added 1 ml of DMF and 0.12 ml (0.84 mmol) of triethylamine. At 0° C., 0.02 ml (0.25 mmol) of ethyl isocyanate were added dropwise. After 5 min, the ice bath was removed, and the reaction mixture was stirred at RT for 3 h. The precipitated solids were then filtered off, washed with acetonitrile, dried under reduced pressure and then purified by means of preparative HPLC (method 14). 38 mg (33% of theory, 100% purity) of the title compound were obtained.

¹H-NMR (400 MHz, DMSO-d₆): δ [ppm]=10.72 (s, 1H), 8.12 (s, 1H), 8.06-8.01 (m, 3H), 7.93 (dd, 1H), 7.83 (d, 1H), 7.70 (d, 1H), 7.63-7.61 (m, 2H), 7.58-7.45 (m, 3H), 6.76 (m, 1H), 3.06 (m, 2H), 2.46 (s, 3H), 0.98 (t, 3H).

LC/MS (Method 1, ESIpos): $R_t$=1.03 min, m/z=547/549 [M+H]⁺.

Example 21

4-{[(6-Bromo-3-methyl-2-phenylquinolin-4-yl)carbonyl]amino}-3-methoxybenzoic Acid

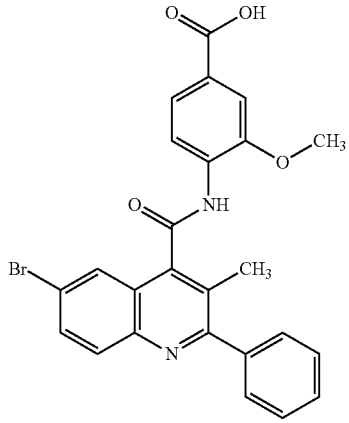 [SMILES: COc1cc(C(=O)O)ccc1NC(=O)c1c(C)c(-c2ccccc2)nc2ccc(Br)cc12]

To a solution of 660 mg (1.31 mmol) of the compound from example 46A in 16.5 ml of THF and 3.5 ml of methanol were added, at RT, 6.6 ml (6.6 mmol) of 1 M sodium hydroxide solution, and the mixture was stirred under reflux for 1 h. After cooling to RT, the organic solvent was removed. The remaining residue was diluted with water, and the mixture was acidified with 1 M hydrochloric acid while stirring. The solids present were filtered off and washed twice with water and once with tert-butyl methyl ether. Drying under reduced pressure gave 599 mg (93% of theory, purity 100%) of the title compound.

¹H-NMR (400 MHz, DMSO-d₆): δ [ppm]=13.02 (br. s, 1H), 10.50 (br. s, 1H), 8.17-7.84 (m, 4H), 7.75-7.43 (m, 7H), 3.93 (s, 3H), 2.43 (s, 3H, partially hidden).

LC/MS (Method 1, ESIpos): $R_t$=1.09 min, m/z=491/493 [M+H]+.

Example 22

4-{[(6-Bromo-3-methyl-2-phenylquinolin-4-yl)carbonyl]amino}-3-hydroxybenzoic Acid

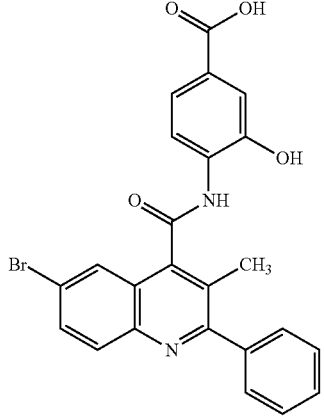

To a suspension of 90 mg (0.18 mmol) of the compound from example 21 in 2 ml of dichloromethane was added, at 0° C., 0.55 ml (0.55 mmol) of a 1 M solution of boron tribromide in dichloromethane.

The mixture was stirred at RT for 2 h. The reaction mixture thus obtained was then combined with an analogously obtained reaction mixture from a proceeding experiment [amount of compound from example 21 used: 10 mg (0.02 mmol)]. After the solvent had been removed, the residue was taken up in DMSO and purified by means of preparative HPLC (method 5). The combined product-containing fractions were concentrated, the residue was taken up in dichloromethane, and the mixture was concentrated again. After drying under reduced pressure, 86 mg (100% purity, 89% of theory, based on a total of 100 mg (0.20 mmol) of the compound from example 21) of the title compound were obtained.

¹H-NMR (400 MHz, DMSO-d₆): [ppm]=12.79 (br. s, 1H), 10.37 (s, 1H), 10.35 (s, 1H), 8.09-7.99 (m, 3H), 7.91 (dd, 1H), 7.66-7.59 (m, 2H), 7.59-7.46 (m, 5H), 2.43 (s, 3H).

LC/MS (Method 1, ESIpos): $R_t$=0.99 min, m/z=477/479 [M+H]⁺.

Example 23

4-{[(6-Bromo-3-methyl-2-phenylquinolin-4-yl)carbonyl]amino}-3-(trifluoromethoxy)benzoic acid

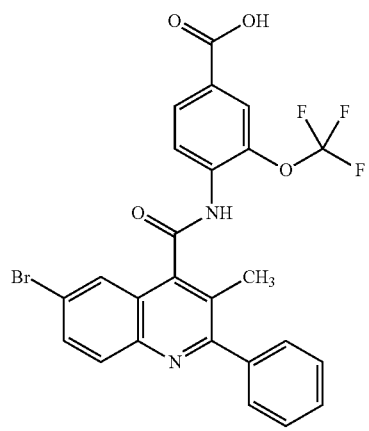 [SMILES: Cc1c(-c2ccccc2)nc2ccc(Br)cc2c1C(=O)Nc1ccc(C(=O)O)cc1OC(F)(F)F]

A solution of 75 mg (0.13 mmol) of the compound from example 47A in 2 ml of a THF/methanol mixture (5:1) was admixed with 0.65 ml (0.65 mmol) of 1 M sodium hydroxide solution and stirred under reflux for 1 h. After cooling to RT, the mixture, without further workup, was purified by means of preparative HPLC (method 6). The acetonitrile-water mixture was removed on a rotary evaporator and the residue was dried under reduced pressure overnight. 49 mg (69% of theory, 100% purity) of the title compound were obtained.

¹H-NMR (400 MHz, DMSO-d₆): [ppm]=13.42 (br. s, 1H), 11.14 (s, 1H), 8.29 (d, 1H), 8.12-8.01 (m, 2H), 7.98-7.91 (m, 3H), 7.68-7.60 (m, 2H), 7.60-7.49 (m, 3H), 2.43 (s, 3H).

LC/MS (Method 1, ESIpos): $R_t$=1.15 min, m/z=545/547 [M+H]⁺.

Example 24

4-{[(6-Bromo-3-methyl-2-phenylquinolin-4-yl)carbonyl]amino}-3-(methylsulfanyl)benzoic Acid

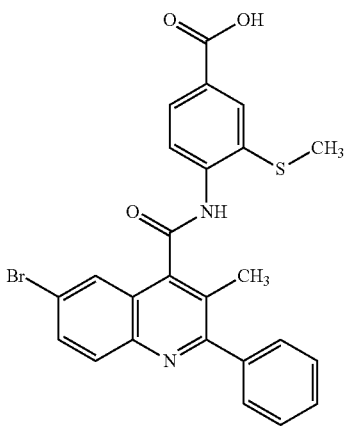

To a solution of 100 mg (0.19 mmol) of the compound from example 48A in 2.5 ml of THF and 0.5 ml of methanol were added, at RT, 0.50 ml (0.50 mmol) of 1 M sodium hydroxide solution, and the mixture was stirred under reflux for 1 h. After cooling to RT, the organic solvent was removed. The remaining residue was diluted with water, and the mixture was acidified with 1 M hydrochloric acid while stirring. After stirring for a few minutes, the solids present were filtered off and washed twice with water. Drying under reduced pressure gave 88 mg (86% of theory, purity 95%) of the title compound.

$^1$H-NMR (400 MHz, DMSO-d$_6$): δ [ppm]=13.17 (br. s, 1H), 10.70 (s, 1H), 8.27 (d, 1H), 8.04 (d, 1H), 7.96-7.90 (m, 2H), 7.86 (dd, 1H), 7.69 (d, 1H), 7.66-7.60 (m, 2H), 7.59-7.49 (m, 3H), 2.56 (s, 3H, partially hidden), 2.50 (s, 3H, partially hidden).

LC/MS (Method 1, ESIpos): R$_t$=1.09 min, m/z=507/509 [M+H]$^+$.

Example 25

4-{[(6-Bromo-3-methyl-2-phenylquinolin-4-yl)carbonyl]amino}-3-(methylsulfinyl)benzoic Acid

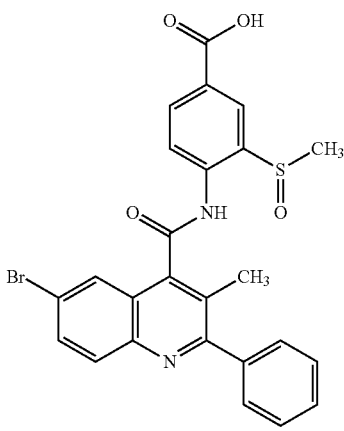 [SMILES: Cc1c(-c2ccccc2)nc2ccc(Br)cc2c1C(=O)Nc1ccc(C(=O)O)cc1S(C)=O]

To a solution of 140 mg (0.26 mmol) of the compound from example 49A in 3.5 ml of THF and 0.7 ml of methanol were added, at RT, 1.31 ml (1.31 mmol) of 1 M sodium hydroxide solution, and the mixture was stirred under reflux for 1 h. After cooling to RT, 0.10 ml (1.31 mmol) of trifluoroacetic acid was added. Subsequently, the mixture was purified by means of preparative HPLC (method 5). The combined product-containing fractions were concentrated, the residue was taken up in dichloromethane, and the mixture was concentrated again. After the residue had been dried under reduced pressure, 126 mg (93% of theory, 100% purity) of the title compound were obtained.

$^1$H-NMR (400 MHz, DMSO-d$_6$): δ [ppm]=13.39 (br. s, 1H), 11.22 (s, 1H), 8.53 (d, 1H), 8.20 (dd, 1H), 8.11-8.03 (m, 2H), 7.97 (dd, 1H), 7.81 (d, 1H), 7.67-7.61 (m, 2H), 7.61-7.50 (m, 3H), 2.92 (s, 3H), 2.50 (s, 3H, hidden).

LC/MS (Method 1, ESIpos): R$_t$=0.97 min, m/z=523/525 [M+H]$^+$.

Example 26

4-{[(6-Bromo-3-methyl-2-phenylquinolin-4-yl)carbonyl]amino}-3-(methylsulfonyl)benzoic Acid

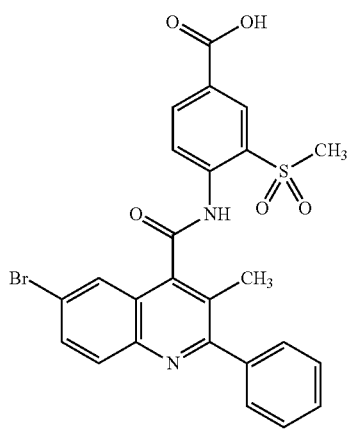 [SMILES: Cc1c(-c2ccccc2)nc2ccc(Br)cc2c1C(=O)Nc1ccc(C(=O)O)cc1S(C)(=O)=O]

To a solution of 100 mg (0.18 mmol) of the compound from example 50A in 2.5 ml of THF and 0.5 ml of methanol were added, at RT, 0.91 ml (0.91 mmol) of 1 M sodium hydroxide solution, and the mixture was stirred under reflux for 1 h. After cooling to RT, 0.07 ml (0.91 mmol) of trifluoroacetic acid was added. Subsequently, the mixture was purified by means of preparative HPLC (method 5). The combined product-containing fractions were concentrated, the residue was taken up in dichloromethane, and the mixture was concentrated again. After the residue had been dried under reduced pressure, 83 mg (85% of theory, 100% purity) of the title compound were obtained.

$^1$H-NMR (400 MHz, DMSO-d$_6$): δ [ppm]=13.55 (br. s, 1H), 10.75 (s, 1H), 8.54 (d, 1H), 8.37 (dd, 1H), 8.32-8.24 (m, 2H), 8.04 (d, 1H), 7.94 (dd, 1H), 7.67-7.61 (m, 2H), 7.60-7.49 (m, 3H), 3.41 (s, 3H), 2.50 (s, 3H, hidden).

LC/MS (Method 1, ESIpos): R$_t$=1.08 min, m/z=539/541 [M+H]$^+$.

Example 27

4-{[(6-Bromo-3-methyl-2-phenylquinolin-4-yl)carbonyl]amino}-5-(ethylsulfonyl)-2-methoxybenzoic Acid

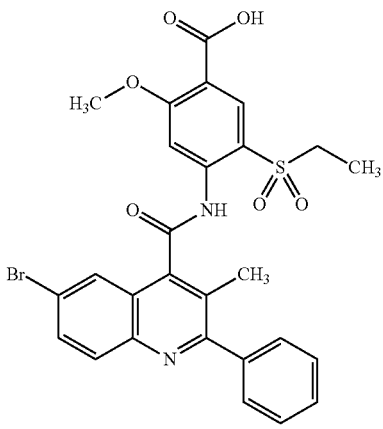 [SMILES: CCS(=O)(=O)c1cc(C(=O)O)c(OC)cc1NC(=O)c1c(C)c(-c2ccccc2)nc2ccc(Br)cc12]

To a solution of 221 mg (0.37 mmol) of the compound from example 51A in 4.7 ml of THF and 1.0 ml of methanol were added, at RT, 1.86 ml (1.86 mmol) of 1 M sodium hydroxide solution, and the mixture was stirred under reflux for 1 h. After cooling to RT, the organic solvent was removed. The remaining residue was diluted with water, and the mixture was acidified with 1 M hydrochloric acid while stirring. The solids formed were filtered off and washed twice with water. Drying under reduced pressure gave 180 mg (84% of theory, purity 100%) of the title compound.

$^1$H-NMR (400 MHz, DMSO-d$_6$): δ [ppm]=13.03 (br. s, 1H), 10.61 (s, 1H), 8.27-8.22 (m, 2H), 8.12 (s, 1H), 8.08-8.01 (m, 1H), 7.95 (dd, 1H), 7.68-7.61 (m, 2H), 7.60-7.49 (m, 3H), 4.02 (s, 3H), 3.47-3.36 (m, 2H, partially hidden), 2.49 (s, 3H, hidden), 1.14 (t, 3H).

LC/MS (Method 1, ESIpos): R$_t$=1.12 min, m/z=583/585 [M+H]$^+$.

Example 28

4-{[(6-Bromo-3-methyl-2-phenylquinolin-4-yl)carbonyl]amino}-3-[(trifluoromethyl)sulfanyl]benzoic Acid

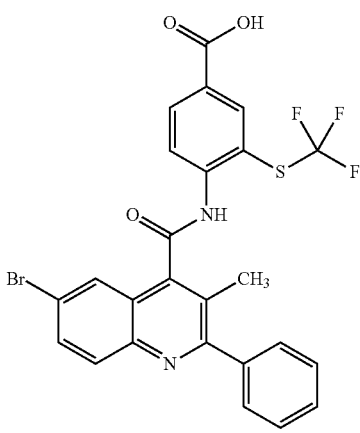 [SMILES: Cc1c(-c2ccccc2)nc2ccc(Br)cc2c1C(=O)Nc1ccc(C(=O)O)cc1SC(F)(F)F]

A mixture of 50 mg (0.09 mmol) of the compound from example 53A in 1.6 ml of THF and 0.3 ml of methanol was admixed with 0.32 ml (0.32 mmol) of 1 M sodium hydroxide solution and then stirred under reflux for 1 h. After cooling to RT, the mixture was adjusted to pH 4 with about 0.03 ml of trifluoroacetic acid and, without further workup, was purified by means of preparative HPLC (method 5). After the solvent-water mixture had been removed, the residue was taken up in dichloromethane, the mixture was concentrated again and the residue was dried under reduced pressure. 35 mg (72% of theory, 100% purity) of the title compound were obtained.

$^1$H-NMR (400 MHz, DMSO-d$_6$): δ [ppm]=13.46 (br. s, 1H), 11.34 (br. s, 1H), 8.50-7.80 (m, 6H), 7.73-7.33 (m, 5H), 2.47 (s, 3H, partially hidden).

LC/MS (Method 1, ESIpos): R$_t$=1.19 min, m/z=561/563 [M+H]$^+$.

Example 29

3-Fluoro-4-{[(6-fluoro-3-methyl-2-phenylquinolin-4-yl)carbonyl]amino}benzoic Acid

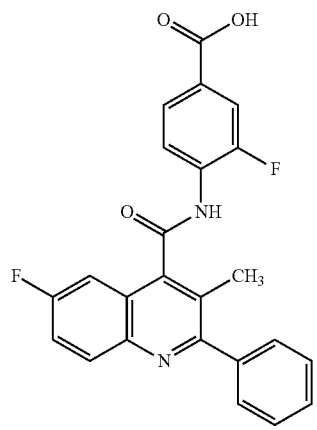 [SMILES: Cc1c(-c2ccccc2)nc2ccc(F)cc2c1C(=O)Nc1ccc(C(=O)O)cc1F]

To a solution of 184 mg (0.43 mmol) of the compound from example 54A in 5.5 ml of THF and 1.1 ml of methanol were added, at RT, 2.14 ml (2.14 mmol) of 1 M sodium hydroxide solution, and the mixture was stirred under reflux for 1 h. After cooling to RT, the organic solvent was removed. The aqueous solution that remained was introduced into 20 ml of 1 M hydrochloric acid while stirring. After stirring for a few minutes, the solids formed were filtered off and washed twice with water and once with pentane. Drying under reduced pressure gave 148 mg (83% of theory, purity 100%) of the title compound.

$^1$H-NMR (400 MHz, DMSO-d$_6$): δ [ppm]=13.24 (br. s, 1H), 11.03 (s, 1H), 8.22 (t, 1H), 8.17 (dd, 1H), 7.88 (dd, 1H), 7.80 (dd, 1H), 7.73 (td, 1H), 7.64-7.59 (m, 2H), 7.59-7.49 (m, 4H), 2.43 (s, 3H).

LC/MS (Method 1, ESIpos): R$_t$=0.99 min, m/z=419 [M+H]$^+$.

Example 30

3-Fluoro-4-{[(6-iodo-3-methyl-2-phenylquinolin-4-yl)carbonyl]amino}benzoic Acid

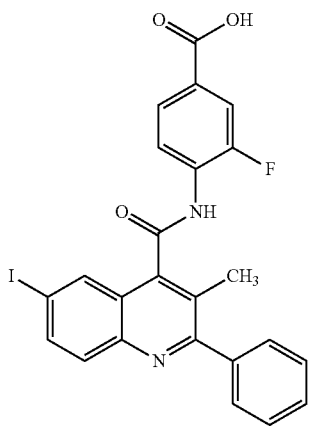 [SMILES: Cc1c(-c2ccccc2)nc2ccc(I)cc2c1C(=O)Nc1ccc(C(=O)O)cc1F]

100 mg (0.23 mmol) of the compound from example 6A and 39 mg (0.23 mmol) of methyl 4-amino-3-fluorobenzoate were dissolved in 1.7 ml of DMF. 64 mg (0.57 mmol) of potassium tert-butoxide were added in portions to the solution. The reaction mixture was stirred at RT for 1 h, and then 1.3 ml (1.3 mmol) of 1 M sodium hydroxide solution were added. The mixture was then stirred at 80° C. for 1 h. After cooling to RT, the mixture, without further workup, was purified by means of preparative HPLC (method 6). After the solvent-water mixture had been removed and the residue had been dried under reduced pressure, 76 mg (62% of theory, 98% purity) of the title compound were obtained.

$^1$H-NMR (400 MHz, DMSO-$d_6$): [ppm]=13.25 (br. s, 1H), 11.04 (s, 1H), 8.19 (t, 1H), 8.18 (d, 1H), 8.06 (dd, 1H), 7.93-7.84 (m, 2H), 7.82 (dd, 1H), 7.66-7.59 (m, 2H), 7.59-7.47 (m, 3H), 2.42 (s, 3H).

LC/MS (Method 1, ESIpos): $R_t$=1.07 min, m/z=527 [M+H]$^+$.

Example 31

4-{[(3,6-Dimethyl-2-phenylquinolin-4-yl)carbonyl]amino}-3-fluorobenzoic acid

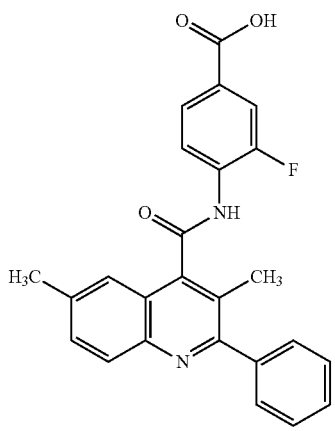 [SMILES: Cc1ccc2nc(-c3ccccc3)c(C)c(C(=O)Nc3ccc(C(=O)O)cc3F)c2c1]

To a solution of 124 mg (0.27 mmol, 93% purity) of the compound from example 55A in 3.5 ml of THF and 0.7 ml of methanol were added, at RT, 1.35 ml (1.35 mmol) of 1 M sodium hydroxide solution, and the mixture was stirred under reflux for 1 h. After cooling to RT, 0.10 ml (1.35 mmol) of trifluoroacetic acid was added. Subsequently, the mixture was purified by means of preparative HPLC (method 5). The combined product-containing fractions were concentrated, the residue was taken up in dichloromethane, and the mixture was concentrated again. Drying under reduced pressure gave 83 mg (75% of theory, purity 100%) of the title compound.

$^1$H-NMR (400 MHz, DMSO-$d_6$): δ [ppm]=13.17 (br. s, 1H), 10.99 (s, 1H), 8.24 (t, 1H), 7.98 (d, 1H), 7.88 (dd, 1H), 7.80 (dd, 1H), 7.68-7.58 (m, 4H), 7.58-7.47 (m, 3H), 2.53 (s, 3H, partially hidden), 2.40 (s, 3H).

LC/MS (Method 1, ESIpos): $R_t$=1.01 min, m/z=415 [M+H]$^+$.

Example 32

4-{[(6-Ethyl-3-methyl-2-phenylquinolin-4-yl)carbonyl]amino}-3-fluorobenzoic Acid

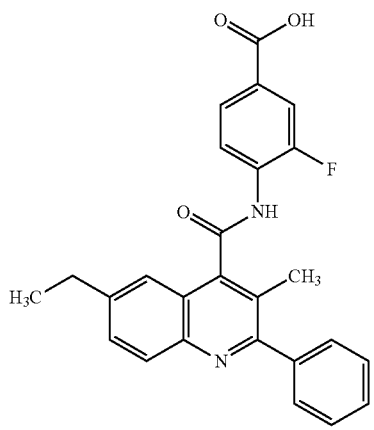 [SMILES: CCc1ccc2nc(-c3ccccc3)c(C)c(C(=O)Nc3ccc(C(=O)O)cc3F)c2c1]

To a solution of 186 mg (0.38 mmol, 91% purity) of the compound from example 56A in 5.0 ml of THF and 1.0 ml of methanol were added, at RT, 1.92 ml (1.92 mmol) of 1 M sodium hydroxide solution, and the mixture was stirred under reflux for 1 h. After cooling to RT, 0.15 ml (2.00 mmol) of trifluoroacetic acid was added. After being left to stand overnight, the mixture was purified by means of preparative HPLC (Method 5). The combined product-containing fractions were concentrated, the residue was taken up in dichloromethane, and the mixture was concentrated again. Drying under reduced pressure gave 139 mg (85% of theory, purity 100%) of the title compound.

$^1$H-NMR (400 MHz, DMSO-$d_6$): [ppm]=13.30 (br. s, 1H), 11.25-10.78 (m, 1H), 8.20 (t, 1H), 8.03 (d, 1H), 7.89 (dd, 1H), 7.81 (dd, 1H), 7.72 (dd, 1H), 7.66-7.60 (m, 3H), 7.59-7.49 (m, 3H), 2.84 (q, 2H), 2.41 (s, 3H), 1.27 (t, 3H).

LC/MS (Method 1, ESIpos): $R_t$=1.06 min, m/z=429 [M+H]+.

Example 33

3-Fluoro-4-{[(6-isopropyl-3-methyl-2-phenylquinolin-4-yl)carbonyl]amino}benzoic Acid

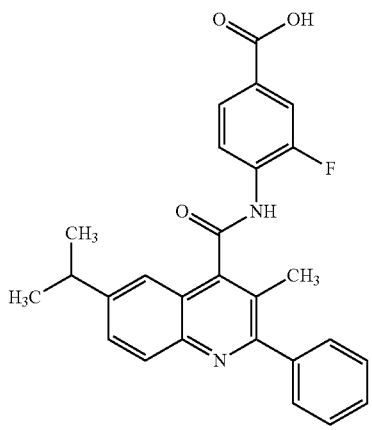 [SMILES: Cc1c(-c2ccccc2)nc2ccc(C(C)C)cc2c1C(=O)Nc1ccc(C(=O)O)cc1F]

To 108 mg (0.24 mmol) of the compound from example 57A were added 2.4 ml of THF and 2.4 ml of 4 M sodium hydroxide solution. The reaction mixture was stirred at 60° C. for 10 h. Thereafter, the organic phase was removed and, without further workup, purified by means of preparative HPLC (method 9). The acetonitrile-water mixture was removed on a rotary evaporator and the residue was stirred with acetonitrile. The solids were filtered off and dried under reduced pressure. 45 mg (43% of theory, 100% purity) of the title compound were obtained.

$^1$H-NMR (400 MHz, DMSO-d$_6$): δ [ppm]=13.26 (br. s, 1H), 11.01 (s, 1H), 8.14 (t, 1H), 8.02 (d, 1H), 7.92-7.71 (m, 3H), 7.67-7.44 (m, 6H), 3.20-3.04 (m, 1H), 2.41 (s, 3H), 1.29 (d, 6H).

LC/MS (Method 1, ESIpos): R$_t$=1.10 min, m/z=443 [M+H]$^+$.

Example 34

3-Fluoro-4-({[3-methyl-2-phenyl-6-(trifluoromethyl)quinolin-4-yl]carbonyl}amino)benzoic acid

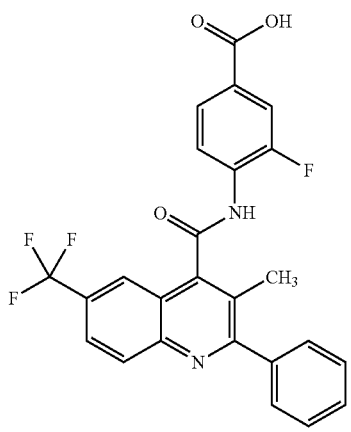 [SMILES: Cc1c(-c2ccccc2)nc2ccc(C(F)(F)F)cc2c1C(=O)Nc1ccc(C(=O)O)cc1F]

To 105 mg (0.22 mol) of the compound from example 58A were added 2.2 ml of THF and 2.2 ml of 4 M sodium hydroxide solution. The reaction mixture was stirred at 60° C. overnight. Thereafter, the organic phase was removed and, without further workup, purified by means of preparative HPLC (method 9). After the solvent-water mixture had been removed, the mixture was dried at 60° C. under reduced pressure overnight. 97 mg (95% of theory, 100% purity) of the title compound were obtained.

$^1$H-NMR (400 MHz, DMSO-d$_6$): [ppm]=13.30 (br. s, 1H), 11.13 (s, 1H), 8.32 (d, 1H), 8.18-8.14 (m, 2H), 8.08 (dd, 1H), 7.90 (dd, 1H), 7.83 (dd, 1H), 7.68-7.66 (m, 2H), 7.61-7.53 (m, 3H), 2.48 (s, 3H).

LC/MS (Method 1, ESIpos): R$_t$=1.13 min, m/z=469 [M+H]$^+$.

Example 35

3-Fluoro-4-({[3-methyl-2-phenyl-6-(trifluoromethoxy)quinolin-4-yl]carbonyl}amino)benzoic Acid

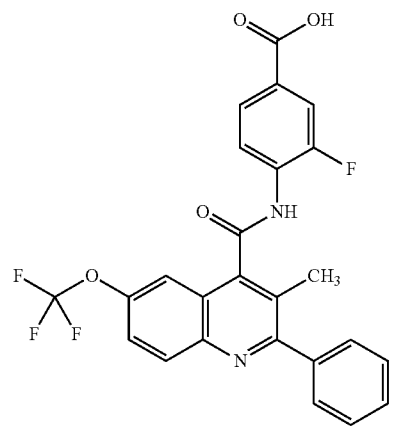 [SMILES: Cc1c(-c2ccccc2)nc2ccc(OC(F)(F)F)cc2c1C(=O)Nc1ccc(C(=O)O)cc1F]

To a solution of 150 mg (0.27 mmol, 91% purity) of the compound from example 59A in 3.5 ml of THF and 0.7 ml of methanol were added, at RT, 1.38 ml (1.38 mmol) of 1 M sodium hydroxide solution, and the mixture was stirred under reflux for 1 h. After cooling to RT, 0.11 ml (1.38 mmol) of trifluoroacetic acid was added. Subsequently, the mixture was purified by means of preparative HPLC (method 5). The combined product-containing fractions were concentrated, the residue was taken up in dichloromethane, and the mixture was concentrated again. Drying under reduced pressure gave 115 mg (87% of theory, purity 100%) of the title compound.

$^1$H-NMR (400 MHz, DMSO-d$_6$): [ppm]=13.25 (br. s, 1H), 11.07 (s, 1H), 8.24 (d, 1H), 8.16 (t, 1H), 7.89 (dd, 1H), 7.82 (dd, 2H), 7.74 (s, 1H), 7.68-7.61 (m, 2H), 7.60-7.48 (m, 3H), 2.45 (s, 3H).

LC/MS (Method 1, ESIpos): R$_t$=1.08 min, m/z=485 [M+H]$^+$.

Example 36

3-Fluoro-4-({[3-methyl-2-phenyl-6-(trimethylsilyl)quinolin-4-yl]carbonyl}amino)benzoic Acid

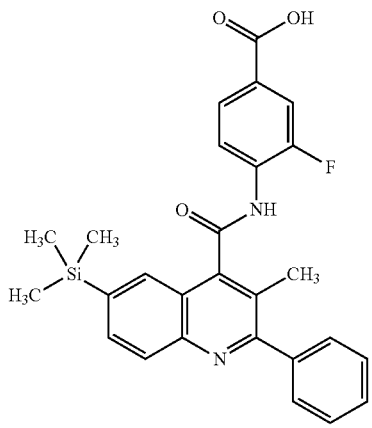 [SMILES: Cc1c(-c2ccccc2)nc2ccc([Si](C)(C)C)cc2c1C(=O)Nc1ccc(C(=O)O)cc1F]

To a mixture of 34 mg (0.06 mmol) of the compound from Example 60A in 1 ml of dichloromethane was added 0.5 ml (6.49 mmol) of trifluoroacetic acid, and the mixture was stirred at RT for 1 h. Then the mixture was concentrated. The residue was taken up in DMSO and purified by means of preparative HPLC (method 5). The combined product-containing fractions were concentrated, the residue was taken up in dichloromethane, and the mixture was concentrated again. Drying under reduced pressure gave 25 mg (81% of theory, purity 100%) of the title compound.

$^1$H-NMR (400 MHz, DMSO-$d_6$): [ppm]=13.19 (br. s, 1H), 11.03 (s, 1H), 8.11-7.99 (m, 3H), 7.97-7.87 (m, 2H), 7.83 (d, 1H), 7.67-7.61 (m, 2H), 7.60-7.47 (m, 3H), 2.44 (s, 3H), 0.32 (s, 9H).

LC/MS (Method 1, ESIpos): $R_t$=1.19 min, m/z=473 [M+H]$^+$.

Example 37

4-({[6-Bromo-3-(fluoromethyl)-2-phenylquinolin-4-yl]carbonyl}amino)-3-fluorobenzoic Acid

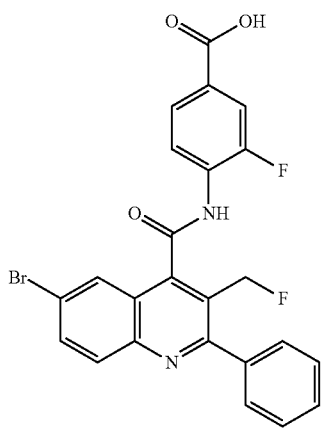 [SMILES: O=C(O)c1ccc(NC(=O)c2c(CF)c(-c3ccccc3)nc3ccc(Br)cc23)c(F)c1]

To a solution of 60 mg (0.12 mmol) of the compound from example 63A in 1.5 ml of THF and 0.3 ml of methanol was added, at RT, 0.59 ml (0.59 mmol) of 1 M sodium hydroxide solution, and the mixture was stirred under reflux for 30 min. After cooling to RT, 0.05 ml (0.60 mmol) of trifluoroacetic acid was added. Subsequently, the mixture was purified by means of preparative HPLC (method 12). 39 mg (66% of theory, 100% purity) of the title compound were obtained.

$^1$H-NMR (500 MHz, DMSO-$d_6$): [ppm]=13.23 (br. s, 1H), 11.16 (s, 1H), 8.23 (t, 1H), 8.15-8.10 (m, 2H), 8.07 (dd, 1H), 7.90 (dd, 1H), 7.82 (dd, 1H), 7.70-7.64 (m, 2H), 7.63-7.54 (m, 3H), 5.57 (dd, 2H).

LC/MS (Method 1, ESIpos): $R_t$=1.05 min, m/z=497/499 [M+H]$^+$.

Example 38

4-({[6-Bromo-3-(difluoromethyl)-2-phenylquinolin-4-yl]carbonyl}amino)-3-fluorobenzoic acid

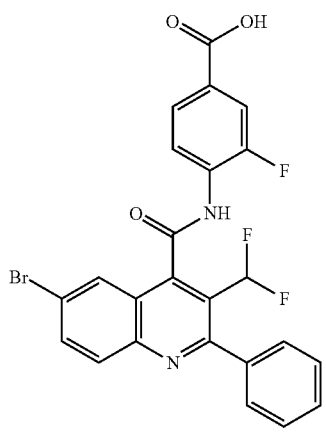 [SMILES: O=C(O)c1ccc(NC(=O)c2c(C(F)F)c(-c3ccccc3)nc3ccc(Br)cc23)c(F)c1]

To a solution of 20 mg (0.04 mmol) of the compound from example 64A in 0.6 ml of THF and 0.13 ml of methanol was added, at RT, 0.19 ml (0.19 mmol) of 1 M sodium hydroxide solution, and the mixture was stirred under reflux for 30 min. After cooling to RT, 0.015 ml (0.19 mmol) of trifluoroacetic acid was added. Subsequently, the mixture was purified by means of preparative HPLC (method 5). The combined product-containing fractions were concentrated, the residue was taken up in dichloromethane, and the mixture was concentrated again. Drying under reduced pressure gave 11 mg (54% of theory, purity 100%) of the title compound.

$^1$H-NMR (400 MHz, DMSO-$d_6$): [ppm]=13.24 (br. s, 1H), 11.13 (s, 1H), 8.26 (t, 1H), 8.18-8.09 (m, 3H), 7.90 (dd, 1H), 7.81 (dd, 1H), 7.65-7.54 (m, 5H), 7.09 (t, 1H).

LC/MS (Method 1, ESIpos): $R_t$=1.05 min, m/z=515/517 [M+H]$^+$.

Example 39

4-{[(6-Bromo-3-ethyl-2-phenylquinolin-4-yl)carbonyl]amino}-3-fluorobenzoic acid

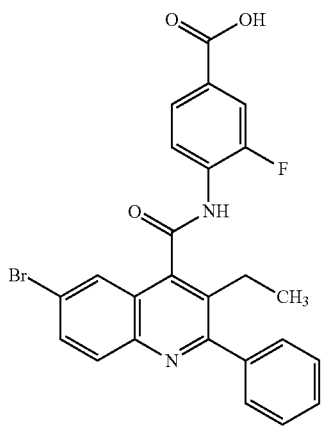 [SMILES: CCc1c(-c2ccccc2)nc2ccc(Br)cc2c1C(=O)Nc1ccc(C(=O)O)cc1F]

To a solution of 187 mg (0.37 mmol) of the compound from example 65A in 5.8 ml of THF and 1.2 ml of methanol were added, at RT, 1.86 ml (1.86 mmol) of 1 M sodium hydroxide solution, and the mixture was stirred under reflux for 30 min. After cooling to RT, the organic solvent was removed by distillation, and 0.14 ml (1.86 mmol) of trifluoroacetic acid was added to the aqueous phase that remained. The solids formed were filtered off, washed twice with 1 ml of water and dried under reduced pressure. 178 mg (98% of theory, 100% purity) of the title compound were obtained.

$^1$H-NMR (400 MHz, DMSO-$d_6$): [ppm]=10.99 (s, 1H), 8.05-7.97 (m, 3H), 7.94 (dd, 1H), 7.84 (dd, 1H), 7.76 (dd, 1H), 7.60-7.48 (m, 5H), 2.83 (d, 2H), 0.99 (t, 3H).

LC/MS (Method 1, ESIpos): $R_t$=1.07 min, m/z=493/495 [M+H]$^+$.

Example 40

4-{[(6-Bromo-2-phenyl-3-propylquinolin-4-yl)carbonyl]amino}-3-fluorobenzoic Acid

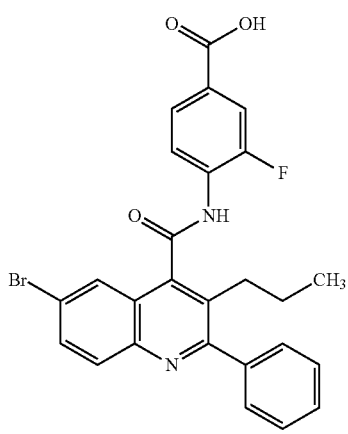 [SMILES: CCCc1c(-c2ccccc2)nc2ccc(Br)cc2c1C(=O)Nc1ccc(C(=O)O)cc1F]

To a solution of 139 mg (0.27 mmol) of the compound from example 66A in 4.2 ml of THF and 0.9 ml of methanol were added, at RT, 1.34 ml (1.34 mmol) of 1 M sodium hydroxide solution, and the mixture was stirred under reflux for 3 h. After cooling to RT, the organic solvent was removed by distillation, and 0.10 ml (1.34 mmol) of trifluoroacetic acid was added to the aqueous phase that remained. The solids formed were filtered off, washed twice with 1 ml of water and dried under reduced pressure. 86 mg (64% of theory, 100% purity) of the title compound were obtained.

$^1$H-NMR (400 MHz, DMSO-$d_6$): [ppm]=10.74 (s, 1H), 8.04-7.99 (m, 2H), 7.94 (dd, 1H), 7.74 (dd, 1H), 7.70-7.62 (m, 2H), 7.59-7.48 (m, 5H), 2.88-2.74 (m, 2H), 1.40 (br. s, 2H), 0.69 (t, 3H).

LC/MS (Method 1, ESIpos): $R_t$=1.14 min, m/z=507/509 [M+H]$^+$.

Example 41

4-{[(6-Bromo-7-chloro-3-methyl-2-phenylquinolin-4-yl)carbonyl]amino}-3-fluorobenzoic Acid

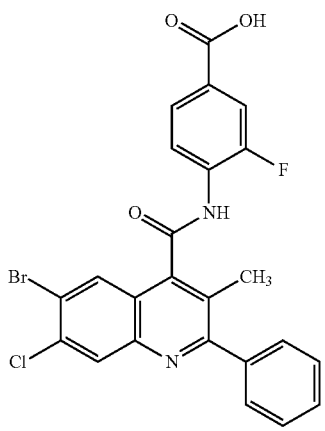 [SMILES: Cc1c(-c2ccccc2)nc2cc(Cl)c(Br)cc2c1C(=O)Nc1ccc(C(=O)O)cc1F]

To a solution of 52 mg (0.10 mmol) of the compound from example 67A in 1.3 ml of THF and 0.25 ml of methanol was added, at RT, 0.49 ml (0.49 mmol) of 1 M sodium hydroxide solution, and the mixture was stirred under reflux for 30 min. After cooling to RT, 0.04 ml (0.50 mmol) of trifluoroacetic acid was added. The solids formed were filtered off and washed twice with 1 ml of THF. After drying under reduced pressure, 13 mg (26% of theory, 100% purity) of a first batch of the title compound were obtained. The filtrate was concentrated, and the residue was taken up in a mixture of DMSO, THF and water, and purified by means of preparative HPLC (method 12). In this way, 30 mg (60% of theory, 100% purity) of a second batch of the title compound were obtained.

$^1$H-NMR (500 MHz, DMSO-$d_6$): [ppm]=13.25 (br. s, 1H), 11.08 (s, 1H), 8.39 (s, 1H), 8.23 (t, 1H), 8.20 (s, 1H), 7.89 (dd, 1H), 7.82 (dd, 1H), 7.66-7.61 (m, 2H), 7.60-7.50 (m, 3H), 2.43 (s, 3H).

LC/MS (Method 1, ESIpos): $R_t$=1.16 min, m/z=513/515 [M+H]$^+$.

Example 42

4-{[(6,7-Dichloro-3-methyl-2-phenylquinolin-4-yl)carbonyl]amino}-3-fluorobenzoic Acid

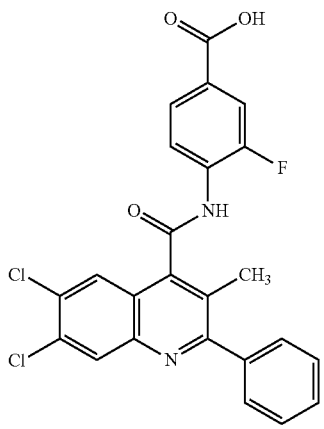 [SMILES: Cc1c(-c2ccccc2)nc2cc(Cl)c(Cl)cc2c1C(=O)Nc1ccc(C(=O)O)cc1F]

100 mg (0.26 mmol) of the compound from example 22A and 44.4 mg (0.26 mmol) of methyl 4-amino-3-fluorobenzoate were dissolved in 2 ml of DMF. 73 mg (0.65 mmol) of potassium tert-butoxide were added in portions to the solution. The reaction mixture was stirred at RT for 1 h, and then 1.3 ml (1.3 mmol) of 1 M sodium hydroxide solution were added. The mixture was then stirred at 80° C. for 1 h. After cooling to RT, the mixture, without further workup, was purified by means of preparative HPLC (method 6). After the solvent-water mixture had been removed and the residue had been dried under reduced pressure, 78 mg (59% of theory, 93% purity) of the title compound were obtained.

$^1$H-NMR (400 MHz, DMSO-d$_6$): [ppm]=13.25 (br. s, 1H), 11.07 (s, 1H), 8.41 (s, 1H), 8.24 (t, 1H), 8.06 (s, 1H), 7.89 (dd, 1H), 7.81 (dd, 1H), 7.69-7.60 (m, 2H), 7.60-7.48 (m, 3H), 2.43 (s, 3H).

LC/MS (Method 1, ESIpos): R$_t$=1.15 min, m/z=469/471 [M+H]$^+$.

Example 43

4-({[6-Bromo-2-(4-fluorophenyl)-3-methylquinolin-4-yl]carbonyl}amino)-3-fluorobenzoic Acid

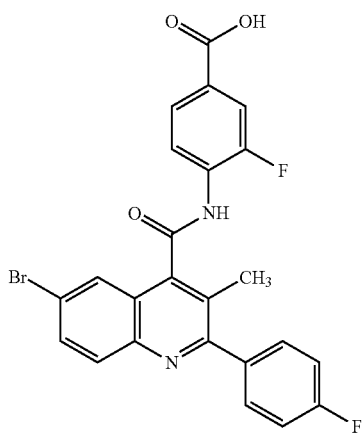 [SMILES: Cc1c(-c2ccc(F)cc2)nc2ccc(Br)cc2c1C(=O)Nc1ccc(C(=O)O)cc1F]

To a solution of 173 mg (0.34 mmol) of the compound from example 68A in 5.4 ml of THF and 1.1 ml of methanol were added, at RT, 1.71 ml (1.71 mmol) of 1 M sodium hydroxide solution, and the mixture was stirred under reflux for 30 min. After cooling to RT, the organic solvent was removed by distillation, and 0.13 ml (1.71 mmol) of trifluoroacetic acid was added to the aqueous phase that remained. The solids formed were filtered off, washed twice with 1 ml of water and dried under reduced pressure. 166 mg (99% of theory, 100% purity) of the title compound were obtained.

$^1$H-NMR (400 MHz, DMSO-d$_6$): [ppm]=13.20 (br. s, 1H), 11.04 (s, 1H), 8.19 (t, 1H), 8.05 (d, 1H), 7.99 (d, 1H), 7.94 (dd, 1H), 7.88 (dd, 1H), 7.81 (dd, 1H), 7.73-7.65 (m, 2H), 7.42-7.33 (m, 2H), 2.44 (s, 3H).

LC/MS (Method 1, ESIpos): R$_t$=1.06 min, m/z=497/499 [M+H]$^+$.

Example 44

4-({[6-Bromo-2-(3-fluorophenyl)-3-methylquinolin-4-yl]carbonyl}amino)-3-fluorobenzoic Acid

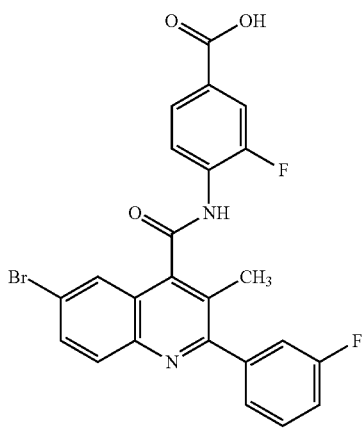 [SMILES: Cc1c(-c2cccc(F)c2)nc2ccc(Br)cc2c1C(=O)Nc1ccc(C(=O)O)cc1F]

To a solution of 96 mg (0.19 mmol) of the compound from example 69A in 3.0 ml of THF and 0.6 ml of methanol was added, at RT, 0.95 ml (0.95 mmol) of 1 M sodium hydroxide solution, and the mixture was stirred under reflux for 3 h. After cooling to RT, the organic solvent was removed by distillation, and 0.07 ml (0.95 mmol) of trifluoroacetic acid was added to the aqueous phase that remained. The solids formed were filtered off, washed twice with 1 ml of water and dried under reduced pressure. Subsequently, the solids were taken up in DMSO and purified by means of preparative HPLC (method 12). 68 mg (72% of theory, 100% purity) of the title compound were obtained.

$^1$H-NMR (400 MHz, DMSO-d$_6$): [ppm]=13.25 (s, 1H), 11.05 (s, 1H), 8.21 (t, 1H), 8.06 (d, 1H), 8.00 (d, 1H), 7.95 (dd, 1H), 7.89 (dd, 1H), 7.82 (dd, 1H), 7.64-7.57 (m, 1H), 7.51-7.44 (m, 2H), 7.42-7.33 (m, 1H), 2.44 (s, 3H).

LC/MS (Method 1, ESIpos): R$_t$=1.09 min, m/z=497/499 [M+H]$^+$.

Example 45

4-({[6-Bromo-2-(2-fluorophenyl)-3-methylquinolin-4-yl]carbonyl}amino)-3-fluorobenzoic Acid

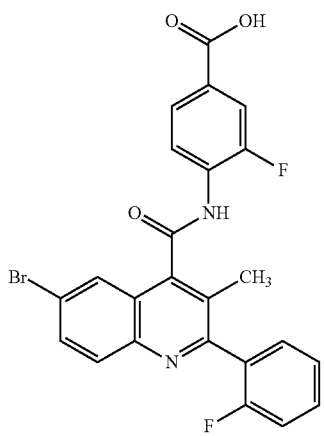 [SMILES: Cc1c(-c2ccccc2F)nc2ccc(Br)cc2c1C(=O)Nc1ccc(C(=O)O)cc1F]

To a solution of 95 mg (0.19 mmol) of the compound from example 70A in 3 ml of THF and 0.6 ml of methanol was added, at RT, 0.94 ml (0.94 mmol) of 1 M sodium hydroxide solution, and the mixture was stirred under reflux for 3 h. After cooling to RT, the organic solvent was removed by distillation, and 0.07 ml (0.94 mmol) of trifluoroacetic acid was added to the aqueous phase that remained. The solids formed were filtered off, washed twice with 1 ml of water and dried under reduced pressure. 83 mg (86% of theory, 96% purity) of the title compound were obtained.

$^1$H-NMR (400 MHz, DMSO-$d_6$): [ppm]=13.25 (br. s, 1H), 11.14 (s, 1H), 8.19 (t, 1H), 8.06 (d, 1H), 8.02 (d, 1H), 7.96 (dd, 1H), 7.89 (dd, 1H), 7.82 (dd, 1H), 7.65-7.50 (m, 2H), 7.45-7.37 (m, 2H), 2.32 (s, 3H).

LC/MS (Method 3, ESIpos): $R_t$=1.34 min, m/z=497/499 [M+H]$^+$.

Example 46

4-({[6-Bromo-3-methyl-2-(pyridin-4-yl)quinolin-4-yl]carbonyl}amino)-3-fluorobenzoic Acid

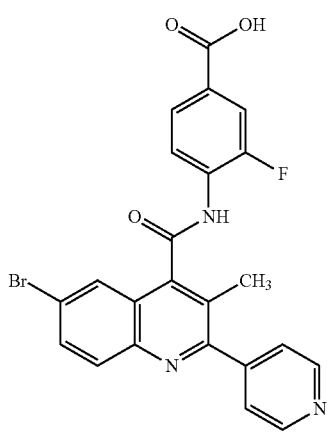 [SMILES: Cc1c(-c2ccncc2)nc2ccc(Br)cc2c1C(=O)Nc1ccc(C(=O)O)cc1F]

A mixture of 90 mg (0.18 mmol) of the compound from example 71A in 1 ml (1 mmol) of 1 M sodium hydroxide solution, 1 ml of methanol and 1 ml of THF was stirred at RT overnight. Subsequently, the mixture was adjusted to pH 7 by adding a few drops of 1 M hydrochloric acid and the solvent was removed under reduced pressure. The residue was purified by means of preparative RP-HPLC (eluent: acetonitrile/10 mM aq. ammonium carbonate gradient). 55 mg (63% of theory) of the title compound were obtained.

$^1$H-NMR (300 MHz, DMSO-$d_6$): [ppm]=8.79 (d, 2H), 8.14 (m, 2H), 8.05 (d, 1H), 7.92 (m, 2H), 7.82 (m, 1H), 7.72 (m, 2H), 2.55 (s, 3H).

LC/MS (Method 4, ESIpos): $R_t$=1.36 min, m/z=479/481 [M+H]+.

Example 47

6-Bromo-N-(4-carbamoylphenyl)-3-methyl-2-phenylquinoline-4-carboxamide

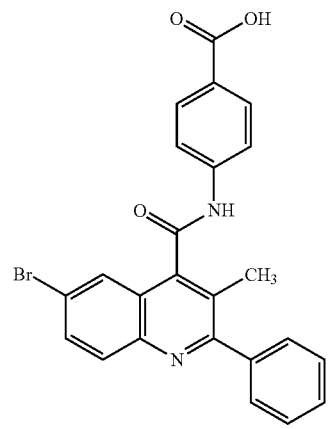 [SMILES: Cc1c(-c2ccccc2)nc2ccc(Br)cc2c1C(=O)Nc1ccc(C(=O)O)cc1]

To 208 mg (0.43 mmol) of the compound from example 35A were gradually added 3.5 ml (30 mmol) of ammonia solution (33% in water), and the mixture was stirred at RT for 1 h. Subsequently, the mixture was diluted with water, and the solids formed were filtered off, washed twice with water and dried under air. The crude product was purified by preparative HPLC (Method 5). The combined product-containing fractions were concentrated, the residue was taken up in a mixture of dichloromethane and methanol, and the mixture was concentrated again. After the residue had been dried under reduced pressure, 113 mg (57% of theory, 100% purity) of the title compound were obtained.

$^1$H-NMR (400 MHz, DMSO-$d_6$): [ppm]=11.10 (s, 1H), 8.05 (d, 1H), 7.97-7.89 (m, 5H), 7.84 (d, 2H), 7.66-7.60 (m, 2H), 7.59-7.47 (m, 3H), 7.31 (br. s, 1H), 2.41 (s, 3H).

LC/MS (Method 1, ESIpos): $R_t$=0.92 min, m/z=460/462 [M+H]$^+$.

Example 48

6-Bromo-N-(4-carbamoyl-2-fluorophenyl)-3-methyl-2-phenylquinoline-4-carboxamide

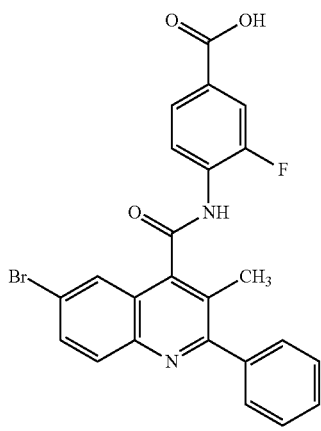 [SMILES: Cc1c(-c2ccccc2)nc2ccc(Br)cc2c1C(=O)Nc1ccc(C(=O)O)cc1F]

To 260 mg (0.52 mmol) of the compound from example 40A were gradually added 4.0 ml (33.9 mmol) of ammonia solution (33% in water), and the mixture was stirred at RT for 30 min. Subsequently, the solids formed were filtered off, washed twice with water and dried under air. The crude product was purified by preparative HPLC (Method 5). The combined product-containing fractions were concentrated, the residue was taken up in a mixture of dichloromethane and methanol, and the mixture was concentrated again. After the residue had been dried under reduced pressure, 181 mg (73% of theory, 100% purity) of the title compound were obtained.

$^1$H-NMR (400 MHz, DMSO-$d_6$): [ppm]=10.96 (s, 1H), 8.12-8.02 (m, 3H), 8.00 (d, 1H), 7.94 (dd, 1H), 7.87-7.80 (m, 2H), 7.66-7.61 (m, 2H), 7.60-7.48 (m, 4H), 2.44 (s, 3H).

LC/MS (Method 1, ESIpos): $R_t$=0.98 min, m/z=478/480 [M+H]$^+$.

Example 49

4-{[(6-Bromo-3-methyl-1-oxido-2-phenylquinolin-4-yl)carbonyl]amino}-3-fluorobenzoic Acid

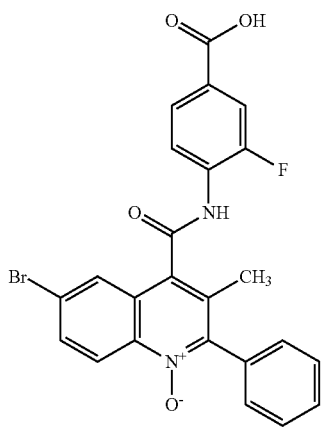 [SMILES: Cc1c(C(=O)Nc2ccc(C(=O)O)cc2F)c2cc(Br)ccc2[n+]([O-])c1-c1ccccc1]

To a suspension of 100 mg (0.21 mmol) of the compound from example 7 in 3 ml of dichloromethane were added, at RT, 113 mg (0.46 mmol, content of 70%, remainder water) of 3-chloroperbenzoic acid, suspended in 1 ml of dichloromethane. The mixture was stirred at RT for 2 h. Subsequently, 0.5 ml of THF was added, and the mixture was left to stand at RT for 3 days. Thereafter, another 113 mg (0.46 mmol, content of 70%) of 3-chloroperbenzoic acid, suspended in 1 ml of dichloromethane, were added, and the mixture was stirred at RT for a further day. Subsequently, a further 57 mg (0.23 mmol, content of 70%) of 3-chloroperbenzoic acid, suspended in 0.5 ml of dichloromethane, were added, and the mixture was stirred at RT for another day. The mixture was then admixed with 20 ml each of saturated aqueous sodium hydrogencarbonate solution and dichloromethane, the phases were separated and then the aqueous phase was extracted once with 20 ml of dichloromethane. The aqueous phase was adjusted to pH 1 by addition of concentrated hydrochloric acid and extracted twice more with 30 ml each time of dichloromethane. The combined organic phases were dried over sodium sulfate, filtered and concentrated. The residue was taken up in DMSO and purified by means of preparative HPLC (method 12). In this way, 67 mg (65% of theory, 100% purity) of the title compound were obtained.

$^1$H-NMR (400 MHz, DMSO-$d_6$): δ [ppm]=13.24 (br. s, 1H), 10.98 (s, 1H), 8.51 (d, 1H), 8.23 (t, 1H), 8.07 (d, 1H), 7.99 (dd, 1H), 7.88 (dd, 1H), 7.80 (dd, 1H), 7.63-7.48 (m, 3H), 7.43 (d, 2H), 2.16 (s, 3H).

LC/MS (Method 1, ESIpos): $R_t$=0.87 min, m/z=495/497 [M+H]$^+$.

Example 50

Sodium 4-{[(6-bromo-3-methyl-2-phenylquinolin-4-yl)carbonyl]amino}-3-fluorobenzoate

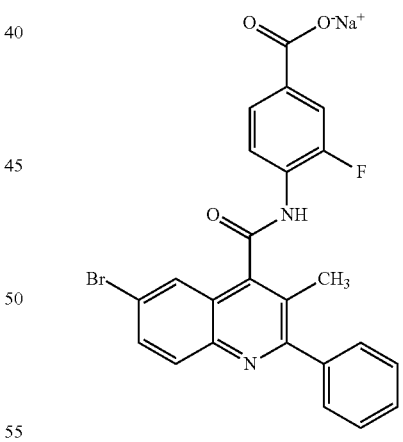

Method A:

50 mg (0.10 mmol) of the compound from Example 7 were dissolved in 1.5 ml of THF, and 1 M sodium hydroxide solution was added dropwise until pH 8 was attained. The mixture was then concentrated to dryness on a rotary evaporator. The residue was dissolved in a little acetonitrile and methanol, and lyophilized overnight. 50 mg (95% of theory, 99% purity) of the title compound were obtained.

$^1$H-NMR (400 MHz, DMSO-$d_6$): [ppm]=10.73 (s, 1H), 8.03-8.01 (m, 2H), 7.93-7.91 (d, 1H), 7.71 (s, 2H), 7.66-7.62 (m, 3H), 7.57-7.50 (m, 3H), 2.44 (s, 3H).

LC/MS (Method 1, ESIpos): $R_t$=1.07 min, m/z=479/481 [M+H]$^+$.

Method B:

To 2.0 g (4.18 mmol) of the compound from example 7 were added 100 ml of 1,4-dioxane, and the mixture was heated briefly to boiling. To the hot solution was added a solution of 167 mg (4.18 mmol) of sodium hydroxide in 20 ml of water. After cooling to RT, the mixture was left to stand at RT under air until the solvent had evaporated. After decanting, 2.3 g of the title compound were obtained (quant., 100% purity, still contains water).

Example 51

4-{[(6-Bromo-3-methyl-2-phenylquinolin-4-yl)carbonyl]amino}-3-fluorobenzoic Acid L-Arginine Salt

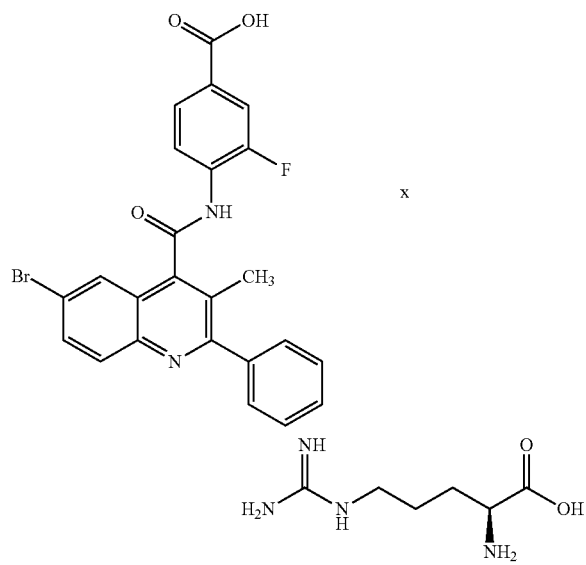

To 1.1 g (2.30 mmol) of the compound from example 7 were added 200 ml of methanol and 5 ml of DMF, and the mixture was heated briefly to boiling. To the hot solution was added a solution of 401 mg (2.30 mmol) of L-(+)-arginine in 30 ml of water. After cooling to RT, the mixture was left to stand at RT under air until the solvent had evaporated. The remaining residue was suspended in 40 ml of water and stirred at RT for one day. Thereafter, the suspension was filtered and the solids were dried at RT under air. 1.0 g (73% of theory, 100% purity) of the title compound was obtained.

$^1$H-NMR (400 MHz, DMSO-d$_6$): δ [ppm]=10.76 (br. s, 1H), 8.04 (d, 1H), 8.00 (d, 1H), 8.0-7.7 (br. m, ~2H), 7.93 (dd, 1H), 7.89-7.82 (m, 1H), 7.77 (dd, 1H), 7.69 (dd, 1H), 7.65-7.60 (m, 2H), 7.55 (d, 3H), 3.30-3.03 (m, 2H, partially hidden), 2.44 (s, 3H), 1.81-1.53 (m, 4H).

LC/MS (Method 1, ESIpos): $R_t$=1.08 min, m/z=479/481 [M+H]$^+$.

Example 52

4-{[(6-Bromo-3-methyl-2-phenylquinolin-4-yl)carbonyl]amino}-3-[(methoxymethyl)sulfanyl]benzoic Acid

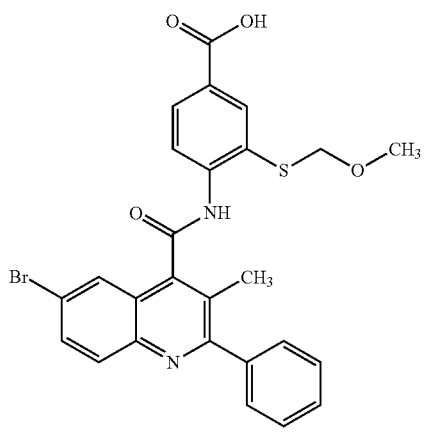 [SMILES: COCSc1cc(C(=O)O)ccc1NC(=O)c1c(C)c(-c2ccccc2)nc2ccc(Br)cc12]

To a solution of 50 mg (0.09 mmol) of the compound from example 72A in 1.5 ml of THF and 0.4 ml of methanol was added, at RT, 0.46 ml (0.46 mmol) of 1 M sodium hydroxide solution, and the mixture was stirred under reflux for 1 h. After cooling to RT, the mixture was admixed with 0.035 ml (0.46 mmol) of trifluoroacetic acid and purified by means of preparative HPLC (method 18). After the solvent had been removed, the residue was taken up in a dichloromethane/methanol mixture and the solution was concentrated again. After the residue had been dried under reduced pressure, 42 mg (87% of theory, 100% purity) of the title compound were obtained.

$^1$H-NMR (400 MHz, DMSO-d$_6$): δ [ppm]=13.14 (br. s, 1H), 10.75 (s, 1H), 8.25 (dd, 2H), 8.04 (d, 1H), 7.97-7.89 (m, 2H), 7.78 (d, 1H), 7.66-7.61 (m, 2H), 7.60-7.49 (m, 3H), 5.09 (s, 2H), 3.34 (s, 3H, hidden), 2.50 (s, 3H, hidden).

LC/MS (Method 1, ESIpos): $R_t$=1.12 min, m/z=537/539 [M+H]$^+$.

Example 53

4-{[(6-Bromo-3-methyl-2-phenylquinolin-4-yl)carbonyl]amino}-3-[(trifluoromethyl)sulfonyl]benzoic Acid

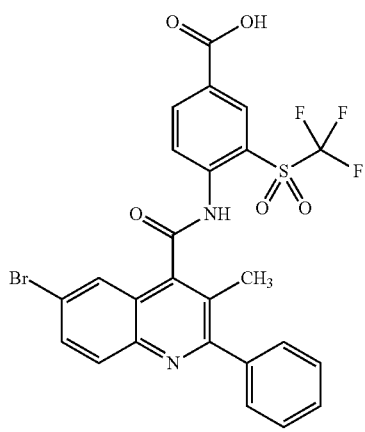 [SMILES: Cc1c(-c2ccccc2)nc2ccc(Br)cc2c1C(=O)Nc1ccc(C(=O)O)cc1S(=O)(=O)C(F)(F)F]

To a solution of 45 mg (0.07 mmol) of the compound from example 75A in 1.2 ml of THF and 0.3 ml of methanol was added, at RT, 0.37 ml (0.37 mmol) of 1 M sodium hydroxide solution, and the mixture was stirred under reflux for 2 h. After cooling to RT, the mixture was admixed with 0.029 ml (0.37 mmol) of trifluoroacetic acid and purified by means of preparative HPLC (method 18). After the solvent had been removed, the residue was taken up in a dichloromethane/methanol mixture and the solution was concentrated again. After the residue had been dried under reduced pressure, 41 mg (94% of theory, 100% purity) of the title compound were obtained.

$^1$H-NMR (400 MHz, DMSO-d$_6$): δ [ppm]=13.91 (br. s, 1H), 11.01 (s, 1H), 8.60 (dd, 1H), 8.58-8.55 (m, 1H), 8.37 (d, 1H), 8.07-8.04 (m, 2H), 7.95 (dd, 1H), 7.66-7.61 (m, 2H), 7.60-7.50 (m, 3H), 2.48 (s, 3H).

LC/MS (Method 1, ESIpos): R$_t$=1.25 min, m/z=593/595 [M+H]+.

Example 54

4-{[(6-Bromo-3-methyl-1-oxido-2-phenylquinolin-4-yl)carbonyl]amino}-3-[(trifluoromethyl)sulfanyl]benzoic Acid

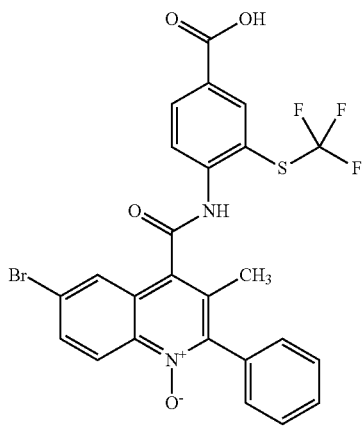 [SMILES: Cc1c(C(=O)Nc2ccc(C(=O)O)cc2SC(F)(F)F)c2cc(Br)ccc2[n+]([O-])c1-c1ccccc1]

To a solution of 43 mg (0.07 mmol) of the compound from example 76A in 1.5 ml of THF and 0.3 ml of methanol was added, at RT, 0.37 ml (0.37 mmol) of 1 M sodium hydroxide solution, and the mixture was stirred under reflux for 1 h. After cooling to RT, the mixture was admixed with 0.028 ml (0.37 mmol) of trifluoroacetic acid and purified by means of preparative HPLC (method 5). After the solvent had been removed, the residue was taken up in dichloromethane and the solution was concentrated again. After the residue had been dried under reduced pressure, 33 mg (78% of theory, 100% purity) of the title compound were obtained.

$^1$H-NMR (500 MHz, DMSO-d$_6$): δ [ppm]=13.45 (br. s, 1H), 11.27 (s, 1H), 8.53 (d, 1H), 8.33 (s, 1H), 8.25-8.21 (m, 2H), 8.01 (dd, 1H), 7.93 (d, 1H), 7.62-7.57 (m, 2H), 7.56-7.50 (m, 1H), 7.45 (d, 2H), 2.19 (s, 3H).

LC/MS (Method 1, ESIpos): R$_t$=1.00 min, m/z=577/579 [M+H]$^+$.

Example 55

4-{[(6-Bromo-5-chloro-3-methyl-2-phenylquinolin-4-yl)carbonyl]amino}-3-fluorobenzoic Acid

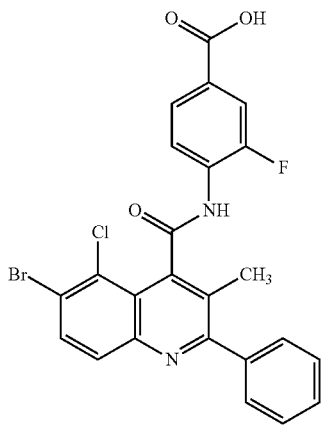

To a solution of 285 mg (0.02 mmol, 4% purity) of the compound from example 79A in 7 ml of THF and 1.5 ml of methanol were added, at RT, 0.09 ml (0.09 mmol) of 1 M sodium hydroxide solution, and the mixture was stirred under reflux for 2 h. After cooling to RT, the mixture was admixed with 0.008 ml (0.11 mmol) of trifluoroacetic acid and left to stand at RT for about 80 h. Thereafter, the precipitate formed was filtered off and washed twice with 0.5 ml of THF. The precipitate newly formed in the filtrate was likewise filtered off. The filtrate was concentrated, and the residue obtained was prepurified by means of preparative HPLC (method 19). The product thus obtained was purified once more by means of preparative HPLC [column: Sunfire C18, 5 μm, 100 mm×30 mm; flow rate: 75 ml/min; detection: 210 nm; injection volume: 2.0 ml; temperature: 40° C.; eluent: water/acetonitrile/(acetonitrile/2% formic acid in water 80:20); gradient: 70:10:20-5:90:5, 10 min]. In this way, 6.1 mg (55% of theory, 100% purity) of the title compound were obtained.

$^1$H-NMR (400 MHz, DMSO-d$_6$): δ [ppm]=13.16 (br. s, 1H), 10.99 (s, 1H), 8.33 (t, 1H), 8.13 (d, 1H), 8.02 (d, 1H), 7.88 (dd, 1H), 7.77 (dd, 1H), 7.66-7.61 (m, 2H), 7.60-7.53 (m, 3H), 2.44 (s, 3H).

LC/MS (Method 1, ESIpos): R$_t$=1.10 min, m/z=513/515 [M+H]$^+$.

Example 56

6-Bromo-N-[2-fluoro-4-(methylcarbamoyl)phenyl]-3-methyl-2-phenylquinoline-4-carboxamide

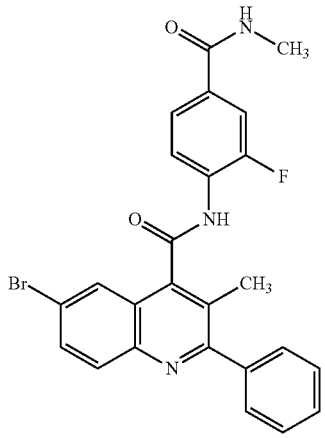 [SMILES: CNC(=O)c1ccc(NC(=O)c2c(C)c(-c3ccccc3)nc3ccc(Br)cc23)c(F)c1]

To 298 mg (0.60 mmol) of the compound from example 40A in 3 ml of THF were gradually added, at 0° C., 1.90 ml (3.80 mmol) of a 2 M solution of methylamine in THF, and the mixture was stirred at RT for 2 h. Subsequently, a further 3 ml of THF and 1 ml (1.90 mmol) of the methylamine solution were added, and the mixture was heated to 70° C. in a microwave apparatus for 30 min. After cooling to RT, another 1 ml (1.90 mmol) of the methylamine solution was added, and the mixture was heated in the microwave at 100° C. for a further 15 min. After cooling to RT, the mixture was admixed with saturated sodium chloride solution, water and 1 M hydrochloric acid, and extracted twice with ethyl acetate. The combined organic phases were washed once with 1 M sodium hydroxide solution, dried over magnesium sulfate and concentrated. The residue was purified by means of preparative HPLC (method 12). 43 mg (15% of theory, 100% purity) of the title compound were obtained.

$^1$H-NMR (400 MHz, DMSO-d$_6$): δ [ppm]=10.96 (s, 1H), 8.55 (q, 1H), 8.09 (t, 1H), 8.04 (d, 1H), 8.00 (d, 1H), 7.94 (dd, 1H), 7.82-7.76 (m, 2H), 7.65-7.61 (m, 2H), 7.59-7.50 (m, 3H), 2.81 (d, 3H), 2.44 (s, 3H).

LC/MS (Method 1, ESIpos): R$_t$=1.00 min, m/z=492/494 [M+H]$^+$.

Example 57

4-({[6-Bromo-2-phenyl-3-(trifluoromethyl)quinolin-4-yl]carbonyl}amino)-3-fluorobenzoic Acid

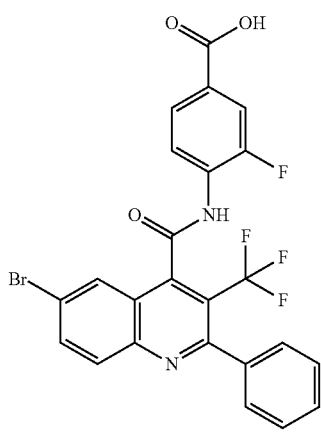 [SMILES: O=C(O)c1ccc(NC(=O)c2c(C(F)(F)F)c(-c3ccccc3)nc3ccc(Br)cc23)c(F)c1]

To a solution of 4.5 mg (0.008 mmol) of the compound from example 81A in 1 ml of THF and 0.5 ml of methanol was added, at RT, 0.03 ml (0.03 mmol) of 1 M sodium hydroxide solution, and the mixture was stirred under reflux for 14 h. After cooling to RT, the mixture was admixed with 0.003 ml (0.035 mmol) of trifluoroacetic acid and concentrated. The residue was purified by means of preparative HPLC (column: Phenomenex Luna C18, 5 μm, 100 mm×21.2 mm; flow rate: 25 ml/min; eluent: water with 1% formic acid/acetonitrile; gradient: 95:5→5:95, 16 min). In this way, 4.5 mg (92% of theory, 90% purity) of the title compound were obtained. Also isolated as a secondary component was 0.5 mg (9% of theory, 92% purity) of the compound listed as example 62 (see therein for analysis).

$^1$H-NMR (500 MHz, DMSO-d$_6$): δ [ppm]=11.27 (s, 1H), 8.28-8.10 (m, 4H), 7.91 (dd, 1H), 7.83 (dd, 1H), 7.56-7.54 (m, 5H).

LC/MS (Method 23, ESIpos): R$_t$=3.54 min, m/z=533/535 [M+H]$^+$.

Example 58

4-{[(6-Bromo-3,8-dimethyl-2-phenylquinolin-4-yl)carbonyl]amino}benzoic Acid

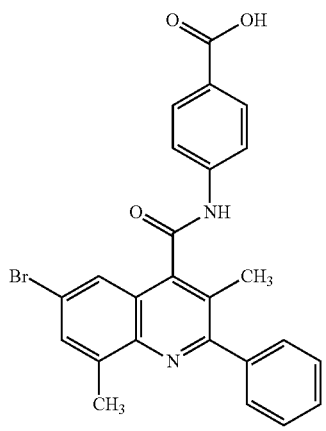 [SMILES: Cc1c(-c2ccccc2)nc2c(C)cc(Br)cc2c1C(=O)Nc1ccc(C(=O)O)cc1]

To a solution of 42 mg (0.08 mmol, 96% purity) of methyl 4-{[(6-bromo-3,8-dimethyl-2-phenylquinolin-4-yl)carbonyl]amino}benzoate (commercially available) in 1.5 ml of THF and 0.3 ml of methanol was added, at RT, 0.4 ml (0.4 mmol) of 1 M sodium hydroxide solution, and the mixture was stirred under reflux for 1 h. After cooling to RT, the mixture was admixed with 0.03 ml (0.4 mmol) of trifluoroacetic acid and purified by means of preparative HPLC (method 5). In this way, 30 mg (78% of theory, 100% purity) of the title compound were obtained.

$^1$H-NMR (400 MHz, DMSO-d$_6$): δ [ppm]=12.83 (br. s, 1H), 11.16 (s, 1H), 8.00 (d, 2H), 7.89 (d, 2H), 7.86-7.84 (m, 1H), 7.73 (d, 1H), 7.70-7.64 (m, 2H), 7.60-7.49 (m, 3H), 2.73 (s, 3H), 2.42 (s, 3H).

LC/MS (Method 1, ESIpos): R$_t$=1.23 min, m/z=475/477 [M+H]$^+$.

Example 59

4-{[(6-Chloro-3-methyl-2-phenylquinolin-4-yl)carbonyl]amino}-3-fluorobenzoic Acid

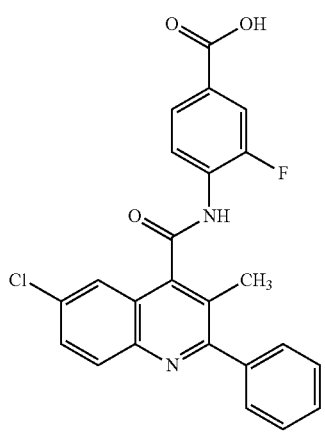

To a solution of 60 mg (0.13 mmol) of the compound from example 82A in 2.7 ml of THF and 0.5 ml of methanol was added, at RT, 0.39 ml (0.39 mmol) of 1 M sodium hydroxide solution, and the mixture was stirred under reflux for 1 h. After cooling to RT, the mixture was admixed with 0.045 ml (0.59 mmol) of trifluoroacetic acid, diluted with 2 ml of DMSO and then purified by means of preparative HPLC (method 18). 51 mg (88% of theory, 100% purity) of the title compound were obtained.

$^1$H-NMR (400 MHz, DMSO-d$_6$): δ [ppm]=13.22 (br. s, 1H), 11.06 (s, 1H), 8.22 (t, 1H), 8.15-8.09 (m, 1H), 7.89 (dd, 1H), 7.86-7.78 (m, 3H), 7.66-7.60 (m, 2H), 7.59-7.49 (m, 3H), 2.43 (s, 3H).

LC/MS (Method 1, ESIpos): R$_t$=1.06 min, m/z=435 [M+H]$^+$.

Example 60

4-{[(6-Bromo-3-methyl-2-phenylquinolin-4-yl)carbonyl]amino}-3-[(methoxymethyl)sulfonyl]benzoic Acid

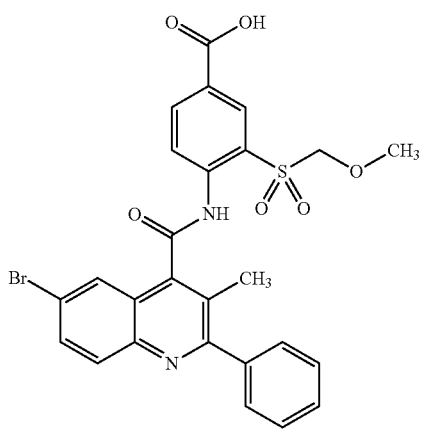 [SMILES: COCS(=O)(=O)c1cc(C(=O)O)ccc1NC(=O)c1c(C)c(-c2ccccc2)nc2ccc(Br)cc12]

To a solution of 70 mg (0.12 mmol) of the compound from example 83A in 2.6 ml of THF and 0.5 ml of methanol was added, at RT, 0.60 ml (0.60 mmol) of 1 M sodium hydroxide solution, and the mixture was stirred under reflux for 1 h. After cooling to RT, the mixture was admixed with 0.047 ml (0.61 mmol) of trifluoroacetic acid and purified by means of preparative HPLC (method 18). 64 mg (91% of theory, 98% purity) of the title compound were obtained.

$^1$H-NMR (400 MHz, DMSO-d$_6$): δ [ppm]=13.50 (br. s, 1H), 10.62 (s, 1H), 8.49 (d, 1H), 8.46-8.37 (m, 2H), 8.21 (d, 1H), 8.05 (d, 1H), 7.95 (dd, 1H), 7.67-7.61 (m, 2H), 7.59-7.50 (m, 3H), 5.02 (s, 2H), 3.42 (s, 3H), 2.49 (s, 3H).

LC/MS (Method 1, ESIpos): R$_t$=1.15 min, m/z=569/571 [M+H]$^+$.

Example 61

4-{[(6-tert-Butyl-3-methyl-2-phenylquinolin-4-yl)carbonyl]amino}-3-fluorobenzoic Acid

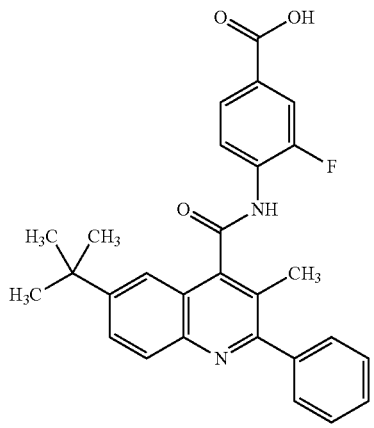

To a solution of 80 mg (0.17 mmol) of the compound from example 85A in 3.5 ml of THF and 0.7 ml of methanol was added, at RT, 0.86 ml (0.86 mmol) of 1 M sodium hydroxide solution, and the mixture was stirred under reflux for 1 h. After cooling to RT, the mixture was admixed with 0.066 ml (0.86 mmol) of trifluoroacetic acid and purified by means of preparative HPLC (method 5). 61 mg (77% of theory, 98% purity) of the title compound were obtained.

$^1$H-NMR (400 MHz, DMSO-d$_6$): δ [ppm]=13.24 (br. s, 1H), 11.01 (s, 1H), 8.07-8.00 (m, 2H), 7.94 (dd, 1H), 7.89 (d, 1H), 7.83 (dd, 1H), 7.77 (d, 1H), 7.64-7.59 (m, 2H), 7.59-7.48 (m, 3H), 2.42 (s, 3H), 1.38 (s, 9H).

LC/MS (Method 1, ESIpos): R$_t$=1.09 min, m/z=457 [M+H]$^+$.

Example 62

3-Bromo-4-({[6-bromo-2-phenyl-3-(trifluoromethyl)quinolin-4-yl]carbonyl}amino)-5-fluorobenzoic Acid

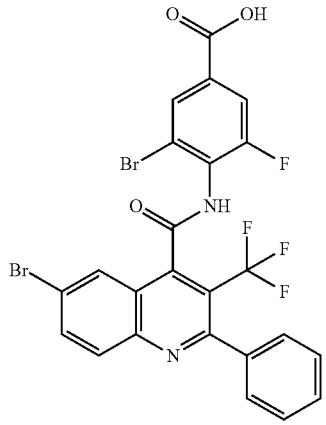 [SMILES: O=C(O)c1cc(F)c(NC(=O)c2c(C(F)(F)F)c(-c3ccccc3)nc3ccc(Br)cc23)c(Br)c1]

The title compound was obtained as a secondary component in the preparation and purification of the compound from example 57 (for description see therein).

$^1$H-NMR (500 MHz, DMSO-d$_6$): δ [ppm]=11.28 (s, 1H), 8.49 (d, 1H), 8.23 (dd, 1H), 8.18 (d, 1H), 8.13-8.10 (m, 1H), 7.94 (dd, 1H), 7.57-7.52 (m, 5H).

LC/MS (Method 1, ESIpos): R$_t$=1.14 min, m/z=611/613/615 [M+H]$^+$.

Example 63

3-Fluoro-4-({[3-methyl-6-(pentafluoro-λ⁶-sulfanyl)-2-phenylquinolin-4-yl]carbonyl}amino)benzoic Acid

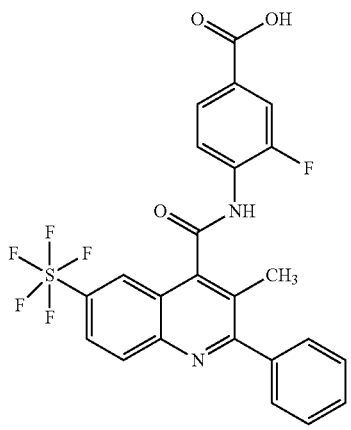 [SMILES: Cc1c(-c2ccccc2)nc2ccc(S(F)(F)(F)(F)F)cc2c1C(=O)Nc1ccc(C(=O)O)cc1F]

110 mg (0.20 mmol) of the compound from example 90A were dissolved in 4 ml of a THF/methanol mixture (5:1), and 1.02 ml (1.02 mmol) of a 1 M solution of lithium hydroxide in water were added. The reaction mixture was stirred at 50° C. for 3 h. Subsequently, the mixture was cooled to RT, adjusted to pH 1-2 with 4 M hydrochloric acid and, without further workup, purified by means of preparative HPLC (method 6). The product fractions were concentrated and the residue was dried under reduced pressure. 85 mg (79% of theory, 100% purity) of the title compound were obtained.

$^1$H-NMR (400 MHz, DMSO-$d_6$): δ [ppm]=13.28 (br. s, 1H), 11.14 (s, 1H), 8.35-8.22 (m, 3H), 8.09 (t, 1H), 7.90 (dd, 1H), 7.84 (dd, 1H), 7.73-7.63 (m, 2H), 7.63-7.50 (m, 3H), 2.49 (s, 3H).

LC/MS (Method 1, ESIpos): $R_t$=1.14 min, m/z=527 [M+H]$^+$.

Example 64

4-({[6-(Difluoromethyl)-3-methyl-2-phenylquinolin-4-yl]carbonyl}amino)-3-fluorobenzoic Acid

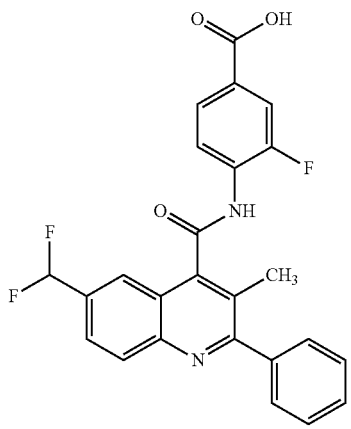 [SMILES: Cc1c(-c2ccccc2)nc2ccc(C(F)F)cc2c1C(=O)Nc1ccc(C(=O)O)cc1F]

55 mg (0.18 mmol) of the compound from example 94A were dissolved in 2 ml of DMF under argon, and 57 mg (0.35 mmol) of N,N'-carbonyldiimidazole were added at RT. The reaction mixture was stirred at 60° C. overnight, and then water and ethyl acetate added. The phases were separated, and the aqueous phase was extracted three times with ethyl acetate. The combined organic phases were dried over sodium sulfate and concentrated. The residue was dissolved in 1.55 ml of dichloromethane, and 29.8 mg (0.26 mmol) of methyl 4-amino-3-fluorobenzoate were added. Subsequently, 0.44 ml (0.44 mmol) of a 1 M solution of potassium tert-butoxide in THF was added. The reaction mixture was stirred at RT overnight, and then 0.88 ml (0.88 mmol) of a 1 M solution of lithium hydroxide in water was added. The reaction mixture was then stirred at 50° C. for 3 h. The mixture was then cooled to RT, adjusted to pH 1-2 with 4 M hydrochloric acid and, without further workup, purified by means of preparative HPLC (method 6). The product fractions were concentrated and the residue was dried under reduced pressure. In this way, 20 mg (23% of theory, 90% purity) of the title compound were obtained.

$^1$H-NMR (400 MHz, DMSO-$d_6$): δ [ppm]=13.24 (br. s, 1H), 11.08 (s, 1H), 8.35-8.17 (m, 2H), 8.09 (s, 1H), 7.98-7.87 (m, 2H), 7.82 (dd, 1H), 7.67-7.62 (m, 2H), 7.60-7.51 (m, 3H), 7.31 (t, 1H), 2.45 (s, 3H).

LC/MS (Method 1, ESIpos): $R_t$=1.03 min, m/z=451 [M+H]$^+$.

Example 65

4-{[(6-Bromo-3-methyl-2-phenylquinolin-4-yl)carbonyl]amino}-2,3-difluorobenzoic Acid

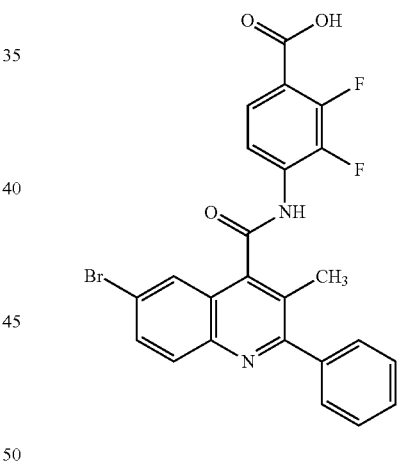

105 mg (0.21 mmol) of the compound from example 95A were dissolved in 5 ml of a THF/methanol mixture (5:1), and 1.03 ml (1.03 mmol) of a 1 M solution of lithium hydroxide in water were added. The reaction mixture was stirred at 50° C. for 3 h, then cooled to RT and adjusted to pH 1-2 with 4 M hydrochloric acid. Subsequently, the mixture, without further workup, was purified by means of preparative HPLC (method 6). The product fractions were concentrated, and the residue was lyophilized and then recrystallized from water. Drying under reduced pressure gave 69 mg (68% of theory, purity 100%) of the title compound.

$^1$H-NMR (400 MHz, DMSO-$d_6$): δ [ppm]=13.51 (br. s, 1H), 11.24 (s, 1H), 8.08-8.03 (m, 1H), 8.03-7.96 (m, 2H), 7.93 (dd, 1H), 7.85-7.74 (m, 1H), 7.66-7.60 (m, 2H), 7.60-7.48 (m, 3H), 2.43 (s, 3H).

LC/MS (Method 1, ESIpos): $R_t$=1.03 min, m/z=497/499 [M+H]$^+$.

Example 66

4-{[(6-Bromo-3-methyl-2-phenylquinolin-4-yl)carbonyl]amino}-2,5-difluorobenzoic Acid

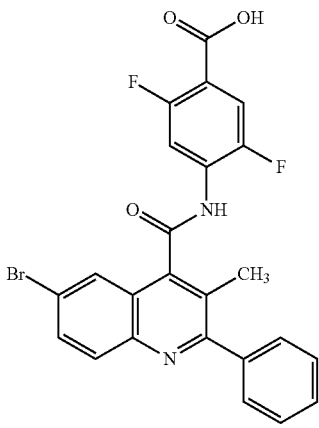

99 mg (0.17 mmol, 85% purity) of the compound from example 96A were dissolved in 5 ml of a THF/methanol mixture (5:1), and 0.82 ml (0.82 mmol) of a 1 M solution of lithium hydroxide in water were added. The reaction mixture was stirred at 50° C. for 3 h, then cooled to RT and adjusted to pH 1-2 with 4 M hydrochloric acid. Subsequently, the mixture, without further workup, was purified by means of preparative HPLC (method 6). The product fractions were concentrated and the residue was dried under reduced pressure. 81 mg (99% of theory, >99% purity) of the title compound were obtained.

$^1$H-NMR (400 MHz, DMSO-$d_6$): δ [ppm]=13.47 (br. s, 1H), 11.23 (s, 1H), 8.25 (dd, 1H), 8.04 (d, 1H), 8.01 (d, 1H), 7.93 (dd, 1H), 7.77 (dd, 1H), 7.66-7.60 (m, 2H), 7.60-7.48 (m, 3H), 2.41 (s, 3H).

LC/MS (Method 1, ESIpos): $R_t$=1.07 min, m/z=497/499 [M+H]$^+$.

Example 67

6-Bromo-N-(2-fluoro-4-{[(trifluoromethyl)sulfonyl]carbamoyl}phenyl)-3-methyl-2-phenylquinoline-4-carboxamide

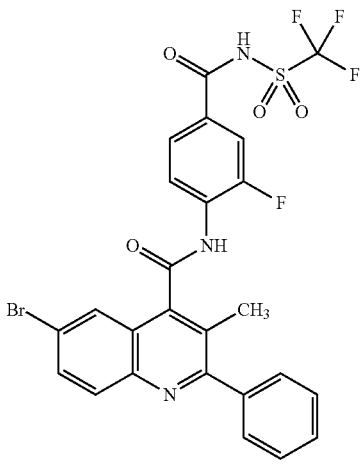 [SMILES: Cc1c(-c2ccccc2)nc2ccc(Br)cc2c1C(=O)Nc1ccc(C(=O)NS(=O)(=O)C(F)(F)F)cc1F]

To a suspension of 20 mg (0.50 mmol) of sodium hydride (60% in mineral oil) in 2.5 ml of THF were added 75 mg (0.50 mmol) of trifluoromethanesulfonamide, and the mixture was stirred at RT for 30 min. Subsequently, 124 mg (0.25 mmol) of the compound from example 40A were added, and the mixture was stirred at RT for a further 30 min. Then the mixture was concentrated. The residue was taken up in DMSO and purified by means of preparative HPLC (method 18). The product-containing fractions were concentrated, and the residue was taken up in a mixture of dichloromethane and methanol, concentrated again and then dried under reduced pressure. 77 mg (50% of theory, 100% purity) of the title compound were obtained.

$^1$H-NMR (400 MHz, DMSO-$d_6$): δ [ppm]=10.90 (s, 1H), 8.07-7.98 (m, 3H), 7.95 (dd, 1H), 7.85 (dd, 1H), 7.75 (dd, 1H), 7.66-7.61 (m, 2H), 7.60-7.50 (m, 3H), 2.44 (s, 3H).

LC/MS (Method 1, ESIpos): $R_t$=1.10 min, m/z=610/612 [M+H]$^+$.

Example 68

6-Bromo-N-{4-[(dimethylsulfamoyl)carbamoyl]-2-fluorophenyl}-3-methyl-2-phenylquinoline-4-carboxamide

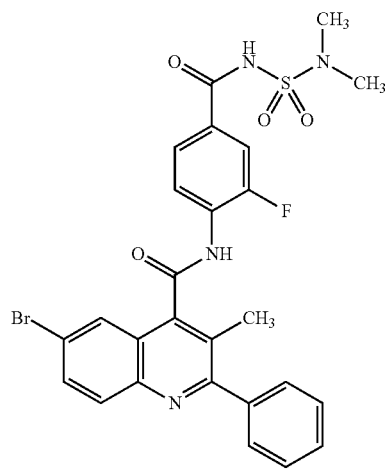 [SMILES: Cc1c(-c2ccccc2)nc2ccc(Br)cc2c1C(=O)Nc1ccc(C(=O)NS(=O)(=O)N(C)C)cc1F]

To a suspension of 20 mg (0.50 mmol) of sodium hydride (60% in mineral oil) in 2.5 ml of THF were added 62 mg (0.50 mmol) of N,N-dimethylsulfonamide, and the mixture was stirred at RT for 30 min. Subsequently, 1 ml of DMF was added and the mixture was stirred at 50° C. for 2 h. After cooling to RT, 124 mg (0.25 mmol) of the compound from example 40A were added, and the mixture was stirred at RT for a further 30 min. Then the mixture was concentrated. The residue was taken up in DMSO and purified by means of preparative HPLC (method 18). The product-containing fractions were concentrated, and the residue was taken up in a mixture of dichloromethane and methanol, concentrated again and then dried under reduced pressure. 40 mg (27% of theory, 100% purity) of the title compound were obtained.

$^1$H-NMR (400 MHz, DMSO-$d_6$): δ [ppm]=11.92 (s, 1H), 11.08 (s, 1H), 8.22 (t, 1H), 8.05 (d, 1H), 7.99 (d, 1H), 7.95 (d, 1H), 7.94-7.87 (m, 2H), 7.66-7.61 (m, 2H), 7.59-7.48 (m, 3H), 2.91 (s, 6H), 2.43 (s, 3H).

LC/MS (Method 1, ESIpos): $R_t$=1.11 min, m/z=585/587 [M+H]$^+$.

Example 69

Potassium 4-{[(6-bromo-3-methyl-2-phenylquinolin-4-yl)carbonyl]amino}-3-fluorobenzoate

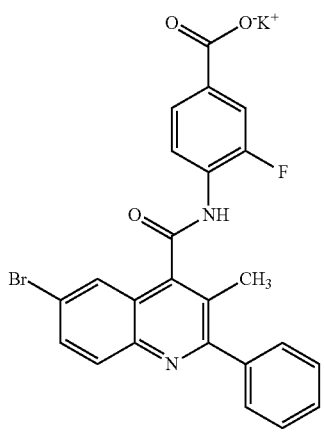

To 1.10 g (2.30 mmol) of the compound from example 7 were added 200 ml of methanol and 5 ml of DMF, and the mixture was heated briefly to boiling. To the hot solution was added a solution of 129 mg (2.30 mmol) of potassium hydroxide in 30 ml of water. After cooling to RT, the mixture was left to stand at RT under air until the solvent had evaporated. A portion of the residue was subjected to heat treatment at 200° C. for 1-1.5 h. After cooling to RT and decanting, 0.50 g (42% of theory, 100% purity) of the title compound was obtained.

$^1$H-NMR (400 MHz, DMSO-d$_6$): δ [ppm]=10.72 (br. s, 1H), 8.05-8.00 (m, 2H), 7.95-7.90 (m, 1H), 7.76-7.68 (m, 2H), 7.67-7.60 (m, 3H), 7.59-7.49 (m, 3H), 2.45 (s, 3H).

LC/MS (Method 1, ESIpos): R$_t$=1.05 min, m/z=479/481 [M+H]$^+$.

Example 70

4-{[(6-Bromo-3-methyl-2-phenylquinolin-4-yl)carbonyl]amino}-3-fluorobenzoic Acid L-Lysine Salt

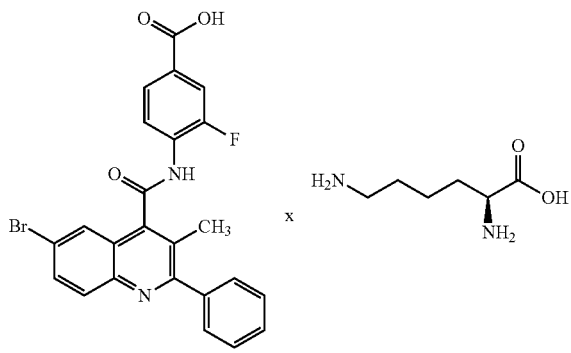 [SMILES: Cc1c(-c2ccccc2)nc2ccc(Br)cc2c1C(=O)Nc1ccc(C(=O)O)cc1F ; NCCCC[C@H](N)C(=O)O]

To 2.0 g (4.18 mmol) of the compound from example 7 were added 100 ml of 1,4-dioxane, and the mixture was heated briefly to boiling. To the hot solution was added a solution of 610 mg (4.18 mmol) of L-lysine in 20 ml of water. After cooling to RT, the mixture was left to stand at RT under air until the solvent had evaporated. The residue was suspended in 20 ml of an ethanol/water mixture (1:1) and stirred at RT for one week. Subsequently, the solids were filtered off and dried under air at RT. 2.2 g of the title compound were obtained (84% of theory, 100% purity, still contains solvent).

$^1$H-NMR (400 MHz, DMSO-d$_6$): δ [ppm]=10.70 (br. s, 1H), 8.03 (d, 1H), 8.00 (d, 1H), 7.93 (dd, 1H), 7.82 (t, 1H), 7.75 (dd, 1H), 7.68 (dd, 1H), 7.65-7.60 (m, 2H), 7.59-7.49 (m, 3H), 3.16 (t, 1H), 2.75 (t, 2H), 2.44 (s, 3H), 1.79-1.29 (m, 6H).

LC/MS (Method 1, ESIpos): R$_t$=1.05 min, m/z=479/481 [M+H]$^+$.

Example 71

2-Hydroxy-N,N,N-trimethylethanaminium 4-{[(6-bromo-3-methyl-2-phenylquinolin-4-yl)carbonyl]amino}-3-fluorobenzoate

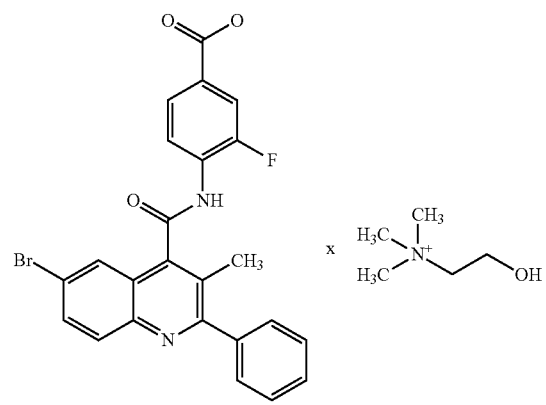

To 2.0 g (4.18 mmol) of the compound from example 7 were added 100 ml of 1,4-dioxane, and the mixture was heated briefly to boiling. To the hot solution was added a mixture of 1.23 g (5.09 mmol) of a 50% by weight aqueous solution of 2-hydroxy-N,N,N-trimethylethanaminium hydroxide (choline hydroxide) and 20 ml of water. After cooling to RT, the mixture was left to stand at RT under air until the solvent had evaporated. 2.5 g of the title compound were obtained (quant., 100% purity, still contains water).

$^1$H-NMR (400 MHz, DMSO-d$_6$): δ [ppm]=10.62 (br. s, 1H), 8.07-7.98 (m, 2H), 7.96-7.87 (m, 1H), 7.74-7.65 (m, 2H), 7.65-7.59 (m, 3H), 7.59-7.47 (m, 3H), 3.87-3.82 (m, 2H), 3.43-3.38 (m, 2H), 3.11 (s, 9H), 2.44 (s, 3H).

LC/MS (Method 1, ESIpos): R$_t$=1.06 min, m/z=479/481 [M+H]$^+$.

Example 72

4-{[(6-Bromo-3-methyl-2-phenylquinolin-4-yl)carbonyl]amino}-3-fluorobenzoic acid 2-amino-2-(hydroxymethyl)propane-1,3-diol Salt

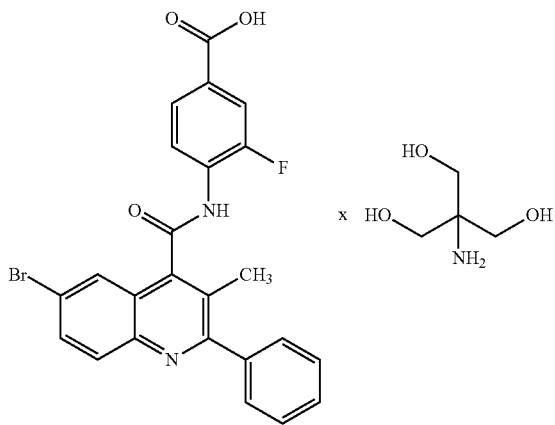 [SMILES: Cc1c(-c2ccccc2)nc2ccc(Br)cc2c1C(=O)Nc1ccc(C(=O)O)cc1F ; NC(CO)(CO)CO]

To 2.0 g (4.18 mmol) of the compound from example 7 were added 100 ml of 1,4-dioxane, and the mixture was heated briefly to boiling. To the hot solution was added a solution of 507 mg (4.18 mmol) of 2-amino-2-(hydroxymethyl)propane-1,3-diol (TRIS) in 20 ml of water. After cooling to RT, the mixture was left to stand at RT under air until the solvent had evaporated. After decanting, 2.5 g of the title compound were obtained (quant., 100% purity, still contains water).

$^1$H-NMR (400 MHz, DMSO-d$_6$): δ [ppm]=10.89 (br. s, 1H), 8.04 (d, 1H), 8.01 (d, 1H), 7.97-7.90 (m, 2H), 7.80 (dd, 1H), 7.72 (dd, 1H), 7.66-7.60 (m, 2H), 7.60-7.49 (m, 3H), 3.44 (s, 6H), 2.45 (s, 3H).

LC/MS (Method 1, ESIpos): R$_t$=1.07 min, m/z=479/481 [M+H]$^+$.

Example 73

4-{[(6-Bromo-3-fluoro-2-phenylquinolin-4-yl)carbonyl]amino}-3-fluorobenzoic Acid

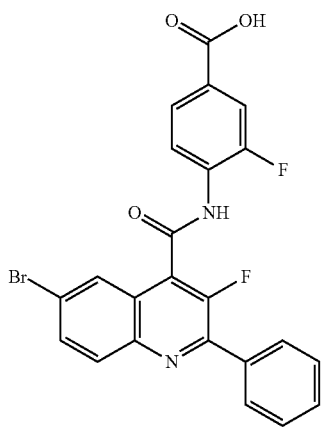 [SMILES: O=C(O)c1ccc(NC(=O)c2c(F)c(-c3ccccc3)nc3ccc(Br)cc23)c(F)c1]

To a solution of 45 mg (0.06 mmol, 69% purity) of the compound from example 98A in 1.0 ml of THF and 0.2 ml of methanol was added, at RT, 0.31 ml (0.31 mmol) of 1 M sodium hydroxide solution, and the mixture was stirred under reflux for 1.5 h. After cooling to RT, 0.03 ml (0.37 mmol) of trifluoroacetic acid was added. Subsequently, the mixture was purified directly by means of preparative HPLC (method 18). 5 mg (16% of theory, 94% purity) of the title compound were obtained.

$^1$H-NMR (400 MHz, DMSO-d$_6$): [ppm]=13.22 (br. s, 1H), 11.21 (s, 1H), 8.33 (t, 1H), 8.17-8.12 (m, 2H), 8.09-8.04 (m, 2H), 8.00 (dd, 1H), 7.89 (dd, 1H), 7.81 (dd, 1H), 7.65-7.57 (m, 3H).

LC/MS (Method 1, ESIpos): R$_t$=1.14 min, m/z=483/485 [M+H]$^+$.

Example 74

4-{[(6-Bromo-3-methoxy-2-phenylquinolin-4-yl)carbonyl]amino}-3-fluorobenzoic Acid

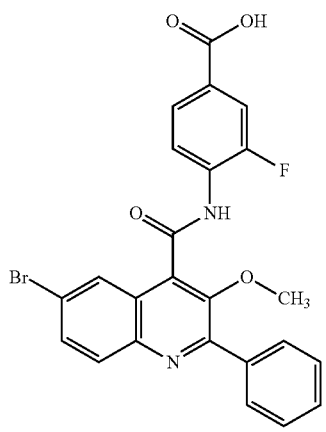

The title compound was obtained as a further product of the reaction described in example 73. In the purification of the reaction mixture by preparative HPLC by method 18 (see example 73), a further product fraction had been obtained, which was purified further by another preparative HPLC [column: Kinetix C18, 5 μm, 100×21.2 mm; flow rate: 60 ml/min; detection: 210 nm; injection volume: 1.0 ml; temperature: 40° C.; eluent: gradient 95% water/0% acetonitrile/5% (acetonitrile/water 80:20+2% formic acid) →30% water/65% acetonitrile/5% (acetonitrile/water 80:20+2% formic acid); run time: 10.8 min]. In this way, 9 mg (29% of theory, 100% purity) of the title compound were obtained.

$^1$H-NMR (400 MHz, DMSO-d$_6$): [ppm]=11.03 (s, 1H), 8.23 (t, 1H), 8.07 (d, 1H), 8.02-7.98 (m, 3H), 7.91 (dd, 1H), 7.88 (d, 1H), 7.80 (d, 1H), 7.61-7.53 (m, 3H), 3.65 (s, 3H).

LC/MS (Method 1, ESIpos): R$_t$=1.08 min, m/z=495/497 [M+H]$^+$.

Example 75

4-{[(3-Chloro-6-iodo-2-phenylquinolin-4-yl)carbonyl]amino}-3-fluorobenzoic Acid

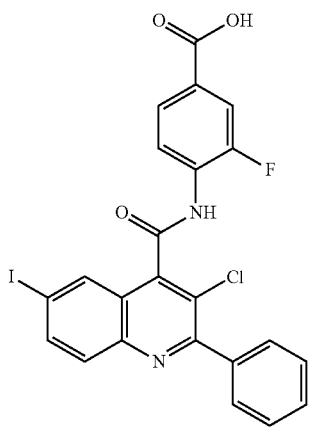 [SMILES: O=C(O)c1ccc(NC(=O)c2c(Cl)c(-c3ccccc3)nc3ccc(I)cc23)c(F)c1]

To a solution of 46 mg (0.07 mmol, 90% purity) of the compound from example 101A in 2.3 ml of THF and 0.5 ml of methanol was added, at RT, 0.44 ml (0.44 mmol) of 1 M sodium hydroxide solution, and the mixture was stirred at RT for 20 h. Subsequently, the mixture was acidified to pH 3 with trifluoroacetic acid and purified by means of preparative HPLC (method 18). 32 mg (77% of theory, 98% purity) of the title compound were obtained.

$^1$H-NMR (400 MHz, DMSO-$d_6$): [ppm]=13.24 (br. s, 1H), 11.20 (s, 1H), 8.31 (t, 1H), 8.21 (d, 1H), 8.17 (dd, 1H), 7.94 (d, 1H), 7.90 (dd, 1H), 7.82 (dd, 1H), 7.78-7.73 (m, 2H), 7.61-7.52 (m, 3H).

LC/MS (Method 1, ESIpos): $R_t$=1.11 min, m/z=547 [M+H]$^+$.

Example 76

4-{[(6-Bromo-3-chloro-2-phenylquinolin-4-yl)carbonyl]amino}-3-fluorobenzoic Acid

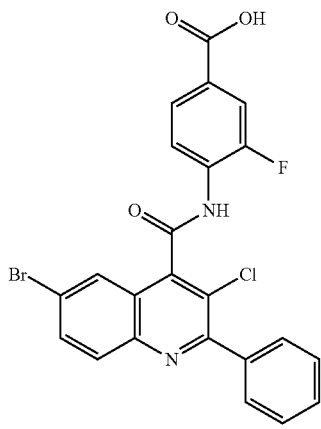

To a solution of 45 mg (0.07 mmol, 85% purity) of the compound from example 104A in 2.3 ml of THF and 0.5 ml of methanol was added, at RT, 0.44 ml (0.44 mmol) of 1 M sodium hydroxide solution, and the mixture was stirred at RT for 20 h. Subsequently, the mixture was acidified to pH 3 with trifluoroacetic acid and prepurified by means of preparative HPLC (method 18). The product thus obtained was dissolved in 10 ml of an acetonitrile/methanol/DMSO/formic acid mixture while heating and purified further by another preparative HPLC [column: Kinetix C18, 5 μm, 100×21.2 mm; flow rate: 25 ml/min; detection: 210 nm; injection volume: 2.75 ml; temperature: 35° C.; eluent: gradient 50% water/45% acetonitrile/5% formic acid (1% in water)→20% water/75% acetonitrile/5% formic acid (1% in water); run time: 6.0 min]. In this way, 22 mg (56% of theory, 95% purity) of the title compound were obtained.

$^1$H-NMR (400 MHz, DMSO-$d_6$): δ [ppm]=13.24 (br. s, 1H), 11.21 (s, 1H), 8.32 (t, 1H), 8.14-8.09 (m, 1H), 8.07-8.02 (m, 2H), 7.92-7.87 (m, 1H), 7.81 (dd, 1H), 7.78-7.73 (m, 2H), 7.61-7.54 (m, 3H).

LC/MS (Method 1, ESIpos): $R_t$=1.09 min, m/z=499/501 [M+H]$^+$.

Example 77

4-{[(6-Bromo-3-cyclopropyl-2-phenylquinolin-4-yl)carbonyl]amino}-3-fluorobenzoic Acid

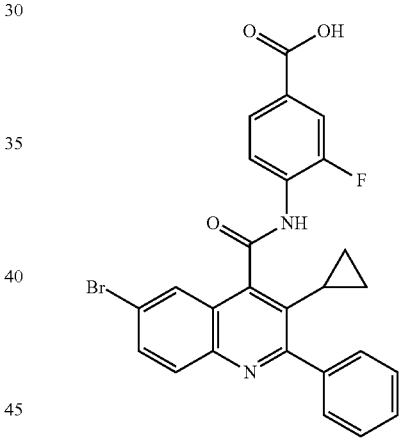

To a solution of 33 mg (0.05 mmol, 77% purity) of the compound from example 106A in 1.5 ml of THF and 0.3 ml of methanol was added, at RT, 0.073 ml (0.073 mmol) of 1 M sodium hydroxide solution, and the mixture was left to stand at RT for 2 h. Subsequently, the mixture was stirred at 60° C. for 5 h and then left to stand again at RT for 2 days. After adding a further 0.15 ml (0.15 mmol) of 1 M sodium hydroxide solution, the mixture was stirred once again at 60° C. for one day. Thereafter, the mixture was acidified to pH 3 with trifluoroacetic acid and purified by means of preparative HPLC (method 18). 19 mg (75% of theory, 100% purity) of the title compound were obtained.

$^1$H-NMR (400 MHz, DMSO-$d_6$): [ppm]=13.24 (br. s, 1H), 11.00 (s, 1H), 8.25 (t, 1H), 8.07-8.02 (m, 2H), 7.94 (dd, 1H), 7.90 (dd, 1H), 7.82 (dd, 1H), 7.76 (dd, 2H), 7.57-7.46 (m, 3H), 2.46-2.30 (m, 1H), 0.68 (d, 2H), 0.33 (d, 2H).

LC/MS (Method 1, ESIpos): $R_t$=1.15 min, m/z=505/507 [M+H]$^+$.

Example 78

4-{[(6-Bromo-3,8-dimethyl-2-phenylquinolin-4-yl)carbonyl]amino}-3-fluorobenzoic Acid

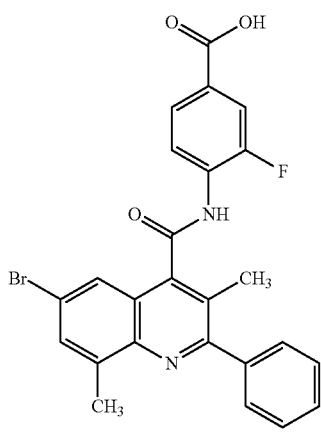

To a solution of 649 mg (1.02 mmol, 80% purity) of the compound from example 108A in 13 ml of THF and 2.6 ml of methanol was added, at RT, 4.3 ml (4.3 mmol) of 1 M sodium hydroxide solution, and the mixture was stirred under reflux for 1.5 h. After cooling to RT, the mixture was acidified to pH 3 with trifluoroacetic acid and then purified by means of preparative HPLC [column: Kinetix C18, 5 µm, 100×21.2 mm; flow rate: 60 ml/min; detection: 210 nm; injection volume: 1.0 ml; temperature: 40° C.; eluent: gradient 50% water/30% acetonitrile/20% (acetonitrile/water 80:20+2% formic acid)→30% water/65% acetonitrile/5% (acetonitrile/water 80:20+2% formic acid); run time: 5.7 min]. 419 mg (83% of theory, 100% purity) of the title compound were obtained.

$^1$H-NMR (400 MHz, DMSO-$d_6$): [ppm]=13.25 (br. s, 1H), 11.02 (s, 1H), 8.19 (t, 1H), 7.89 (dd, 1H), 7.86-7.83 (m, 1H), 7.81 (td, 2H), 7.70-7.64 (m, 2H), 7.60-7.49 (m, 3H), 2.73 (s, 3H), 2.45 (s, 3H).

LC/MS (Method 1, ESIpos): $R_t$=1.19 min, m/z=493/495 [M+H]$^+$.

B. ASSESSMENT OF PHARMACOLOGICAL EFFICACY

The pharmacological activity of the compounds of the invention can be demonstrated by in vitro and in vivo studies as known to the person skilled in the art. The application examples which follow describe the biological action of the compounds of the invention, without restricting the invention to these examples.

Abbreviations and Acronyms

BSA bovine serum albumin
CRTH2 chemoattractant receptor-homologous molecule expressed on T helper type 2 cells
DMEM Dulbecco's modified Eagle's medium
DMSO dimethyl sulfoxide
DP PGD2 receptor
EC$_{50}$ half-maximum effective concentration
em. emission
EP PGE2 receptor
ex. excitation
FCS fetal calf serum
FP PGF2α receptor
HEPES 2-[4-(2-hydroxyethyl)piperazin-1-yl]ethanesulfonic acid
IC$_{50}$ half-maximum inhibitory concentration
IP PGI2 receptor
MES 2-(N-morpholino)ethanesulfonic acid
Pen/Strep penicillin/streptomycin
PGD2 prostaglandin D2
PGE2 prostaglandin E2
PGF2α prostaglandin F2α
PGI2 prostaglandin I2
TC tissue culture
TP thromboxane A2 receptor
Tris tris(hydroxymethyl)aminomethane
v/v volume to volume ratio (of a solution)
w/w weight to weight ratio (of a solution)

B-1. In Vitro Test of Inhibition of Human FP Receptor Activity

Variant B-1A:

For the characterization of test substances in respect of FP antagonism, PGF2α-induced calcium flux in FP-expressing CHEM1 cells (Millipore, HTS093C) was used.

3000 cells in 25 µl of full medium [DMEM F12, 10% FCS, 1.35 mM sodium pyruvate, 20 mM HEPES, 4 mM GlutaMAX™, 2% sodium bicarbonate, 1% Pen/Strep, 1% 100× non-essential amino acids] are sown per well of a 384 multititer plate (from Greiner, TC plate, black with clear base) and incubated at 37° C./5% CO$_2$ for 24 hours. Prior to the measurement, the medium is replaced by 30 µl of Fluo-8 AM loading buffer [calcium-free Tyrode (130 mM NaCl, 5 mM KCl, 20 mM HEPES, 1 mM MgCl$_2$, 4.8 mM NaHCO$_3$, pH 7.4), 2 mM CaCl$_2$, 1× SmartBlock (from CANDOR Bioscience GmbH), 4.5 mM Probenecid, 5 µM Fluo-8 AM, 0.016% Pluronic®, 0.04% Brilliant black] and incubated at 37° C./5% CO$_2$ for 30 minutes. The test substance is prepared in DMSO in various concentrations as a dose-response curve (starting concentration 10 mM, dilution factor 3.16) and prediluted 1:50 with calcium-free Tyrode/2 mM CaCl$_2$. 10 µl of the prediluted substance solution are added to the Fluo-8-laden cells and incubated at 37° C./5% CO$_2$ for 10 minutes. The FP receptor is activated by adding 20 µl of 3 nM (final concentration) PGF2α in calcium-free Tyrode/2 mM CaCl$_2$/0.04% Brilliant black, and the calcium flux is determined by measuring the fluorescence at ex. 470 nm/em. 525 nm in a fluorescence measuring instrument (FLIPR Tetra®, Molecular Devices) for 120 seconds.

Table 1A below lists the IC$_{50}$ values from this assay for individual working examples of the invention (some as mean values from multiple independent individual determinations):

TABLE 1A

| Example no. | FP receptor activity IC$_{50}$ [µmol/l] |
|---|---|
| 1 | 0.166 |
| 2 | 0.148 |
| 3 | 0.170 |
| 4 | 0.880 |
| 5 | 0.905 |
| 6 | 0.079 |
| 7 | 0.020 |
| 8 | 0.795 |
| 9 | 0.065 |
| 10 | 0.041 |
| 11 | 0.053 |
| 12 | 0.022 |

TABLE 1A-continued

| Example no. | FP receptor activity IC$_{50}$ [µmol/l] |
|---|---|
| 13 | 0.150 |
| 14 | 0.617 |
| 15 | 0.045 |
| 16 | 0.278 |
| 17 | 0.060 |
| 18 | 0.335 |
| 19 | 0.650 |
| 20 | 0.530 |
| 21 | 0.204 |
| 22 | 0.290 |
| 23 | 0.057 |
| 24 | 0.124 |
| 25 | 0.720 |
| 26 | 0.086 |
| 27 | 0.097 |
| 28 | 0.017 |
| 29 | 0.890 |
| 30 | 0.006 |
| 31 | 0.165 |
| 32 | 0.245 |
| 33 | 0.272 |
| 34 | 0.093 |
| 35 | 0.290 |
| 36 | 0.078 |
| 37 | 0.039 |
| 38 | 0.265 |
| 39 | 0.190 |
| 40 | 0.560 |
| 41 | 0.025 |
| 42 | 0.033 |
| 43 | 0.052 |
| 44 | 0.033 |
| 45 | 0.205 |
| 46 | 0.140 |
| 47 | 0.197 |
| 48 | 0.102 |
| 49 | 0.120 |
| 50 | 0.037 |
| 51 | 0.091 |
| 52 | 0.017 |
| 53 | 0.031 |
| 54 | 0.102 |
| 55 | 0.049 |
| 56 | 0.285 |
| 57 | 0.437 |
| 58 | 0.557 |
| 59 | 0.203 |
| 60 | 0.027 |
| 61 | 0.131 |
| 62 | 0.301 |
| 63 | 0.246 |
| 64 | 0.362 |
| 65 | 0.105 |
| 66 | 0.282 |
| 67 | 0.239 |
| 68 | 0.318 |
| 69 | 0.104 |
| 70 | 0.089 |
| 71 | 0.090 |
| 72 | 0.079 |
| 74 | 0.220 |
| 75 | 0.009 |
| 76 | 0.017 |
| 77 | 0.027 |
| 78 | 0.154 |

Variant B-1B:

For the characterization of test substances in respect of FP antagonism, the PGF2α-induced calcium flux in recombinant FP-expressing CHO cells which additionally express the Ca$^{2+}$ sensor protein GCaMP6 was used.

3000 cells in 25 µl of full medium [DMEM F12, 10% FCS, 1.35 mM sodium pyruvate, 20 mM HEPES, 4 mM GlutaMAX™, 2% sodium bicarbonate, 1% Pen/Strep, 1% 100× non-essential amino acids] are sown per well of a 384 multititer plate (from Greiner, TC plate, black with clear base) and incubated at 37° C., 5% CO$_2$ for 24 hours. Prior to the measurement, the medium is replaced by 30 µl of buffer [calcium-free Tyrode (130 mM NaCl, 5 mM KCl, 20 mM HEPES, 1 mM MgCl$_2$, 4.8 mM NaHCO$_3$, pH 7.4), 2 mM CaCl$_2$, 0.01% BSA] and incubated at 37° C., 5% CO$_2$ for 30 minutes. The test substance is prepared in DMSO in various concentrations as a dose-response curve (starting concentration 10 mM, dilution factor 3.16) and prediluted 1:50 with calcium-free Tyrode/2 mM CaCl$_2$/0.01% BSA. 10 µl of the prediluted substance solution are added to the cells and incubated at 37° C., 5% CO$_2$ for 10 minutes. The FP receptor is activated by adding 20 µl of 3 nM (final concentration) PGF2α in calcium-free Tyrode/2 mM CaCl$_2$, and the calcium flux is determined by measuring the fluorescence at ex. 470 nm/em. 525 nm in a fluorescence measuring instrument (FLIPR Tetra®, MolecularDevices) for 120 seconds.

Table 1B below lists the IC$_{50}$ values from this assay for individual working examples of the invention (some as mean values from multiple independent individual determinations):

TABLE 1B

| Example no. | FP receptor activity IC$_{50}$ [µmol/l] |
|---|---|
| 7 | 0.034 |
| 50 | 0.044 |
| 51 | 0.038 |
| 52 | 0.006 |
| 61 | 0.079 |
| 65 | 0.060 |
| 67 | 0.134 |
| 68 | 0.182 |
| 69 | 0.059 |
| 70 | 0.053 |
| 71 | 0.047 |
| 72 | 0.043 |
| 73 | 0.098 |

B-2. In Vitro FP Receptor Binding Inhibition Test

For the FP receptor binding test, human recombinant prostanoid FP receptors, expressed in HEK293 cells, in modified MES buffer, pH 6.0, are used. This test is conducted commercially (at Eurofins Panlabs, catalog #268510). 80 µg of membrane are incubated with 1 nM [$^3$H]-PGF2α at 25° C. for 60 minutes. The amount of membrane protein can vary from batch to batch and is adjusted if required. Unspecific binding is determined in the presence of 1 µM cloprostenol. The membranes are filtered, washed and then analyzed in order to determine the specific binding of [$^3$H]-PGF2α. Substances are tested for inhibitory activity at a concentration of 10 µM or in the form of a dose-response curve [lit.: Abramovitz et al., *J. Biol. Chem.* 1994, 269 (4): 2632].

B-3. In Vitro CRTH2 Receptor Binding Inhibition Test

For this test, human recombinant prostanoid CRTH2 receptors, expressed in CHO-K1 cells, in modified Tris-HCl buffer, pH 7.4, are used. This test is conducted commercially (at Eurofins Panlabs, catalog #268030). 4 µg of membrane are incubated with 1 nM [$^3$H]-PGD2 at 25° C. for 120 minutes. The amount of membrane protein can vary from batch to batch and is adjusted if required. Unspecific binding is determined in the presence of 1 µM PGD2. The membranes are filtered, washed and then analyzed in order to determine the specific binding of [$^3$H]-PGD2. Substances are tested for inhibitory activity at a concentration of 10 µM or in the form of a dose-response curve [lit.: Sugimoto et al., *J. Pharmacol. Exp. Ther.* 2003, 305 (1): 347].

B-4. In Vitro DP Receptor Binding Inhibition Test

For this test, human recombinant prostanoid DP receptors, expressed in Chem-1 cells, in modified HEPES buffer, pH 7.4, are used. This test is conducted commercially (at Eurofins Panlabs, catalog #268060). 10 µg of membrane are incubated with 2 nM [$^3$H]-PGD2 at 25° C. for 120 minutes. The amount of membrane protein can vary from batch to batch and is adjusted if required. Unspecific binding is determined in the presence of 1 µM PGD2. The membranes are filtered, washed and then analyzed in order to determine the specific binding of [$^3$H]-PGD2. Substances are tested for inhibitory activity at a concentration of 10 µM or in the form of a dose-response curve [lit.: Wright et al., *Br. J. Pharmacol.* 1998, 123 (7): 1317; Sharif et al., *Br. J. Pharmacol.* 2000, 131 (6): 1025].

B-5. In Vitro EP1 Receptor Binding Inhibition Test

For this test, human recombinant prostanoid EP1 receptors, expressed in HEK293 cells, in modified MES buffer, pH 6.0, are used. This test is conducted commercially (at Eurofins Panlabs, catalog #268110). 14 µg of membrane are incubated with 1 nM [$^3$H]-PGE2 at 25° C. for 60 minutes. The amount of membrane protein can vary from batch to batch and is adjusted if required. Unspecific binding is determined in the presence of 10 µM PGE2. The membranes are filtered, washed and then analyzed in order to determine the specific binding of [$^3$H]-PGE2. Substances are tested for inhibitory activity at a concentration of 10 µM or in the form of a dose-response curve [lit.: Abramovitz et al., *Biochim. Biophys. Acta* 2000, 1483 (2): 285; Funk et al., *J. Biol. Chem.* 1993, 268 (35): 26767].

B-6. In Vitro EP2 Receptor Binding Inhibition Test

For this test, human recombinant prostanoid EP2 receptors, expressed in HEK293 cells, in modified MES/KOH buffer, pH 6.0, are used. This test is conducted commercially (at Eurofins Panlabs, catalog #268200). 25 mg/ml of membrane are incubated with 4 nM [$^3$H]-PGE2 at 25° C. for 120 minutes. The amount of membrane protein can vary from batch to batch and is adjusted if required. Unspecific binding is determined in the presence of 10 µM PGE2. The membranes are filtered, washed and then analyzed in order to determine the specific binding of [$^3$H]-PGE2. Substances are tested for inhibitory activity at a concentration of 10 µM or in the form of a dose-response curve [lit.: Bastien et al., *J. Biol. Chem.* 1994, 269 (16): 11873; Boie et al., *Eur. J. Pharmacol.* 1997, 340 (2-3): 227].

B-7. In Vitro EP3 Receptor Binding Inhibition Test

For this test, human recombinant prostanoid EP3 receptors, expressed in HEK293 cells, in modified MES buffer, pH 6.0, are used. This test is conducted commercially (at Eurofins Panlabs, catalog #268310). 3 µg of membrane are incubated with 0.5 nM [$^3$H]-PGE2 at 25° C. for 120 minutes. The amount of membrane protein can vary from batch to batch and is adjusted if required. Unspecific binding is determined in the presence of 10 µM PGE2. The membranes are filtered, washed and then analyzed in order to determine the specific binding of [$^3$H]-PGE2. Substances are tested for inhibitory activity at a concentration of 10 µM or in the form of a dose-response curve [lit.: Schmidt et al., *Eur. J. Biochem.* 1995, 228 (1): 23].

B-8. In Vitro EP4 Receptor Binding Inhibition Test

For this test, human recombinant prostanoid EP4 receptors, expressed in Chem-1 cells, in modified MES buffer, pH 6.0, are used. This test is conducted commercially (at Eurofins Panlabs, catalog #268420). 3 µg of membrane are incubated with 1 nM [$^3$H]-PGE2 at 25° C. for 120 minutes. The amount of membrane protein can vary from batch to batch and is adjusted if required. Unspecific binding is determined in the presence of 10 µM PGE2. The membranes are filtered, washed and then analyzed in order to determine the specific binding of [$^3$H]-PGE2. Substances are tested for inhibitory activity at a concentration of 10 µM or in the form of a dose-response curve [lit.: Davis et al., *Br. J. Pharmacol.* 2000, 130 (8): 1919].

B-9. In Vitro IP Receptor Binding Inhibition Test

For this test, human recombinant prostanoid IP receptors, expressed in HEK293 cells, in modified HEPES buffer, pH 6.0, are used. This test is conducted commercially (at Eurofins Panlabs, catalog #268600). 15 µg of membrane are incubated with 5 nM [$^3$H]-iloprost at 25° C. for 60 minutes. The amount of membrane protein can vary from batch to batch and is adjusted if required. Unspecific binding is determined in the presence of 10 µM iloprost. The membranes are filtered, washed and then analyzed in order to determine the specific binding of [$^3$H]-iloprost. Substances are tested for inhibitory activity at a concentration of 10 µM or in the form of a dose-response curve [lit.: Armstrong et al., *Br. J. Pharmacol.* 1989, 97 (3): 657; Boie et al., *J. Biol. Chem.* 1994, 269 (16): 12173].

B-10. In Vitro TP Receptor Binding Inhibition Test

For this test, human recombinant prostanoid TP receptors, expressed in HEK-293 EBNA cells, in modified Tris/HCl buffer, pH 7.4, are used. This test is conducted commercially (at Eurofins Panlabs, catalog #285510). 18.4 µg of membrane are incubated with 5 nM [$^3$H]-SQ-29 548 at 25° C. for 30 minutes. The amount of membrane protein can vary from batch to batch and is adjusted if required. Unspecific binding is determined in the presence of 1 M SQ-29 548. The membranes are filtered, washed and then analyzed in order to determine the specific binding of [$^3$H]-SQ-29 548. Substances are tested for inhibitory activity at a concentration of 10 µM or in the form of a dose-response curve [lit.: Saussy Jr. et al., *J. Biol. Chem.* 1986, 261: 3025; Hedberg et al., *J. Pharmacol. Exp. Ther.* 1988, 245: 786].

B-11. In Vitro Test for DP Agonism and Antagonism

For the characterization of test substances in respect of DP agonism and antagonism, PGD2-induced calcium flux in DP-expressing CHEM1 cells (Millipore, HTS091C) was used: 3000 cells in 25 µl of full medium [DMEM, 4.5 g/l glucose, 10% heat-inactivated FCS, 1% 100× non-essential amino acids, 10 mM HEPES, 0.25 mg/ml Geneticin (G418), 100 U/ml penicillin and streptomycin] are sown per well of a 384 multititer plate (from Greiner, TC plate, black with clear base) and incubated at 37° C./5% $CO_2$ for 24 hours. Prior to the measurement, the medium is replaced by 30 l of calcium dye loading buffer (FLIPR Calcium Assay, Molecular Devices) and incubated at 37° C./5% $CO_2$ for 60 minutes. The test substance is prepared in DMSO in various concentrations as a dose-response curve (starting concentration 10 mM, dilution factor 3.16) and prediluted 1:50 with, for example, calcium-free Tyrode (130 mM NaCl, 5 mM KCl, 20 mM HEPES, 1 mM $MgCl_2$, 4.8 mM $NaHCO_3$, pH 7.4)/2 mM $CaCl_2$. For the measurement of DP agonism, in a fluorescence measuring instrument (FLIPR Tetra®, Molecular Devices), 10 µl of the prediluted substance solution are added to the calcium dye-laden cells, and the calcium flux is determined by measuring the fluorescence at ex. 470 nm/em. 525 nm for 120 seconds. Thereafter, the cells are incubated at 37° C./5% $CO_2$ for 10 minutes. For the measurement of DP antagonism, the DP receptor is activated in the FLIPR Tetra® by adding 20 µl of ~76 nM (2×$EC_{50}$, final concentration) PGD2 in, for example, calcium-free Tyrode/2 mM $CaCl_2$, and the calcium flux is determined by measuring the fluorescence at ex. 470 nm/em. 525 nm for 120 seconds [lit.: T. Matsuoka et al. (2000) *Science* 287: 2013-2017; S. Narumiya and G. A. Fitzgerald (2001) *J. Clin. Invest.* 108: 25-30].

B-12. In Vitro Test for EP1 Agonism and Antagonism

For the characterization of test substances in respect of EP 1 agonism and antagonism, PGE2-induced calcium flux in EP1-expressing CHEM1 cells (Millipore, HTS099C) was used: 3000 cells in 25 µl of full medium [DMEM, 4.5 g/l glucose, 10% heat-inactivated FCS, 1% 100× non-essential amino acids, 10 mM HEPES, 0.25 mg/ml Geneticin (G418), 100 U/ml penicillin and streptomycin] are sown per well of a 384 multititer plate (from Greiner, TC plate, black with clear base) and incubated at 37° C./5% $CO_2$ for 24 hours. Prior to the measurement, the medium is replaced by 30 µl of calcium dye loading buffer (FLIPR Calcium Assay, Molecular Devices) and incubated at 37° C./5% $CO_2$ for 60 minutes. The test substance is prepared in DMSO in various concentrations as a dose-response curve (starting concentration 10 mM, dilution factor 3.16) and prediluted 1:50 with, for example, calcium-free Tyrode (130 mM NaCl, 5 mM KCl, 20 mM HEPES, 1 mM $MgCl_2$, 4.8 mM $NaHCO_3$, pH 7.4)/2 mM $CaCl_2$. For the measurement of EP1 agonism, in a fluorescence measuring instrument (FLIPR Tetra®, Molecular Devices), 10 µl of the prediluted substance solution are added to the calcium dye-laden cells, and the calcium flux is determined by measuring the fluorescence at ex. 470 nm/em. 525 nm for 120 seconds. Thereafter, the cells are incubated at 37° C./5% $CO_2$ for 10 minutes. For the measurement of EP 1 antagonism, the EP 1 receptor is activated in the FLIPR Tetra® by adding 20 µl of ~6 nM (2×$EC_{50}$, final concentration) PGE2 in, for example, calcium-free Tyrode/2 mM $CaCl_2$, and the calcium flux is determined by measuring the fluorescence at ex. 470 nm/em. 525 nm for 120 seconds [lit.: Y. Matsuoka et al. (2005) *Proc. Natl. Acad. Sci. USA* 102: 16066-16071; S. Narumiya and G. A. Fitzgerald (2001) *J. Clin. Invest.* 108: 25-30; K. Watanabe et al. (1999) *Cancer Res.* 59: 5093-5096].

B-13. In Vitro Test for EP2 Agonism and Antagonism

For the characterization of test substances in respect of EP2 agonism and antagonism, PGE2-induced calcium flux in EP2-expressing CHEM9 cells (Millipore, HTS185C) was used: 3000 cells in 25 µl of plating medium [DMEM, 4.5 g/l glucose, 4 mM glutamine, 10% heat-inactivated FCS, 1% 100× non-essential amino acids, 10 mM HEPES, 100 U/ml penicillin and streptomycin] are sown per well of a 384 multititer plate (from Greiner, TC plate, black with clear base) and incubated at 37° C./5% $CO_2$ for 24 hours. Prior to the measurement, the medium is replaced by 30 µl of calcium dye loading buffer (FLIPR Calcium Assay, Molecular Devices) and incubated at 37° C./5% $CO_2$ for 60 minutes. The test substance is prepared in DMSO in various concentrations as a dose-response curve (starting concentration 10 mM, dilution factor 3.16) and prediluted 1:50 with, for example, calcium-free Tyrode (130 mM NaCl, 5 mM KCl, 20 mM HEPES, 1 mM $MgCl_2$, 4.8 mM $NaHCO_3$, pH 7.4)/2 mM $CaCl_2$. For the measurement of EP2 agonism, in a fluorescence measuring instrument (FLIPR Tetra®, Molecular Devices), 10 µl of the prediluted substance solution are added to the calcium dye-laden cells, and the calcium flux is determined by measuring the fluorescence at ex. 470 nm/em. 525 nm for 120 seconds. Thereafter, the cells are incubated at 37° C./5% $CO_2$ for 10 minutes. For the measurement of EP2 antagonism, the EP2 receptor is activated in the FLIPR Tetra® by adding 20 µl of ~22 nM (2×$EC_{50}$, final concentration) PGE2 in, for example, calcium-free Tyrode/2 mM $CaCl_2$, and the calcium flux is determined by measuring the fluorescence at ex. 470 nm/em. 525 nm for 120 seconds [lit.: C. R. Kennedy et al. (1999) *Nat. Med.* 5: 217-220; S. Narumiya and G. A. Fitzgerald (2001) *J. Clin. Invest.* 108: 25-30; N. Yang et al. (2003) *J. Clin. Invest.* 111: 727-735].

B-14. In Vitro Test for EP3 Agonism and Antagonism

For the characterization of test substances in respect of EP3 agonism and antagonism, PGE2-induced calcium flux in EP3 (splice variant 6)-expressing CHEM1 cells (Millipore, HTS092C) was used: 3000 cells in 25 µl of plating medium [DMEM, 4.5 g/l glucose, 4 mM glutamine, 10% heat-inactivated FCS, 1% 100× non-essential amino acids, 10 mM HEPES, 100 U/ml penicillin and streptomycin] are sown per well of a 384 multititer plate (from Greiner, TC plate, black with clear base) and incubated at 37° C./5% $CO_2$ for 24 hours. Prior to the measurement, the medium is replaced by 30 µl of calcium dye loading buffer (FLIPR Calcium Assay, Molecular Devices) and incubated at 37° C./5% $CO_2$ for 60 minutes. The test substance is prepared in DMSO in various concentrations as a dose-response curve (starting concentration 10 mM, dilution factor 3.16) and prediluted 1:50 with, for example, calcium-free Tyrode (130 mM NaCl, 5 mM KCl, 20 mM HEPES, 1 mM $MgCl_2$, 4.8 mM $NaHCO_3$, pH 7.4)/2 mM $CaCl_2$. For the measurement of EP3 agonism, in a fluorescence measuring instrument (FLIPR Tetra®, Molecular Devices), 10 µl of the prediluted substance solution are added to the calcium dye-laden cells, and the calcium flux is determined by measuring the fluorescence at ex. 470 nm/em. 525 nm for 120 seconds. Thereafter, the cells are incubated at 37° C./5% $CO_2$ for 10 minutes. For the measurement of EP3 antagonism, the EP3 receptor is activated in the FLIPR Tetra® by adding 20 µl of ~2 nM (2×$EC_{50}$, final concentration) PGE2 in, for example, calcium-free Tyrode/2 mM $CaCl_2$, and the calcium flux is determined by measuring the fluorescence at ex. 470 nm/em. 525 nm for 120 seconds [lit.: M. Kotani et al. (1995) *Mol. Pharmacol.* 48: 869-879; M. Kotani et al. (1997) *Genomics* 40: 425-434; T. Kunikata et al. (2005) *Nat. Immunol.* 6: 524-531; S. Narumiya and G. A. Fitzgerald (2001) *J. Clin. Invest.* 108: 25-30; F. Ushikubi et al. (1998) *Nature* 395: 281-284].

B-15. In Vitro Test for EP4 Agonism and Antagonism

For the characterization of test substances in respect of EP4 agonism and antagonism, PGE2-induced calcium flux in EP4-expressing CHEM1 cells (Millipore, HTS142C) was used: 3000 cells in 25 µl of plating medium [DMEM, 4.5 g/l glucose, 4 mM glutamine, 10% heat-inactivated FCS, 1% 100× non-essential amino acids, 10 mM HEPES, 100 U/ml penicillin and streptomycin] are sown per well of a 384 multititer plate (from Greiner, TC plate, black with clear base) and incubated at 37° C./5% $CO_2$ for 24 hours. Prior to the measurement, the medium is replaced by 30 µl of calcium dye loading buffer (FLIPR Calcium Assay, Molecular Devices) and incubated at 37° C./5% $CO_2$ for 60 minutes. The test substance is prepared in DMSO in various concentrations as a dose-response curve (starting concentration 10 mM, dilution factor 3.16) and prediluted 1:50 with, for example, calcium-free Tyrode (130 mM NaCl, 5 mM KCl, 20 mM HEPES, 1 mM $MgCl_2$, 4.8 mM $NaHCO_3$, pH 7.4)/2 mM $CaCl_2$. For the measurement of EP4 agonism, in a fluorescence measuring instrument (FLIPR Tetra®, Molecular Devices), 10 µl of the prediluted substance solution are added to the calcium dye-laden cells, and the calcium flux is determined by measuring the fluorescence at ex. 470 nm/em. 525 nm for 120 seconds. Thereafter, the cells are incubated at 37° C./5% $CO_2$ for 10 minutes. For the measurement of EP4 antagonism, the EP4 receptor is activated in the FLIPR Tetra® by adding 20 µl of ~26 nM (2×$EC_{50}$, final concentration) PGE2 in, for example, calcium-free Tyrode/2 mM $CaCl_2$, and the calcium flux is determined by measuring the fluorescence at ex. 470 nm/em. 525 nm for 120 seconds [lit.: S. Narumiya and G. A. Fitzgerald (2001) *J. Clin. Invest.* 108: 25-30; M. Nguyen et al. (1997) *Nature* 390: 78-81; K. Yoshida et al. (2002) *Proc. Natl. Acad. Sci. USA* 99: 4580-4585].

B-16. In Vitro Test for IP Agonism and Antagonism

For the characterization of test substances in respect of IP agonism and antagonism, iloprost-induced calcium flux in IP-expressing CHEM1 cells (Millipore, HTS131C) was used: 3000 cells in 25 µl of plating medium [DMEM, 4.5 g/l glucose, 4 mM glutamine, 10% heat-inactivated FCS, 1% 100× non-essential amino acids, 10 mM HEPES, 100 U/ml penicillin and streptomycin] are sown per well of a 384 multititer plate (from Greiner, TC plate, black with clear base) and incubated at 37° C./5% $CO_2$ for 24 hours. Prior to the measurement, the medium is replaced by 30 µl of calcium dye loading buffer (FLIPR Calcium Assay, Molecular Devices) and incubated at 37° C./5% $CO_2$ for 60 minutes. The test substance is prepared in DMSO in various concentrations as a dose-response curve (starting concentration 10 mM, dilution factor 3.16) and prediluted 1:50 with, for example, calcium-free Tyrode (130 mM NaCl, 5 mM KCl, 20 mM HEPES, 1 mM $MgCl_2$, 4.8 mM $NaHCO_3$, pH 7.4)/2 mM $CaCl_2$. For the measurement of IP agonism, in a fluorescence measuring instrument (FLIPR Tetra®, Molecular Devices), 10 µl of the prediluted substance solution are added to the calcium dye-laden cells, and the calcium flux is determined by measuring the fluorescence at ex. 470 nm/em. 525 nm for 120 seconds. Thereafter, the cells are incubated at 37° C./5% $CO_2$ for 10 minutes. For the measurement of IP antagonism, the IP receptor is activated in the FLIPR Tetra® by adding 20 µl of ~106 nM (2×$EC_{50}$, final concentration) iloprost in, for example, calcium-free Tyrode/2 mM $CaCl_2$, and the calcium flux is determined by measuring the fluorescence at ex. 470 nm/em. 525 nm for 120 seconds [lit.: S. Narumiya et al. (1999) *Physiol. Rev.* 79: 1193-1226; T. Murata et al. (1997) *Nature* 388: 678-682; Y. Cheng et al. (2002) *Science* 296: 539-541; C. H. Xiao et al. (2001) *Circulation* 104: 2210-2215; G. A. Fitzgerald (2004) *N. Engl. J. Med.* 351: 1709-1711].

B-17. In Vitro Test for TP Agonism and Antagonism

For the characterization of test substances in respect of TP agonism and antagonism, U46619-induced calcium flux in TP-expressing CHEM1 cells (Millipore, HTS081C) was used: 3000 cells in 25 µl of plating medium [DMEM, 10% heat-inactivated FCS, 10% heat-inactivated FCS, 1% 100× non-essential amino acids, 10 mM HEPES, 0.25 mg/ml Geneticin (G418), 100 U/ml penicillin and streptomycin] are sown per well of a 384 multititer plate (from Greiner, TC plate, black with clear base) and incubated at 37° C./5% $CO_2$ for 24 hours. Prior to the measurement, the medium is replaced by 30 µl of calcium dye loading buffer (FLIPR Calcium Assay, Molecular Devices) and incubated at 37° C./5% $CO_2$ for 60 minutes. The test substance is prepared in DMSO in various concentrations as a dose-response curve (starting concentration 10 mM, dilution factor 3.16) and prediluted 1:50 with, for example, calcium-free Tyrode (130 mM NaCl, 5 mM KCl, 20 mM HEPES, 1 mM $MgCl_2$, 4.8 mM $NaHCO_3$, pH 7.4)/2 mM $CaCl_2$. For the measurement of TP agonism, in a fluorescence measuring instrument (FLIPR Tetra®, Molecular Devices), 10 µl of the prediluted substance solution are added to the calcium dye-laden cells, and the calcium flux is determined by measuring the fluorescence at ex. 470 nm/em. 525 nm for 120 seconds. Thereafter, the cells are incubated at 37° C./5% $CO_2$ for 10 minutes. For the measurement of TP antagonism, the TP receptor is activated in the FLIPR Tetra® by adding 20 µl of ~88 nM (2×$EC_{50}$, final concentration) U46619 in, for example, calcium-free Tyrode/2 mM $CaCl_2$, and the calcium flux is determined by measuring the fluorescence at ex. 470 nm/em. 525 nm for 120 seconds [lit.: S. Ali et al. (1993) *J. Biol. Chem.* 268: 17397-17403; K. Hanasaki et al. (1989) *Biochem. Pharmacol.* 38: 2967-2976; M. Hirata et al. (1991) *Nature* 349: 617-620].

B-18. Animal Model of Bleomycin-Induced Pulmonary Fibrosis

Bleomycin-induced pulmonary fibrosis in the mouse or rat is a widely used animal model of pulmonary fibrosis. Bleomycin is a glycopeptide antibiotic employed in oncology for the therapy of testicular tumors and Hodgkin- and Non-Hodgkin tumors. It is eliminated renally, has a half-life of about 3 hours and, as cytostatic, influences various phases of the division cycle [Lazo et al., *Cancer Chemother.* 15, 44-50 (1994)]. Its anti-neoplastic effect is based on an oxidatively damaging effect on DNA [Hay et al., Arch. 65, 81-94 (1991)]. Lung tissue is at a particular risk when exposed to bleomycin since it contains only a small number of cysteine hydrolases which, in other tissues, lead to inactivation of bleomycin. Following administration of bleomycin, the animals suffer an acute respiratory distress syndrome (ARDS) with subsequent development of pulmonary fibrosis.

Administration of bleomycin may be by single or repeat intratracheal, inhalative, intravenous or intraperitoneal administration. Treatment of the animals with the test substance (by gavage, by addition to the feed or drinking water, using an osmotic minipump, by subcutaneous or intraperitoneal injection or by inhalation) starts at the day of the first bleomycin administration or therapeutically 3-14 days later and extends over a period of 2-6 weeks. At the end of the study, a bronchio-alveolar lavage to determine the cell content and the pro-inflammatory and pro-fibrotic markers and a histological assessment of pulmonary fibrosis are carried out.

B-19. Animal Model of DQ12 Quartz-Induced Pulmonary Fibrosis

DQ12 quartz-induced pulmonary fibrosis in the mouse or rat is a widely used animal model of pulmonary fibrosis [Shimbori et al., *Exp. Lung Res.* 36, 292-301 (2010)]. DQ12 quartz is quartz which is highly active owing to breaking or grinding. In mice and rats, intratracheal or inhalative administration of DQ12 quartz leads to alveolar proteinosis followed by interstitial pulmonary fibrosis. The animals receive a single or repeat intratracheal or inhalative instillation of DQ12 quartz. Treatment of the animals with the test substance (by gavage, by addition to the feed or drinking water, using an osmotic minipump, by subcutaneous or intraperitoneal injection or by inhalation) starts at the day of the first silicate instillation or therapeutically 3-14 days later and extends over a period of 3-12 weeks. At the end of the study, a bronchio-alveolar lavage to determine the cell content and the pro-inflammatory and pro-fibrotic markers and a histological assessment of pulmonary fibrosis are carried out.

B-20. Animal Model of DQ12 Quartz or FITC-Induced Pulmonary Inflammation

In the mouse and the rat, intratracheal administration of DQ12 quartz or fluorescein isothiocyanate (FITC) leads to an inflammation in the lung [Shimbori et al., *Exp. Lung Res.* 36, 292-301 (2010)]. At the day of the instillation of DQ12 quartz or FITC or a day later the animals are treated with the test substance for a duration of 24 h up to 7 days (by gavage, by addition to the feed or drinking water, using an osmotic minipump, by subcutaneous or intraperitoneal injection or by inhalation). At the end of the experiment, a bronchioalveolar lavage to determine the cell content and the pro-inflammatory and pro-fibrotic markers is carried out.

C. WORKING EXAMPLES OF PHARMACEUTICAL COMPOSITIONS

The compounds of the invention can be converted to pharmaceutical preparations as follows:

Tablet:

Composition:

100 mg of the compound of the invention, 50 mg of lactose (monohydrate), 50 mg of corn starch (native), 10 mg of polyvinylpyrrolidone (PVP 25) (BASF, Ludwigshafen, Germany) and 2 mg of magnesium stearate.

Tablet weight 212 mg. Diameter 8 mm, radius of curvature 12 mm.

Production:

The mixture of compound of the invention, lactose and starch is granulated with a 5% solution (w/w) of the PVP in water. The granules are dried and then mixed with the magnesium stearate for 5 minutes. This mixture is compressed using a conventional tableting press (see above for format of the tablet). The guide value used for the pressing is a pressing force of 15 kN.

Suspension for Oral Administration:

Composition:

1000 mg of the compound of the invention, 1000 mg of ethanol (96%), 400 mg of Rhodigel® (xanthan gum from FMC, Pennsylvania, USA) and 99 g of water.

10 ml of oral suspension correspond to a single dose of 100 mg of the compound of the invention.

Production:

The Rhodigel is suspended in ethanol; the compound of the invention is added to the suspension. The water is added while stirring. The mixture is stirred for about 6 h until the swelling of the Rhodigel is complete.

Solution for Oral Administration:

Composition:

500 mg of the compound of the invention, 2.5 g of polysorbate and 97 g of polyethylene glycol 400. 20 g of oral solution correspond to a single dose of 100 mg of the compound of the invention.

Production:

The compound of the invention is suspended in the mixture of polyethylene glycol and polysorbate with stirring. The stirring operation is continued until dissolution of the compound of the invention is complete.

i.v. solution:

The compound of the invention is dissolved in a concentration below the saturation solubility in a physiologically acceptable solvent (e.g. isotonic saline solution, glucose solution 5% and/or PEG 400 solution 30%). The solution is subjected to sterile filtration and dispensed into sterile and pyrogen-free injection vessels.

The invention claimed is:

1. A method for treatment of idiopathic pulmonary fibrosis in a human or an animal, comprising administering to the human or animal in need thereof a compound of the formula (I)

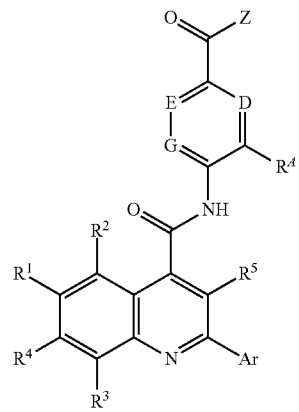

in which
$R^A$ is hydrogen, halogen, pentafluorosulfanyl, cyano, nitro, $(C_1\text{-}C_4)$-alkyl, hydroxyl, $(C_1\text{-}C_4)$-alkoxy, amino or a group of the formula —NH—C(=O)—$R^6$, —NH—C(=O)—NH—$R^6$ or —S(=O)$_n$—$R^7$,
where $(C_1\text{-}C_4)$-alkyl and $(C_1\text{-}C_4)$-alkoxy may be up to trisubstituted by fluorine,
and in which
$R^6$ is hydrogen or $(C_1\text{-}C_4)$-alkoxy which may be up to trisubstituted by fluorine,
$R^7$ is $(C_1\text{-}C_4)$-alkyl which may be substituted by hydroxyl, methoxy or ethoxy or up to trisubstituted by fluorine,
and
n is the number 0, 1 or 2,
D is C—$R^D$ or N,
E is C—$R^E$ or N,
G is C—$R^G$ or N,
where not more than two of the ring members D, E and G at the same time are N,
and in which
$R^D$ and $R^E$ are each independently hydrogen, fluorine, chlorine, methyl, trifluoromethyl, methoxy or trifluoromethoxy,
and
$R^G$ is hydrogen, fluorine, chlorine, bromine, methyl or trifluoromethyl,
Z is OH or a group of the formula —NH—$R^8$, —NH—SO$_2$$R^9$ or —NH—SO$_2$—NR$^{10A}$R$^{10B}$, in which
$R^8$ is hydrogen or $(C_1\text{-}C_4)$-alkoxy which may be up to trisubstituted by fluorine,
$R^9$ is $(C_1\text{-}C_4)$-alkoxy which may be up to trisubstituted by fluorine, or phenyl,
and
$R^{10A}$ and $R^{10B}$ are each independently hydrogen or $(C_1\text{-}C_4)$-alkyl which may be up to trisubstituted by fluorine,
$R^1$ is halogen, trifluoromethoxy, (trifluoromethyl)sulfanyl, pentafluorosulfanyl, $(C_1\text{-}C_4)$-alkyl, trimethylsilyl, cyclopropyl or cyclobutyl,
where $(C_1\text{-}C_4)$-alkyl may be up to trisubstituted by fluorine
and
cyclopropyl and cyclobutyl may be up to disubstituted by fluorine,
$R^2$, $R^3$ and $R^4$ are each independently hydrogen, fluorine, chlorine, methyl or trifluoromethyl,
$R^5$ is $(C_1\text{-}C_4)$-alkyl which may be up to trisubstituted by fluorine, or is fluorine, chlorine, methoxy or cyclopropyl,
and
Ar is phenyl which may be mono- or disubstituted identically or differently by fluorine and chlorine, or is pyridyl or thienyl, and an N-oxide, salt, solvate, salt of the N-oxide and solvate of the N-oxide and salt thereof.

2. The method of claim 1, wherein the compound of the formula (I) is in a medicament, wherein the medicament comprises the compound of the formula (I) in combination with one or more inert, nontoxic, pharmaceutically suitable excipients.

3. The method of claim 2 wherein the medicament further comprises at least one compound selected from the group consisting of
PDE 5 inhibitor,
sGC activator,
sGC stimulator,
prostacyclin analog,
IP receptor agonist,
endothelin antagonist,
compound that inhibit the signal transduction cascade, and
pirfenidone.

4. The method of claim 1, wherein the compound is a compound of formula (I) in which
$R^A$ is hydrogen, fluorine, chlorine, bromine, cyano, methyl, trifluoromethyl, methoxy, trifluoromethoxy or a group of the formula —S(=O)$_n$—R$^7$ in which
$R^7$ is methyl or trifluoromethyl,
and
n is the number 0 or 2,
D is C—R$^D$ or N, in which
$R^D$ is hydrogen or fluorine,
E is C-H,
G is C—R$^G$ or N, in which
$R^G$ is hydrogen, fluorine or chlorine,
Z is OH,
$R^1$ is chlorine, bromine, iodine, methyl, ethyl, isopropyl, trifluoromethyl, trifluoromethoxy, (trifluoromethyl)sulfanyl, pentafluorosulfanyl or trimethylsilyl,
$R^2$ and $R^3$ are each hydrogen,
$R^4$ is hydrogen, fluorine or chlorine,
$R^5$ is methyl, chlorine or cyclopropyl,
and
Ar is phenyl which may be monosubstituted by fluorine, or pyridyl, and a salt, solvate and solvate of the salt thereof.

5. The method of claim 1, wherein the compound is a compound of formula (I) in which
$R^A$ is fluorine, chlorine, cyano, methyl, trifluoromethyl, methoxy, trifluoromethoxy or a group of the formula —S(=O)$_n$—R$^7$ in which
$R^7$ is methyl or trifluoromethyl,
and
n is the number 0 or 2,
D is C-H,
E is C-H,
G is C—R$^G$ or N, in which
$R^G$ is hydrogen, fluorine or chlorine,
Z is OH,
$R^1$ is chlorine, bromine, methyl, trifluoromethyl or trimethylsilyl,
$R^2$ and $R^3$ are each hydrogen,
$R^4$ is hydrogen or chlorine,
$R^5$ is methyl,
and
Ar is phenyl which may be monosubstituted by fluorine, or 4-pyridyl,
and a salt, solvate and solvate of the salt thereof.

6. The method of claim 1, wherein the compound is 6-{[6-Bromo-3-methyl-2-phenylquinolin-4-yl)carbonyl]amino}-5-fluoronicotinic acid

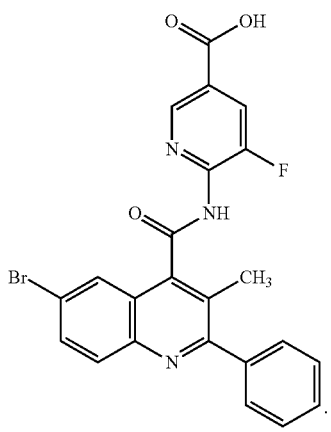 [SMILES: Cc1c(-c2ccccc2)nc2ccc(Br)cc2c1C(=O)Nc1ncc(C(=O)O)cc1F]

7. The method of claim 1, wherein the compound is 4-{[(6-Bromo-3-methyl-2-phenylquinolin-4-yl)carbonyl]amino}-3 fluorobenzoic acid

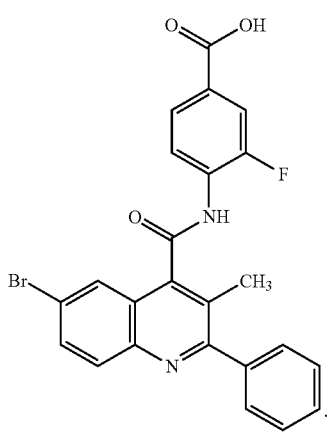 [SMILES: Cc1c(-c2ccccc2)nc2ccc(Br)cc2c1C(=O)Nc1ccc(C(=O)O)cc1F]

8. The method of claim 1, wherein the compound is 3-Fluoro-4-{[6-iodo-3-methyl-2-phenylquinolin-4-yl)carbonyl]-amino}-benzoic acid

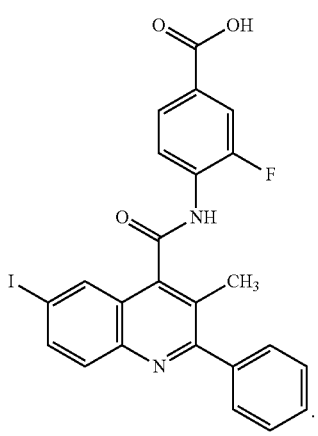 [SMILES: Cc1c(-c2ccccc2)nc2ccc(I)cc2c1C(=O)Nc1ccc(C(=O)O)cc1F]

9. The method of claim 1, wherein the compound is 4-{[(6-Bromo-3-chloro-2-phenylquinolin-4-yl)carbonyl]amino}-3-fluorobenzoic acid

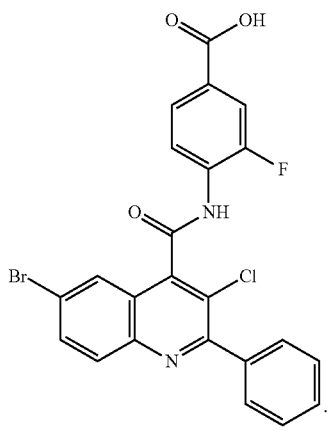 [SMILES: O=C(O)c1ccc(NC(=O)c2c(Cl)c(-c3ccccc3)nc3ccc(Br)cc23)c(F)c1]
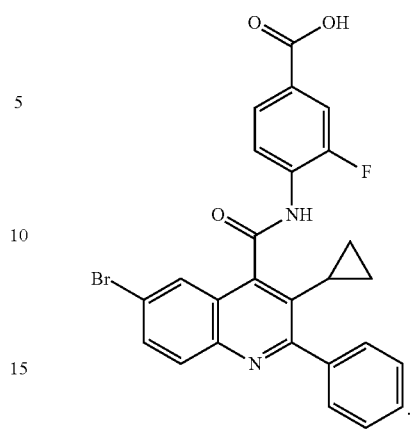
10. The method of claim 1, wherein the compound is 4-{[(6-Bromo-3-cyclopropyl-2-phenylquinolin-4-yl)carbonyl]amino}-3-fluorobenzoic acid
* * * * *